(12) United States Patent
Yu et al.

(10) Patent No.: US 6,489,338 B2
(45) Date of Patent: Dec. 3, 2002

(54) IMIDAZOPYRIDINE AND IMIDAZOPYRIMIDINE ANTIVIRAL AGENTS

(75) Inventors: Kuo-Long Yu, Zionsville, IN (US); Rita L. Civiello, Killingworth, CT (US); Keith D. Combrink, Wallingford, CT (US); Hatice Belgin Gulgeze, New Haven, CT (US); Ny Sin, Meriden, CT (US); Xiangdong Wang, Guilford, CT (US); Nicholas A. Meanwell, East Hampton, CT (US); Brian Lee Venables, Milford, CT (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 09/840,279

(22) Filed: Apr. 23, 2001

(65) Prior Publication Data

US 2002/0016309 A1 Feb. 7, 2002

Related U.S. Application Data

(60) Provisional application No. 60/263,363, filed on Jan. 22, 2001, and provisional application No. 60/211,447, filed on Jun. 13, 2000.

(51) Int. Cl.[7] .................... A61K 31/437; C07D 471/04
(52) U.S. Cl. ......................... 514/303; 546/118
(58) Field of Search ........................... 546/118; 514/303

(56) References Cited

U.S. PATENT DOCUMENTS 4,324,794 A    4/1982    Tidwell et al. ............... 424/273
5,256,668 A    10/1993   Hsu et al. .................... 514/269

FOREIGN PATENT DOCUMENTS

| AU | A-14704 | 12/1998 |
| EP | 0058146 A1 | 6/1985 |
| WO | WO 99/38508 | 8/1999 |
| WO | WO 00/04900 | 2/2000 |
| WO | WO 01/00615 A1 | 1/2001 |

OTHER PUBLICATIONS

G. Crank et al, "Photochemistry of Heterocyclics. III* Photolysis of Various 2–Substituted Benzimidazoles," Australian Journal of Chemistry, 35(4), pp. 775–784, 1982.
JAMA, 277(1), pp. 12–13, 1997.
E. De Clercq, Int. J. Antimicrobial Agents, 7, pp. 193–202, 1996.
R. R. Tidwell, et al, J. Med. Chem., 26, pp. 294–298, 1983.
E. J. Dubovi, et al, Antimicrobial Agents & Chemotherapy, 19(4), pp. 649–656, 1981.
P. R. Wyde, et al, Antiviral Research, 38, pp–31–42, 1998.
S. Shigeta, et al, Antiviral Chemistry & Chemotherapy, 3(3), pp. 171–177, 1992.
W. R. Roderick, et al, J. Med. Chem., 15(6), pp. 655–658, 1972.
B. Cakir, et al, Gazi Eczacilik Fak. Der., 5(1), pp. 71–77, 1988.

*Primary Examiner*—Richard L. Raymond
(74) *Attorney, Agent, or Firm*—Samuel J. DuBoff

(57) ABSTRACT

The present invention concerns antiviral compounds, their methods of preparation and their compositions, and use in the treatment of viral infections. More particularly, the invention provides imidazopyridine and imidazopyrimidine derivatives (Formula I) for the treatment of respiratory syncytial virus infection.

7 Claims, No Drawings

IMIDAZOPYRIDINE AND IMIDAZOPYRIMIDINE ANTIVIRAL AGENTS

This application claims the benefit of U.S. Provisional Application Nos. 60/263,363 filed Jan. 22, 2001 and 60/211,447 filed Jun. 13, 2000, respectively.

BACKGROUND OF THE INVENTION

1. Field of the Invention

The present invention concerns antiviral compounds, their methods of preparation and their compositions, and use in the treatment of viral infections. More particularly, the invention provides imidazopyridine and imidazopyrimidine derivatives (Formula I) for the treatment of respiratory syncytial virus infection.

2. Background Art

Respiratory syncytial virus (RSV) is the leading cause of serious lower respiratory tract infection in infants, children, elderly and immunocompromised persons. Severe infection of the virus may result in bronchiolitis or pneumonia which may require hospitalization or result in death. (*JAMA*, 1997, 277, 12). Currently only Ribavirin is approved for the treatment of this viral infection. Ribavirin is a nucleoside analogue which is administered intranasally as an aerosol. The agent is quite toxic, and its efficacy has remained controversial. Other than Ribavirin, RespiGam and Synagis are an immunoglobulin and monoclonal antibody, respectively, that neutralize RSV. They are the only two biologics that have been approved for prophylactic use in high risk pediatric patients for RSV infection. Both RespiGam and Synagis are very expensive and require parental administration.

Many agents are known to inhibit respiratory syncytial virus (De Clercq, *Int. J. Antiviral Agents,* 1996, 7, 193). Y. Tao et al. (EP 0 058 146 A1, 1998) disclosed that Cetirizine, a known antihistamine, exhibited anti-RSV activity. Tidwell et al.,*J. Med. Chem.* 1983, 26, 294 (U.S. Pat. No. 4,324,794, 1982), and Dubovi et al., *Antimicrobial Agents and Chemotherapy,* 1981, 19, 649, reported a series of amidino compounds with the formula shown below as inhibitors of RSV.

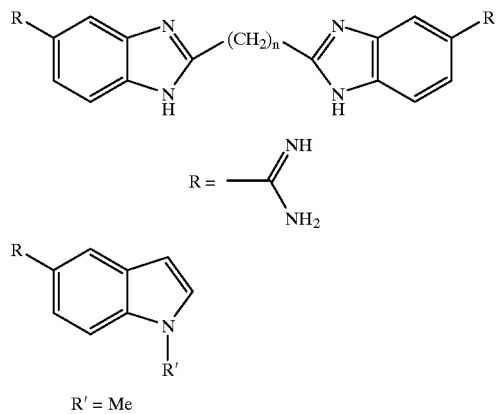

Hsu et al., U.S. Pat. No. 5,256,668 (1993) also disclosed a series of 6-aminopyrimidones that possess anti-viral activity against RSV.

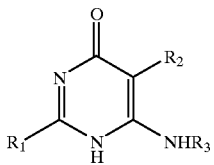

In addition, Y. Gluzman, et al., (AU Patent, Au-A-14,704, 1997) and P. R. Wyde et al. (*Antiviral Res.* 1998, 38, 31) disclosed a series of triazine containing compounds that were useful for the treatment and/or prevention of RSV infection.

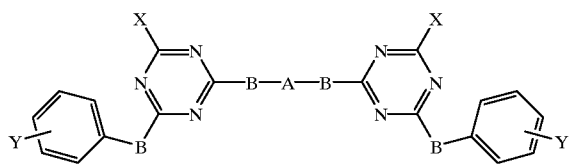

Another series of compounds structurally related to this invention are pyrido[1,2-a]benzoazoles and pyrimidio[1,2a]benzimidazoles disclosed by S. Shigeta et al in *Antiviral Chem. & Chemother.* 1992, 3, 171. These compounds have demonstrated inhibition of orthomyxovirus and paramyxovirus replication in HeLa cells. The structures of these compounds are shown in formulas Id and Ie, in which F=NH, S, or O; Q=—NHCOPh, —COOH, COOEt, or CN; T=COMe, CN, or COOEt; G=O or NH.

Formula Id

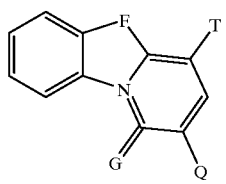

Formula Ie

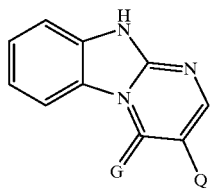

A bis-benzimidazole with an ethylenediol linker shown below has also been reported as a potent inhibitor of rhinoviruses (Roderick, et al. *J. Med. Chem.* 1972, 15, 655).

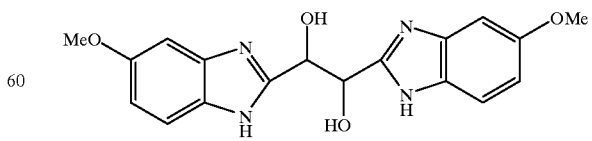

Other structurally related compounds are bis-benzimidazoles which possess antifungal activity (B. Cakir, et al. *Eczacilik Fak. Derg.* 1988, 5, 71).

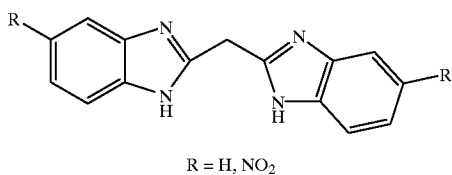

R = H, NO₂

Most recently Yu et al. have discovered a series of benzimidazoles (Formula II) for the treatment and prevention of RSV infection (WO 00/04900). In addition, Theodore Nitz has also found a series of compounds with Formula III that inhibit RSV in Hep-2 cell tissue culture assay (WO 99/38508). Although many other agents are known to inhibit respiratory syncytial virus (De Clercq, *Int. J. Antiviral Agents,* 1996, 7, 193) none of them have been used in human clinical trials. Thus, there is a medical need for a convenient and less expensive anti-viral agent for the treatment and prevention of RSV infection.

Formula II

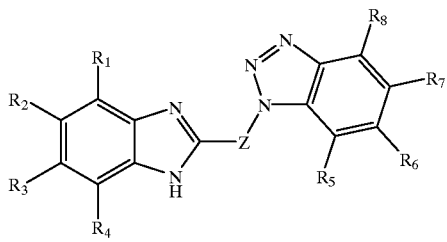

Formula III

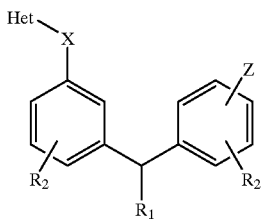

SUMMARY OF THE INVENTION

This invention relates to compounds having the Formula I, and pharmaceutically acceptable salts thereof Formula I

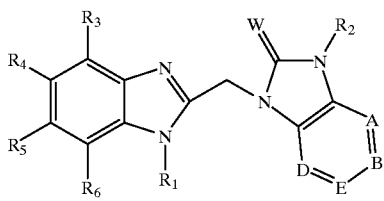

wherein:
W is O or S;
$R_1$ is —(CR'R")$_n$—X;
X is H, $C_{1-12}$ alkyl, $C_{2-12}$ alkenyl, $C_{2-12}$ alkynyl, $C_{3-7}$ cycloalkyl, $C_{4-7}$ cycloalkenyl, each of said alkyl, alkenyl, alkynyl, cycloalkyl and cycloalkenyl being optionally substituted with one to six of the same or different halogen atoms; halogen, CN, OR', OCOR"", NR'R", NR'COR", NR'CONR"R'", NR'SO$_2$R", NR'COOR", COR', CR'"NNR'R", CR'NOR", COOR', CONR'R", SO$_m$R', PO(OR')$_2$, aryl, heteroaryl or non-aromatic heterocycle;
m is 0–2; n is 2–6;
$R_2$ is
(i) H, $C_{1-12}$ alkyl, $C_{2-12}$ alkenyl, $C_{2-12}$ alkynyl, $C_{3-7}$ cycloalkyl, $C_{4-7}$ cycloalkenyl, —(CH$_2$)$_t$, $C_{3-7}$ cycloalkyl, —(CH$_2$)$_t$, $C_{4-7}$ cycloalkenyl, each of said alkyl, alkenyl, alkynyl, cycloalkyl and cycloalkenyl being optionally substituted with one to six of the same or different halogen atoms; SO$_2$R", SO$_2$NR'R" or CN; wherein t is 1–6;
(ii) —(CR'R")$_{n'}$—Y, wherein Y is CN, OR', OCONR'R", NR'R", NCOR', NR'SO$_2$R", NR'COOR", NR'CONR"R'", COR', CR'"NNR'R", CR'NOR", COOR', CONR'R", SO$_m$R', SO$_2$NR'R" or PO(OR')$_2$; wherein
m is 0–2 and n' is 1–6;
(iii) —(CR'R")$_{n"}$—C$_6$H$_4$—Z, wherein the Z group may be in the ortho, meta or para position relative to the —(CH$_2$)$_{n"}$ group; Z is CN, OR', OCONR'R", NO$_2$, NR'R", NCOR', NR'SO$_2$R", NR'COOR", NR'CONR"R'", COR', CR'"NNR'R", CR'NOR", COOR', CONR'R", SO$_m$R', SO$_2$NR'R" or PO(OR')$_2$;
m is 0–2; n" is 0–6; or
(iv) —(CR'R")n'''-heteroaryl, wherein n''' is 0–6;
(v) —(CR'R")n'''-non-aromatic heterocycle, wherein n''' is 0–6;
$R_3$, $R_4$, $R_5$ and $R_6$ are each independently hydrogen, halogen, $C_{1-6}$ alkyl, $C_{1-6}$ alkyl substituted with one to six of the same or different halogen atoms, OR', CN, COR', COOR', CONR'R", or NO$_2$;
A, B, E, D are each independently C—H, C—Q—, N, or N—O; provided at least one of A, B, E or D is not C—H or C—Q; wherein Q is halogen, $C_{1-3}$ alkyl or $C_{1-3}$ alkyl substituted with one to three of the same or different halogen atoms; and
R', R", R'" are each independently H, $C_{1-6}$ alkyl, $C_{26}$ alkenyl, $C_{2-6}$ alkynyl, $C_{3-7}$ cycloalkyl, $C_{4-7}$ cycloalkenyl, each of said alkyl, alkenyl, alkynyl, cycloalkyl and cycloalkenyl being optionally substituted with one to six of the same or different halogen atoms; or R' and R" taken together form a cyclic alkyl group having 3 to 7 carbon atoms; benzyl or aryl;
R"" is $C_{1-6}$ alkyl, $C_{2-6}$ alkenyl, $C_{2-6}$ alkynyl, $C_{3-7}$ cycloalkyl, $C_{4-7}$ cycloalkenyl, NR'R", CR'NR"R'", aryl, heteroaryl, non-aromatic heterocycle; and
Non-aromatic heterocycle is a 3–7 membered non-aromatic ring containing at least one and up to 4 non-carbon atoms selected from the group consisting of O, S, N, and NR';
Aryl is phenyl, naphthyl, indenyl, azulenyl, fluorenyl and anthracenyl;
Heteroaryl is a 4–7 membered aromatic ring which contains one to five heteroatoms independently selected from the group consisting of O, S, N or NR', wherein said aromatic ring is optionally fused to group B';
B' is an aromatic group selected from the group consisting of phenyl, 1-naphthyl, 2-naphthyl, indenyl, azulenyl, fluorenyl, and anthracenyl;
Aryl, B', said 4–7 membered aromatic ring, and said 3–7 membered non-aromatic ring may each independently contain one to five substituents which are each independently selected from $R_7$, $R_8$, $R_9$, $R_{10}$ or $R_{11}$; and $R_7$, $R_8$, $R_9$, $R_{10}$ and $R_{11}$ are each independently (i) H, $C_{1-6}$ alkyl, $C_{2-6}$ alkenyl, $C_{2-6}$ alkynyl, $C_{3-7}$ cycloalkyl, $C_{4-7}$ cycloalkenyl, each of said alkyl, alkenyl, alkynyl, cycloalkyl, cycloalkenyl being optionally substituted with one to six of the same or different halogen atoms; and (ii) halogen, CN, $NO_2$, OR', NR'R", COR', COOR', CONR'R", OCOR', NR'COR", $SO_mR'$, $SO_2NR'R"$, $PO(OR')_2$.

A preferred embodiment includes compounds of Formula I wherein heteroaryl is selected from the group consisting of 2-furyl, 3-furyl, 2-thienyl, 3-thienyl, 2-pyridyl, 3-pyridyl, 4-pyridyl, pyrrolyl, oxazolyl, thiazolyl, imidazolyl, pyrazolyl, isoxazolyl, isothiazolyl, 1,2,3-oxadiazolyl, 1,2,4-oxadiazolyl, 1,2,4-oxadiazol-5-one, 1,2,3-triazolyl, 1,3,4-thiadiazolyl, pyridazinyl, pyrimidinyl, pyrazinyl, 1,3,5-triazinyl, 1,3,5-trithianyl, indolizinyl, indolyl, isoindolyl, 3H-indolyl, indolinyl, benzo[b]furanyl, benzo[b]thiophenyl, 1H-indazolyl, benzimidazolyl, benzthiazolyl, purinyl, 4H-quinolizinyl, quinolinyl, isoquinolinyl, cinnolinyl, phthalazinyl, quinazolinyl, quinoxalinyl, 1,8-naphthyridinyl, pteridinyl, carbazolyl, acridinyl, phenazinyl, phenothiazinyl, tetrazole and phenoxazinyl.

Another preferred embodiment includes compounds of Formula I wherein:

$R_1$ is —$(CH_2)_n$—X;

X is H, $C_{1-6}$ alkyl, $C_{2-6}$ alkenyl, $C_{2-6}$ alkynyl, $C_{3-6}$ cycloalkyl, $C_{3-6}$ cycloalkenyl, each of said alkyl, alkenyl, alkynyl, cycloalkyl and cycloalkenyl being optionally substituted with one to six of the same or different halogen atoms; halogen, CN, OR', OCOR"", NR'R", NR'COR", NR'COOR", COR', CR'"NNR'R", CR'NOR", COOR', CONR'R", $SO_mR'$, aryl or heteroaryl;

m is 0–2; n is 2–4;

$R_2$ is (i) H, $C_{1-6}$ alkyl, $C_{2-6}$ alkenyl, $C_{2-6}$ alkynyl, $C_{3-6}$ cycloalkyl, $C_{3-6}$ cycloalkenyl, —$(CH_2)_t$ $C_{3-7}$ cycloalkyl, —$(CH_2)_t$ $C_{4-7}$ cycloalkenyl, each of said alkyl, alkenyl, alkynyl, cycloalkyl and cycloalkenyl being optionally substituted with one to six of the same or different halogen atoms; $SO_2R"$, $SO_2NR'R"$ or CN; wherein t is 1–6;

(ii) —$(CH_2)_{n'}$—Y, wherein Y is CN, OR', COR', COOR', CONR'R", $SO_mR'$, $SO_2NR'R"$, $PO(OR')_2$ wherein m is 0–2 and n' is 1–6; or (iii) —$(CH_2)n"$—$C_6H_4$—Z, wherein the Z group may be in the ortho, meta or para position relative to the —$(CH_2)n"$ group; Z is CN, OR', COR' or $SO_mR'$; m is 0–2; n" is 0–3;

$R_3$, $R_4$, $R_5$, and $R_6$ are each independently hydrogen, halogen, $C_{1-6}$ alkyl, optionally substituted with one to six of the same or different halogen atoms; and A, B, E, D are each independently C—H or N; provided at least one of A, B, E or D is not C—H.

Another preferred embodiment includes compounds of Formula I wherein:

$R_3$, R4, $R_5$ and $R_6$ are each H;

A, B and D are each C—H; and

E is N.

Another preferred embodiment includes compounds of Formula I wherein:

$R_3$, $R_4$, $R_5$ and $R_6$ are each H;

A, B and E are each C—H; and

D is N.

In another embodiment of the invention there is provided a method for treating mammals infected with RSV, and in need thereof, which comprises administering to said mammal a therapeutically effective amount of one or more of the aforementioned compounds of having Formula I, including pharmaceutically acceptable salts thereof.

Another embodiment includes a pharmaceutical composition which comprises a therapeutically effective amount of one or more of the aforementioned anti-RSV compounds having Formula I, including pharmaceutically acceptable salts thereof, and a pharmaceutically acceptable carrier.

The term pharmaceutically acceptable salt includes solvates, hydrates, acid addition salts and quarternary salts. The acid addition salts are formed from a compound of Formula I and a pharmaceutically acceptable inorganic or organic acid including but not limited to hydrochloric, hydrobromic, sulfuric, phosphoric, methanesulfonic, acetic, citric, malonic, fumaric, maleic, oxalic acid, sulfamic, or tartaric acids. Quaternary salts include chloride, bromide, iodide, sulfate, phosphate, methansulfonate, citrate, acetate, malonate, fumarate, oxalate, sulfamate, and tartrate. Halogen means bromine, chlorine, fluorine and iodine.

DETAILED DESCRIPTION OF THE INVENTION

The following definitions apply unless indicated otherwise:

An "aryl" group refers to an all carbon monocyclic or fused-ring polycyclic (i.e., rings which share adjacent pairs of carbon atoms) groups having a completely conjugated pi-electron system. Examples, without limitation, of aryl groups are phenyl, napthalenyl and anthracenyl.

As used herein, a "heteroaryl" group refers to a monocyclic or fused ring (i.e., rings which share an adjacent pair of atoms) group having in the ring(s) one or more atoms selected from the group consisting of nitrogen, oxygen and sulfur and, in addition, having a completely conjugated pi-electron system. Examples, without limitation, of heteroaryl groups are furyl, thienyl, benzothienyl, thiazolyl, imidazolyl, oxazolyl, oxadiazolyl, thiadiazolyl, benzthiazolyl, triazolyl, tetrazolyl, isoxazolyl, isothiazolyl, pyrrolyl, pyranyl, pyrazolyl, pyridyl, pyrimidinyl, quinolinyl, isoquinolinyl, purinyl, carbazolyl, benzoxazolyl, benzimidazolyl, indolyl, isoindolyl, and pyrazinyl.

As used herein, a "non-aromatic heterocycle" group refers to a monocyclic or fused ring group having in the ring(s) one or more atoms selected from the group consisting of nitrogen, oxygen and sulfur. The rings may also have one or more double bonds. However, the rings do not have a completely conjugated pi-electron system. Examples, without limitation, of non-aromatic heterocycle groups are azetidinyl, piperidyl, piperazinyl, imidazolinyl, thiazolidinyl, 3-pyrrolidin-1-yl, morpholinyl, thiomorpholinyl, tetrahydropyranyl, oxazolidonyl, oxazolonyl, 2-pyrrolidinonyl, hydantoinyl, meleimidyl and oxazolidinedionyl.

An "alkyl" group refers to a saturated aliphatic hydrocarbon including straight chain and branched chain groups. Preferably, the alkyl group has 1 to 20 carbon atoms (whenever a numerical range; e.g., "1–20", is stated herein, it means that the group, in this case the alkyl group may contain 1 carbon atom, 2 carbon atoms, 3 carbon atoms, etc. up to and including 20 carbon atoms). More preferably, it is a medium size alkyl having 1 to 10 carbon atoms. For example, the term "$C_{1-6}$ alkyl" as used herein and in the claims (unless specified otherwise) mean straight or branched chain alkyl groups such as methyl, ethyl, propyl, isopropyl, butyl, isobutyl, t-butyl, amyl, hexyl and the like.

A "cycloalkyl" group refers to a saturated all-carbon monocyclic or fused ring (i.e., rings which share and adjacent pair of carbon atoms) group wherein one or more rings does not have a completely conjugated pi-electron system. Examples, without limitation, of cycloalkyl groups are cyclopropane, cyclobutane, cyclopentane, cyclohexane, cycloheptane, and adamantane.

A "cycloalkenyl" group refers to an all-carbon monocyclic or fused ring (i.e., rings which share and adjacent pair of carbon atoms) group wherein one or more rings contains one or more carbon-carbon double bonds but does not have a completely conjugated pi-electron system. Examples, without limitation, of cycloalkenyl groups are cyclopentene, cyclohexadiene, and cycloheptatriene.

An "alkenyl" group refers to an alkyl group, as defined herein, consisting of at least two carbon atoms and at least one carbon-carbon double bond.

An "alkynyl" group refers to an alkyl group, as defined herein, consisting of at least two carbon atoms and at least one carbon-carbon triple bond.

A "hydroxy" group refers to an —OH group.

An "alkoxy" group refers to both an —O-alkyl and an —O-cycloalkyl group as defined herein.

An "O-carboxy" group refers to a R"C(O)O-group, with R" as defined herein.

An "amino" group refers to an —NH$_2$ group.

A "N-amido" group refers to a R$^x$C(=O)NR$^y$— group, with R$^x$ selected from the group consisting of alkyl, cycloalkyl, aryl, heteroaryl, and heteroalicyclic and R$^y$ selected from hydrogen or alkyl.

A "cyano" group refers to a —CN group.

It is known in the art that nitrogen atoms in heteroaryl systems can be "participating in a heteroaryl ring double bond", and this refers to the form of double bonds in the two tautomeric structures which comprise five-member ring heteroaryl groups. This dictates whether nitrogens can be substituted as well understood by chemists in the art. The disclosure and claims of the present invention are based on the known general principles of chemical bonding. It is understood that the claims do not encompass structures known to be unstable or not able to exist based on the literature.

Compounds of Formula I can be prepared either by coupling 2-substituted-benzimidazoles (II), where X is a halide or sulfonate such as mesylate or tosylate, with 2-oxo-imidazopyridines or 2-oxo-imidazopyrimidines (III) in the presence of base, preferably phosphazene bases such as t-butylimino-tri(pyrrolidino)phosphorane (BTPP), cesium carbonate or sodium hydride (Scheme I-A) or by reacting Ia with a R$_2$-LG, where LG is a leaving group, preferably a halide or sulfonate such as mesylate or tosylate (Scheme I-B). Alternatively, compounds of Formula I can be synthesized according to the procedure described in Scheme I-C. Coupling of 2-substituted-benzimidazoles (IV) containing protecting groups (P) such as p-methoxybenzyl, mesyl, or 2-cyanoethyl with 2-oxo-imidazopyridines or 2-oxo-imidazopyrimidines in the presence of base is followed by removal of the protecting group using appropriate conditions. Deprotection can be accomplished by treatment with ceric ammonium nitrate (CAN), treatment with hydrazine or tetrabutylammonium fluoride (TBAF), or treatment with potassium tert-butoxide to respectively remove p-methoxybenzyl, mesyl, or 2-cyanoethyl groups and give intermediates V. Compounds of Formula I can then be prepared by reacting V with R$_1$-LG where LG is a leaving group preferably a halide or sulfonate such as mesylate or tosylate.

Scheme I: Preparation of Formula I (A)

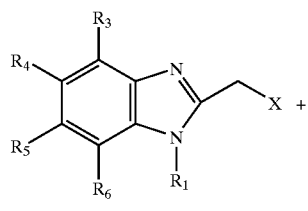

II

X = Cl, Br, I or OSO$_2$R

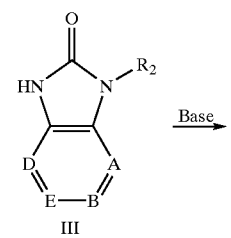

III

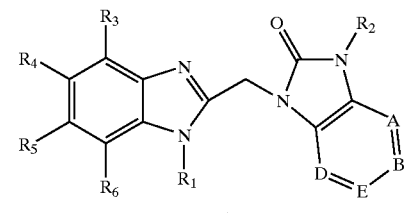

Formula I (B)

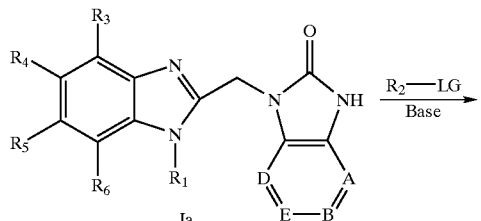

Ia

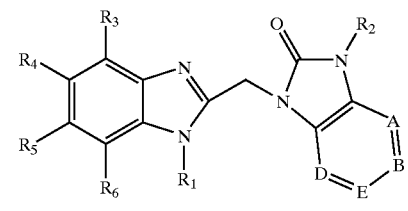

Formula I (C)

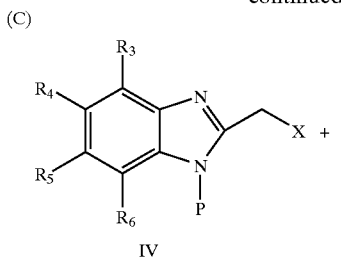

IV

X = Cl, Br, I
P = protecting group
such as:

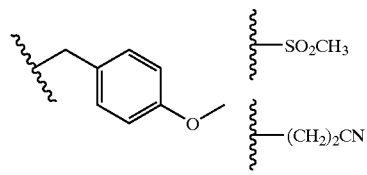

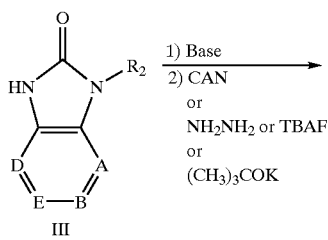

III

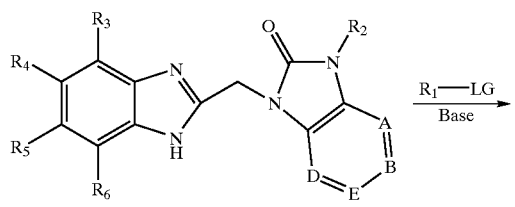

V

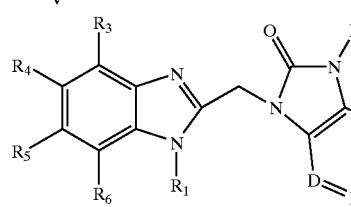

Formula I

The synthesis of 2-substituted-benzimidazoles (IIa) is shown in Schemes II A-C. Treatment of substituted or unsubstituted 2-hydroxymethylbenzimidazole (VI) with 1.05 equivalents of base, preferably sodium hydride or cesium carbonate, followed by the addition of $R_1$-LG, where LG is a leaving group such as halide or sulfonate, gives compound VII. Treatment of the alcohol with thionyl chloride provides 2-chloromethyl-benzimidazole Ia (Scheme II-A). In a separate synthetic route, depicted in Scheme II-B, 2-fluoro-nitrobenzene (VIII) reacts with an amine to afford compound IX. Reduction of the nitro group provides a phenylenediamine derivative X which is cyclized with gly- colic acid in 4–6 N HCl to give alcohol VII. Alternatively, 2-amino-nitrobenzene (IX) is acylated with 2-benzyloxyacetyl chloride to provide XI (Scheme II-C). Reduction of the nitro group followed by ring closure in ethanol in the presence of catalytic amount of acetic acid provides XII. Removal of the benzyl group using boron tribromide or palladium hydroxide on carbon and cyclohexene yields VII.

Preparation of compounds IVa–IVd containing protecting groups is depicted in Schemes IID-F. In Scheme II–D, 2-chloromethylbenzimidazole reacts with methane sulfonyl chloride (Ms–Cl) and triethylamine to give compound IVa. The chloride can be refluxed with potassium iodide in acetone to produce compound IVb. A p-methoxybenzyl protecting group is installed in Scheme II-E. Reaction of 4-methoxybenzyl chloride with 2-hydroxymethyl benzimidazole (VI) in the presence of base, preferably sodium hydride, gives compound of Formula XIV. Treatment of alcohol XIV with (bromomethylene)dimethylaiimonium bromide provides compound IVc. Compound IVd can be prepared as described in Scheme II-F. Michael addition of 2-hydroxymethylbenzimidazole (VI) with acrylonitrile yields compound XV which is then converted to the chloride IVd by treatment with thionyl chloride.

Scheme II: Preparation of Benzimidazoles Ia

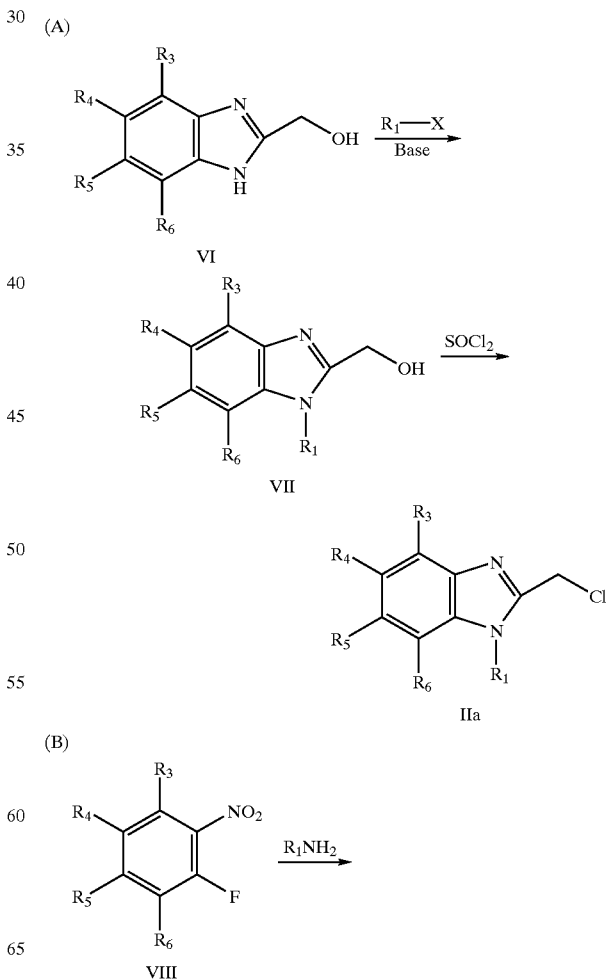

-continued
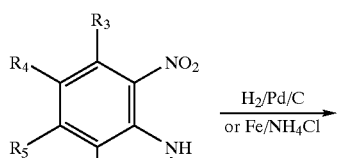
IX
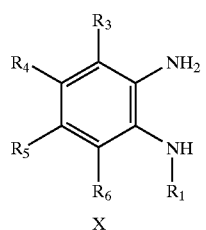
X
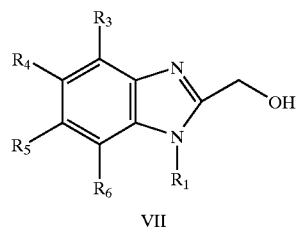
VII
(C)
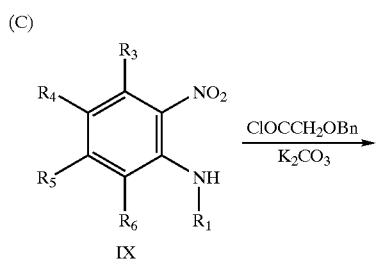
IX
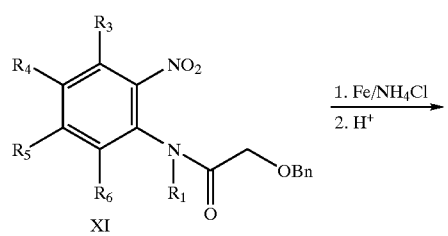
XI
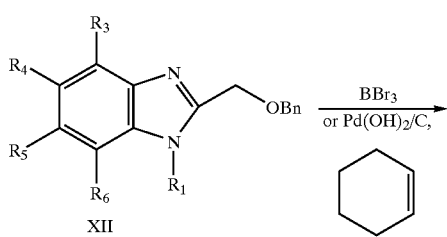
XII
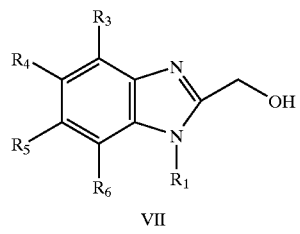
VII
-continued
(D)
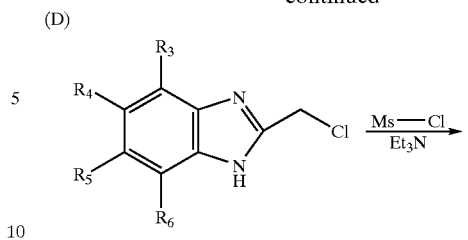
XIII
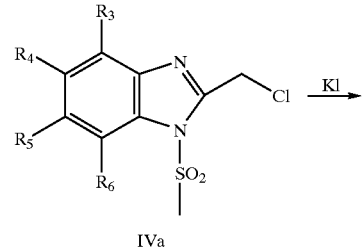
IVa
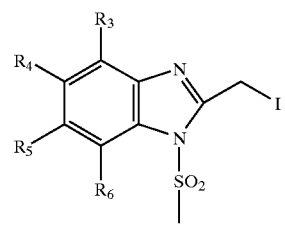
IVb
(E)
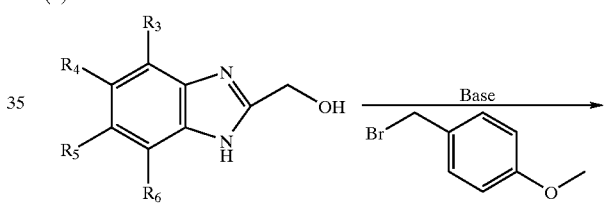
VI
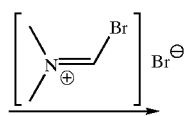
XIV
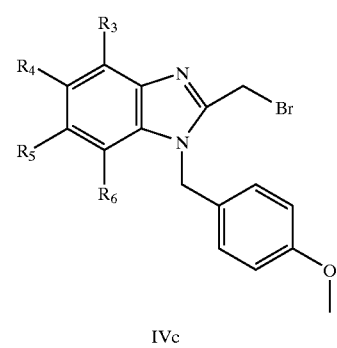
IVc

Scheme III: Preparation of 2-oxo-imidazopyridines and 2-oxo imidazopyrimidines (F)
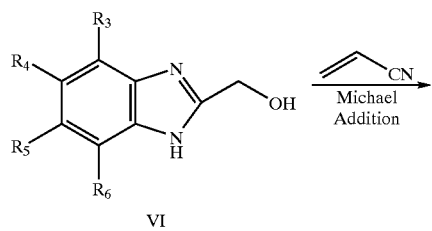
VI

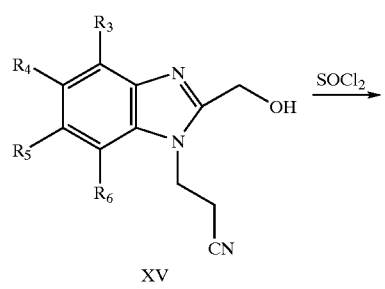
XV

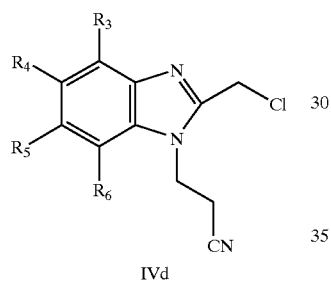
IVd (A)
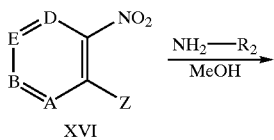
XVI

Z = Cl, OCH₃

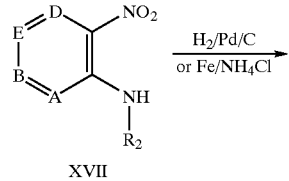
XVII

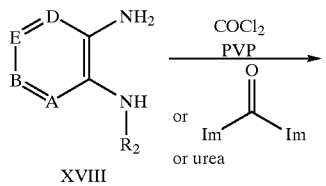
XVIII

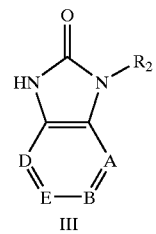
III (B)
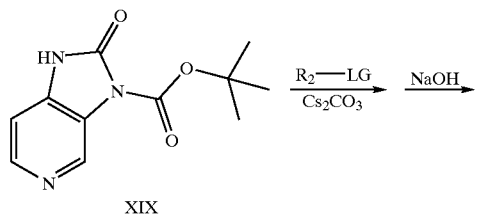
XIX

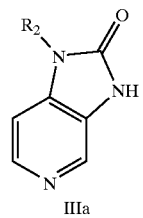
IIIa (C)
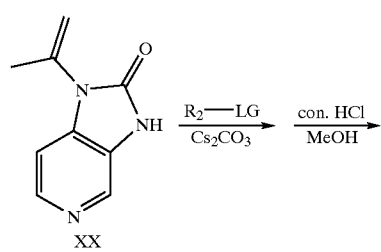
XX

2-Oxo-imidazopyridines and 2-oxo-imidazopyrimidines can be synthesized using the procedure depicted in Scheme III. Displacement of Z, which is a halide, preferably chlorine, or an alkoxy group, preferably methoxy, of nitro-pyridines XVI (2-chloro-3-nitro-pyridine, 4-alkoxy-3-nitropyridine and 3-alkoxy-2-nitropyridine) with an amine gives XVII (Scheme III-A). Reduction of the nitro group and cyclization of the resulting diamine (XVIII) using phosgene/polyvinylpyridine, carbonyldiimidazole or urea provides N3-substituted 2-oxo-imidazopyridine III. N-substituted 2-oxo-5-imidazo-pyridines IIIa are prepared from known compound XIX by N-alkylation and deprotection of the t-butoxycarbonyl with aqueous sodium hydroxide (Scheme III-B). On the other hand, N-alkylation of XX and acid hydrolysis of the isopropenyl group gives 2-oxo-imidazo-6-pyridine IIIb (Scheme III-C). 2-Oxo-imidazopyrimidines (IIIc) can be prepared directly by reacting 2-oxo-imidazopyrimidine (XXI) with R₂-LG where LG is a leaving group as described above, to give IIIc, as illustrated in Scheme III-D. Alternatively, 4,6-dichloro-5-nitropyrimidine (XXII) is treated with an amine to generate XXIII (Scheme III-E). Catalytic reduction of both the nitro group and the carbon-chlorine bond, and cyclization of the resulting diamine (XIV) with phosgene provides IIId.

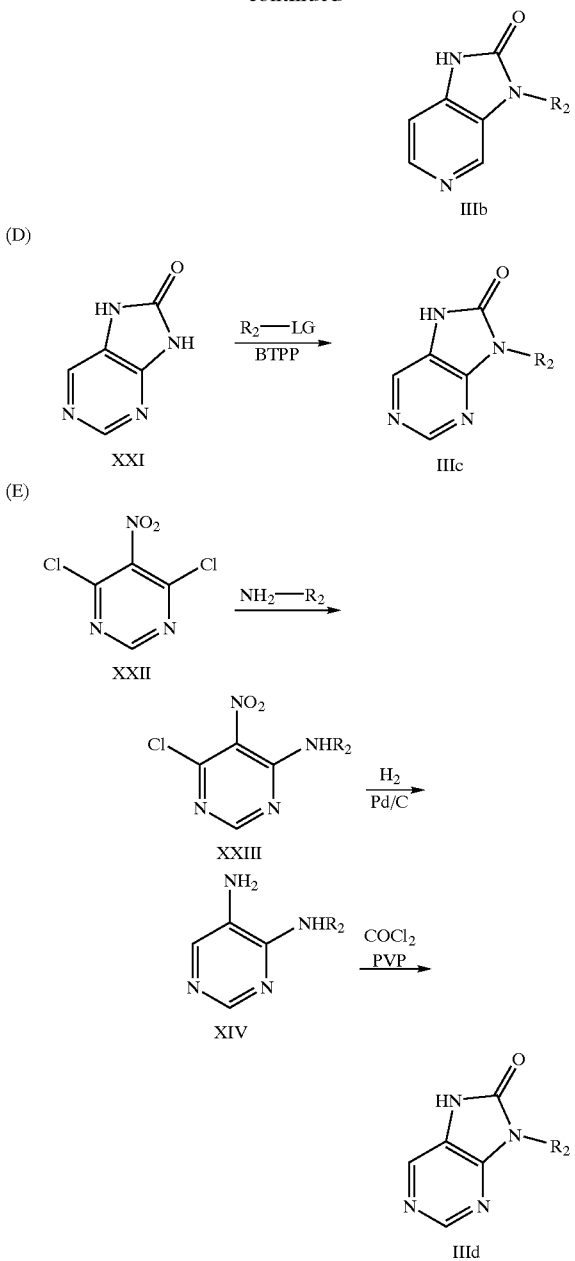

Experimental Section

Proton nuclear magnetic resonance (¹H NMR) spectra were recorded on a Bruker Avance 500, AC-300, Bruker DPX-300 or a Varian Gemini 300 10 spectrometer. All spectra were determined in $CDCl_3$, $CD_3OD$, or DMSO-$d_6$ and chemical shifts are reported in δ units relative to tetramethylsilane (TMS). Splitting patterns are designated as follows: s, singlet; d, doublet; t, triplet; m, multiplet; b, broad peak; dd, doublet of doublets; dt, doublet of triplets. Mass spectroscopy was performed on a Finnigan SSQ 7000 quadrupole mass spectrometer in both positive and negative electrospray ionization (ESI) modes or on a LC-MS using Shimadzu LC-10AS with micromass platform LC single quadrupole mass spectrometer in positive electrospray ionization. High resolution mass spectroscopy was recorded using a Finnigan MAT 900. Infrared (IR) spectra were recorded on a Perkin-Elmer system 2000 FT-IR. Elemental analysis was performed with a Perkin-Elmer series II, model 2400 CHN/O/S analyzer. Column chromatography was performed on silica gel from VWR Scientific. Preparative HPLC was performed using a Shimadzu LC-8A on a C18 column eluted with mixture of MeOH in water with 0.1% trifluoroacetic acid.

Abbreviations used in the experimental section:

BEMP: 2-t-butylimino-2-diethylamino-1,3-dimethyl-perhydro-1,3,2-diazaphosphorine BTPP: t-butylimino-tri(pyrrolidino)phosphorane CAN: ceric ammonium nitrate DBU: 1,8-diazabicyclo[5,4,0]undec-7-ene DIEA: N,N-diisopropylethylamine DMF: dimethylformamide DMSO: dimethyl sulfoxide $Et_2O$: diethyl ether EtOAc: ethyl acetate EtOH: ethyl alcohol MeOH: methanol Prep HPLC: preparative high performance liquid chromatography Prep TLC: preparative thin layer chromatography TBAF: tetrabutylammonium fluoride TFA: trifluoroacetic acid THF: tetrahydrofuran I. Preparation of Benzimidazoles:

Compounds 1–25, 59–111, and 138–143 are benzimidazole intermediates synthesized according to the procedures described in Scheme II.

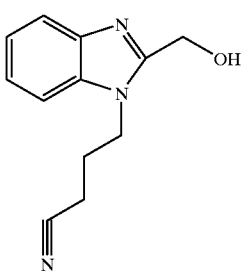

To a solution of 2-hydroxymethylbenzimidazole (29.63 g, 200 mmol) in a mixture of DMF/THF (150 mL, 1:1) was added sodium hydride (60% in mineral oil, 8.4 g, 210 mmol) in several portions at room temperature. After stirring for 1 hour, 4-bromobutyronitrile (29.6 g, 200 mmol) was added and the resulting solution was stirred at 80° C. for 16 hours. The solvent was evaporated and the residue diluted with water and extracted with EtOAc. The combined extracts were dried over $MgSO_4$ and evaporated. The residue was purified by flash chromatography (gradient, EtOAc/hexane, 1:1 to 2:1, then EtOAc/MeOH, 10:1) to give 22.11 g (51% yield) of 1 as a white solid.

¹H NMR ($CDCl_3$) δ 2.27–2.32 (m, 2 H), 2.41 (t, J=6.0 Hz, 2 H), 4.41 (t, J=7.2 Hz, 2 H), 7.26–7.38 (m, 3 H), 7.67–7.70 (m, 1 H); MS m/e 216 (MH⁺).

General Procedure for Converting 2-Hydroxymethyl-benzimidazoles to 2-Chloromethyl-benzimidazoles.

The procedure described below was used for the synthesis of compounds 2, 4, 9, 11A+11B, 15, 19, 23, 25, 70, 72, 76, 81, 88, 92, 94, 96, 98, 100, 102, 108, and 111 and 143.

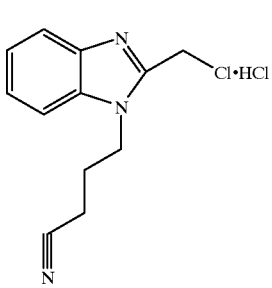

2

To alcohol 1 (22 g, 102.2 mmol) suspended in CH$_2$Cl$_2$ (100 mL), thionyl chloride (15.81 g, 132.9 mmol) was slowly added with ice-water bath cooling. The ice bath was removed. The solution was stirred at room temperature for 1 hour and then evaporated. The residue was triturated with EtOAc to give a nearly quantitative yield of 2 as light gray powder.

$^1$H NMR (CDCl$_3$) δ 2.32–2.38 (m, 2 H), 2.70 (t, J=7.3 Hz, 2 H), 4.69 (t, J=7.6 Hz, 2 H), 5.33 (s, 2 H), 7.69–7.74 (m, 2 H), 7.85–7.87 (m, 1 H), 8.00–8.02 (m, 1 H); MS m/e 234 (MH$^+$). Anal. Calcd for C$_{12}$H$_{12}$N$_3$•HCl•0.25 H$_2$O: C, 52.48; H, 4.95; N, 15.30 Found: C, 52.52; H, 4.88; N, 15.26

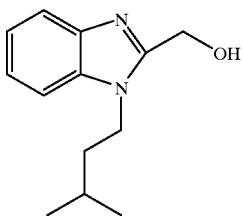

3

Compound 3 was prepared using the same procedure described for compound 1, except that 4-bromobutyronitrile was replaced with 3-methylbutylbromide.

$^1$H NMR (CDCl$_3$) δ 1.71–1.78 (m, 3 H), 4.28 (t, J=7.5 Hz, 2 H), 5.02 (s, 2 H), 7.33–7.41 (m, 3 H), 7.75 (d, J=7.9 Hz, 2 H); MS m/e 219 (MH$^+$).

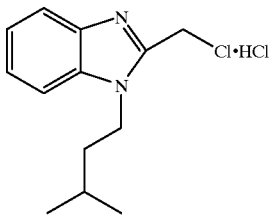

4

Compound 4 was prepared according to the same procedure described for compound 2.

$^1$H NMR (CDCl$_3$) δ 1.08 (d, J=6.4 Hz, 6 H), 1.83–1.89 (m, 3 H), 4.57–4.60 (m, 2 H), 5.30 (s, 2 H), 7.68–7.73 (m, 2 H), 7.84–7.86 (m, 1 H), 7.93–7.95 (m, 1H); MS m/e 237 (MH$^+$).

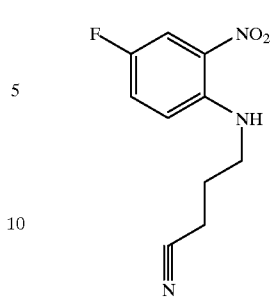

5

A solution of 2,5-difluoronitrobenzene (15.4 g, 96.8 mmol), 4-aminobutyronitrile (7.4 g, 88 mmol) and diisopropylethylamine (23 ml, 132 mmol) in DMF (250 ml) was stirred at room temperature for 32 hours. After filtration, the solvent was evaporated and the orange solid was recrystallized from MeOH (250 ml) to afford 5 (14 g, 65% yield) as orange crystals.

$^1$H NMR (CDCl$_3$) δ 2.06–2.12 (m, 2 H), 2.54 (t, J=7.0 Hz, 2 H), 3.48–3.53 (m, 2 H), 6.85–6.88 (m, 1 H), 7.27–7.31 (m, 1 H), 7.89–7.92 (m, 1 H); MS m/e 224 (MH$^+$).

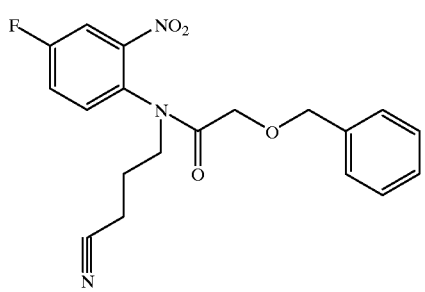

6

To a suspension of nitrile 5 (10.8 g, 48.4 mmol) and potassium carbonate (20.1 g, 145 mmol) in CH$_3$CN (200 ml) was added benzyloxyacetyl chloride (7.64 ml, 48.4 mmol) dropwise. After stirring at room temperature for 12 hours, the mixture was diluted with EtOAc (500 ml) and filtered. The filtrate was washed with 1 N HCl, brine, dried over MgSO$_4$ and evaporated. The residue was purified by flash chromatography (gradient, EtOAc/hexane, 1:2 to 1:1) to yield 6 (7.5 g, 42% yield) as a viscous pale yellow oil.

$^1$H NMR (CDCl$_3$) δ 1.86–1.98 (m, 2 H), 2.38–2.51 (m, 2 H), 3.34–3.39 (m, 1 H), 3.80–3.87 (m, 2 H), 4.06–4.14 (m, 1 H), 4.40–4.48 (m, 2 H), 7.18–7.19 (m, 1 H), 7.26–7.40 (m, 5 H), 7.72–7.74 (m, 1 H); MS m/e 394 (MH$^+$).

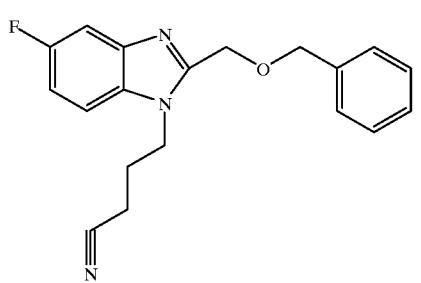

7

In a flask equipped with a mechanical stirrer, a suspension of compound 6 (6.40 g, 17.25 mmol), iron powder (2.89 g, 51.8 mmol) and ammonium chloride (4.61 g, 86.2 mmol) in a mixture of MeOH and H₂O (200 ml, 1:1) was stirred at reflux for 4 hours. The mixture was filtered through a pad of Celite and washed with MeOH. The filtrate was evaporated and the residue was taken up in EtOAc (500 ml), washed with brine, dried over MgSO₄, and evaporated. To the residue was added CH₃CN (100 ml) and acetic acid (1 ml), and the mixture was stirred at reflux for 4 hours. The solvent was evaporated and the residue was purified by flash chromatography (gradient, EtOAc/hexane, 1:2 to 2:1) to give 7 (4.42 g, 75% yield) as a viscous oil which solidified upon standing.

$^1$H NMR (CDCl₃) δ 2.15–2.20 (m, 2 H), 2.31 (t, J=7.0 Hz, 2 H), 4.35 (t, J=7.2 Hz, 2 H), 4.62 (s, 2 H), 4.83 (s, 2 H), 7.07–7.11 (m, 1 H), 7.29–7.38 (m, 6 H), 7.43–7.46 (dd, J=2.4, 9.2 Hz, 1 H); MS m/e 324 (MH⁺).

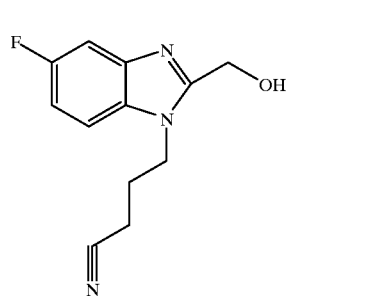

8

To a solution of 7 (3.23 g, 10 mmol) in CH₂Cl₂ (100 ml) at 0° C. was added boron tribromide (2.84 ml, 30 mmol). After stirring for 1 hour, the mixture was quenched with saturated NaHCO₃ solution with ice bath cooling and extracted with EtOAc. The combined extracts were dried over MgSO₄ and evaporated. The residue was purified by flash chromatography (gradient, CH₂Cl₂/MeOH, 40:1 to 20:1) to give 8 (1.68 g, 72% yield) as an off-white solid.

$^1$H NMR (CDCl₃) δ 2.25–2.30 (m, 2 H), 2.43 (t, J=7.1 Hz, 2 H), 4.41 (t, J=7.1 Hz, 2 H), 4.85 (s, 2 H), 7.04–7.081 (m, 1 H), 7.29–7.34 (m, 2 H); MS m/e 234 (MH⁺).

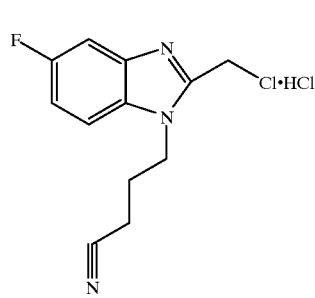

9

Compound 9 was prepared according to the same procedure described for compound 2.

$^1$H NMR (CD₃OD) δ 2.30–2.36 (m, 2 H), 2.70 (t, J=7.2 Hz, 2 H), 4.67 (t, J=7.6 Hz, 2 H), 5.30 (s, 2 H), 7.49–7.54 (dt, J=2.4, 9.2 Hz, 1 H), 7.62–7.64 (dd, J=2.4, 8.0 Hz, 1 H), 8.01–8.04 (dd, J=2.0, 9.2 Hz, 1 H); MS m/e 252 (MH⁺).

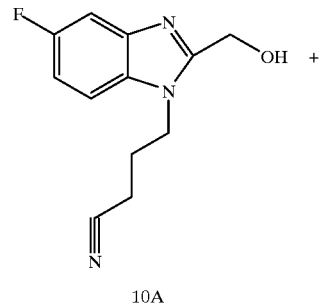

10A

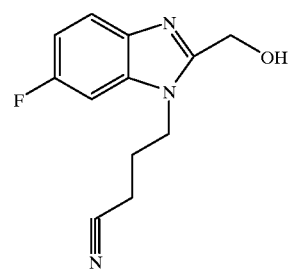

10B

A mixture of 10A and 10B was prepared from 5-fluoro-2-hydroxymethyl-benzimidazole using the same procedure described for compound 1.

$^1$H NMR (CDCl₃) δ 2.26–2.30 (m, 2 H), 2.42–2.46 (m, 2 H), 4.36–4.42 (m, 2 H), 4.87 (s, 2 H), 7.03–7.07 (m, 1.5 H), 7.30–7.32 (m, 1 H), 7.60–7.63 (m, 0.5 H); MS m/e 234 (MH⁺).

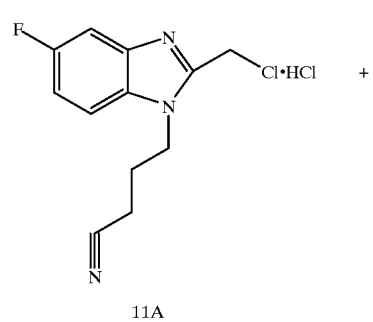

11A

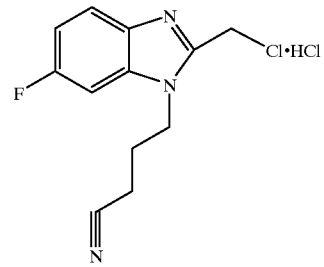

11B

Compounds 11A and 11B were prepared according to the same procedure described for compound 2.

$^1$H NMR (CDCl₃) δ 2.24–2.30 (m, 2 H), 2.44–2.47 (m, 2 H), 4.32–4.39 (m, 2 H), 4.829 (s, 1 H), 4.831 (s, 1 H), 7.01–7.11 (m, 1.5 H), 7.30–7.33 (dd, J=4.4, 8.8 Hz, 0.5 H), 7.40–7.42 (dd, J=2.3, 9.0 Hz, 0.5 H), 7.66–7.68 (dd, J=4.8, 8.8 Hz, 0.5 H); MS m/e 252 (MH⁺).

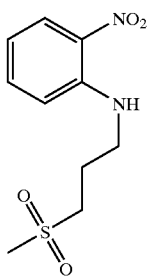

12

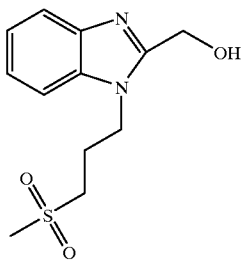

14

2-Fluoronitrobenzene (35.4 g, 250.9 mmol), 3-(methylthio)propylamine (24.0g, 228.1 mmol) and potassium carbonate (47.3 g, 342 mmol) were stirred in $CH_3CN$ (100 mL) at room temperature overnight. After stirring for an additional hour at reflux, the mixture was cooled to room temperature and filtered. The filtrate was evaporated. To the residue in DMF (150 mL), magnesium monoperoxyphthalate hexahydrate (MMPP, 168 g, 340 mmol) was added in several portions with ice-water cooling. The mixture was stirred at room temperature for 3 hours and the solvent was evaporated. The residue was dissolved in $CH_2Cl_2$ and washed with 1 N NaOH, water, brine, dried over $MgSO_4$ and evaporated. The residue was triturated with hot EtOAc to give 12 (48.7 g, 75% yield) as an orange solid.

$^1$H NMR ($CDCl_3$) δ 2.25–2.35 (m, 2 H), 2.97 (s, 3 H), 3.17 (t, J=7.2 Hz, 2 H), 3.59 (t, J=6.9 Hz, 2 H), 6.68–6.74 (m, 1 H), 6.89 (d, J=8.1 Hz, 1 H), 7.45–7.51 (m, 1 H), 8.20 (dd, J=1.5, 8.7 Hz, 1 H); MS m/e 259 (MH$^+$); Anal. Calcd for $C_{10}H_{14}N_2O_4S$: C, 46.50; H, 5.46; N, 10.84 Found: C, 46.53; H, 5.54; N, 10.90.

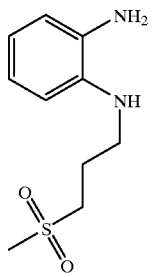

13

To a suspension of 12 (48.5 g, 187.8 mmol) in a mixture of $CHCl_3$ and MeOH (150 mL, 1:3) was added 10% palladium on carbon (6 g) under nitrogen. The reduction was carried out in a Parr shaker with hydrogen pressure maintained between 40 and 60 psi for 25 minutes. The catalyst was removed by filtration through a pad of Celite and the filtrate was evaporated to give crude 13.

$^1$H NMR ($CD_3OD$) δ 2.11–2.21 (m, 2 H), 2.98 (s, 3 H), 3.28–3.36 (m, 4 H), 6.75 (dt, J=0.9, 7.2 Hz, 1 H), 6.85 (d, J=7.5 Hz, 1 H), 7.06–7.12 (m, 2 H); MS m/e 229 (MH$^+$).

The crude diamine 13 obtained above was stirred at reflux overnight with glycolic acid (15.7 g, 207 mmol) in 6 N HCl (150 mL). The solution was cooled in an ice bath and neutralized with concentrated $NH_4OH$ solution, extracted with EtOAc, dried over $MgSO_4$ and evaporated. The residue was purified by chromatography (gradient, EtOAc/hexane, 1:1 to EtOAc/MeOH, 10:1) to give a product which crystallized from EtOAc/MeOH to afford 25.7 g (51% yield in two steps) of 14.

$^1$H NMR ($CD_3OD$) δ 2.38–2.44 (m, 2 H), 2.97 (s, 3 H), 3.24 (t, J=7.6 Hz, 2 H), 4.54 (t, J=7.6Hz, 2 H), 7.27 (t, J=1.1, 8.1 Hz, 1 H), 7.33 (dt, J=1.1, 8.0Hz, 1 H), 7.62 (d, J=8.1 Hz, 1 H), 7.64 (dd, J=1.0, 8.0 Hz, 1 H); MS m/e 269 (MH$^+$).

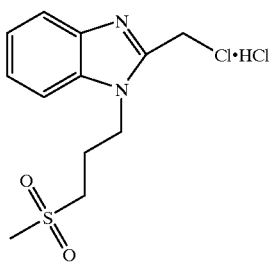

15

Compound 15 was prepared according to the same procedure described for compound 2.

$^1$H NMR ($CD_3OD$) δ 2.46–2.52 (m, 2 H), 3.03 (s, 3 H), 3.37 (t, J=7.1 Hz, 2 H), 4.77 (t, J=7.8 Hz, 2 H), 5.31 (s, 2 H), 7.68–7.73 (m, 2 H), 7.86 (dd, J=2.8, 6.9 Hz, 1 H), 8.03 (dd, J=1.7, 6.1 Hz, 1 H); MS m/e 287 (MH$^+$).

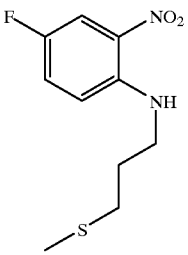

16

To a solution of 2,5-difluoronitrobenzene (15.1 g, 95.06 mmol) in $CH_3CN$ (150 mL) was added potassium carbonate (26.3 g, 190.11 mmol) and 3-(methylthio)propylamine (10.0 g, 95.06 mmol). The mixture was stirred vigorously with the aid of a mechanical stirrer for 16 hours at room temperature. The solid was filtered and the filtrate was evaporated. The residue was diluted with EtOAc (600 mL) and washed with water and brine. The organic layer was dried over anhydrous MgSO$_4$ and evaporated to give crude 16 as an orange solid (25 g, 70% pure).

1H NMR (CDCl$_3$) δ 1.97–2.01 (m, 2 H), 2.11 (s, 3 H), 2.62 (t, J=6.9 Hz, 2 H), 3.43 (q, J=6.3 Hz, 2 H), 6.87 (dd, J=4.6, 9.3 Hz, 1 H), 7.22–7.24 (m, 1 H), 7.85 (dd, J=3.1, 9.3 Hz, 1 H), 7.95 (bs, 1 H); MS m/e 245 (MH$^+$).

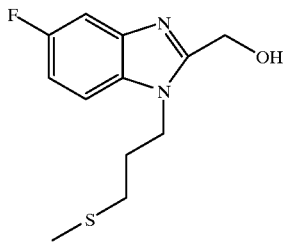

17

A solution of 16 (25 g) in MeOH (300 mL) was added to a mixture of iron powder (12.0 g, 214.9 mmol) and ammonium chloride (19.2 g, 358.2 mmol) in water (100 mL). The reaction mixture was vigorously stirred with a mechanical stirrer and heated at 90° C. for 16 hours. The mixture was filtered through a plug of Celite which was rinsed with hot methanol. The solvent was evaporated to give the crude diamine. LC-MS m/e 215 (MH$^+$).

The diamine (500 mg crude, 2.33 mmol) and glycolic acid (266 mg, 3.50 mmol) were heated at reflux in 4 N hydrochloric acid (15 mL) for 16 hours. The aqueous solution was cooled and neutralized with concentrated NH$_4$OH (15 mL). The aqueous solution was then extracted with EtOAc. The organic extracts were dried over anhydrous MgSO$_4$, filtered and evaporated. The residue was purified by flash chromatography (gradient, EtOAc/hexanes, 2:1 to EtOAc/MeOH, 10:1) to give 17 (150 mg, 25% yield).

$^1$H NMR (CD$_3$OD) δ 2.08 (s, 3 H), 2.12–2.20 (m, 2 H), 2.53 (t, J=6.9 Hz, 2 H), 4.43 (t, J=6.3 Hz, 2 H), 4.85 (s, 2 H), 7.07 (dt, J=2.4, 9.2 Hz, 1 H), 7.30 (dd, J =2.4, 9.3 Hz, 1 H), 7.53 (dd, J=4.6, 8.9 Hz, 1 H); MS m/e 255 (MH$^+$).

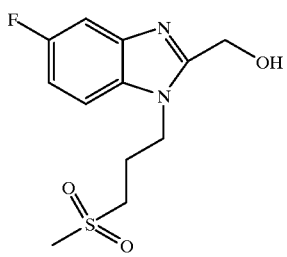

18

To a solution of sulfide 17 (150 mg, 0.59 mmol) in DMF (5 mL) was added magnesium monoperoxyphthate hexahydrate (MMPP, 583 mg, 1.18 mmol). The reaction mixture was stirred at room temperature for 16 hours. The solvent was evaporated, and the residue was diluted with water and extracted with EtOAc. The combined extracts were washed with saturated aqueous sodium bicarbonate solution and dried over anhydrous MgSO$_4$, filtered and evaporated. The residue was purified by flash chromatography (gradient, straight EtOAc to EtOAc/MeOH, 10:1) to give 18 (129 mg, 76% yield) as a white solid.

$^1$H NMR (CD$_3$OD) δ 2.37–2.47 (m, 2 H), 3.00 (s, 3 H), 3.26 (t, J=7.4 Hz, 2 H), 4.55 (t, J=7.5 Hz, 2 H), 7.14 (dt, J2.4, 9.4Hz, 1 H), 7.34 (dd, J=2.4, 9.2 Hz, 1 H), 7.62 (dd, J=4.5, 8.9 Hz, 1H); IR (KBr, cm$^{-1}$) 3139, 1624, 1591, 1489, 1478, 1446, 1416, 1308, 1270, 1143, 1134, 1047, 951, 859, 802, 527, 500; MS m/e 287 (MH$^+$); Anal. Calcd for C$_{12}$H$_{15}$FN$_2$O$_3$S: C, 50.33; H, 5.28; N, 9.78 Found: C, 50.17; H, 5.17; N, 9.57.

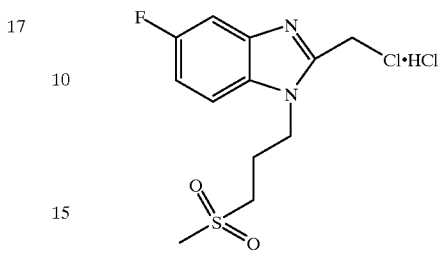

19

Compound 19 was prepared according to the same procedure described for compound 2.

$^1$H NMR (DMSO-d$_6$) δ 2.15–2.20 (m, 2 H), 3.00 (s, 3 H), 3.26 (t, J=7.2 Hz, 2 H), 4.47 (t, J=7.8 Hz, 2 H), 5.11 (s, 2 H), 7.27 (dt, J=2.4, 9.4 Hz, 1 H), 7.51 (dd, J =2.4, 9.0Hz, 1 H), 7.76 (dd, J=4.8, 9.0 Hz, 1 H); IR (KBr, cm$^{-1}$) 3429, 2577, 1635, 1536, 1496, 1290, 1277, 1130, 962, 927, 784; MS m/e 305 (MH$^+$).

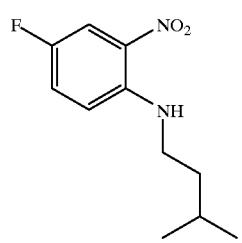

20

To a solution of 2,5-difluoronitrobenzene (45 g, 282.86 mmol) in CH$_3$CN (500 mL) was added potassium carbonate (78 g, 565.72 mmol) and isoamylamine (25 g, 282.86 mmol). The reaction mixture was stirred at room temperature for 18 hours with the aid of a mechanical stirrer. The potassium carbonate was filtered and the filtrate was evaporated to give an orange oil. The oil was diluted with EtOAc, washed with water and brine, dried over MgSO$_4$, and evaporated. Purification by flash column chromatography (hexanes/EtOAc, 20:1) gave 53 g (83% yield) of compound 20.

$^1$H NMR (CDCl$_3$) δ 0.98 (d, J=6.5 Hz, 6 H), 1.61–1.65 (m, 2 H), 1.74–1.78 (m, 1 H), 3.30 (t, J=7.3 Hz, 2 H), 6.83 (dd, J=4.6, 9.5 Hz, 1 H), 7.23–7.27 (m, 1 H), 7.85 (dd, J=3.1, 9.2 Hz, 1 H).

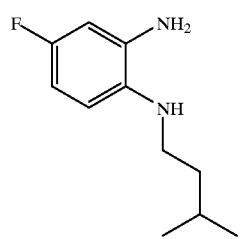

21

To a solution of compound 20 (53 g, 235.14 mmol) and concentrated HCl (15 mL) in MeOH (200 mL) was added 10% palladium on carbon (5 g) and the mixture was agitated under $H_2$ at 55 psi for 1.5 hours. The catalyst was removed by filtration through a pad of Celite and the filtrate was concentrated to give 47 g (87% yield) of diamine 21 as the HCl salt.

$^1$H NMR (CDCl$_3$) δ 0.97 (d, J=6.2 Hz, 6 H), 1.65–1.77 (m, 3 H), 3.36 (t, J=8.0 Hz, 2 H), 6.50–6.57 (m, 1 H), 6.71 (dd, J=2.7, 10.5 Hz, 1 H), 7.28 (dd, J=5.5, 8.8 Hz, 1 H); MS m/e 197 (MH$^+$).

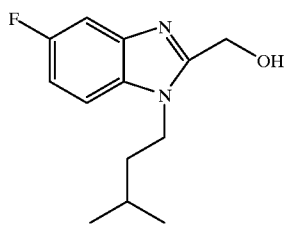

22

A mixture of diamine 21 (47 g, 200.66 mmol) and glycolic acid (16 g, 210.70 mmol) in 4 N HCl (500 mL) was stirred at reflux for 18 hours. The reaction mixture was cooled first to room temperature and then to 0° C. The reaction was diluted with concentrated ammonium hydroxide (200 mL) until the pH was adjusted to approximately 8. The product was extracted with EtOAc, dried over MgSO$_4$, and evaporated. The crude product was recrystallized with EtOAc/hexanes to give 27 g (37% yield) of compound 22 as brown crystals.

$^1$H NMR (CDCl$_3$) δ 1.02 (d, J=6.0 Hz, 6 H), 1.68–1.75 (m, 3 H), 3.19 (bs, 1 H), 4.22 (t, J=7.7 Hz, 2 H), 4.93 (s, 2 H), 7.06 (dt, J=2.2, 9.1 Hz, 1 H), 7.26–7.28 (m, 1 H), 7.37 (dd, J=2.1, 8.9 Hz, 1 H); MS m/e 237 (MH$^+$).

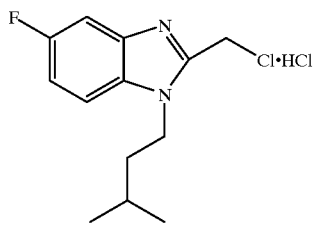

23

Compound 23 was prepared according to the same procedure described for compound 2.

$^1$H NMR (CDCl$_3$) δ 1.08 (d, J=6.4 Hz, 6 H), 1.79–1.90 (m, 3 H), 4.44 (bt, J=8.2 Hz, 2 H), 5.32 (s, 2 H), 7.36 (dt, J=2.2, 8.9, 1 H), 7.54–7.59 (m, 2 H); MS m/e 255 (MH$^+$).

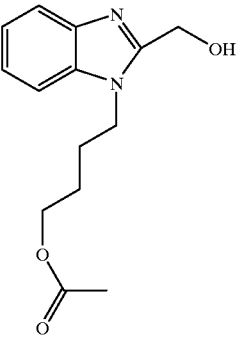

24

Compound 24 was prepared using the same procedure described for compound 1, except that 4-biomobutyromitrile was replaced with 4-bromobutyl acetate.

$^1$H NMR (CDCl$_3$) δ 1.68–1.72 (m, 2 H), 1.91–1.94 (,2 H), 2.03 (s, 3 H), 4.07 (t, J=6.4 Hz, 2 H), 4.26 (t, J=7.5 Hz, 2 H), 4.86 (s, 2 H), 6.86 (bs, 1 H), 7.20–7.29 (m, 3 H), 7.65 (dd, J=1.8, 6.7 Hz, 1 H); MS m/e 263 (MH$^+$).

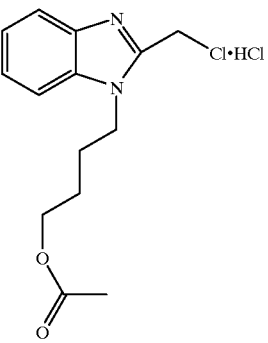

25

Compound 25 was prepared according to the same procedure described for compound 2.

$^1$H NMR (CDCl$_3$) δ 1.80–1.86 (m, 2 H), 2.03 (s, 3 H), 2.06–2.12 (m, 2 H), 4.14 (t, J=6.1 Hz, 2 H), 4.55 (t, J=8.1 Hz, 2 H), 5.42 (s, 2 H), 7.48 (t, J=7.3 Hz, 1 H), 7.55 (t, J=7.3 Hz, 1 H), 7.64 (d, J=8.5 Hz, 1 H), 7.78 (d, J=8.2 Hz, 1 H); MS m/e 281 (MH$^+$).

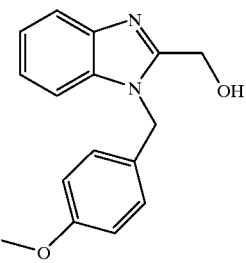

59

Compound 59 was prepared using the same procedure described for compound 1, except that 4-bromobutyronitrile was replaced with 4-methoxybenzyl chloride.

$^1$H NMR (CDCl$_3$) δ 3.77 (s, 3 H), 4.99 (s, 2 H), 5.45 (s, 2 H), 6.84 (d, J=8.6 Hz, 2 H), 7.11 (d, J=8.6 Hz, 2 H), 7.28–7.34 (m, 3 H), 7.75 (d, J=6.8, 1 H); MS m/e 269 (MH⁺).

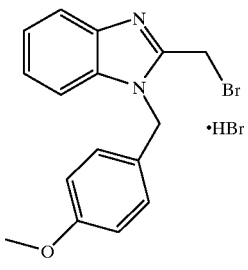

60

Compound 59 (4,75 g, 17.7 mmol) was combined with CH₂Cl₂ (100 mL) and the mixture was treated with (bromomethylene)dimethylammonium bromide (5.25 g, 23.0 mmol). The reaction was stirred at room temperature for 30 minutes and then filtered to isolate a white solid. The solid was rinsed with CH₂Cl₂, then with diethyl ether. The solid was triturated with water (50 mL), isolated by filtration, rinsed with water, then with acetone, and finally with Et₂O. The white powder was labeled crop 1 and set aside. All liquids were combined and concentrated in vacuo to give an off-white solid which was triturated with a mixture of acetone (50 mL) and Et₂O (300 mL). The liquid was decanted and the solid was suspended in acetone and isolated by filtration to give crop 2. Crops 1 and 2 were determined to be spectroscopically identical and were combined to give 6.65 g (91% yield) of compound 60 as a white powder.

¹H NMR (DMSO-d₆) δ 3.72 (s, 3 H), 5.18 (s, 2 H), 5.68 (s, 2 H), 6.92 (d, J=8.7 Hz, 2 H), 7.29 (d, J=8.7 Hz, 2 H), 7.44–7.47 (m, 2 H), 7.62–7.63 (m, 1 H), 7.78–7.80 (m, 1 H); MS m/e 332 (MH⁺).

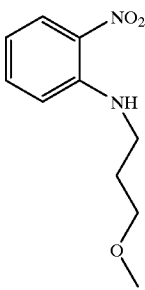

61

Compound 61 was prepared according to the same procedure described for compound 16 using 3-methoxypropylamine instead of 3-(methylthio) propylamine.

¹H NMR (CDCl₃) δ 1.95–2.00 (m, 2 H), 3.37 (s, 3 H), 3.39–3.43 (m, 2 H), 3.52 (t, J=5.7 Hz, 2 H), 6.61 (t, J=8.2 Hz, 1 H), 6.86 (d, J=8.8 Hz, 1 H), 7.41 (t, J=7.9 Hz, 1 H), 8.14 (dd, J=1.4, 8.7 Hz, 1 H), 8.26 (bs, 1 H); MS m/e 211 (MH⁺).

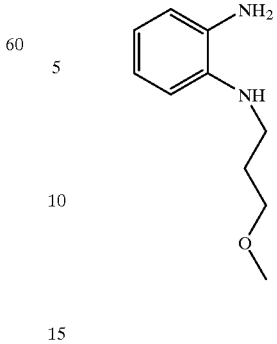

62

Compound 62 was prepared from compound 61 according to the same procedure described for compound 13 and was used immediately upon isolation.

MS m/e 181 (MH⁺).

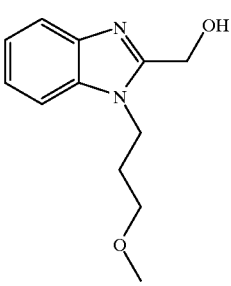

63

Compound 63 was prepared from compound 62 according to the same procedure described for compound 14.

¹H NMR (CDCl₃) δ 2.09–2.14 (m, 2 H), 3.30 (t, J=5.7 Hz, 2 H), 3.33 (s, 3 H), 4.35 (t, J=6.9 Hz, 2 H), 4.89 (s, 2 H), 7.22–7.26 (m, 2 H), 7.35–7.37 (m, 1 H), 7.69–7.70 (m, 1 H); MS m/e 221 (MH⁺).

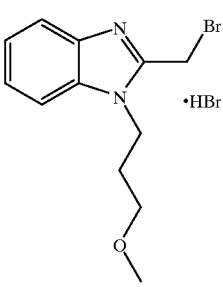

64

A solution of compound 63 (1.50 g, 6.81 mmol) in CH₃CN (20 mL) was treated with (bromomethylene) dimethylammonium bromide. The reaction mixture was stirred at room temperature for 18 hours. The reaction was quenched with H₂O (3 mL) and the solvent was evaporated and dried under vacuum to give compound 64 which was used immediately upon isolation.

MS m/e 283, 285 (MH+).

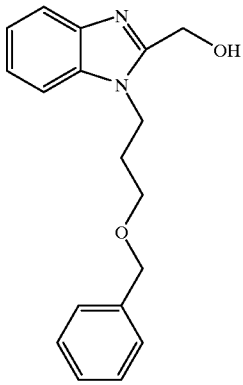

65

Compound 65 was prepared according to the same procedure described for compound 1, except that 4-bromobutyronitrile was replaced with benzyl 4-bromobutylether.

¹H NMR (CD₃OD) δ 1.65–1.71 (m, 2 H), 1.94–1.99 (m, 2 H), 3.52 (t, J=6.2 Hz, 2 H), 4.36 (t, J=7.7 Hz, 2 H), 4.47 (s, 2 H), 4.84 (s, 2 H), 7.22–7.27 (m, 3 H), 7.27–7.31 (m, 4 H), 7.48 (d, J=7.4 Hz, 1 H), 7.61 (dd,J=1.4, 7.1 Hz, 1 H); MS m/e 311 (MH+).

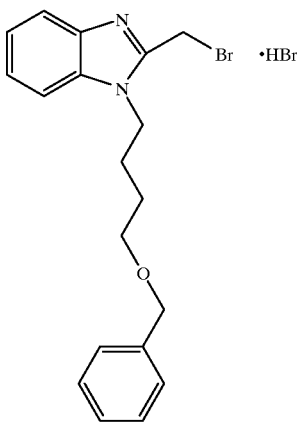

66

Compound 66 was prepared according to the same procedure described for compound 64.

MS m/e 373, 375 (MH+).

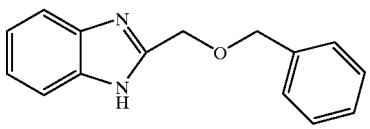

67

To a suspension of 1,2-phenylenediamine (50 g, 462 mmol) in THF (150 mL) cooled at 0C was slowly added a solution of benzyloxyacetyl chloride (171 g, 924 mmol) in THF (100 mL). The reaction mixture was stirred for 3 hours. The reaction mixture was cooled to 0° C. with an ice bath and 4N HCl (300 mL) was slowly added to the reaction mixture. The ice bath was removed and the mixture was heated at reflux for 18 hours. The majority of the THF was evaporated. The aqueous material was neutralized with 10 N NaOH, extracted with EtOAc, dried over MgSO₄, and evaporated to give a tan solid. The solid was recrystallized from EtOAc to give 45 g (41% yield) of compound 67. ¹H NMR (CD₃OD) δ 4.65 (s, 2 H), 4.77 (s, 2 H), 7.22–7.41 (m, 7 H), 7.56 (dd, J 3.2, 6.1 Hz, 2 H); MS m/e 239 (MH+).

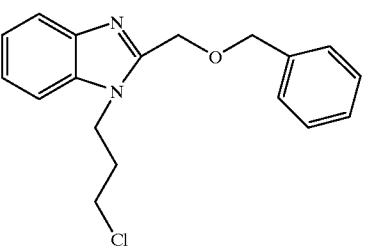

68

To a solution of compound 67 (6.00 g, 25.18 mmol) in DMF (50 mL) was added sodium hydride (60% dispersion in mineral oil, 1.46 g, 36.52 mmol). The reaction mixture was cooled to 0° C. and stirred for 30 minutes. To the cooled mixture 1 -bromo-3 -chloropropane (5.3 5 g, 3 2.99 mmol) was added and the reaction mixture was stirred for 4.5 hours. The mixture was diluted with H₂O (75 mL) and extracted with Et₂O (3×300 mL). The combined organic extracts were dried over MgSO₄ and evaporated. Purification by flash column chromatography on silica (gradient, hexanes/FtOAc 2:1 to 1:1) gave 6.86 g (87% yield) of compound 68.

¹H NMR (CDCl₃) δ 2.22–2.36 (m, 2 H), 3.53 (t, J=6.0 Hz, 2 H), 4.45 (t, J=7.0 Hz, 2 H), 4.62 (s, 2 H), 4.90 (s, 2 H), 7.28–7.44 (m, 7 H), 7.42–7.48 (m, 1 H), 7.79–7.82 (m, 1 H); MS m/e 315, 317 (MH+).

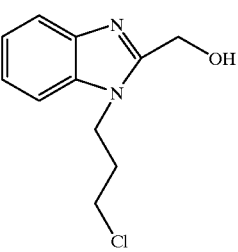

69

A solution of compound 68 (4.00 g, 12.71 mmol) in CH₂Cl₂ (75 mL) was cooled to 0° C. with an ice bath. To this solution was added boron tribromide (0.99M in CH₂Cl₂, 20 mL, 19.76 mmol) slowly via syringe. The reaction mixture was stirred at 0° C. for 2 hours. The reaction was quenched at 0° C. with MeOH (75 mL). The solvent was evaporated with a room temperature rotary evaporator bath. More MeOH was added and was again evaporated. The resulting solid was dried under high vacuum for 48 hours to give 3.70 g (95% yield) of compound 69.

¹H NMR (CD₃OD) δ 2.39–2.44 (m, 2 H), 3.72 (t, J=6.0 Hz, 2 H), 4.61 (t, J7.2 Hz, 2 H), 5.19 (s, 2 H), 7.62–7.68 (m, 2 H), 7.80–7.82 (m, 1 H), 7.93–7.95 (m, 1 H); MS m/e 225, 227 (MH+).

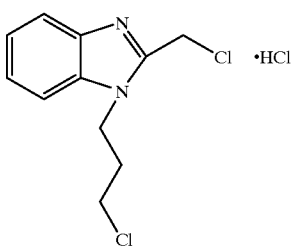

70

Compound 70 was prepared according to the same procedure described for compound 2.
MS m/e 244 (MH+).

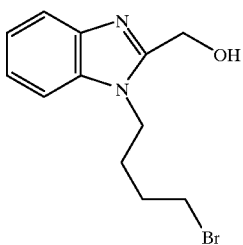

71

Compound 71 was prepared according to the same procedure described for compound 1 using 1,4-dibromobutane and the reaction was carried out at 0° C.
¹H NMR (CD₃OD) δ 1.91–1.95 (m, 2 H), 2.01–2.08 (m, 2 H), 3.48 (t, J=6.6 Hz, 2 H), 4.38 (t, J=7.4 Hz, 2 H), 4.86 (s, 2 H), 7.23–7.27 (m, 1 H), 7.29–7.32 (m, 1H), 7.54 (d, J=8.0 Hz, 1 H), 7.62 (d, J=8.0 Hz, 1 H); MS m/e 282, 284 (MH+).

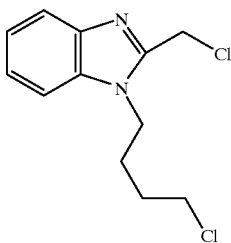

72

Compound 72 was prepared according to the same procedure described for compound 2 and was used immediately upon isolation.

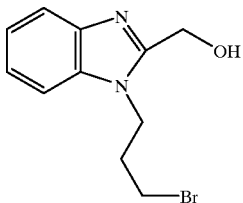

73

Compound 73 was prepared according to the same procedure described for compound 1 using 1,3 dibromopropane and the reaction was carried out at 0° C.
¹H NMR (CDCl₃) δ 2.42–2.47 (m, 2 H), 3.43 (t, J=6.1 Hz, 2 H), 4.43 (t, J=7.0 Hz, 2 H), 4.94 (s, 2 H), 7.25–7.32 (m, 2 H), 7.42–7.44 (m, 1 H), 7.68–7.70 (m, 1 H); MS m/e 268, 270 (MH+).

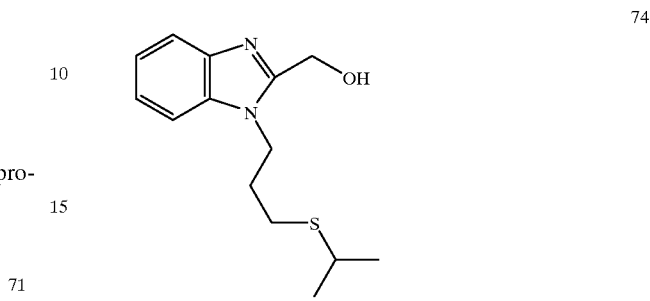

74

2-Propanethiol (305 mg, 4.00 mmol) and sodium hydride (60% dispersion in mineral oil, 240 mg, 6.00 mmol) were stirred together in DMF (20 mL) and then cooled to 0° C. To this mixture was added compound 73 (542 mg, 2.00 mmol) and the reaction mixture was allowed to warm to room temperature over 2 hours. The reaction mixture was quenched with water and extracted with EtOAc. The combined organic extracts were washed with water and brine, dried over MgSO₄, and evaporated. Purification by column chromatography (gradient, CH₂Cl₂/MeOH, 40:1 to 20:1) gave 310 mg (59% yield) of compound 74 as an off-white oil.

¹H NMR (CD₃OD) δ 1.22 (d, J=6.7 Hz, 6 H), 2.10–2.18 (m, 2 H), 2.58 (t, J=7.0 Hz, 2 H), 2.90–2.93 (m, 1 H), 4.45 (t, J=7.3 Hz, 2 H), 4.87 (s, 2 H), 7.23–7.32 (m, 2 H), 7.55 (d, J=8.0 Hz, 1 H), 7.62 (d, J=7.9 Hz, 1 H); MS m/e 265 (MH+).

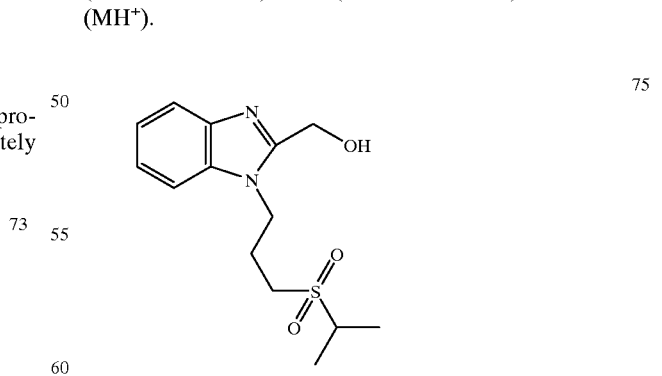

75

Compound 75 was prepared from compound 74 according to the same procedure described for compound 18.

$^1$H NMR (CD$_3$Cl) δ 1.32–1.36 (m, 6 H), 2.44–2.50 (m, 2 H), 3.00–3.02 (m, 2 H), 3.06–3.10 (m, 1 H), 4.48 (t, J=7.3 Hz, 2 H), 4.87 (s, 2 H), 7.23–7.30 (m, 2 H), 7.42 (d, J=7.7 Hz, 1 H), 7.65 (d, J=7.8 Hz, 1 H); MS m/e 297 (MH$^+$).

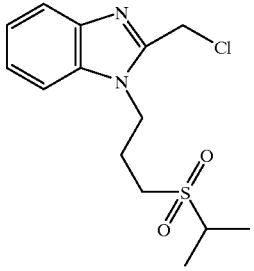

76

Compound 76 was prepared according to the same procedure described for compound 2 and was used immediately upon isolation.

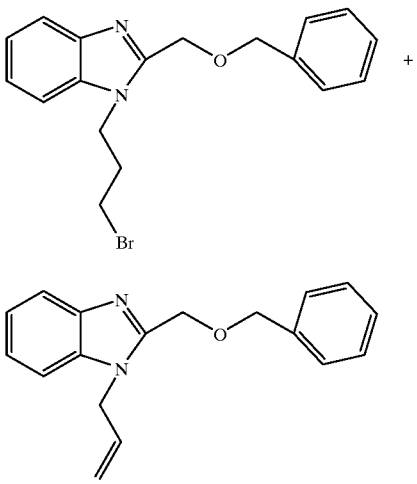

77A

77B

To a solution of compound 67 (18.25 g, 76.59 mmol) in DMF (85 mL) was added sodium hydride (60% dispersion in mineral oil, 3.37 g, 84.25 mmol). The reaction mixture was stirred for 30 minutes and then cooled to 0° C. 1,3-Dibromopropane was slowly added to the cooled solution. The temperature was raised to room temperature after 20 minutes as no starting material remained. The reaction mixture was diluted with H$_2$O and extracted with EtOAc. The combined organic extracts were dried over MgSO$_4$ and evaporated. Column chromatography (hexanes/EtOAc, 2:1) gave 5.2 g of a 60/40 mixture of the desired bromide compound 77A (8% yield) and an undesired elimination product 77B. This mixture was used in the next step without further purification.

Bromide 77A: MS m/e 360, 361 (MH$^+$);
Elimination product 77B: MS m/e 279 (MH$^+$).

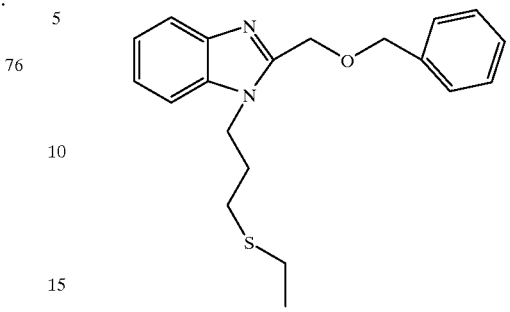

78

To a solution of ethanethiol (1.04 g, 16.77 mmol) in DMF (60 mL) was added sodium hydride (60% dispersion in mineral oil, 670 mg, 16.77 mmol). The mixture was stirred for 15 minutes at room temperature and then cooled to 0° C. In a separate flask, the mixture containing compounds 77A and 77B (5.2 g mixture, 3.0 g, 8.38 mmol) as dissolved in DMF (10 mL), cooled to 0° C. and added slowly to the ethanethiol mixture. The reaction mixture was stirred for 1 hour while the temperature was slowly allowed to rise to room temperature. The DMF was evaporated under reduced pressure. The residue was dissolved in EtOAc and washed with H$_2$O. The organic layer was dried over MgSO$_4$ and evaporated. This material containing compound 78 was used immediately as a mixture without further purification.

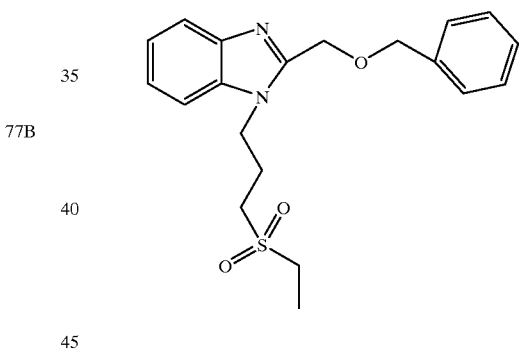

79

Compound 79 was prepared from crude 78 according to the same procedure as compound 18 and was purified by flash column chromatography on silica (gradient, EtOAc/hexanes, 2:1 to straight EtOAc).

$^1$H NMR (CDCl$_3$) δ 1.21 (t, J=7.5 Hz, 3 H), 2.35–2.42 (m, 2 H), 2.73 (q, J=7.5 Hz, 2 H), 2.84–2.88 (m, 2 H), 4.43 (t, J=7.2 Hz, 2 H), 4.60 (s, 2 H), 4.87 (s, 2 H), 7.27–7.34 (m, 5 H), 7.42 (dd, J=1.5, 7.0Hz, 1 H), 7.77 (dd, J=1.6, 6.9Hz, 1 H), 8.00(s,2H); MS m/e 373 (MH$^+$).

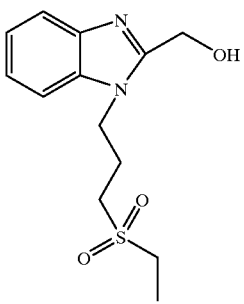

80

A solution of compound 79 (1.95 g, 5.24 mmol) in CH₂Cl₂ (50 mL) was cooled to 0° C. with an ice bath. To this solution was added boron tribromide (0.99 M in CH₂Cl₂, 9.0 mL, 9.00 mmol) slowly via syringe. The reaction mixture was stirred for 40 minutes at 0° C. before quenching at 0C by cautious addition of anhydrous MeOH (50 mL). The solvent was evaporated with a room temperature rotary evaporator bath. More anhydrous MeOH was added and the solvent was again evaporated. The resulting solid was dried under high vacuum for 48 hours to give 1.82 g (96% yield) of compound 80.

¹H NMR (DMSO-d₆) δ 1.22 (t, J=7.4 Hz, 3 H), 2.23–2.89 (m, 2 H), 3.11 (q, J 7.4 Hz, 2 H), 3.29 (t, J=7.7 Hz, 2 H), 4.53 (t, J=7.5 Hz, 2 H), 5.08 (s, 2 H), 7.58–7.65 (m, 2 H), 7.80 (dd, J=1.0, 7.3 Hz, 1 H), 8.04 (d, J=7.75 Hz, 1 H); MS m/e 283 (MH⁺).

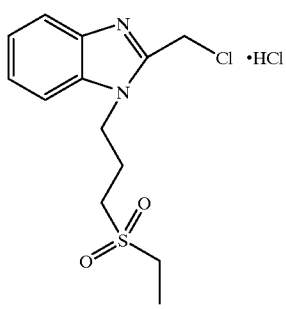

81

Compound 81 was prepared according to the same procedure described for compound 2.

MS m/e 301 (MH⁺).

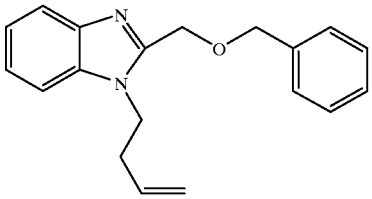

82

To a solution of compound 67 (1.43 g, 6.00 mmol) in DMF (25 mL) was added sodium hydride (60% dispersion in mineral oil, 260 mg, 6.60 mmol) and the mixture was cooled to 0° C. To the mixture was added 4-bromo-1-1-butene (972 mg, 7.20 mmol) and the mixture was allowed to stir at room temperature for 18 hours. The reaction mixture was quenched with H₂O and extracted with EtOAc. The organic extracts were washed with water and then brine, dried over MgSO₄, and evaporated. Flash column chromatography (gradient, hexanes/EtOAc, 4:1 to 1: 1) gave 5 80 mg (33% yield) of compound 82 as a viscous oil.

¹H NMR (CDCl₃) δ 2.55–2.59 (m, 2 H), 4.31 (t, J=7.5 Hz, 2 H), 4.59 (s, 2 H), 4.88 (s, 2 H), 5.01 (d, J=7.8 Hz, 1 H), 5.04 (d, J=10.4 Hz, 1 H), 5.71–5.80 (m, 1 H), 7.26–7.39 (m, 8 H), 7.79 (d, J=7.6 Hz, 1 H); MS m/e 293 (MH⁺).

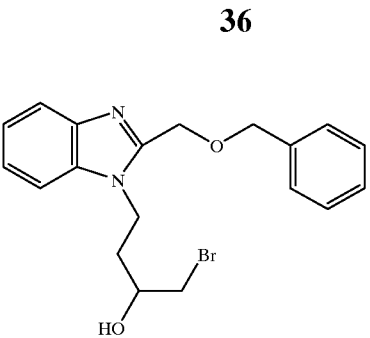

83

To a solution of compound 82 (468 mg, 1.92 mmol) and water (71 mg, 3.93 mmol) in DMSO (5 mL) was added N-bromosuccinimide (NBS, 700 mg, 3.93 mmol) at room temperature and the mixture was stirred for 1 hour. The resulting solution was diluted with EtOAc and washed with H₂O. The organic extracts were dried with MgSO₄ and evaporated. The residue was purified by flash chromatography (gradient, hexane:EtOAc 3:1 to 1:2) to give 214 mg (56% yield) of compound 83 as a off-white viscous oil.

¹H NMR (CDCl₃) δ 1.90–1.97 (m, 1 H), 2.12–2.18 (m, 1 H), 3.22–3.30 (m, 2 H), 3.61–3.66 (m, 1 H), 4.38–4.50 (m, 2 H), 4.59–4.64 (m, 2 H), 4.87–4.92 (m, 2 H), 7.28–7.37 (m, 7 H), 7.42–7.46 (m, 1 H), 7.78–7.80 (m, 1 H); MS m/e 389, 391 (MH⁺).

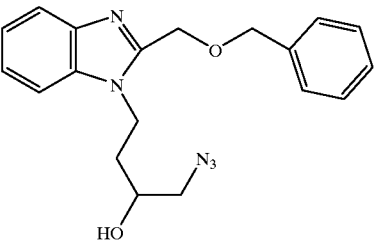

84

A mixture of compound 83 (214 mg, 0.55 mmol) and sodium azide (107 mg, 1.65 mmol) in DMF (5 mL) was stirred at 50° C. for 1 hour. The resulting solution was diluted with EtOAc and washed with water. The organic extracts were dried with MgSO₄ and evaporated to give 190 mg (98% yield) of compound 84 as a off-white viscous oil.

¹H NMR (CDCl₃) δ 1.84–1.91 (m, 1 H), 2.02–2.09 (m, 1 H), 3.08–3.14 (m, 2 H), 3.52–3.56 (m, 1 H), 4.36–4.41 (m, 1 H), 4.44–4.50 (m, 1 H), 4.60–4.67 (m, 2 H), 4.88–4.93 (m, 2 H), 7.26–7.38 (m, 7 H), 7.42–7.44 (m, 1 H), 7.79–7.81 (m, 1 H); MS m/e 352 (MH⁺).

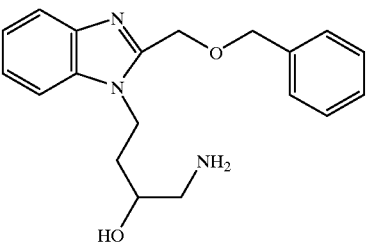

85

Compound 85 was prepared from compound 84 according to the same reduction procedure described for compound 13.

¹H NMR (CD₃OD) δ 1.86–1.94 (m, 1 H), 2.03–2.10 (m, 1 H), 2.70–2.74 (m, J=3.2, 12.8 Hz, 1 H), 2.84–2.88 (dd,

J=3.2, 12.8 Hz, 1 H), 3.70–3.75 (m, 1 H), 4.44–4.54 (m, 2 H), 4.60–4.65 (m, 2 H), 4.88–4.93 (m, 2 H), 7.27–7.38 (m, 7 H), 7.59 (d, J=8.0 Hz, 1 H), 7.65 (d, J=8.0 Hz, 1 H); MS m/e 326 (MH⁺).

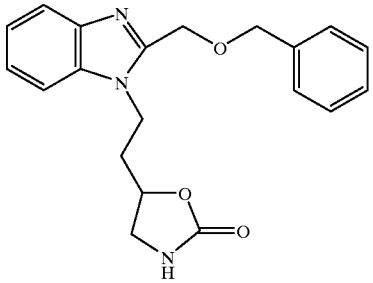

86

A solution of compound 85 (162 mg, 0.50 mmol), carbonyldiimidazole (89 mg, 0.55 mmol) and pyridine (198 mg, 2.50 mmol) in CH₂Cl₂ (5 mL) was stirred at room temperature for 2 hours. The mixture was diluted with CH₂Cl₂ and washed with water. The organic extracts were dried over MgSO₄ and evaporated. The residue was purified by flash chromatography (gradient, CH₂Cl₂:MeOH, 40:1 to 20:1) to give 130 mg (74% yield) of compound 86 as a off-white viscous oil.

¹H NMR (CD₃OD) δ 2.16–2.21 (m, 2 H), 3.06–3.09 (m, 1 H), 3.52–3.59 (m, 1 H), 4.41–4.50 (m, 2 H), 4.58–4.65 (m, 3 H), 4.80–4.84 (m, 2 H), 7.26–7.38 (m, 6 H), 7.55–7.58 (m, 1 H), 7.82–7.85 (m, 1 H), 8.51–8.53 (m, 1 H); MS m/e 352 (MH⁺).

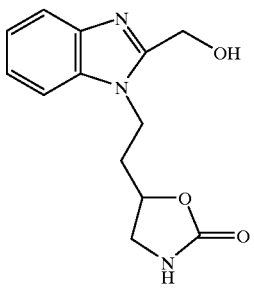

87

Compound 86 (130 mg, 0.37 mmol), palladium hydroxide on carbon (Pearlman's catalyst, 50 mg), EtOH (2 mL) and cyclohexene (1 mL) were stirred at reflux for 1 hour. The reaction mixture was filtered through a pad of Celite. The filtrate was concentrated and purified by flash column chromatography (gradient, CH₂Cl₂/MeOH, 30:1 to 10:1) to give 20 mg (21% yield) of compound 87 as a viscous white oil.

¹H NMR (CD₃OD) δ 2.26–2.33 (m, 2 H), 3.21–3.24 (m, 1 H), 3.65 (t, J=8.8 Hz, 1 H), 4.50–4.54 (m, 2 H), 4.67–4.70 (m, 1 H), 4.89–4.92 (m, 2 H), 7.24–7.34 (m, 2 H), 7.57 (d, J=8.0 Hz, 1 H), 7.63 (d, J=7.9 Hz, 1 H); MS m/e 294 (MH⁺).

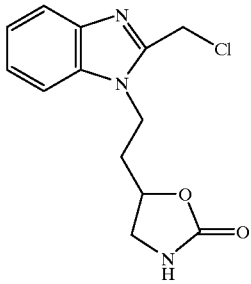

88

Compound 88 was prepared according to the same procedure described for chloride 2 and was used immediately upon isolation.

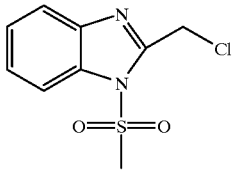

89

To a solution of 2-(chloromethyl)benzimidazole (80 g, 0.48 mol) and methanesulfonyl chloride (58.3 mL, 0.75 mol) in CH₂Cl₂ (0.5 L), triethylamine (136 mL, 0.97 mol) was added dropwise under nitrogen. The resulting mixture was stirred at room temperature for 6 hours. The mixture was filtered and the filtrate was evaporated. The residue was triturated with MeOH and filtered to afford 74.9 g (64% yield) of compound 89 as a brown solid.

¹H NMR (CDCl₃), 3.44 (s, 3 H), 5.11 (s, 2 H), 7.40–7.49 (m, 2 H), 7.76–7.82 (m, 1 H), 7.85–7.91 (m, 1H); IR (KBr, cm⁻¹) 3027, 2920, 1371, 1349, 1177, 1144, 1059; MS m/e 245 (MH⁺); Anal. Calcd for C₉H₉ClN₂O₂S: C, 44.18; H, 3.71; N, 11.45 Found: C, 44.09; H, 3.57; N, 11.49.

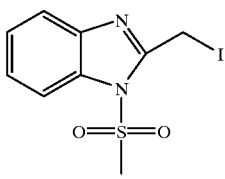

90

A solution of potassium iodide (206 g, 1.24 mol) and compound 89 (74.8 g, 0.414 mol) in acetone (1 L) was stirred at reflux under nitrogen for 4 hours. The solid was filtered and the filtrate was evaporated. The crude product was triturated in MeOH and filtered to give 83 g (60% yield) of compound 90 as a solid.

¹H NMR (CDCl₃) δ 3.48 (s, 3 H), 4.97 (s, 2 H), 7.40–7.50 (m, 2 H), 7.75–7.85 (m, 2 H); IR (KBr, cm⁻¹) 3022, 2916, 1366, 1173, 1055, 966, 763, 745; MS m/e 336 (MH⁺); Anal. Calcd for C₉H₉IN₂O₂S: C, 32.16; H, 2.70; N, 8.33 Found: C, 32.05; H, 2.63; N, 8.22.

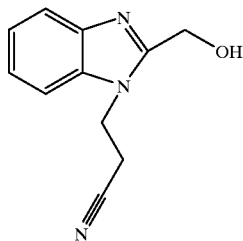

91

Compound 91 was prepared according to the Michael addition procedure described by Popov, I. I. in *Khim Geterotskl. Soedin.* 1996, 6, 781–792.

$^1$H NMR (CDCl$_3$) δ 3.08 (t, J=6.8 Hz, 2 H), 4.63 (t, 3 6.8 Hz, 2 H), 4.77 (d, J 5.7 Hz, 2 H), 5.73 (t, J=5.7 Hz, 1 H), 7.17–7.28 (m, 2 H), 7.64 (d, J=1.2 Hz, 1 H), 7.70 (d, J=1.2 Hz, 1H);

MS m/e 202 (MH$^+$); Anal. Calcd for C$_{11}$H$_{11}$N$_3$O: C 65.66; H, 5.51; N, 20.88 Found: C, 65.94; H, 5.57; N, 21.08.

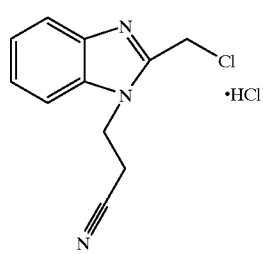

92

Compound 92 was prepared according to the same procedure described for compound 2.

$^1$H NMR (CDCl$_3$) δ 3.02 (t, J=7.0Hz, 2 H), 4.65 (t, J=7.0 Hz, 2 H), 4.99 (s, 2 H), 7.34–7.44 (m, 3 H), 7.79–7.82 (m, 1 H); MS m/e 220 (MH$^+$); Anal. Calcd for C$_{11}$H$_{10}$ClN$_3$: C, 60.09; H, 4.65; N, 19.13 Found: C, 60.09; H,4.65; N, 19.11.

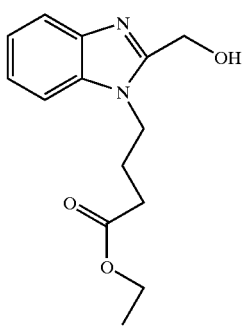

93

Compound 93 was prepared according to the same procedure described for compound 1 except that 4-bromobutyronitrile was replaced with ethyl 4-bromobutyrate.

$^1$H NMR (CDCl$_3$) 5 1.24 (t, J=7.0 Hz, 3 H), 2.15–2.22 (m, 2 H), 2.38–2.42 (m, 2 H), 4.12 (q, J=7.1 Hz, 211), 4.29–4.34 (m, 211), 4.96 (s, 211), 7.22–7.30 (m, 2 H), 7.38–7.43 (m, 1 H), 7.66–7.70 (m, 1 H); MS m/e 250 (MH$^+$).

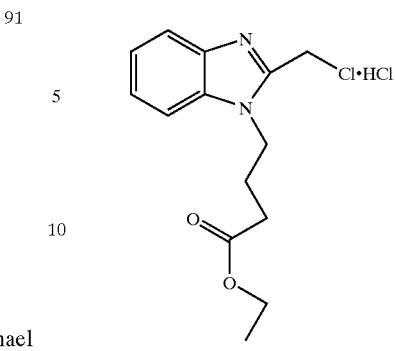

94

Compound 94 was prepared according to the same procedure described for chloride 2 and was used immediately upon isolation.

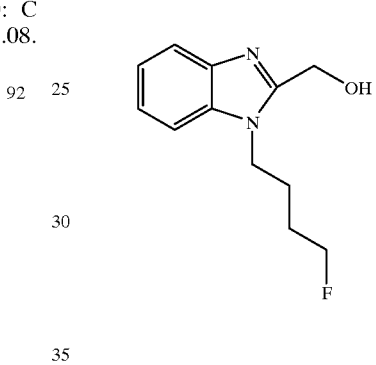

95

Compound 95 was prepared according to the same procedure described for compound 1 except that 4-bromobutyronitrile was replaced with 1-bromo-4-fluorobutane.

$^1$H NMR (DMSO-d,) 8 1.65–1.75 (m, 2 H), 1.85–1.90 (m, 2 H), 4.32 (t, J=7.5 Hz, 2 H), 4.41 (t, J=6.0 Hz, 1 H), 4.51 (t, J=6.0 Hz, 1H), 4.71 (d, J=5.8 Hz, 2 H), 5.62 (t, J=5.8 Hz, 1 H), 7.18 (t, J=7.0 Hz, 1 H), 7.23 (t, J=6.3 Hz, 1 H), 7.56–7.60 (m, 2 H); MS m/e 222 (MH$^+$).

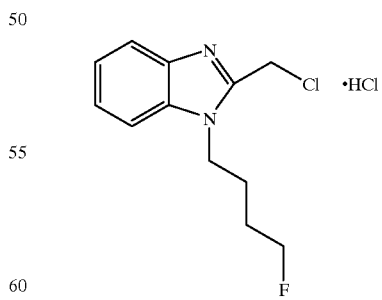

96

Compound 96 was prepared according to the same procedure described for chloride 2 and was used immediately upon isolation.

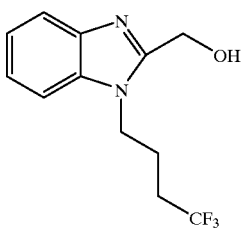

97

Compound 97 was prepared according to the same procedure described for compound 1 except that 4-bromobutyronitrile was replaced with 1-bromo-4,4,4-trifluorobutane.

$^1$H NMR (DMSO-$d_6$) δ 1.99–2.05 (m, 2 H), 2.34–2.40 (m, 2 H), 4.35–4.38 (m, 2 H), 4.73 (s, 2 H), 7.20 (t, J=7.2 Hz, 1 H), 7.26 (t, J=7.4 Hz, 1 H), 7.60–7.63 (m, 1 H), 7.96 (s, 1 H); MS m/e 258 (MH$^+$).

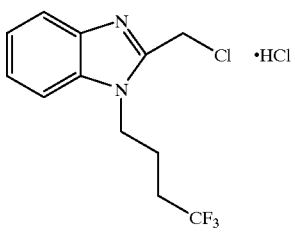

98

Compound 98 was prepared according to the same procedure described for chloride 2 and was used immediately upon isolation.

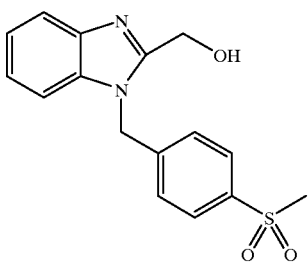

99

Compound 99 was prepared according to the same procedure described for compound 1 except that 4-bromobutyronitrile was replaced with 4-methylsulfonylbenzyl bromide.

$^1$H NMR (DMSO-$d_6$) 3.16 (s, 3 H), 4.75 (d, J=5.6Hz, 2 H), 5.70 (s, 2 H), 5.73–5.75 (m, 1 H), 7.17–7.21 (m, 2 H), 7.36–7.38 (m, 1 H), 7.42 (d, J=8.2 Hz, 2 H), 7.64–7.65 (m, 1 H), 7.87 (d, J=8.2 Hz, 1 H); MS m/e 316 (MH$^+$).

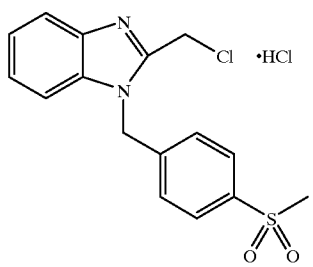

100

Compound 100 was prepared according to the same procedure described for chloride 2 and was used immediately upon isolation.

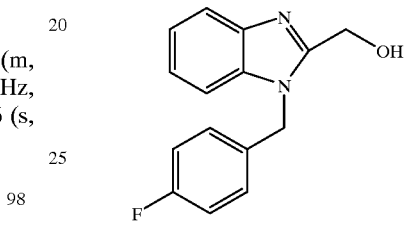

101

Compound 101 was prepared according to the same procedure described for compound 1 except that 4-bromobutyronitrile was replaced with 4-fluorobenzyl bromide.

$^1$H NMR (DMSO-$d_6$) δ 4.74 (s, 2 H), 5.55 (s, 2 H), 7.13–7.18 (m, 3 H), 7.28–7.30 (m, 2 H), 7.38–7.40 (m, 1 H), 7.59–7.63 (m, 1 H); MS m/e 256 (MH$^+$).

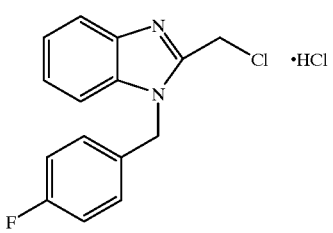

102

Compound 102 was prepared according to the same procedure described for chloride 2 and was used immediately upon isolation.

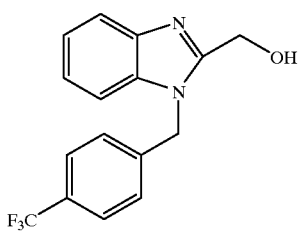

103

Compound 103 was prepared according to the same procedure as compound 1 except that 4-bromobutyronitrile was replaced with 4-trifluoromethylbenzyl bromide.

¹H NMR (DMSO-d₆) δ 4.74 (s, 2 H), 5.68 (s, 2 H), 7.11–7.20 (m, 2 H), 7.35–7.39 (m, 2 H), 7.62–7.64 (m, 1 H), 7.64–7.72 (m, 2 H); MS m/e 369 (MH⁺).

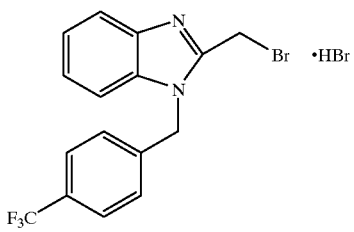

104

Compound 104 was prepared according to the same procedure described for compound 64 and was used immediately upon isolation.

105

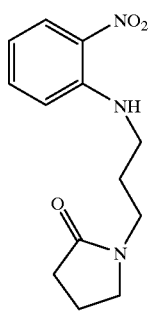

Compound 105 was prepared according to the same procedure described for compound 16 using 1-(3-aminopropyl)-2-pyrrolidinone instead of 3-(methylthio)propylamine.

¹H NMR (CDCl₃) δ 1.93 (m, 2 H), 2.02–2.07 (m, 2 H), 2.39 (t, J=8.05 Hz, 2 H), 3.32–3.36 (m, 2H), 3.36–3.45 (m, 4 H), 6.64 (t, J=7.0 Hz, 1 H), 6.83 (d, J=8.7 Hz, 1 H), 7.42 (t, J=8.7 Hz, 1 H), 8.07 (bs, 1 H), 8.16 (d, J=7.0 Hz, 1 H); MS in/e 263 (MH⁺); Anal. Calcd for $C_{13}H_{17}N_3O_3 \cdot 0.24$ H2O: C, 58.34; H, 6.58; N, 15.70 Found: C, 58.05; H, 6.20; N, 11.41.

106

Compound 106 was prepared according to the same reduction procedure described for compound 13.

¹H NMR (CDCl₃) δ 1.83–1.88 (m, 2 H), 1.99–2.05 (m, 2 H), 2.41 (t, J=8.0 Hz, 2 H), 3.16 (t, J=6.5 Hz, 2 H), 3.33–3.43 (m, 4 H), 6.63–6.65 (m, 2 H), 6.70 (d, J=7.1 Hz, 1 H), 6.78 (t, J=7.5 Hz, 1 H), 7.26 (s, 1 H); MS m/e 233 (MH⁺).

107

Compound 107 was prepared according to the same procedure described for compound 14.

¹H NMR (DMSO-d₆) δ 1.87–1.92 (m, 2 H), 1.95–2.00 (m, 2 H), 2.21 (t, J=8.0 Hz, 2 H), 3.25–3.34 (m, 4 H), 4.26 (t, J=7.6 Hz, 2 H), 4.72 (s, 2 H), 5.65 (bs, 2 H); MS m/e 273 (MH⁺).

108

Compound 108 was prepared according to the same procedure described for chloride 2 and was used immediately upon isolation.

109

A mixture of 2,3-diaminotoluene (10.21 g, 83.57 mmol) and glycolic acid (9.5 3 g, 125.3 6 mmol) in 6 N HCl (1 00 mL) were stirred at I100° C. for 14 hours. The reaction mixture was cooled and made basic (pH 7–8) with ammonium hydroxide. A dark brown solid was collected by filtration, washed with H₂and dried to give 12.47 g (92% yield) of compound 109.

¹H NMR (DMSO-d₆) δ 2.50 (s, 3 H), 4.70 (s, 2 H), 6.93 (d, J=7.3 Hz, 1 H), 7.04 (t, J=7.6Hz, 1 H), 7.31 (d, J=7.9Hz, 1 H).

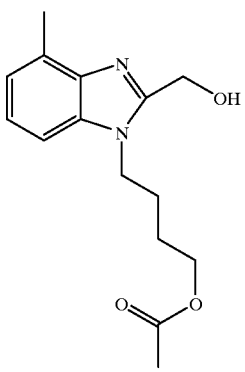

110

Compound 110 was prepared according to the same procedure described for compound 24 except that the base employed was cesium carbonate.

$^1$H NMR (CDCl$_3$) δ 1.67–1.73 (m, 2 H), 1.89–1.96 (m, 2 H), 2.02 (s, 3 H), 2.59 (s, 3 H), 4.05–4.10 (m, 2 H), 4.27 (t, J=7.5 Hz, 2 H), 4.89 (s, 2 H), 7.01–7.03 (m, 1 H), 7.12–7.15 (m, 2 H); MS m/e 277 (MH$^+$).

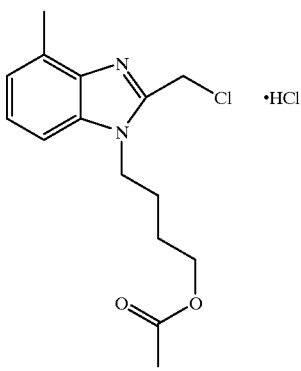

111

Compound 111 was prepared according to the same procedure described for chloride 2 and was used immediately upon isolation. MS m/e 295 (MH$^+$).

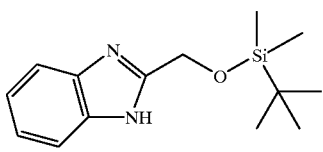

138

To a solution of 2-hydroxymethylbenzimidazole (5.92 g, 40.0 mmol) and imidazole (6.81 g, 100.0 mmol) in THF (100 mL) was added t-butyldimethylsilyl chloride (12.65 g, 84.0 mmol) in several portions. The resulting mixture was stirred at room temperature for 2 hours and filtered. The filtrate was diluted with EtOAc and washed with H$_2$O and brine. The organic layer was dried over MgSO$_4$ and evaporated. The residue was recrystallized from hexanes/EtOAc to give 8.50 g (81%) of compound 138 as white needles.

$^1$H NMR (CDCl$_3$) δ 0.15–0.16 (m, 6 H), 0.95–0.97 (m, 9 H), 5.02–5.03 (m, 2 H), 7.24–7.27 (m, 2 H), 7.59 (bs, 2 H); MS m/e 263 (MH$^+$).

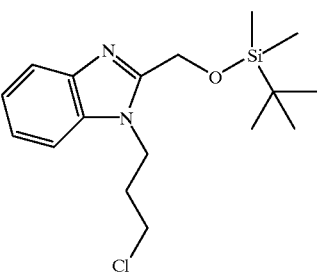

139

Compound 139 was prepared according to the same procedure described for compound 68 except that cesium carbonate was used instead of sodium hydride as the base.

$^1$H NMR (CDCl$_3$) δ 0.13–0.14 (m, 6 H), 0.91–0.92 (m, 9 H), 2.35–2.37 (m, 2 H), 3.58 (t, J=6.0 Hz, 2 H), 4.50 (t, J=7.0 Hz, 2 H), 5.01 (s, 2 H), 7.26–7.32 (m, 2 H), 7.44 (d, J=8.0 Hz, 1 H), 7.77 (d, J=10.0 Hz, 1 H); MS m/e 339 (MH$^+$).

140

Compound 140 was prepared through the coupling of compound 139 and cyclopropylsulfide according to the same procedure described for compound 74 except using cesium carbonate instead of sodium hydride as the base. The cyclopropylsulfide was prepared according to a literature procedure by E. Block, A. Schwan, and D. Dixon in *Journal of the American Chemical Society*, 1992, 114, 3492–3499.

$^1$H NMR (CDCl$_3$) δ 0.12–0.13 (m, 6 H), 0.54–0.56 (m, 2 H), 0.84–0.86 (m, 2 H), 0.90–0.91 (m,9 H), 1.87–1.92 (m, 1 H), 2.20–2.25 (m,2 H), 2.62 (t, J=7.0 Hz, 2 H), 4.43 (t, J=7.4 Hz, 2 H), 5.00 (s, 2 H), 7.26–7.32 (m,2 H), 7.44 (d, J=8.0 Hz, 1 H), 7.77 (d, J=10.0 Hz, 1 H); MS m/e 377 (MH$^+$).

141

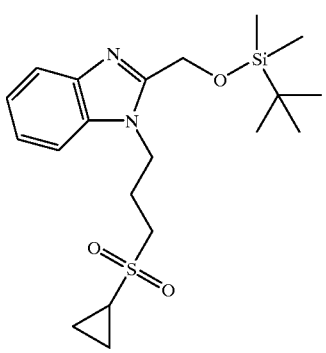

Compound 141 was prepared from compound 140 by the same procedure described for compound 18.

¹H NMR (CDCl₃) δ 0.13–0.14 (m, 6 H), 0.91–0.92 (m, 9 H), 1.01–1.03 (m, 2 H), 1.23–1.24 (m, 2 H), 2.31–2.34 (m, 1 H), 2.48–2.52 (m, 2 H), 3.07 (t, J=7.2 Hz, 2 H), 4.51 (t, J=7.1 Hz, 2 H), 5.00 (s, 2 H), 7.26–7.32 (m, 2 H), 7.44 (d, J=8.0 Hz, 1 H), 7.77 (d, J=10.0 Hz, 1 H); MS m/e 409 (MH⁺).

142

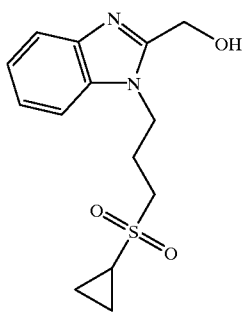

To solution of compound 141 (27 mg, 0.07 mmol) in THF (0.5 ml) was added TBAF (1 M THF solution, 0.13 mL, 0.13 mmol) at 0° C. and the mixture was stirred for 10 minutes. The solvent was evaporated and the residue was passed through a short plug of silica (CH₂Cl₂/MeOH, 10:1) to give crude compound 142 which was used immediately upon isolation.

143

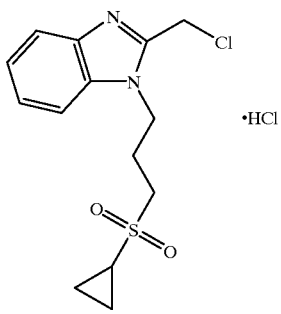

Compound 143 was prepared according to the same procedure described for compound 2 and was used immediately upon isolation.

II. Preparation of 2-Oxo-imidazopyridines and 2-Oxo-imidazopyrimidines:

Compounds 26–58 and 112–126 are intermediates prepared according to the procedures depicted in Scheme III.

26

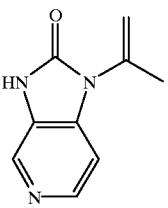

3,4-Diaminopyridine (30 g, 274.9 mmol), ethyl acetoacetate (53.66 g, 412 mmol) and DBU (1 mL) were stirred at reflux in xylene (300 mL) under a Dean-Stark trap. After stirring for 3.5 hours, the solvent was evaporated and the residue was purified by flash chromatography (EtOAc; EtOAc:MeOH =10:1) to give a solid which was recrystallized from CH₂Cl2/EtOAc to afford 26 (21.45 g, 45% yield) as white crystals.

¹H NMR (CDCl₃) δ 2.19 (s, 3 H), 5.22 (s, 1 H), 5.46 (s, 1 H), 7.19 (d, J=5.4 Hz, 1 H), 8.20 (d, J=5.4 Hz, 1 H), 8.23 (s, 1 H); MS m/e 176 (MH⁺).

27

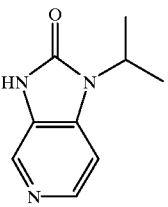

Compound 26 (1.0 g, 5.71 mmol) in the presence of 10% palladium on carbon (0.1 g) in MeOH (10 mL) was hydrogenated in a Parr shaker at 40 psi for 2 days. The catalyst was removed by filtration and the filtrate was evaporated to give compound 27 as a white solid.

¹H NMR (CDCl₃) δ 1.57 (d, J=7.0 Hz, 6 H), 4.72–4.76 (m, 1 H), 7.19 (d, J=5.8 Hz, 1 H), 8.30 (d, J=5.8 Hz, 1 H), 8.58 (s, 1 H); MS m/e 178 (MH⁺).

28A

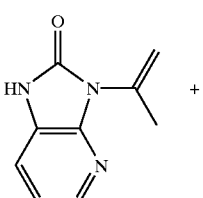

+

28B

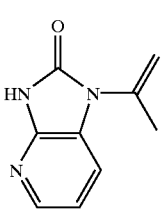

The same procedure described for compound 26 was carried out using 2,3-diaminopyridine to give 28A and 28 B which were separated by flash chromatography (gradient, CH₂Cl₂/acetone,5:1 to 4:1).

Compound 28A

¹H NMR (CD₃OD) δ 2.31 (s, 3 H), 5.40 (s, 1 H), 5.51 (s, 1 H), 7.04 (dd, J=5.2, 7.7 Hz, 1 H), 7.38 (dd, J=1.4, 7.7 Hz, 1 H), 8.09 (dd, J=1.4, 5.2 Hz, 1 H); MS m/e 176 (MH⁺).

Compound 28B

¹H NMR (CD₃OD) δ 2.26 (s, 3 H), 5.21 (s, 1 H), 5.38 (s, 1 H), 7.11 (dd, J=5.5, 7.9 Hz, 1 H), 7.40 (dd, J=1.3, 7.9 Hz, 1 H), 8.09 (dd, J=1.3, 5.5 Hz, 1 H); MS m/e 176 (MH⁺).

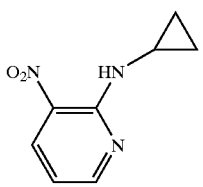

29

2-Chloro-3-nitropyridine (7.0 g, 50.0 mmol), cyclopropylamine (3.71g, 65 mmol) and potassium carbonate (13.82 g, 100 mmol) were stirred in CH₃CN (100 mL) at room temperature overnight and at reflux for an additional hour. The solid was filtered and the filtrate was evaporated. Water was added to the residue and the mixture was extracted with EtOAc. The combined extracts were dried over MgSO₄ and filtered. Evaporation of the solvent gave 29 (8.40 g, 94% yield) as a dark brown solid.

¹H NMR (CD₃OD) δ 0.63–0.69 (m, 2 H), 0.93–0.97 (m, 2 H), 3.01–3.06 (m, 1 H), 6.70–6.72 (dd, J=4.5, 8.3 Hz, 1 H), 8.24 (bs, 1 H), 8.42 (dd, J=1.7, 8.3 Hz, 1 H), 8.52 (dd, J=1.7, 4.5 Hz, 1 H); MS m/e 180 (MH⁺).

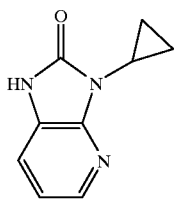

30

Compound 29 (8.29 g, 46.28 mmol) was reduced with iron using the procedure described for compound 7. To the crude diamine in THF (50 mL) was added 1 equivalent of carbonyldiimidazole and the mixture was stirred at room temperature overnight. The solvent was evaporated and the residue was diluted with CH₂Cl₂; washed with water, dried over MgSO₄ and evaporated. The residue was purified by flash chromatography (gradient, EtOAc/hexane, 1:1 to EtOAc/MeOH, 10: 1) to give 30 (1.93 g, 24% yield over two steps) as a light orange solid.

¹H NMR (CDCl₃) δ 1.19 (d, J=3.4 Hz, 2 H), 1.20 (s, 2H), 3.01–3.04 (m, 2 H), 7.02 (dd, J=5.3, 7.7 Hz, 1 H), 7.32 (dd, J=1.4, 7.7 Hz, 1 H), 8.12 (dd, J=1.4, 5.3 Hz, 1 H), 9.61 (bs, 1 H); MS m/e 176 (MH⁺).

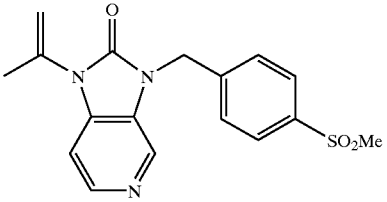

31

A mixture of 26 (2.0 g, 11.4 mmol), Cs₂CO₃ (5.58 g, 17.1 mmol) and p-methylsulfonylbenzyl chloride (2.34 g, 11.4 mmol) in acetone (50 mL) was stirred at reflux for 2 hours. The solid was removed by filtration and the filtrate was evaporated. The residue was purified by flash chromatography (gradient, CH₂Cl₂/MeOH, 40:1 to 20:1) to afford 31 ( 3.24 g, 83% yield) as a white solid.

¹H NMR (DMSO-d₆) δ 2.18 (s, 3 H), 3.20 (s, 3 H), 5.23 (s, 2 H), 5.26 (s, 1 H), 5.45 (d, J=1.2 Hz, 1 H)), 7.21 (d, J=5.3 Hz, 1 H), 7.63 (d, J=8.4 Hz, 2 H), 7.92 (d, J=8.4 Hz, 2 H), 8.25 (d, J=5.1 Hz, 1H), 8.41 (s, 1 H); MS m/e 344 (MH⁺).

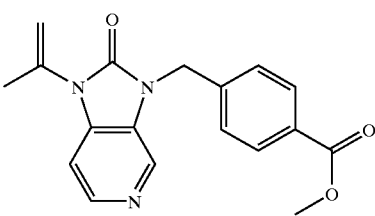

32

Compound 32 was prepared using the same procedure for compound 31, except that methylsulfonylbenzyl chloride was replaced with methyl p-bromomethylbenzoate.

¹H NMR (DMSO-d₆) δ 2.05 (s, 3H), 3.70 (s, 3H), 5.06 (s, 2H), 5.12 (s, 1H), 5.32 (d, J=1.4 Hz, 1H), 7.07–7.09 (dd, J=0.45, 5.4 Hz, 1H), 7.37 (d, J=8.4 Hz, 2H), 7.80–7.82 (m, 2H), 8.11 (d, J=5.3 Hz, 1H), 8.23 (s, 1H); MS m/e 324 (MH⁺).

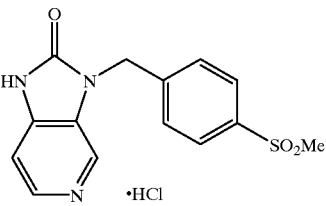

33

A solution of 31 (3.24 g, 9.45 mmol) in concentrated HCl (5 ml) and MeOH (50 ml) was stirred at reflux for 2 hours. The solvent was evaporated and the residue was triturated in hot MeOH to yield 33 (2.80 g, 87% yield) as a white solid as the HCl salt.

¹H NMR (DMSO-d₆) δ 3.18 (s, 3 H), 5.17 (s, 2 H), 7.07 (d, J=5.2 Hz, 1 H), 7.58 (d, J=8.0 Hz, 2 H), 7.91 (d, J=8.2 Hz, 2 H), 8.17 (d, J=5.0 Hz, 1 H), 8.29 (s, 1 H); MS m/e 304 (MH⁺).

34

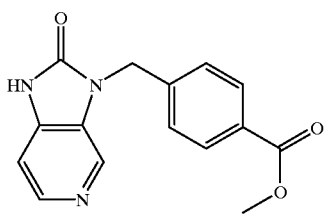

A solution of 32 (1.30 g, 4.02 mmol) in concentrated HCl (10 ml) and MeOH (10 ml) was stirred at reflux for 1 hour. The solution was neutralized with $K_2CO_3$ to pH 6, and extracted with EtOAc. The organic layer was dried and evaporated to dryness. The crude product was triturated with hot $CH_2Cl_2$ to yield 34 (0.85 g, 75% yield) as off-white solid.

$^1$H NMR (DMSO-$d_6$) δ 3.90 (s, 3 H), 5.20 (s, 2 H), 7.13 (d, J=5.2 Hz, 1 H), 7.53 (d, J=8.2 Hz, 2 H), 8.00 (d, J=8.2 Hz, 2 H), 8.22 (d, J=5.2 Hz, 1 H), 8.31 (s, 1 H); MS m/e 284 (MH$^+$).

35

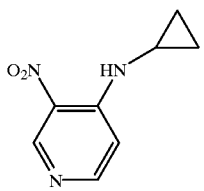

A solution of 4-methoxy-3-nitro-pyridine (7.71 g, 50 mmol) and cyclopropylamine (7.14g, 125 mmol) in EtOH (20 mL) was stirred at reflux under a dry-ice trap condenser for 2 hours. The solvent was evaporated to give 35 as a yellow solid.

$^1$H NMR (CD$_3$OD) δ 0.72–0.75 (m, 2 H), 0.99–1.03 (m, 2 H), 2.63–2.68 (m, 1 H), 7.19 (d, J=6.2 Hz, 1 H), 8.26 (bs, 1 H), 8.35 (d, J=6.2 Hz, 1 H), 9.22 (s, 1 H); IR (KBr, cm$^1$) 3369, 1613, 1560, 1515, 1406, 1254, 1195, 1039, 881, 846, 769, 545; MS m/e 180 (MH$^+$).

36

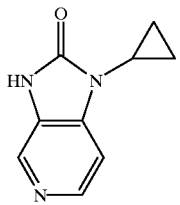

To a solution of 35 (12.28 g, 68.6 mmol) in anhydrous MeOH (120 mL) was added 10% palladium on carbon (3 g) in several portions under nitrogen. The reduction was carried out using a balloon containing hydrogen (1 atm) for 16 hours. The catalyst was removed by filtration through a pad of Celite and rinsed with MeOH. The filtrate was concentrated to a slurry and $Et_2O$ was added to precipitate the diamine product as a light yellow solid (10.1 g, 99% yield).

To a slurry of the diamine and polyvinylpyridine (22.0 g) in acetonitrile (70 mL) of a 20% phosgene solution in toluene was added dropwise (70 mL, 135.4 mmol). After stirring at room temperature for 2 hours, the reaction was quenched with water. Polyvinylpyridine was removed by filtration and rinsed with MeOH. The filtrate was concentrated and $Et_2O$ was added to precipitate product 36 (15.5g, 98% yield) as a light brown solid.

$^1$H NMR (CD$_3$OD) δ 0.95–0.98 (m, 2 H), 1.07–1.14 (m, 2 H), 2.91–2.96 (m, 1 H), 7.32 (dd, J=0.5, 5.3 Hz, 1 H), 7.18 (s, 1 H), 8.21 (d, J=5.3 Hz, 1 H); MS m/e 176 (MH$^+$).

2-Oxo-imidazopyridine 39 was prepared using the same procedure described for the preparation of 36, except that cyclopropylamine was replaced with 2 equivalents of trifluoroethylamine hydrochloride and diisopropylethylamine, and the reaction was carried out in a sealed tube at 120–130° C. for 2 days.

37

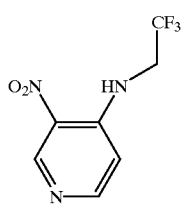

$^1$H NMR (CDCl$_3$) δ 4.02 (q, J=7.9 Hz, 2 H), 6.83 (d, J=5.5 Hz, 1 H), 8.43 (d over bs, 2 H), 9.28 (s, 1 H); IR (KBr, cm$^{-1}$): 3287, 3241, 1629, 1611, 1363, 1254, 1150, 1047, 870; MS m/e 222 (MH$^+$); Anal. Calcd for $C_7H_6F_3N_3O_2$: C, 38.02; H, 2.73; N, 19.00 Found: C, 38.00; H, 2.69; N, 19.19.

38

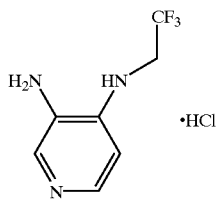

$^1$H NMR (CD$_3$OD) δ 4.23 (q, J=9.0 Hz, 2 H), 7.05 (d, J=6.6 Hz, 1 H), 7.74 (d, J=1.1 Hz, 1 H), 7.84 (d, J=1.1, 6.6 Hz, 1 H); IR (KBr, cm$^1$): 3343, 3202, 3062, 1625, 1578, 1529, 1257, 1154, 949; MS m/e 192 (MH$^+$); Anal. Calcd for $C_7H_8F_3N_3$·HCl: C, 36.94; H, 3.99; N, 18.46 Found: C, 37.19; H, 3.86; N, 18.79.

39

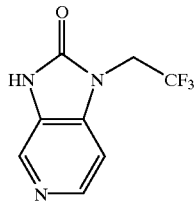

$^1$H NMR (DMSO-$d_6$) δ 4.99 (q, J=9.2 Hz, 2 H), 7.90 (d, J=6.3 Hz, 1 H), 8.61 (d, J=6.3 Hz, 1 H), 8.63 (s, 1 H); IR (KBr, cm$^{-1}$): 3423, 2994, 1744, 1517, 1347, 1254, 1263, 1173, 1000, 811; MS m/e 218 (MH$^+$).

2-Oxo-imidazopyridine 41 was prepared using the same procedure described for compound 36, except that cyclopropylamine was replaced with t-butylamine and the reaction was carried out in a sealed tube at 80° C. This com pound was used as a crude intermediate for the coupling reaction.

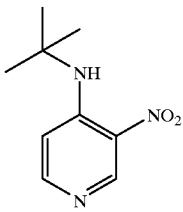

40

¹H NMR (CDCl₃) δ 1.54 (s, 9 H), 7.21 (d, J=6.3 Hz, 1 H), 8.17 (d, J=6.3 Hz, 1 H), 9.08 (s, 1 H); MS m/e 196 (MH⁺).

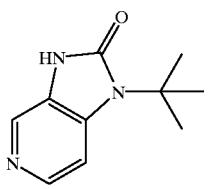

41

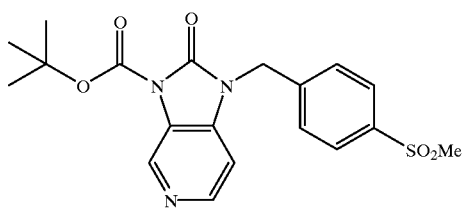

42

A mixture of 1,2-dihydro-2-oxo-3H-imidazol[4,5-c]pyridine-3-carboxylic acid, 1,1-dimethyl ethyl ester (470 mg, 2.0 mmol) (prepared according to the procedure described by N. Meanwell et al. in *J. Org. Chem.* 1995, 60, 1565), Cs₂CO₃ (978 mg, 3.0 mmol) and p-methylsulfonylbenzyl chloride (451 mg, 2.2 mmol) in acetone (10 mL) was stirred at reflux for 2 hours. The mixture was filtered and the filtrate was evaporated. The residue was purified by flash chromatography (gradient, CH₂Cl₂/MeOH, 40:1 to 20:1) to afford 42 (500 mg, 62% yield) as a white solid.

¹H NMR (CDCl₃) δ 1.71 (s, 9 H), 3.04 (s, 3 H), 5.15 (s, 2 H), 6.90 (m, 1 H), 7.54 (m, 2 H), 7.93 (m, 2 H), 8.40 (m, 1 H), 9.01 (m, 1 H); MS m/e 404 (MH⁺).

43

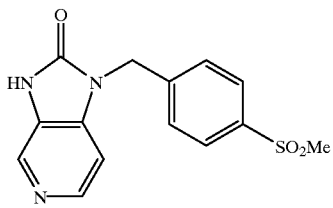

A mixture of 42 (260 mg, 0.64 mmol) and 1 N NaOH (3.22 ml) in THF (5 ml) and water (1 ml) was stirred at the ambient temperature overnight. The mixture was diluted with saturated NH₄Cl and extracted with CH₂Cl₂. The combined extracts were dried over MgSO₄ and evaporated. The residue was triturated with EtOAc to produce 43 (180 mg, 93% yield) as a white solid.

¹H NMR (DMSO-d₆) δ 3.34 (s, 3 H), 5.16 (s, 2 H), 7.19 (d, J=5.2 Hz, 1 H), 7.56 (d, J=8.4Hz, 2 H), 7.89 (d, J=8.4Hz, 2 H), 8.15 (d, J=5.2Hz, 1 H), 8.22 (s, 1 H), 11.34 (s, 1 H); MS m/e 304 (MH⁺).

2-Oxo-imidazopyridine 45 was prepared using the same procedure for compound 43, except that p-methylsulfonylbenzyl chloride was replaced with cyclopropylmethyl bromide. This compound was used as a crude intermediate for the coupling reaction.

44

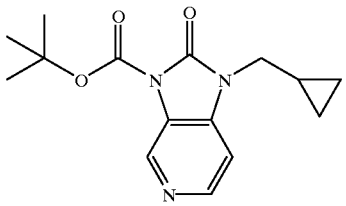

¹H NMR (CD₃OD) δ 0.44–0.45 (m, 2 H), 0.56–0.58 (m, 2 H), 1.21–1.25 (m, 1 H), 1.69 (s, 9 H), 3.79 (d, J=7.1 Hz, 2 H), 7.35 (d, J=5.4Hz, 1 H), 8.34 (d, J5.4 Hz, 1 H), 8.84 (s, 1 H); MS m/e 290 (MH⁺).

45

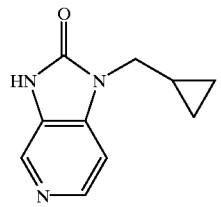

¹H NMR (CD₃OD) δ 7.54 (d, J=1.2 Hz, 1 H), 8.19 (d, J=1.2 Hz, 1 H), 8.23 (s, 1 H), 8.67 (s, 1 H); MS m/e 137 (MH⁺).

46

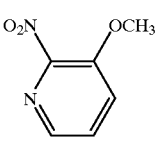

To a solution of 3-hydroxy-2-nitropyridine (100 g, 0.71 mol) in acetone (800 mL) was added potassium carbonate (148 g, 1.07 mol) followed by dimethyl sulfate (99 g, 0.79 mol). The reaction mixture was stirred vigorously using a mechanical stirrer and heated to 60° C. for 4.5 hours. The mixture was filtered while still warm. The filtrate was stripped of solvent to give a crude brown solid. The solid was diluted with water and extracted with EtOAc. The organic extracts were dried over anhydrous MgSO₄, filtered and evaporated. The residue was purified by flash chromatography (CH₂Cl₂/EtOAc, 1:1) to give 46 as a bright yellow solid (81 g, 74% yield).

¹H NMR (CDCl₃) δ 3.98 (s, 3 H), 7.51–7.57 (m, 2 H), 8.10 (dd, J=1.5, 7.5 Hz, 1 H); MS m/e 155 (MH⁺).

47

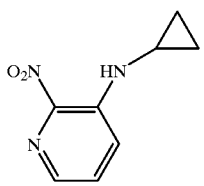

Compound 47 was obtained from 46 using the same procedure for the preparation of 35 except that the reaction was carried out with 1.5 equivalents of cyclopropylamine in a sealed tube at 120° C. for 2 days.

$^1$H NMR (CDCl$_3$) δ 0.67–0.72 (m, 2 H), 0.89–1.00 (m, 2 H), 2.58–2.65 (m, 1 H), 7.50 (dd, J=4.0, 8.6 Hz, 1 H), 7.82 (J=8.6 Hz, 1 H), 7.83 (d, J=8.6 Hz, 1 H), 7.97 (dd, J=1.4, 4.0 Hz, 1 H); MS m/e 155 (MH$^+$).

48

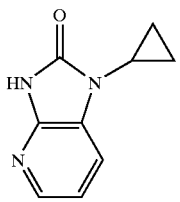

A solution of 47 (300 mg, 1.67 mmol) in MeOH (25 mL) was agitated under H$_2$ (10 psi) in the presence of 10% palladium on carbon (60 mg) for 15 min. The catalyst was removed by filtration through a pad of Celite. To the filtrate was added urea (402 mg, 6.70 mmol), and the mixture was evaporated. The solid residue was then heated at 170° C. for 16 hours. The resulting black solid was heated in boiling ethanol and filtered. The filtrate was evaporated and the residue was purified by flash chromatography (gradient, straight CH$_2$Cl$_2$ to CH$_2$Cl$_2$/MeOH, 20:1) to give compound 48 as a yellow solid (82 mg, 28% yield). $^1$H NMR (CDCl$_3$) δ 0.99–1.04 (m, 2 H), 1.12–1.15 (m, 2 H), 2.89–2.93 (m, 1 H), 7.05 (dd, J=5.3, 7.8Hz, 1 H), 7.41 (dd, J=1.3; 7.8Hz, 1 H), 8.05 (d, J=5.3Hz, 1 H); MS m/e 176 (MH$^+$).

49

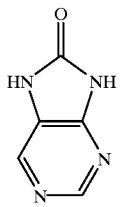

Compound 49 was prepared from 4,5-diaminopyrimidine and urea using the same procedure described for compound 48.

50

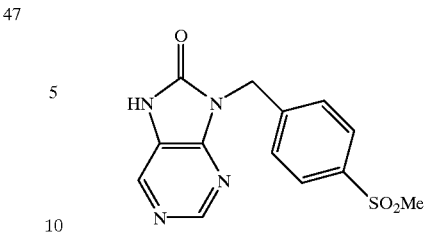

To a slurry of 49 (136 mg, 1.0 mmol) in THF (5 mL) was added BTPP (946 mg, 3.0 mmol) and p-methylsulfonylbenzyl chloride (205 mg, 1.0 mmol) at ambient temperature. After stirring overnight, the solution was diluted with EtOAc, washed with water, dried over MgSO$_4$ and evaporated. The residue was purified by flash chromatography (gradient, CH$_2$Cl$_2$/MeOH, 40:1 to 20:1) to afford compound 50 (52 mg, 34% yield) as a white solid.

$^1$H NMR (CD$_3$OD) δ 3.08 (s, 3 H), 5.26 (s, 2 H), 7.67 (d, J=8.4 Hz, 2 H), 7.91–7.93 (m, 2 H), 8.34 (s, 1 H), 8.74 (s, 1 H); MS m/e 305 (MH$^+$).

51

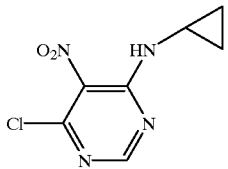

To a suspension of 4,6-dichloro-5-nitropyrimidine (3.88 g, 20.0 mmol) and triethylamine (4.05 g, 40.0 mmol) in THF (50 ml) was added cyclopropylamine (1.14 g, 20.0 mmol) dropwise at 0° C. After stirring at 0° C. for 2 hours, the slurry was filtered. The filtrate was diluted with EtOAc, washed with water, dried over MgSO$_4$, and evaporated. The residue was purified by flash chromatography (gradient, CH$_2$Cl$_2$/MeOH, 100:1 to 40:1) to afford compound 51 (2.75 g, 64% yield) as a yellow solid.

$^1$H NMR (DMSO-d$_6$) δ 0.61–0.64 (m, 2 H), 0.74–0.78 (m, 2 H), 2.92 (bs, 1 H), 8.43 (bs, 1 H), 8.51 (s, 1 H); MS m/e 215 (MH$^+$).

52

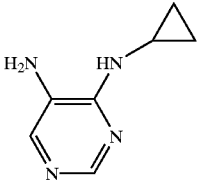

Pyrimidine 51 was reduced using catalytic hydrogenation with 10% palladium on carbon in MeOH at 40 psi (Parr shaker) for 1 hour to afford compound 52.

$^1$H NMR (DMSO-d$_6$) δ 0.74–0.76 (m, 2 H), 0.79–0.83 (m, 2 H), 3.06–3.11 (m, 1 H), 6.17 (bs, 2 H), 7.47 (d, J=1.5 Hz, 1 H), 8.37 (d, J=1.0 Hz, 1 H), 9.09 (d, J 3.8 Hz, 1 H); MS m/e 151 (MH$^+$).

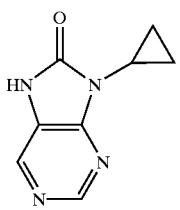

53

Compound 53 was obtained by cyclization of diamine 52 according to the same procedure described for compound 36 using phosgene and polyvinylpyridine.

¹H NMR (CD₃OD) δ 1.14–1.19 (m, 2 H), 1.20–1.27 (m, 2 H), 3.11–3.18 (m, 1 H), 8.47 (d, J=0.45 Hz, 1 H), 9.01 (s, 1 H); MS m/e 177 (MH⁺).

2-Oxo-imidazopyrimidine 56 was prepared using the same procedure for compound 53, except that cyclopropylamine was replaced with t-butylamine. The compound was used as a crude intermediate for the coupling reaction without further purification.

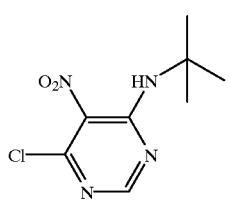

54

¹H NMR (CDCl₃) δ 1.52 (s, 9 H), 7.26 (bs, 1 H), 8.37 (s, 1 H); MS m/e 231 (MH⁺).

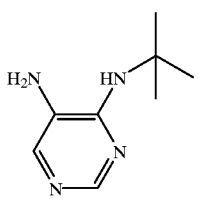

55

¹H NMR (CD₃OD) δ 1.57 (s, 9 H), 7.49 (d, J=1.3 Hz, 1 H), 8.27 (d, J=1.3 Hz, 1 H); MS m/e 167 (MH⁺).

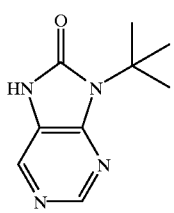

56

2-Oxo-imidazopyrimidine 58 was prepared according to the same procedure described for compound 53, except that cyclopropylamine was replaced with 2,2,2-trifluoroethylamine. The crude intermediate was used in the coupling reaction without further purification.

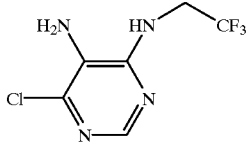

57

¹H NMR (CD₃OD) δ 4.30–4.36 (m, 2 H), 8.46 (s, 1 H); MS m/e 226 (MH⁺).

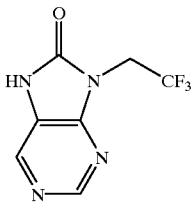

58

2-Oxo-imidazopyridine 113 was prepared according to the same procedure for the preparation of 36, except that cyclopropylamine was replaced with 2 equivalents of 3-amino-5-methylisoxazole, and the reaction was carried out in MeOH at 100° C. for 18 hours in a sealed pressure tube.

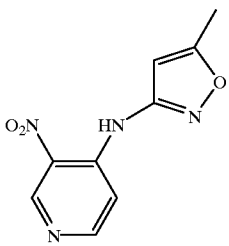

112

¹H NMR (CD₃OD) δ 0.88 (s, 3 H), 4.71 (s, 1 H), 6.79 (d, J=6.2 Hz, 1 H), 6.95 (d, J=6.2 Hz, 1 H), 7.69 (d, 1 H); IR (KBr, cm⁻¹) 3323, 3125, 3097, 1604, 1581, 1521, 1499, 1228, 1179; MS m/e 221 (MH⁺); Anal. Calcd for C₉H₈N₄O₃: C, 49.09; H, 3.66; N, 25.44 Found: C, 49.04; H, 3.63; N, 25.06.

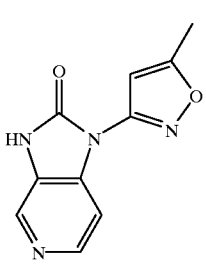

113

¹H NMR (CD₃OD) δ 2.50 (s, 3 H), 6.94 (s, 1 H), 7.95 (dd, J=0.6, 6.55 Hz, 1 H), 8.31 (s, 1 H), 8.32 (d, J5.5 Hz, 1 H); IR (KBr, cm⁻¹) 3546, 3463, 2679, 1744, 1720, 1596, 1474, 1457, 1193, 1129, 809, 633; MS m/e 217 (MH⁺).

114

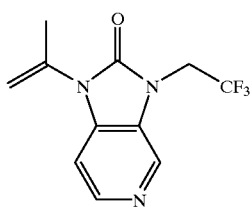

A mixture of compound 26 (400 mg, 2.28 mmol) and BTPP (1.57 g, 5.02 mmol) in THF (10 mL) was stirred for 20 minutes after which 2,2,2-trifluoroethyl p-toluenesulfonate (605 mg, 2.40 mmol) was added to the mixture. The reaction mixture was stirred at 45° C. for 18 hours and then at 60° C. for an additional 24 hours. The solvent was evaporated and the residue was diluted with H$_2$O and extracted with EtOAc. The combined organic extracts were dried over MgSO$_4$ and evaporated. Purification by flash column chromatography (EtOAc/MeOH, 20:1) gave 295 mg (50% yield) of 114 as a white solid.

$^1$H NMR (CDCl$_3$) δ 2.24 (s, 3 H), 4.51 (q, J=8.6 Hz, 2 H), 5.24 (s, 1 H), 5.43 (d, J=1.1 Hz, 1 H), 7.10 (d, J=5.5Hz, 1 H), 8.39 (s, 1 H), 8.40 (d, J=5.5 Hz, 1 H); IR(KBr,cm$^1$)3026, 1727, 1605, 1503, 1169, 1156, 1126, 827; MS m/e 258 (MW+).

115

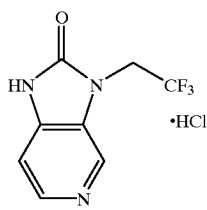

Compound 114 (272 mg, 1.06 mmol) and concentrated HCl (12 mL) in MeOH (20 mL) were refluxed for 72 hours. The solvent was evaporated and the residue was dried under vacuum to give 263 mg (99% yield) of compound 115 as the HCl salt.

$^1$H NMR (DMSO-d$_6$) δ 4.93 (q, J=9.2 Hz, 2 H), 7.61 (d, J=6.3 Hz, 1 H), 8.54 (d, J=6.3 Hz, 1 H), 8.89 (s, 1 H); MS m/e 218 (MH$^+$).

116

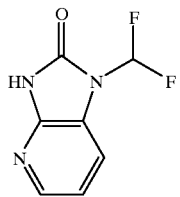

Compound 28B (1.2 g, 6.86 mmol) and BTPP (3.21 g, 10.28 mmol) in CH$_2$Cl$_2$ were mixed together in a sealed flask and cooled to -78° C. Chlorodifluoromethane (gas, approximately 2 g, 23.26 mmol) was bubbled into the solution in the sealed flask. The flask was sealed and the temperature was raised to 0° C. for 10 minutes and then to room temperature for 3 minutes. The reaction mixture was diluted with H$_2$O and extracted with CH$_2$Cl$_2$. The combined extracts were dried over MgSO$_4$ and evaporated. To the residue was added 6 N HCl in MeOH (1:1 mixture, 10 mL). The mixture was stirred at reflux for 6 hours. The reaction was neutralized with solid Na$_2$CO$_3$. The solvent was concentrated and the resulting aqueous solution was extracted with CH$_2$Cl$_2$. The combined extracts were dried over MgSO$_4$ and evaporated. Purification by flash column chromatography (gradient, straight EtOAc to EtOAc/MeOH, 5:1) gave 398 mg (31% yield) of 116.

$^1$H NMR (CDCl$_3$) δ 7.14 (dd, J=5.7, 7.4 Hz, 1 H), 7.36 (t, J=58.7 Hz, 1 H), 7.62 (d, J=7.8 Hz, 1 H), 8.21 (d, J=5.3 Hz, 1 H), 9.40 (bs, 1 H); MS m/e 186 (MH$^+$).

Compound 119 was prepared using the same procedure described for the preparation of 36, except that cyclopropylamine was replaced with 2 equivalents of cyclopentylamine, and the reaction was carried out in a sealed pressure tube at 120° C. for 2 hours.

117

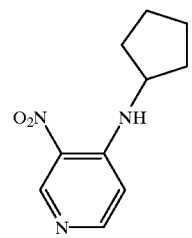

$^1$H NMR (CDCl$_3$) δ 1.62–1.69 (m, 2 H), 1.70–1.76 (m, 2 H), 1.79–1.85 (m, 2 H), 2.10–2.16 (m, 2 H), 3.96–4.01 (m, 1 H), 6.76 (d, J=6.2 Hz, 1 H), 8.23 (bs, 1 H), 8.27 (d, J=6.2 Hz, 1 H), 9.21 (s, 1 H); MS m/e 208 (MH$^+$).

118

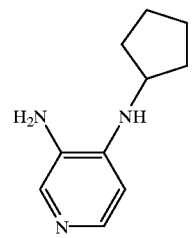

$^1$H NMR (CDCl$_3$) δ 1.48–1.53 (m, 2 H), 1.61–1.64 (m, 2 H), 1.69–1.74 (m, 2 H), 2.00–2.06 (m, 2 H), 3.12 (bs, 2 H), 3.77–3.83 (m, 1 H), 4.22 (bd, J=4.5 Hz, 1 H), 6.47 (d, J=5.4 Hz, 1 H), 7.85 (s, 1 H), 7.92 (d, J=5.4 Hz, 1 H); MS m/e 178 (MH$^+$).

119

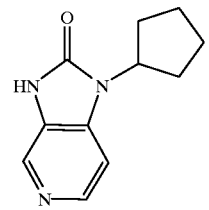

$^1$H NMR (DMSO-d$_6$) δ 1.61–1.68 (m, 2 H), 1.85–1.95 (m, 4 H), 1.97–2.02 (m, 2 H), 4.11 (bs, 1 H), 4.67–4.74 (m, 1 H), 7.20 (d, J=5.3 Hz, 1 H), 8.16 (d, J=5.4 Hz, 1 H), 8.19 (s, 1 H); MS m/e 204 (MH$^+$).

Compound 122 was prepared using the same procedure described for the preparation of 36, except that cyclopropylamine was replaced with 2 equivalents of cyclobutylamine, and the reaction was carried out in a sealed pressure tube at 100° C.

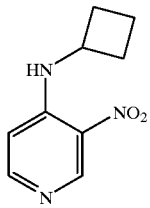

120

$^1$H NMR (CDCl$_3$) δ 1.89–1.97 (m, 2 H), 2.05–2.09 (m, 2 H), 2.50–2.56 (m, 2 H), 4.06–4.13 (m, 1 H), 6.56–6.62 (m, 1 H), 8.23 (s, 1 H), 8.27 (d, J=5.6 Hz, 1 H), 9,21 (s, 1 H); MS m/C 194 (MH$^+$).

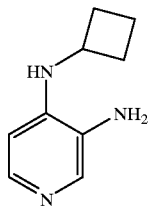

121

$^1$H NMR (DMSO-d$_6$) δ 1.70–1.79 (m, 2 H), 1.83–1.91 (m, 2 H), 2.32–2.50 (m, 2 H), 3.85–3.91 (m, 1 H), 4.59 (s, 2 H), 5.49 (d, J=6.2 Hz, 1H), 6.22 (d, J=5.3 Hz, 1 H), 7.55 (d, J=5.2 Hz, 1 H), 7.63 (s, 1 H); MS m/e 164 (MH$^+$).

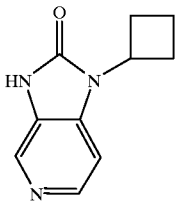

122

$^1$H NMR (CD$_3$OD) δ 1.92–2.04 (m, 2 H), 2.43–2.49 (m, 2 H), 2.88–2.97 (m, 2 H), 4.93–4.98 (m, 1 H), 7.83 (d, J=6.6 Hz, 1 H), 8.41–8.43 (m, 2 H); MS m/e 190 (MH$^+$).

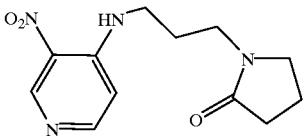

123

To a solution of 4-chloro-3-nitropyridine (4.9 g, 30.80 mmol) and 2-(3-aminopropyl)-2-pyrrolidinone (4.4 g, 30.80 mmol) in CH$_3$CN (50 mL) was added K$_2$CO$_3$ (4.25 g, 30.8 mmol) and the mixture was stirred for 8 hours. Additional 1-(3-aminopropyl)-2-pyrrolidinone (0.2 g, 1.41 mmol) was added and the mixture was stirred for 24 hours at room temperature. The mixture was filtered and concentrated to give 8.0 g (98% yield) of the compound 123 as an orange oil.

$^1$H NMR (CDCl$_3$) δ 1.89–1.99 (m, 2 H); 2.02–2.15 (m, 2 H), 2.35 (t, J=8.05 Hz, 2 H); 3.36–3.47 (m, 6 H), 6.70 (d, J=6.2 Hz, 1 H), 8.28 (d, J=6.27 Hz, 1 H), 8.37–8.40 (s, 1 H), 9.20 (s, 1 H); MS m/e 264 (MH$^+$).

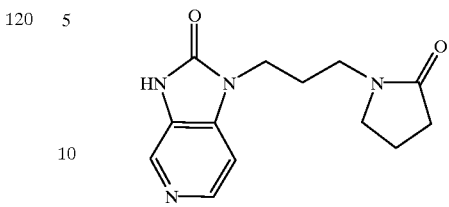

124

A mixture of 123 (2.0 g, 7.6 mmol) and 10% palladium on carbon (200 mg) in EtOH (50 mL) was hydrogenated at 50 psi for 18 hours, filtered and concentrated to give 1.6 g (90% yield) of the diamine as a black oil. The oil was dissolved in CH$_2$Cl$_2$ (40 mL), treated with carbonyl diimidazole (1.22 mg, 7.5 mmol) and stirred for 12 hours at room temperature. The solvent was evaporated and the residue was subjected to flash column chromatography (gradient, 3% MeOH/CH$_2$Cl$_2$ to 10% MeOH/CH$_2$Cl$_2$) to give 1.09 g (62% yield) of compound 124 as an orange gum.

$^1$H NMR (CDCl$_3$) 5 2.01–2.05 (m, 4 H), 2.39 (t, J=7.9 Hz, 2 H) 3.37–3.43 (m, 4 H), 3.90 (t, J=7.2 Hz, 2 H), 7.01 (d, J=5.4 Hz, 1 H), 8.29 (d, J=5.4 Hz, 1 H), 8.37 (s, 1 H); MS m/e 260 (MH$^+$).

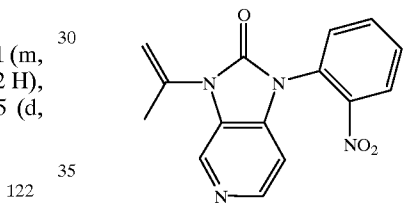

125

A mixture of 28A (1.00 g, 5.71 mmol), o-fluoronitrobenzene (0.88 g, 6.28 mmol) and Cs$_2$CO$_3$ (5.58 g, 17.1 mmol) in DMF was stirred at room temperature for 12 hours. The reaction mixture was diluted with EtOAc and washed with water and brine, dried over MgSO$_4$, and concentrated. Purification by flash chromatography (gradient, CH$_2$Cl$_2$/hexane, 40:1 to 20:1) gave 1.10 g (65% yield) of 125 as a yellow foam.

$^1$H NMR (CDCl$_3$) δ 2.28–2.32 (m, 3 H), 5.45–5.49 (m, 2 H), 7.01–7.05 (m, 1 H), 7.11–7.15 (m, 1 H), 7.62–7.68 (m, 2 H), 7.80–7.84 (m, 1 H), 8.14–8.22 (m, 2 H); MS m/e 297 (MH$^+$).

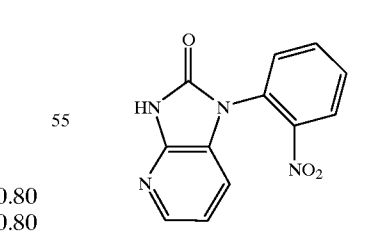

126

Compound 126 was prepared from compound 125 according to the same procedure described for compound 115.

$^1$H NMR (DMSO-d$_6$) δ 7.06–7.09 (m, 1 H), 7.33–7.34 (m, 1 H), 7.75–7.79 (m, 1 H), 7.85–7.87 (m, 1 H), 7.94–7.98 (m, 1 H), 8.04–8.05 (m, 1 H), 8.21–8.23 (m, I H); MS m/e 257 (MH$^+$).

III. Preparation of R$_1$-LGs:

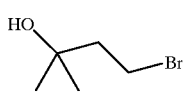
127

Compound 127 was prepared according to the procedure described by A. Yebga et al. in *Eur. J Med. Chem.*, 1995, 30, 769–777.

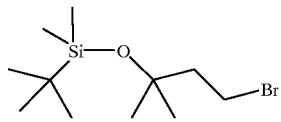
128

Compound 128 was prepared according to the procedure described by J. C. Heslin and C. J. Moody in *J. Chem. Soc. Perkins Trans. I*, 1988, 6, 1417–1423.

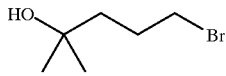
129

Compound 129 was prepared according to the same procedure described for compound 127.

$^1$H NMR (CDCl$_3$) δ 1.22 (s, 6 H), 1.57–1.60 (m, 2 H), 1.92–1.98 (m, 3 H), 3.42 (t, J=6.7 Hz, 2 H).

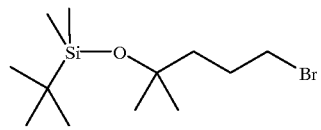
130

To neat 2,6-lutidine (11.42 g, 106.60 mmol) cooled with an ice bath to 0° C. was added t-butyldimethylsilyltrifluoromethane sulfonate (16.91 g, 63.96 mmol). After 30 minutes, a solution of compound 129 (7.72 g, 42.64 mmol) in CH$_2$Cl$_2$ (15 mL) was added. The resulting brown reaction mixture was stirred at 0° C. for 2.5 hours. The reaction mixture was poured onto ice (50 mL) and saturated aqueous sodium bicarbonate solution (50 mL) and extracted with CH$_2$Cl$_2$. The combined organic extracts were dried over MgSO$_4$ and evaporated. The crude brown oil was purified by flash column chromatography (pentane:Et$_2$O, 15:1) to give compound 130 as a colorless oil.

$^1$H NMR (CDCl$_3$) δ 0.07 (s, 6 H), 0.85 (s, 9 H), 1.21 (s, 6 H), 1.52–1.55 (m, 2 H), 1.93–1.99 (m, 2 H), 3.42 (t, J=6.7 Hz, 2 H).

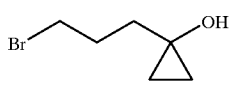
131

Compound 131 was prepared according to the procedure described by O Kulinkovich et al. in *Tetrahedron Letters*, 1996, 37, 1095–1096. To a solution of ethyl-4-bromobutyrate (16.36 g, 83.85 mmol) in Et$_2$O (200 mL) was added titanium (IV) isopropoxide (2.38 g, 8.39 mmol). Ethylmagnesium bromide (3.0 M in Et$_2$O, 58.7 mL, 176.09 mmol) was added to the mixture slowly via addition funnel over 30 minutes maintaining the temperature between 10–20° C. The reaction mixture was stirred for 6 hours at room temperature and then poured slowly into chilled 10% aqueous H$_2$SO$_4$ (300 mL) and stirred. The layers were separated and the aqueous layer was further extracted with Et$_2$O. The combined organic extracts were dried over MgSO$_4$ and evaporated. The crude oil was purified by flash column chromatography (gradient, hexanes/Et$_2$O 3:1 to 1:1) to give 10.3g (67% yield) of compound 131 as a yellow oil.

$^1$H NMR (CDCl$_3$) δ 0.42–0.48 (m, 2 H), 0.69–0.76 (m, 2 H), 1.63–1.70 (m, 2 H), 2.05–2.14 (m, 2 H), 3.45–3.50 (m, 2 H);

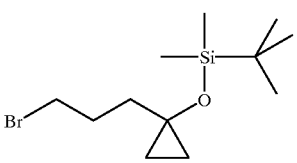
132

Compound 132 was prepared from compound 131 according to the same procedure described for compound 130 and was used immediately for coupling upon isolation.

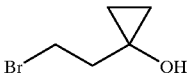
133

Compound 133 was prepared according to the same procedure described for compound 131 using ethyl 3-bromopropionate.

$^1$H NMR (CDCl$_3$) 60.51 (t, J=6.1 Hz, 2 H), 0.76 (t, J=6.2Hz, 2 H), 2.07 (t, J=7.3 Hz, 2 H), 3.57 (t, J=7.3 Hz, 2 H).

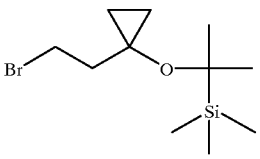
134

Compound 134 was prepared from compound 133 according to the same procedure described for compound 130.

$^1$H NMR (CDCl$_3$) δ 0.10 (s, 6 H), 0.50 (t, J=6.3 Hz, 2 H), 0.74 (t, J=6.3 Hz, 2 H), 0.85 (s, 9 H), 2.03 (t, J=8.0 Hz, 2 H), 3.56 (t, J=8.0 Hz, 2 H).

135

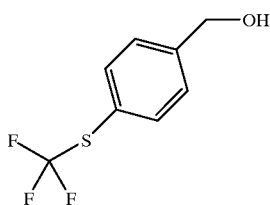

A solution of 4-(trifluoromethylthio) benzoic acid (5.00 g, 22.50 mmol) and triethylamine (2.36g, 23.40 mmol) in THF (50 mL) was cooled to 0° C. and to the solution was added ethyl chloroformate (2.53 g, 23.40 mmol). The mixture was filtered and the added dropwise to a cooled solution of sodium borohydride (3.54 g, 93.38 mmol) in a mixture of H$_2$O and THF (1 :1 ratio, 50 mL). The reaction mixture was stirred for 2 hours keeping the temperature below 15° C. and then for 18 hours at room temperature. The reaction was quenched with 1N HCl and the organic layer was separated. The aqueous layer was extracted with Et$_2$O and all organic layers were combined, dried over Na$_2$SO$_4$, and evaporated. The resulting solid was dissolved in EtOAc and was washed with saturated aqueous NaHCO$_3$. The organic layer was dried over Na$_2$SO$_4$ and evaporated to give 3.53 g (75% yield) of compound 135 as a white solid.

$^1$H NMR (DMSO-d$_6$) δ 4.57 (d, J=5.7 Hz, 2 H), 5.38 (t, J=5.7 Hz, 1 H), 7.48 (d, J=7.3 Hz, 2 H), 7.68 (d, J=7.3 Hz, 1 H).

136

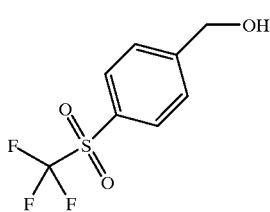

A mixture of compound 135 (3.50 g, 16.81 mmol), hydrogen peroxide (30%, 19.05 g, 168.10 mmol) and glacial acetic acid (40 mL) was stirred at 80° C for several minutes and then at 50° C. for 48 hours. The solution was poured into H$_2$O and extracted with Et$_2$O. The combined extracts were washed with aqueous 10% NaHCO$_3$, dried over Na$_2$SO$_2$, and evaporated to give 3.6 g (89% yield) of compound 136 as a white solid.

$^1$H NMR (DMSO-d$_6$) δ 4.70 (d, J=7.1 Hz, 2 H), 5.61 (bs, 1 H), 7.78 (d, J=7.2 Hz, 2 H), 8.10 (d, J=7.2 Hz, 2 H).

137

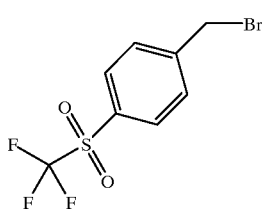

A solution of alcohol 136 (2.0 g, 8.32 mmol) in Et$_2$O (50 mL) was cooled to −5° C. with an ice/salt bath. To this solution was added phosphorous tribromide and the resulting mixture was stirred at −5° C. for 5 hours and then at room temperature for 18 hours. The reaction mixture was poured into ice water and the aqueous layer was extracted with Et$_2$O. The combined organic layers were washed with saturated aqueous NaHCO$_3$, saturated aqueous NaCl, dried over Na$_2$SO$_4$, and evaporated to give 1.45 g (56% yield) of 137 as a clear oil.

$^1$H NMR (DMSO-d$_6$) δ 4.87 (s, 2 H), 7.91 (d, J=8.5 Hz, 2 H), 8.15 (d, J=8.4 Hz,2H).

IV. Preparation of Examples of Formula I:

Unless a specific procedure is described, Examples 1–166 are prepared according to the general coupling procedures described below:

General Coupling Procedure of 2-Chloromethyl-benzimidazoles (II) and 2-Oxo-imidazopyridines or 2-Oxo-imidazopyrimidines in Scheme I-A.

Examples 1–3, 8–12, 14–16, 23–46, 65, 69–70, 72, 90, 94, 102, 104, 111–113, 120, 122, 126, 128–131, 135–136, 140–151, 156–157, 154–155, 157 and 160–163, and 166 were prepared according to the following procedure:

To a solution of II and 2-oxo-imidazopyridine or 2-oxo-imidazopyrimidine (1 equivalent of each) in THF or CH$_2$Cl$_2$ or DMF is added 3–4 equivalents of BTPP or Cs$_2$CO$_3$. The mixture is stirred at 0° C. or room temperature for 1–16 hours. The solvent is evaporated, and the residue is diluted with water and extracted with EtOAc. The crude product is then purified by chromatography on silica gel or by reverse phase preparative HPLC.

General Procedure of Reacting Ia with R$_2$-LG in Scheme I-B.

Examples 5–7, 18, 100, and 138 were prepared according to the following procedure:

To a solution of Ia and 1.5–3 equivalents of BTPP, Cs$_2$CO$_3$, or BEMP on polystyrene resin in THF or DMF is slowly added R$_2$-LG at room temperature. When the reaction is completed, the solvent is evaporated or resin is filtered and filtrate is evaporated. The residue is purified by dissolving in EtOAc or CH$_2$Cl$_2$ and washing with water followed by flash chromatography, or by trituration of the solid collected from the reaction in solvents such as MeOH, or by reverse phase preparative HPLC.

General Procedure of Reacting V with R$_1$-LG in Scheme I-C.

Examples 48, 67–68, 76, 78, 80, 82, 84, 88, 124, and 152–153 were prepared according to the following procedure.

To a mixture of V and 1.5–3 equivalents of sodium hydride or BEMP on polystryene resin in THF, DMF or CH$_3$CN is added R$_1$-LG. The reaction is stirred at temperatures ranging from 0° C. to 80° C. for 30 minutes to 18 hours In examples where BEMP on polystyrene resin is utilized, the resin is filtered. The filtrate is evaporated and the residue is purified by flash column chromatography on silica or reverse phase preparative HPLC. In examples where sodium hydride is used as base, the reaction mixture is diluted with water, extracted with EtOAc or CH$_2$Cl$_2$, and purified by flash column chromatography on silica or reverse phase preparative HPLC.

EXAMPLE 1

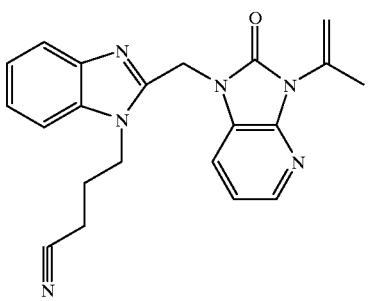

¹H NMR (CDCl₃) δ 2.05–2.11 (m, 2 H), 2.29 (s, 3 H), 2.50 (t, J=7.1 Hz, 2 H), 4.58 (t, J=7.6 Hz, 2 H), 5.36 (s, 1 H), 5.48 (s, 3 H), 7.06 (dd, J=5.2, 7.8 Hz, 1 H), 7.35–7.45 (m, 3 H), 7.84 (d, J=7.4 Hz, 1 H), 7.94 (bd, J=6.4 Hz, 1 H), 8.08 (dd, J=1.2, 5.2 Hz, 1 H); IR (KBr, cm¹) 3423, 2952, 2243, 1698, 1656, 1618, 1452, 1403, 1336, 1247, 1152, 790, 766, 743; MS m/e 373 (MH⁺); Anal. Calcd for $C_{21}H_{20}N_6O$: C, 67.73; H, 5.41; N, 22.57 Found: C, 67.35; H, 5.35; N, 22.41.

EXAMPLE 2

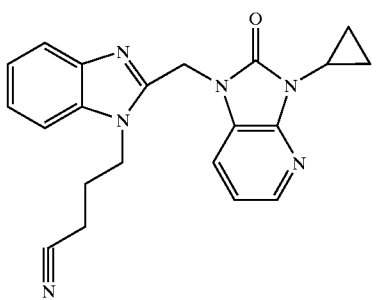

¹H NMR (CDCl₃) δ 1.13–1.21 (m, 4 H), 2.06–2.12 (m, 2 H), 2.51 (,J=7.2 Hz, 2 H), 3.01–3.05 (m, 1 H), 4.57 (,J=7.5 Hz, 2 H), 5.42 (s, 2 H), 7.01–7.05 (m, 1 H), 7.3 4–7.47 (m, 3 H), 7.81–7.86 (m, 2 H), 8. 10 (d, J=4.8 Hz, 1 H); IR (KBr, cm⁻¹) 3424, 2244, 1702, 1333, 1474, 1461, 1280, 1164, 789; MS m/e 373 (MH⁺).

EXAMPLE 3

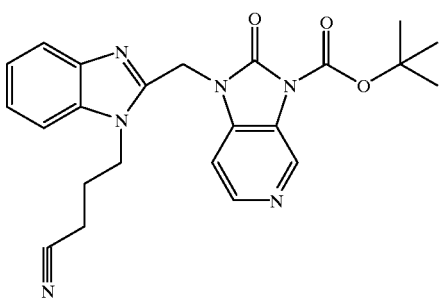

¹H NMR (CD₃OD) δ 1.68 (s, 9 H), 2.18–2.21 (m, 2 H), 2.60 (t, J=7.2 Hz, 2 H), 4.50 (t, J=7.6 Hz, 2 H), 5.48 (s, 2 H), 7.23–7.25 (m, 1 H), 7.30 (t, J=7.2 Hz, I H), 7.35 (d, J=5.4 Hz, 1 H), 7.54 (d, J=8.0 Hz, 1 H), 7.56 (d, J=8.0 Hz, 1 H), 8.31 (d, J=5.4 Hz, 1 H), 8.88 (s, 1 H); MS m/e 433 (MH⁺).

EXAMPLE 4

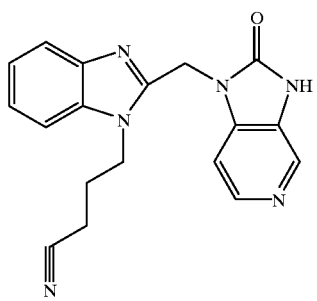

The t-butoxycarbonyl group of Example 4 was removed by treating with aqueous 1 N NaOH solution using the procedure described for the preparation of intermediate compound 43.

¹H NMR (CD₃OD) 62.05–2.11 (m, 2 H), 2.63 (t, J=7.4Hz, 2 H), 4.41 (t, J=7.5 Hz, 2 H), 5.39 (s, 2 H), 7.16–7.19 (m, 1 H), 7.24–7.27 (m, 2 H), 7.55 (d, J=8.0 Hz, 1 H), 7.61 (d, J=8.0 Hz, 1 H), 8.17 (d, J=5.2 Hz, 1 H), 8.25 (s, 1 H), 11.34 (s, 1 H); MS m/e 333 (MH⁺).

EXAMPLE 5

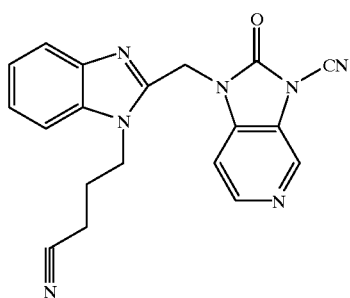

¹H NMR (DMSO-d₆) δ 2.14–2.17 (m, 2 H), 2.65 (t, J=7.4 Hz, 2 H), 4.41 (t, J 7.5 Hz, 2 H), 5.52 (s, 2 H), 7.18 (t, J=8.0Hz, 1 H), 7.28 (t, J=8.0 Hz, 1 H), 7.51 (d, J=5.3 Hz, 1 H), 7.55 (d, J=8.0 Hz, 1 H), 7.64 (d, J=8.2 Hz, 1 H), 8.47 (d, J =5.3 Hz, 1 H), 8.65 (s, 1 H); IR (KBr, cm¹) 3436, 2987, 2263, 1760, 1608, 1384, 1125, 748; MS m/e 358 (MH⁺); Anal. Calcd for $C_{19}H_{15}N_7O \cdot 0.6EtOAc$: C, 62.65; H, 4.87; N, 23.90 Found: C, 62.33; H, 4.76; N, 24.14.

EXAMPLE 6

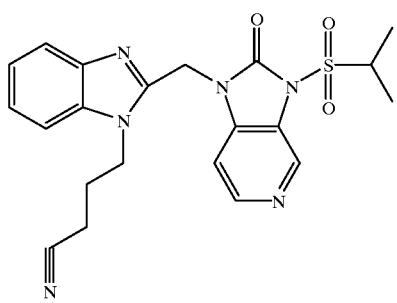

¹H NMR (CD₃OD) 5 1.53 (d, J=6.8 Hz, 6 H), 2.27–2.32 (m, 2 H), 2.65 (t, J=7.2 Hz, 2 H), 4.08–4.12 (m, 1 H), 4.57

(t, J=7.5 Hz, 2 H), 5.68 (s, 2 H), 7.30 (t, J=7.3 Hz, 1 H), 7.39 (t, J=7.2 Hz, 1 H), 7.56 (d, J=8.0 Hz, 1 H), 7.67 (d, J=8.2 Hz, 1 H), 7.88 (d, J=6.3 Hz, 2 H), 8.61 (d, J=6.3 Hz, 1 H), 8.94 (s, 1 H); IR (KBr, cm$^{-1}$) 3420, 2314, 2251, 2075, 2008, 1752, 1623, 1509, 1369, 1180, 738; HRMS m/e 439.1552 (MH$^+$).

EXAMPLE 7

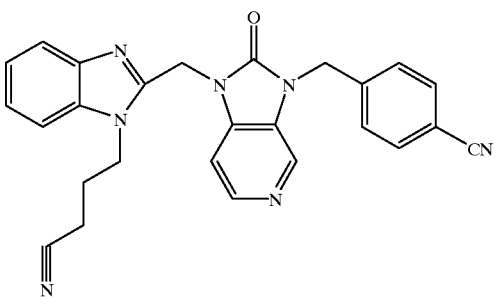

$^1$H NMR (DMSO-d$_6$) δ 2.11–2.12 (m, 2 H), 2.63 (t, J=7.4 Hz, 2 H), 4.42 (t, J=7.4 Hz, 2 H), 5.28 (s, 2 H), 5.50 (s, 2 H), 7.18 (t, J=8.0 Hz, 1 H), 7.26 (t, J=8.0 Hz, 1 H), 7.35 (d, J=5.3 Hz, 1 H), 7.55–7.57 (m, 3 H), 7.62 (d, J=8.1 Hz, 1 H), 7.86 (d, J=8.2 Hz), 8.24 (d, J=5.2 Hz, 1H), 8.40 (s, 1 H); IR (KBr, cm$^{-1}$) 3424, 2953, 2250, 2229, 1716, 1609, 1503, 825, 744; MS m/e 448 (MH$^+$); Anal. Calcd for C$_{26}$H$_{21}$N$_7$O•90.25H$_2$O: C, 69.09; H, 4.79; N, 21.69 Found: C, 69.00; H, 4.81; N, 21.77.

EXAMPLE 8

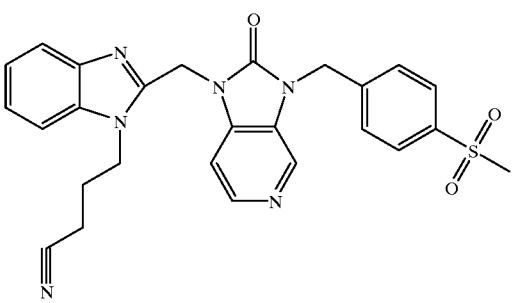

$^1$H NMR (DMSO-d$_6$) δ 2.10–2.13 (m, 2 H), 2.64 (t, J=7.4 Hz, 2 H), 3.20 (s, 3 H), 4.43 (t, J=7.4Hz, 2 H), 5.30 (s, 2 H), 5.51 (s, 2 H), 7.19 (t, J=8.0Hz, 1 H), 7.27 (t, J=7.2 Hz, 1 H), 7.35 (d, J=5.2 Hz, 1 H), 7.55 (d, J=8.0 Hz, 1 H), 7.62–7.65 (m, 3 H), 7.93 (d, J=8.3 Hz, 2 H), 8.24 (d, J=5.2 Hz, 1 H), 8.43 (s, 1 H); IR (KBr, cm$^{-1}$) 3424, 2246, 1707, 1614, 1501, 1407, 1306, 1148; MS m/e 501 (MH$^+$); Anal. Calcd for C$_{26}$H$_{24}$N$_6$O$_3$S: C, 62.38; H, 4.83; N, 16.78 Found: C, 62.31; H, 4.73; N, 16.75.

EXAMPLE 9

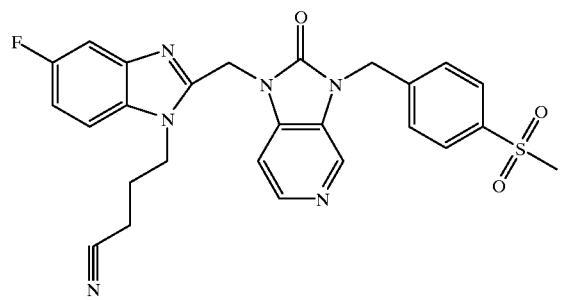

$^1$H NMR (DMSO-d$_6$) δ 2.11–2.14 (m, 2 H), 2.65 (t, J=7.4 Hz, 2 H), 3.21 (s, 3 H), 4.44 (t, J=7.4 Hz, 2 H), 5.30 (s, 2 H), 5.51 (s, 2 H), 7.16 (m, 1 H), 7.36 (d, J=5.2 Hz, 1 H), 7.40 (q, J=2.4, 9.7 Hz, 1 H), 7.63–7.68 (m, 3 H), 7.94 (d, J=8.4 Hz, 2 H), 8.25 (d, J=5.2 Hz, 1 H), 8.44 (s, 1 H); IR (KBr, cm$^{-1}$) 3423, 2926, 2248, 1707, 1613, 1602, 1148; MS m/e 519 (MH$^+$); Anal. Calcd for C$_{26}$H$_{23}$FN$_6$O$_3$S: C, 60.22; H, 4.47, N, 16.20 Found C, 60.06; H, 4.69, N, 16.21.

EXAMPLE 10

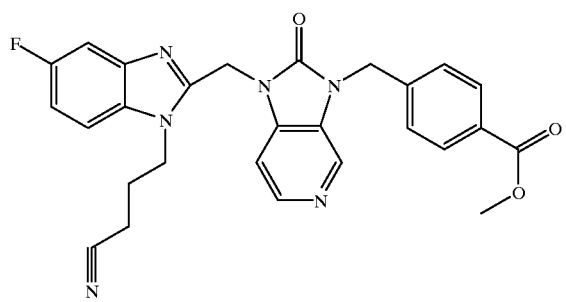

$^1$H NMR (DMSO-d$_6$) δ 2.09–2.13 (m, 2 H), 2.64 (t, J=7.4 Hz, 2 H), 3.84 (s, 3 H), 4.43 (t, J=7.4 Hz, 2 H), 5.26 (s, 2 H), 5.50 (s, 2 H), 7.13–7.17 (m, 1 H), 7.34–7.40 (m, 2 H), 7.51 (d, J=8.3 Hz, 2 H), 7.64–7.67 (m, 1 H), 7.96–7.97 (m, 2 H), 8.23 (d, J=5.2 Hz, 1 H), 8.39 (s, 1H); IR (KBr, cm$^{-1}$) 3432, 2954, 2245, 1719, 1698, 1499, 1284, 1139; MS m/e 499 (MH$^+$); Anal. Calcd for C$_{21}$H$_{23}$FN$_6$O$_3$: C, 65.05; H, 4.65; N, 16.85 Found: C, 65.25; H, 4.65; N, 16.87.

EXAMPLE 11

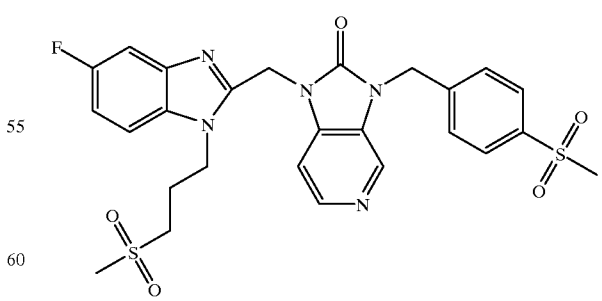

$^1$H NMR (DMSO-d$_6$) δ 2.17–2.23 (m, 2 H), 3.02 (s, 3 H), 3.20 (s, 3H), 3.26 (t, J=8.0 Hz, 2 H), 4.51 (t, J=7.7 Hz, 2 H), 5.29 (s, 2 H), 5.50 (s, 2 H), 7.16 (dt, J=2.4, 9.2 Hz, 1 H), 7.36 (d, J=4.9 Hz, 1 H), 7.40 (dd, J=2.4, 9.5 Hz, 1 H), 7.63 (d,

J=8.2 Hz, 2 H), 7.68 (dd, J=4.9, 8.9 Hz, 1 H), 7.93 (d, J=8.3 Hz, 2 H), 8.25 (d, J=5.2 Hz, 1 H), 8.43 (s, 1 H); IR (KBr, cm$^{-1}$) 3442, 2925, 2360, 1712, 1614, 31500, 1490, 1296, 147, 761, 530; MS m/e 572 (MH$^+$); Anal. Calcd for C$_{26}$H$_{26}$FN$_5$O$_5$S$_2$: C, 54.62; H, 4.5 8; N, 12.2 5 Found: C, 54.48; H, 4.69; N, 12.14.

EXAMPLE 12

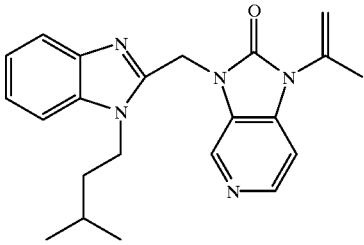

$^1$H NMR (CDCl$_3$) δ 0.98 (s, 3 H), 0.95 (s, 3 H), 1.44–1.52 (m, 2 H), 1.60–1.73 (m, 1 H), 2.25 (s, 3 H), 4.28–4.33 (m, 2 H), 5.20 (s, 1 H), 5.41 (s, 3 H), 7.02 (d, J=5.1 hz, 1 H), 7.27–7.31 (m, 3 H), 7.77–7.80 (m, 1 H), 8.31 (d, J=5.1 Hz, 1 H), 8.73 (s, 1 H); MS m/e 376 (MH$^+$); IR (KBr, cm$^{-1}$) 2957, 1712, 1603, 1494, 1398, 1330, 1167, 1138, 816, 740; Anal. Calcd for C$_{22}$H$_{25}$N$_5$O: C, 70.38; H, 6.71; N, 18.65 Found: C, 70.24; H, 6.67; N, 18.71.

EXAMPLE 13

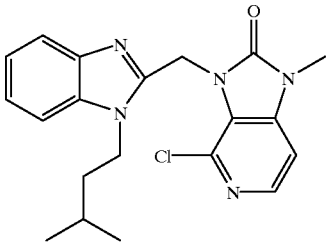

To a solution of 4-chloro-1-methyl-1,3-dihydro-imidazo[4,5 c]pyridin-2-one (Salor of Aldrich Chemical, 100 mg, 0.55 mmol) in DMF (10 mL) was added sodium hydride (26 mg, 60% dispersion in mineral oil) at room temperature. After stirring for 30 min, a neutral form of compound 4 (155 mg, 0.654 mmol) was added. The resulting mixture was stirred overnight and evaporated. The residue was diluted with water and extracted with Et$_2$O. The combined extracts were dried over MgSO$_4$ and evaporated. The residue was purified by flash chromatography (gradient, EtOAc, then EtOAc/MeOH, 20:1 to 10:1) to give the Example 13 (78 mg, 38% yield).

$^1$H NMR (CDCl$_3$) δ 1.07 (d, J=6.3 Hz, 6 H), 1.72–1.86 (m, 3 H), 3.52 (s, 3 H), 4.27 (t, J=7.7 Hz, 2 H), 5.64 (s, 2 H), 6.98 (d, J=5.3 Hz, 1 H), 7.18–7.30 (m, 2 H), 7.35 (d, J=7.5 Hz, 1 H), 7.66 (d, J=7.4 Hz, 1 H), 8.13 (d, J=5.3 Hz, 1 H); IR (KBr, cm) 3449, 2954, 1735, 1613, 1586, 1503, 1441, 1133, 775; MS m/e 384 (MH$^+$); Anal. Calcd for C$_{20}$H$_{22}$ClN$_5$O•1.10 H$_2$O: C, 59.50; H, 6.04; N, 17.35 Found: C, 59.46; H, 5.47; N, 16.68

EXAMPLE 14

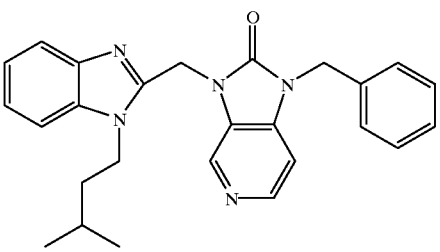

$^1$H NMR (CDCl$_3$) o 1.07 (d, J=6.1Hz, 6 H), 1.78–1.84 (m, 3 H), 4.42 (bt, J=8.0 Hz, 2 H), 5.21 (s, 2 H), 5.77 (s, 2 H), 7.14 (d, J=6.2 Hz, 1 H), 7.33–7.49 (m, 8 H), 7.94 (d, J=8.0 Hz,1 H), 8.34 (d, J=6.3 Hz, 1 H), 9.00 (s, 1 H); MS m/e 376 (MH$^+$).

EXAMPLE 15

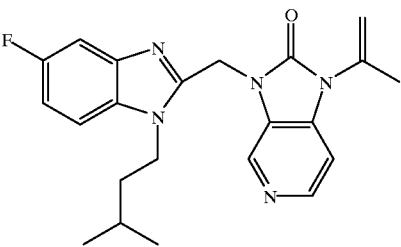

$^1$H NMR (CD$_3$OD) δ 0.97 (d, J=6.3 Hz, 6 H), 1.44–1.49 (m, 2 H), 1.62–1.73 (m, 1 H),2.25 (s, 3 H), 4.27–4.33 (m, 2 H), 5.21 (s, 1 H), 5.38 (s, 2 H), 5.42 (s, 1 H), 7.02–7.08 (m, 2 H), 7.23 (dd, J=4.5, 9.0 Hz, 1 H), 7.45 (dd, J=2.4, 9.3 Hz, 1 H), 8.33 (d, J=5.1 Hz, 1 H), 8.17 (s, 1 H); IR (KBr, cm$^{-1}$) 2960, 1713, 1605, 1495, 1455, 1399, 1333, 1163, 1140, 848, 813; MS m/e 394 (MH$^+$); Anal. Calcd for C$_{22}$H$_{24}$FN$_5$O: C, 67.16; H, 6.15; N, 17.80 Found: C, 67.25; H, 5.96; N, 17.88.

EXAMPLE 16

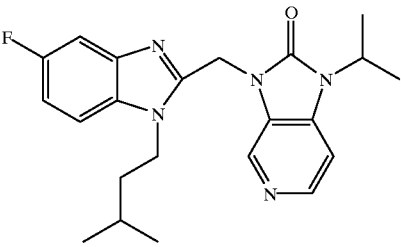

$^1$H NMR (CDCl$_3$) δ 0.97 (d, J=6.9 Hz, 6 H), 1.43–1.50 (m, 2 H), 1.55 (d, J=7.2 Hz, 6 H), 1.55–1.75 (m, 1 H), 4.26–4.31 (m, 2 H), 4.70–4.80 (m, 1 H), 5.37 (s, 2 H), 7.01–7.08 (m, 2 H), 7.22 (dd, J=4.8, 8.9 Hz, 1 H), 7.44 (dd, J=2.7, 9.3 Hz, 1H), 8.29 (d, J=5.4 Hz, 1 H), 8.68 (s, 1 H); IR (KBr, cm$^1$) 2956, 1706, 1493, 1456, 1389, 1332, 1133, 1113, 847; MS m/e 396 (MH$^+$); Anal. Calcd for C$_{22}$H$_{26}$FN$_5$O•0.33H$_2$O: C, 65.82; H, 6.69; N, 17.44 Found: C, 65.83; H, 6.30; N, 17.43.

EXAMPLE 17

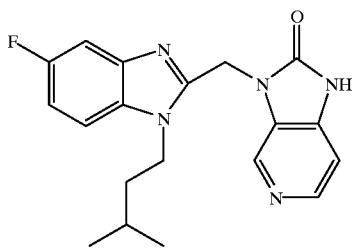

A solution of Example 15 (4.0 g, 10.17 mmol) in a mixture of MeOH (10 mL) and 6 N HCl (20 mL) was stirred at reflux overnight. The solution was cooled to room temperature and neutralized with concentrated NaOH solution, and evaporated. The residue was taken up with $CH_2Cl_2$, dried over $MgSO_4$, and evaporated. The residue was triturated with hot EtOAc and filtered to give Example 17 (3.22 g, 90% yield) as a white solid.

$^1$H NMR (CDCl$_3$) δ 0.99 (d, J=6.6 Hz, 6 H), 1.50–1.55 (m, 2 H), 1.71–1.77 (m, 1 H), 4.25–4.31 (m, 2 H), 5.36 (s, 2 H), 6.97 (d, J=5.1 Hz, 1 H), 7.06 (dt, J=2.4, 9.3 Hz, 1 H), 7.23 (dd, J=4.5, 8.7 Hz, 1 H), 7.43 (dd, J=2.4, 9.3 Hz, 1 H), 8.29 (d, J=5.1 Hz, 1 H), 8.62 (s, 1 H), 9.89 (bs, 1 H); IR (KBr, cm$^{-1}$) 2958, 1720, 1622, 1491, 1455, 1139, 1014, 958, 894, 813; MS m/e 375 (MH$^+$); Anal. Calcd for C$_{19}$H$_{20}$FN$_5$O: C, 64.58; H, 5.70; N, 19.82 Found: C, 64.26; H, 5.58; N, 19.85.

EXAMPLE 18

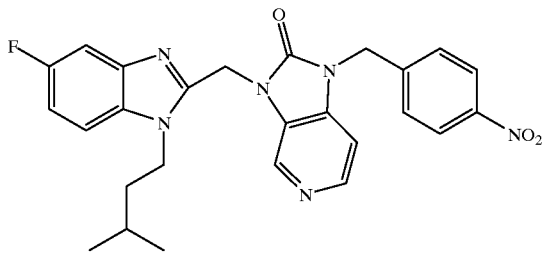

$^1$H NMR (CDCl$_3$) δ 0.99 (d, J=6.7 Hz, 6 H), 1.54–1.59 (m, 2 H), 1.69–1.73 (m, 1 H), 4.29 (t, J=9.2 H, 2 H), 5.20 (s, 2 H), 5.43 (s, 2 H), 6.86 (d, J=.4 Hz, 1 H), 7.05 (dt, J=2.4, 9.1 Hz, 1 H), 7.24 (dd, J=4.5, 8.9 Hz, 1 H), 7.41 (dd, J=2.4, 9.3 Hz, 1 H), 7.49 (d, J=8.7 Hz, 2 H), 8.21 (d, J=8.7 Hz, 2 H), 8.29 (d, J=5.2 Hz, 1 H), 8.76 (s, 1 H); IR(KBr,cm$^{-1}$) 3424, 2959, 1716, 1611, 1524, 1492, 1346, 1176, 1137, 800; MS m/e 489 (MH$^+$). Anal. Calcd for C$_{26}$H$_{25}$FN$_6$O$_3$: C, 63.92; H, 5.16; N, 17.20 Found: C, 63.95; H, 5.13; N, 17.22.

EXAMPLE 19

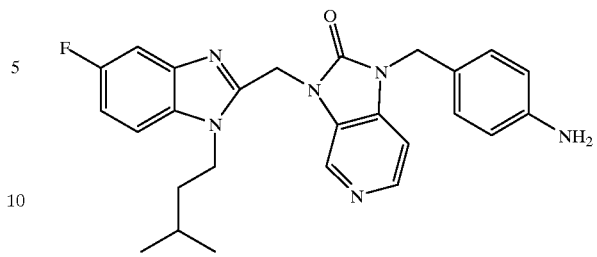

A mixture of Example 18 (1.52 g, 3.11 mmol) and 10% palladium on carbon (150 mg) in MeOH (50 mL) and concentrated hydrochloric acid (1 mL) was aggitated under hydrogen at 55 psi for 1.5 hours. The reaction mixture was filtered through a pad of Celite, rinsing thoroughly with MeOH. The filtrate was evaporated and dried under vacuum to give Example 19 as an HCl salt (1.82 g, quantitative yield).

$^1$H NMR (CD$_3$OD) δ 1.09 (d, J=6.0 Hz, 6 H), 1.84–1.90 (m, 3 H), 4.64 (t, J=7.6 Hz, 2 H), 5.40 (s, 2 H), 5.94 (s, 2 H), 7.43–7.47 (m, 3 H), 7.52 (dd, J=2.3, 8.1 Hz, 1 H), 7.70 (d, J=8.3 Hz, 2 H), 7.87 (d, J=6.5 Hz, 1 H), 7.93 (dd, J=4.2, 9.1 Hz, 1 H), 8.59 (d, J=6.4 Hz, 1 H), 9.01 (s, 1 H); IR (KBr, cm$^{-1}$) 3411, 2869, 1748, 1655, 1621, 1517, 1496, 1130, 810; MS m/e 459 (MH$^+$); Anal. Calcd for C$_{26}$H$_{27}$FN$_6$O$_3$·3HCl·2.5H$_2$O: C, 50.95; H, 5.76; N, 13.71 Found: C, 50.72; H, 5.47; N, 13.66.

EXAMPLE 20

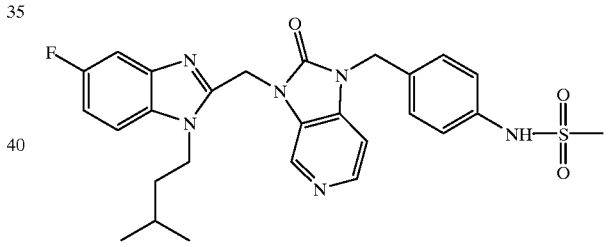

To a mixture of Example 19 (350 mg, 0.66 mmol) and triethylamine (200 mg, 1.98 mmol) in CH$_2$Cl$_2$ cooled to 0° C. was added methanesulfonyl chloride (75 mg, 0.66 mmol). The reaction mixture was allowed to warm to room temperature and then stirred for 16 hours. The reaction mixture was diluted with CH$_2$Cl$_2$ (100 mL) and washed with saturated aqueous sodium bicarbonate solution (10 mL) and brine solution (10 mL). The aqueous layer was back-extracted with CH$_2$Cl$_2$. The combined organic extracts were dried over anhydrous MgSO$_4$, and evaporated. Trituration of the resulting pale yellow solid with Et$_2$O gave the title compound (quantitative yield).

$^1$H NMR (CD$_3$OD) δ 1.06 (d, J=6.3 Hz, 6 H), 1.75–1.81 (m, 3 H), 2.93 (s, 3 H), 4.46 (t, J=8.2 Hz, 2 H), 5.28 (s, 2 H), 5.64 (s, 2 H), 7.18 (t, J=2.5, 9.2 Hz, 1 H), 7.23–7.29 (m, 3 H), 7.46 (d, J=8.6 Hz, 2 H), 7.60 (dd, J=4.4, 8.9 Hz, 1 H), 7.77 (d, J=6.5 Hz, 1 H), 8.48 (d, J=6.7 Hz, 1 H), 8.78 (s, 1 H); IR(KBr, cm$^{-1}$) 3441, 2959, 1736, 1617, 1515, 1332, 1150, 1040, 821; MS m/e 537 (MH$^+$); Anal. Calcd for C$_{27}$H$_{29}$FN$_6$O$_3$S·4.5H$_2$O: C, 52.50; H, 6.20; N, 13.61 Found: C, 52.20; H, 5.79; N, 12.79.

EXAMPLE 21

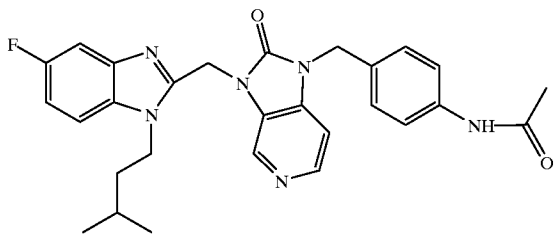

To a mixture of Example 19 (400 mg, 0.75 mmol) and triethylamine (229 mg, 2.26 mmol) in $CH_2Cl_2$ cooled to 0° C. was added acetyl chloride (74 mg, 0.94 mmol) followed by a catalytic amount of dimethylaminopyridine (10 mg). The reaction was allowed to warm to room temperature and a pale yellow precipitate came out of solution. After 1 hour, the reaction mixture was diluted with $CH_2Cl_2$ and washed with saturated aqueous sodium bicarbonate solution and brine. The aqueous layer was back-extracted with $CH_2Cl_2$. The combined organic extracts were dried over anhydrous $MgSO_4$, and evaporated. Trituration of the resulting white solid with $Et_2O$ gave Example 21 (321 mg, 85% yield).

$^1H$ NMR ($CD_3OD$) δ 0.96 (d, J=0.96 Hz, 6 H), 1.54–1.59 (m, 2 H), 1.67–1.70 (m, 1 H), 2.10 (s, 3 H), 4.36 (t, J=8.2Hz, 2 H), 5.13 (s, 2 H), 5.51 (s, 2 H), 7.11 (dt, J=2.5, 9.2 Hz, 1 H), 7.21 (d, J=5.4 Hz, 1 H), 7.30 (dd, J=2.4,9.3 Hz, 1 H), 7.37 (d, J=8.6 Hz, 2 H), 7.49 (dd, J=4.5, 9.0 Hz, 1 H), 7.54 (d, J=8.6 Hz, 2 H), 8.19 (d,J=5.4 Hz, 1 H), 8.35 (s, 1 H); IR (KBr, $cm^{-1}$) 3424, 2960, 1724, 1691, 1610, 1517, 1507, 1455, 1402, 1319, 1136, 810; MS m/e 501 ($MH^+$); Anal. Calcd for $C_{28}H_{29}FN_6O_2 \cdot 0.5H_2O$: C, 66.00; H, 5.93; N, 16.49 Found: C, 65.79; H, 6.12; N, 16.29.

EXAMPLE 22

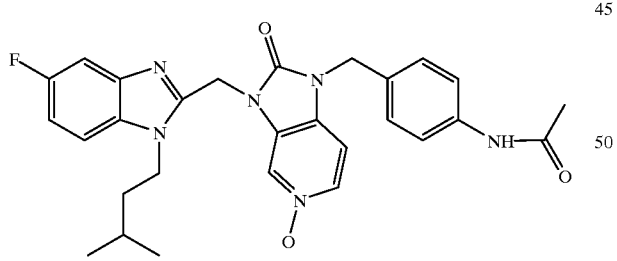

To a solution of the Example 20 (50 mg, 0.10 mmol) in DMF (5 mL) was added m-chloroperbenzoic acid (34 mg, 0.20 mmol). The mixture was stirred at room temperature for 16 hours. The solvent was evaporated under reduced pressure. The resulting residue was triturated with water and filtered. The aqueous filtrate was extracted with EtOAc and the combined extracts were dried over $MgSO_4$, and evaporated. The residue combined with the solid obtained from trituration were subjected to flash chromatography (gradient, $CH_2Cl_2$/5% ammonium hydroxide in MeOH, 40:1 to 20:1) to give Example 22 as a white solid (21 mg, 41% yield).

$^1H$ NMR (DMSO-$d_6$) δ 0.95 (d, J=6.5 Hz, 6 H), 1.57–1.60 (m, 2 H), 1.66–1.74 (m, 1 H), 2.02 (s, 3 H), 4.32 (t, J=7.7 Hz, 2 H), 5.05 (s, 2 H), 5.41 (s, 2 H), 7.13 (t, J=8.7 Hz, 1 H), 7.24 (d, J=6.7 Hz, 1 H), 7.29 (d, J=8.2 Hz, 1 H), 7.41 (d, J =8.6 Hz, 1 H), 7.54 (d, J=8.2 Hz, 1 H), 7.55–7.59 (m, 1 H), 7.96 (d, J=6.3 Hz, 1 H), 8.37 (s, 1 H); IR (KBr, $cm^{-1}$) 3428, 2956, 1720, 1678, 1600, 1551, 1514, 1465, 1407, 1320, 1162, 1146, 802; MS m/e 517 ($MH^+$); Anal. Calcd for $C_{28}H_{29}FN_6O_3 \cdot 0.5H_2O$: C, 63.99; H, 5.75; N, 15.99 Found: C, 64.08; H, 5.57; N, 15.82.

EXAMPLE 23

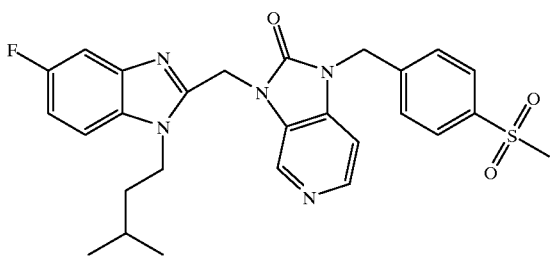

$^1H$ NMR ($CD_3OD$) δ 0.98 (d, J=6.6 Hz, 6 H), 1.59–1.64 (m, 2 H), 1.69–1.73 (mi, 1 H), 3.09 (s, 3 H), 4.39 (t, J=8.1 Hz, 2 H), 5.31 (s, 2 H), 5.52 (s, 2 H), 7.12 (dt, J=2.5, 9.2 Hz, 1 H), 7.23 (d, J=5.4 Hz, 1 H), 7.29 (dd, J=2.4, 9.2 Hz, 1 H), 7.51 (dd, J=4.5, 8.9 hz, 1 H), 7.66 (d, J=8.4 Hz, 2 H), 7.94 (d, J=8.4 Hz, 2 H), 8.22 (d, J=1.7 Hz, 1 H), 8.39 (s, 1 H); IR (KBr, $cm^{-1}$) 3423, 2959, 1715, 1613, 1602, 1497, 1454, 1407, 1307, 1148, 1090, 808, 520; MS m/e 522 ($MH^+$).

EXAMPLE 24

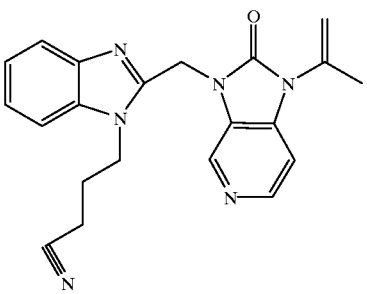

$^1H$ NMR ($CD_3OD$) δ 1.85–1.90 (m, 2 H), 1.90 (s, 3 H), 2.27 (t, J=7.5 Hz, 2 H), 4.29–4.34 (t, J=7.5 Hz, 2 H), 5.03 (s, 1 H), 5.65 (s, 1 H), 6.86 (d, J=5.5 Hz, 1 H), 7.12–7.22 (m, 3 H), 7.60–7.63 (m, 1 H), 8.16 (d, J5.5 Hz, 1 H), 8.65(s,1 H); IR (KBr, $cm^{-1}$) 3396, 2244, 1710, 1660, 1604, 1493, 1458, 1399, 1332, 1166, 1140, 824, 742; MS m/e 373 ($MH^+$); Anal. Calcd for $C_{22}H_{25}N_5O \cdot 0.25 H_2O$: C, 66.92; H, 5.48; N, 22.30 Found: C, 66.58; H, 5.56; N, 22.34.

EXAMPLE 25

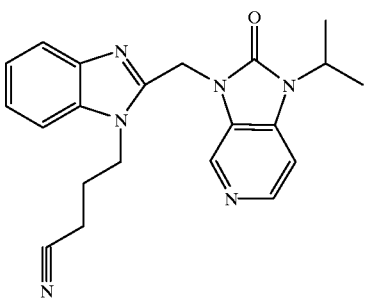

¹H NMR (CDCl₃) δ 1.56 (d, J=6.9 Hz, 6 H), 1.98–2.08 (m, 2 H), 2.45 (t, J=7.2 Hz, 2 H), 4.49 (t, J=7.2 Hz, 2 H), 4.70–4.74 (m, 1 H), 5.40 (s, 2 H), 7.06 (d, 3J 5.2 Hz, 1 H), 7.33–7.39 (m, 3 H), 7.78–7.81 (m, 1 H), 8.31 (d, J=5.2 Hz, 1 H), 8.81 (s, 1 H); IR (KBr, cm⁻¹) 3412, 2981, 2246, 1700, 1608, 1496, 1459, 1391, 1117, 748; MS m/e 375 (MH⁺).

EXAMPLE 26

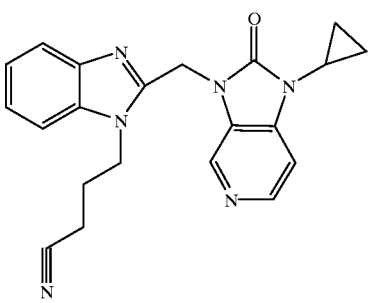

¹H NMR (CDCl₃) δ 1.03–1.06 (m, 2 H), 1.97–1.24 (m, 2 H), 2.13–2.18 (m, 2 H), 2.47 (t, J4.2 Hz, 2 H), 2.96–3.00 (m, 1 H), 4.51 (t, J4.4 Hz, 2 H), 4.16 (s, 2 H), 7.27–7.35 (m, 4 H), 7.38 (dd, J=0.8,4.2 Hz, 1 H), 7.77 (dd, J=0.9, 4.4 Hz, 1 H), 8.37 (d, J=3.4 Hz, 1 H), 8.56 (s, 1 H); IR (KBr, cm¹) 3405, 2245, 1702, 1608, 1500, 1408, 1172, 1024, 820, 743; MS m/e 373 (MH⁺); Anal. Calcd for C₂₁H₂₀N₈O•0.875H₂O: C, 64.98; H, 5.64; N, 21.65 Found: C, 65.06; H, 5.36; N, 21.51.

EXAMPLE 27

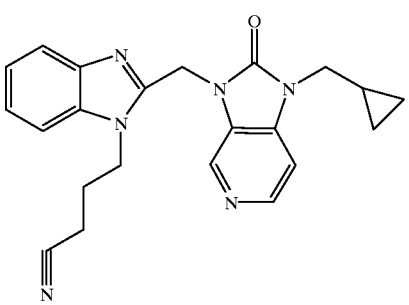

¹H NMR(CD₃OD) δ 0.53–0.54 (m, 2 H), 0.64–0.66 (m, 2 H), 1.31–1.37 (m, 1 H), 2.30–2.34 (m, 2 H), 2.68 (t, J=7.2 Hz, 2 H), 4.02 (d, J=7.2 Hz, 2 H), 4.63 (t, J=7.4 Hz, 2 H), 5.72 (s, 2 H), 7.39 (t, J=7.0 Hz, 1 H), 7.43 (t, J=7.1 Hz, 1 H), 7.63 (d, J=7.9 Hz, 1 H), 7.73 (d, J=8.1 Hz, 2 H), 7.92 (d, J=6.5 Hz, 1 H), 8.55 (d, J =6.5 Hz, 1 H), 8.81 (s, 1 H); IR (KBr, cm) 3448, 2250, 1748, 1676, 1522, 1201, 1131, 720; MS m/e 387 (MH⁺).

EXAMPLE 28

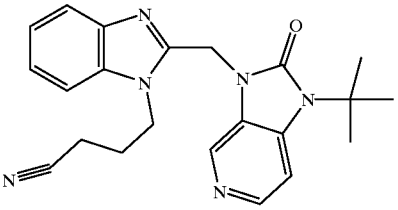

¹H NMR (CDCl₃) δ 1.81 (s, 9 H), 2.05–2.06 (m, 2 H), 2.46 (t, J=7.2 Hz, 2 H), 4.48 (t, J=7.6 Hz, 2 H), 5.38 (s, 2 H), 7.31–7.36 (m, 4 H), 7.78 (m, 1 H), 8.24 (d, J=5.8 Hz, 1 H), 8.84 (s, 1 H); IR (KBr, cm¹) 3406, 2937, 2246, 1706, 1493, 1458, 1387, 1157, 1138, 746; MS m/e 389 (MH⁺).

EXAMPLE 29

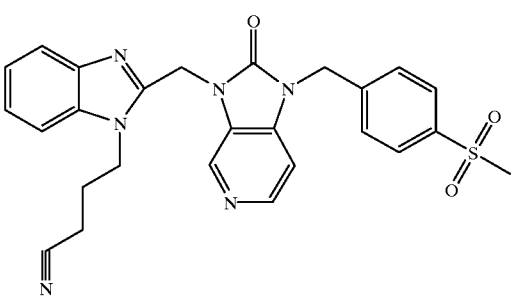

¹H NMR (DMSO-d₆) δ 2.09–2.12(m, 2 H), 2.63 (t, J=7.4 Hz, 2 H), 4.43 (t, J=7.5 Hz, 2 H), 5.28 (s, 2 H), 5.52 (s, 2 H), 7.21 (t, J=7.2 Hz, 1 H), 7.26 (t, J=7.2 Hz, 1 H), 7.57 (d, J=8.0 Hz, 1 H), 7.60–7.63 (m, 4 H), 7.92 (d, J=8.4 Hz, 2 H), 8.23 (d, J=5.3 Hz, 1 H), 8.50 (s, 1 H); IR (KBr, cm⁻¹) 3426, 2246, 1716, 1407, 1150, 760; MS m/e 501 (MH⁺); Anal. Calcd for C₂₇H₂₈FN₅O₃S: C, 62.17; H, 5.17; N, 13.43 Found: C, 62.03; H, 5.45; N, 13.34.

EXAMPLE 30

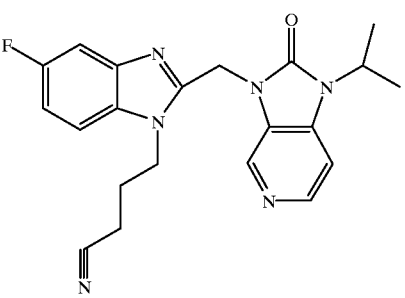

¹H NMR (CDCl₃) δ 1.54 (d, J=7.0 Hz, 6 H), 1.99–2.05 (m,2 H), 2.45 (t, J=7.2 Hz, 2 H), 4.47 (t, J=7.6Hz, 2 H), 4.70 (m, 1H), 5.36 (s, 2 H), 7.06–7.10 (m, 2 H), 7.27–7.30 (m, 1 H), 7.45 (q, J=2.4, 9.1 Hz, 1 H), 8.31 (d, J=4.0 Hz, 1 H), 8.78 (s, 1 H); R (KBr, cm) 3432, 2953, 2360, 2245, 1718, 1698, 1284, 1139; MS m/e 393 (MH+); Anal. Calcd for $C_{21}H_{21}FN_6O$: C, 64.27; H, 5.39; N, 21.41 Found: C, 64.23, H, 5.44; N, 21.24.

EXAMPLE 31

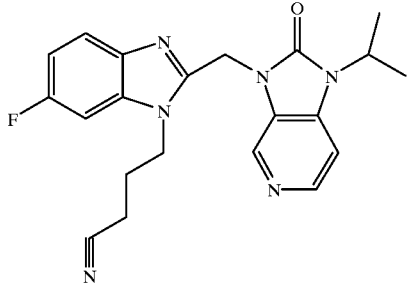

$^1$H NMR (CDCl$_3$) δ 1.53 (d, J=7.0 Hz, 6 H), 1.96–2.03 (m, 2 H), 2.45 (t, J=7.2 Hz, 2 H), 4.41 (t, J=7.6 Hz, 2 H), 4.70 (m, 1 H), 5.34 (s, 2 H), 6.99–7.06 (m, 3 H), 7.67–7.70 (m, 1 H), 8.29 (d, J=4.0 Hz, 1H), 8.76 (s, 1 H); IR (KBr, cm$^1$) 3423, 2941, 2247, 1710, 1492, 1390, 808; MS m/e 393 (MH+).

EXAMPLE 32

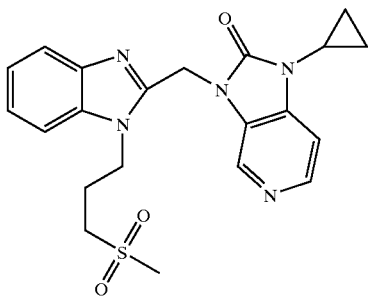

$^1$H NMR (CDCl$_3$) δ 1.03–1.06 (m, 2 1.17–1.22 (m, 2H), 2.25–2.31 (m, 2 H), 2.93 (s, 3 H), 2.98–3.01 (m, 1 H), 3.10 (t, J=7.4 Hz, 2 H), 4.54 (t, J=7.5 Hz, 2 H), 5.42 (s, 2 H), 7.25–7.39 (m, 4 H), 7.76 (d, J=7.1 Hz, 1 H), 8.36 (d, J=5.3Hz, 1 H), 8.79 (s, 1 H); IR (KBr, cm$^{-1}$) 3423, 2927, 1718, 1608, 1499, 1459, 1409, 1311, 1289, 1128, 748; MS m/e 426(MH+); Anal. Calcd for $C_{21}H_{23}N_5O_3S$: C, 59.27; H, 5.44; N, 16.45 Found: C, 59.03; H, 5.52; N, 16.31.

EXAMPLE 33

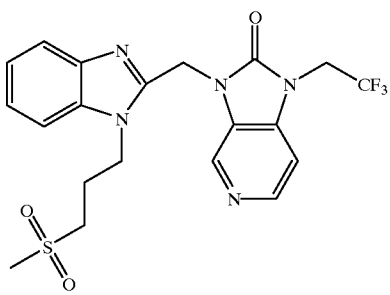

$^1$H NMR (DMSO-d$_6$) δ 2.13–2.20 (m, 2 H), 3.01 (s, 3 H), 3.26 (t, J=7.8 Hz, 2 H), 4.50 (t, J=7.5 Hz, 2 H), 4.91 (q, J=9.3 Hz, 2 H), 5.53 (s, 2 H), 7.20 (t, J=7.3 Hz, 1 H), 7.28 (t, J=7.7 Hz, 1 H), 7.45 (d, J=5.3 Hz, 1 H), 7.64 (d, J=8.1 Hz, 1 H) 8.32 (d, J=5.3 Hz, 1 H), 8.52 (s, 1 H); IR (KBr, cm$^{-1}$) 3441, 1725, 1498, 1460, 1408, 1294, 1265, 1167, 1125, 746; MS m/e 468 (MH+); Anal. Calcd for $C_{20}H_{20}F_3N_5O_3S$•0.375 H$_2$O: C, 50.66; H, 4.41; N, 14.76 Found: C, 50.83; H, 4.34; N, 14.41.

EXAMPLE 34

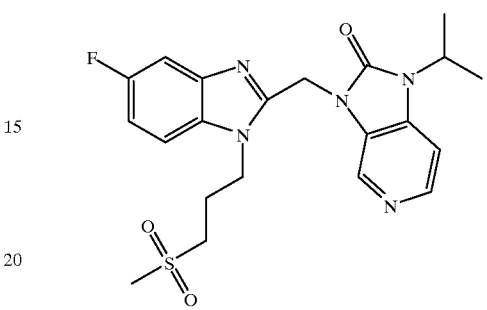

$^1$H NMR (CD$_3$OD) δ 1.47 (d, J=6.9 Hz, 6 H), 2.14–2.17 (m, 2 H), 3.00 (s, 3 H), 3.24 (t, J=7.8 Hz, 2 H), 4.50 (d, J=7.5 Hz, 2 H), 4.63–4.66 (m, 1 H), 5.44 (s, 2 H), 7.16 (dt, J=2.5, 9.2 Hz, 1 H), 7.41–7.45 (m, 2 H), 7.67 (dd, J=4.8, 8.9 Hz, 1 H), 8.23 (d, J=5.4 Hz, 1 H), 8.47 (s, 1 H); IR (KBr, cm$^{-1}$)3423, 2984, 2937, 1702, 1608, 1495, 1457, 1391, 1293, 1135, 1116, 963, 809; MS m/e 446 (MH+); Anal. Calcd for $C_{21}H_{24}FN_5O_3S$: C, 56.61; H, 5.43; N1, 15.71 Found: C, 56.46; H, 5.55; N, 15.62.

EXAMPLE 35

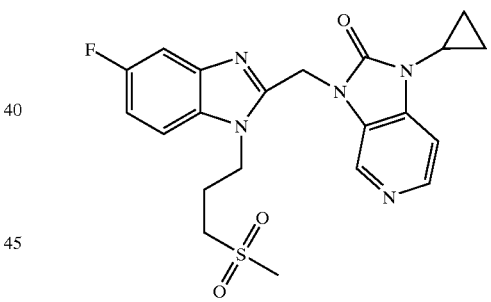

$^1$H NMR (CD$_3$OD) δ 0.91–0.93 (m, 2 H), 1.06–1.07 (m, 2 H), 2.99–3.01 (m, 1 H), 3.00 (s, 3 H), 3.23 (t, J=7.7 Hz, 2 H), 4.49 (t, J=7.5 Hz, 2 H), 5.41 (s, J=2 H), 7.15 (dt, J=, 1 H), 7.29 (dd, J=2.0, 5.3 Hz, 1 H), 7.43 (dd, J=2.5, 9.8 Hz, 1 H), 7.67 (dd, J=4.7, 8.9 Hz, 1 H), 8.26 (d, J=5.3 Hz, 1 H), 8.44 (s, 1 H); IR (KBr, cm$^{-1}$) 3423, 3014, 1708, 1609, 1498, 1455, 1415, 1315, 1294, 1171, 1131, 957, 819; MS m/e 444 (MH+); Anal. Calcd for $C_{21}H_{22}FN_5O_3S$: C, 56.87; H, 5.00; N, 15.79 Found: C, 56.76; H, 5.15; N, 15.69.

Example 35 was converted to an oxalate salt by adding 1 equivalent of oxalic acid to a MeOH solution of 35 and evaporating the solvent.

$^1$H NMR (CD$_3$OD) δ 2.26 (s, 3 H), 2.26–2.36 (m, 2 H), 2.64 (t, J=7.5 Hz, 2 H), 4.62 (t, J=7.5 Hz, 2 H), 5.29 (s, 1 H), 5.45 (s, 1 H), 5.58 (s, 2 H), 7.16 (dd, J=5.4, 8.1 Hz, 1 H), 7.34–7.44 (m, 2 H), 7.54–7.71 (m, 2 H), 7.70 (dl, J=8.1 Hz, 1 H), 8.01 (dd, J=0.9, 5.4 Hz, 1 H); IR (KBr, cm$^{-1}$) 3405, 2954, 2244, 1702, 1611, 1476, 1456, 1400, 1276, 1188, 1158, 795, 749; MS m/e 373 (MH⁺); Anal. Calcd for C₂₁H₂₀N₆O•C₂H₂O₄•0.25H₂O: C, 59.16; H, 4.86; N, 18.00 Found: C, 58.90; H, 4.83; N, 18.24.

EXAMPLE 36

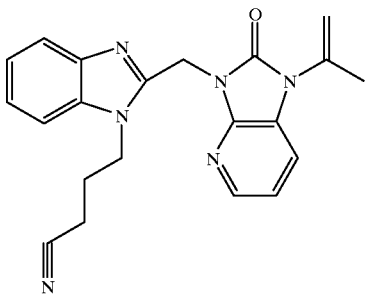

¹H NMR (CDCl₃) 62.19–2.45 (m, 2 H), 2.45 (s, 3 H), 2.48 (t, J=7.1 Hz, 2 H), 4.61 (t, J=7.4 Hz, 2 H), 5.19 (s, 1 H), 5.34 (s, 1H), 5.48 (s, 2 H), 7.03 (dd, J=5.2, 7.9 Hz, 1 H), 7.26–7.33 (m, 3 H), 7.80 (d, J=8.0 Hz, 1 H), 8.10 (dd, J=1.4, 5.2 Hz, 1 H).

EXAMPLE 37

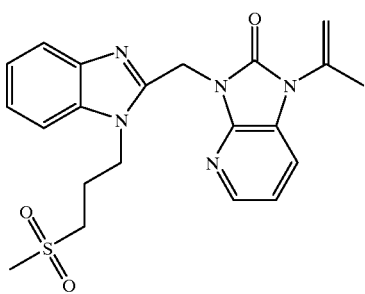

¹H NMR (CDCl₃) δ 2.28–2.34 (s over m, 5 H), 2.94 (s, 3 H), 3.16 (t, J=7.2 Hz, 2 H), 4.59 (t, J=7.9 Hz, 2 H), 5.37 (s, 1 H), 5.47 (s, 1 H), 5.54 (s, 2 H), 7.08 (dd, J =5.3, 7.8 Hz, 1 H), 7.39–7.43 (m, 2 H), 7.51 (d, J=7.7 Hz, 1 H), 7.85 (d, J=7,3 Hz, 1 H), 8.05 (bs, 1 H), 8.09 (dd, J=1.0, 5.2 Hz, 1 H); IR (KBr, cm⁻¹) 3423, 1708, 1618, 1453, 1402, 1295, 1131, 750; MS m/e 426(M); Anal. Calcd for C₂₁H₂₃N₅O₃S: C, 59.28; H, 5.44; (t, 16.45 Found: C, 59.11; H, 5.36; N, 16.35.

EXAMPLE 38

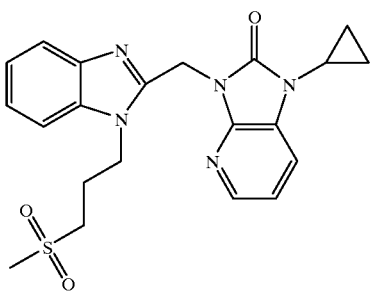

¹H NMR (CDCl₃) δ 1.06–1.11 (m, 4 H), 2.49–2.54 (m, 2 H), 2.94–2.99 (m, 1 H), 3.24 (t, J=6.7 Hz, 2 H), 4.75 (t, J=7.1 Hz, 2 H), 5.70 (s, 2 H), 7.05 (dd, J=5.3, 7.7 Hz, 1 H), 7.37–7.44 (m, 3 H), 7.54 (d, J=8.0 Hz, 1 H), 7.91 (d, J=8.0 Hz, 1 H), 7.98 (d, J=4.8 Hz, 1 H); IR (KBr, cm⁻¹) 3435, 1716, 1617, 1486, 1460, 1425, 1295, 1131, 747; MS m/e 426 (MH⁺).

EXAMPLE 39

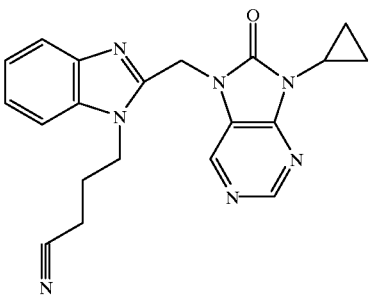

¹H NMR (DMSO-d₆) δ 1.02–1.07 (m, 4 H), 2.08–2.14 (m, 2 H), 21.64 (,J=7,4 Hz, 2 H), 3.02–3.03 (m, 1 H), 4.42 (t, J=7.4 Hz, 2 H), 5.44 (s, 1 H), 7.19 (t, J=7.5 Hz, 1 H), 7.28 (t, J=7.2 Hz, 1 H), 7.56 (d, J=8.0 Hz, 1 H), 7.63 (d, J=8.0 Hz, 1 H), 8.46 (s, 1 H), 8.66 (s, 1 H); IR (KBr, cm⁻¹) 3452, 2244, 1731, 1718, 1612, 1488, 1422, 1407, 1317, 746; MS m/e 374 (MH⁺); Anal. Calcd for C₂₀H₁₉N₇O: C, 64.33; H, 5.12; N, 26.25; Found: C, 64.00; H, 5.20; N, 26.12.

EXAMPLE 40

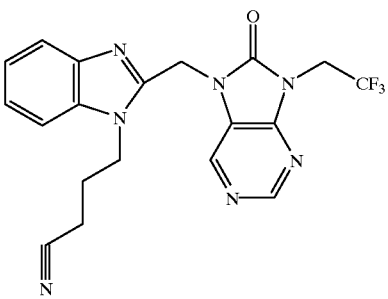

¹H NMR (CDCl₃) δ 2.07–2.13 (m, 2 H), 2.48 (t, J=6.9 Hz, 2 H), 4.52 (d, J=7.6 Hz, 2 H), 4.59–4.64 (m, 2 H), 5.47 (s, 2 H), 7.33–7.44 (m, 3 H), 7.80 (d, J=7.5 Hz, 1 H), 8.76 (s, 1 H), 8.88 (s, 1 H); MS m/e 416 (MH⁺); Anal. Calcd for C₁₉H₁₆F₃N₇O: C, 54.94; H, 3.88; N, 23.60 Found: C, 54.87; H, 3.78; N, 23.66.

EXAMPLE 41

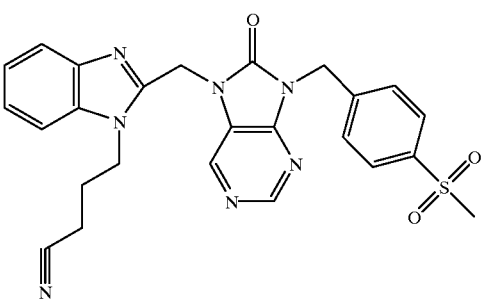

¹H NMR (CDCl₃) δ 2.12–2.15 (,2 H), 2.43 (t, J=7.0 Hz, 2 H), 3.02 (s, 3 H), 4.51 (,J=7.4 Hz, 2 H), 5.22 (s, 2 H), 5.45

(s, 2 H), 7.32–7.42 (m, 3 H), 7.69 (d, J 8.4 Hz, 2 H), 7.77–7.79 (m, 1 H), 7.91–7.93 (m, 2 H), 8.73 (s, 1 H), 8.83 (s, 1 H); MS m/e 502 (MH⁺).

EXAMPLE 42

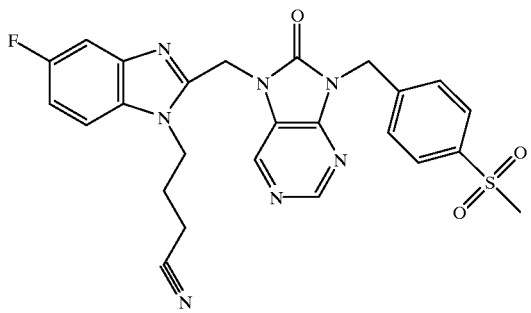

¹H NMR (CDCl₃) δ 2.12–2.15 (m, 2 H), 2.44 (t, J=7.0 Hz, 2 H), 3.02 (s, 3 H), 4.49 (t, J=7.4 Hz, 2 H), 5.23 (s, 2 H), 5.41 (s, 2 H), 7.10–7.14 (m, 1 H), 7.32–7.34 (m, 1 H), 7.43 (dd, J=2.4, 9.0 Hz, 1 H), 7.69 (d, J=8.3 Hz, 2H), 7.92 (d, J =8.3 Hz, 2 H), 8.74 (s, 1 H), 8.80 (s, 1 H); IR (KBr, cm) 3441, 2928, 2244, 1718, 1609, 1492, 1406, 1300, 1150; MS m/e 520 (MH⁺); Anal. Calcd. for $C_{25}H_{22}FN_3O_3S$: C, 57.79; H, 4.26; N, 18.87 Found: C, 57.49; H, 4.11; N, 18.55.

EXAMPLE 43

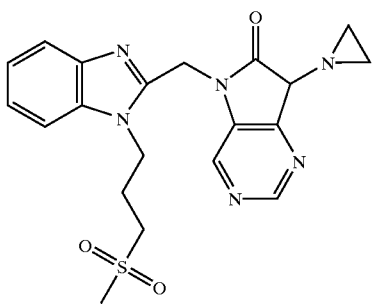

¹H NMR (CDCl₃) δ 1.17–1.18 (m, 2 H), 2.31–2.37 (m, 2 H), 2.97 (s, 3 H), 3.01–3.06 (m, 1 H), 3.15 (t, J=7.2 Hz, 2 H), 4.58 (t, J=7.5 Hz, 2 H), 5.41 (s, 1 H), 7.30–7.36 (m, 2 H), 7.42 (d, J=7.4 Hz, 1 H), 7.76–7.78 (dd, J=1.2, 7.2 Hz, 1 H), 8.73(s, 1 H), 8.74 (s, 1 H); IR (KBr, cm⁻¹) 3424, 1721, 1615, 1493, 1407, 1313, 1126, 750; MS m/e 427 (MH⁺); Anal. Calcd for $C_{20}H_{22}N_6OS \cdot H_2O$: C, 54.04; H, 5.44; N, 18.91 Found: C, 53.95; H, 5.54; N. 18.75.

EXAMPLE 44

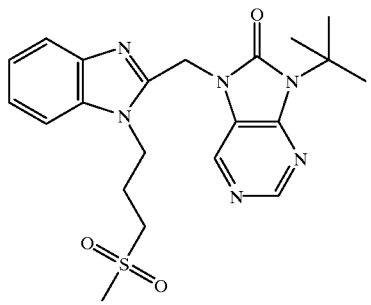

¹H NMR (CDCl₃) δ 1.84 (s, 9 H), 2.30–2.35 (m, 2 H), 3.13 (t, J=7.2 Hz, 2H), 4.58 (t, J=7.6 Hz, 2 H), 5.38 (s, 1 H), 7.30–7.35 (m, 2 H), 7.42 (d, J=7.4 Hz, 1 H), 7.76–7.78 (dd, J=1.2,7.2 Hz, 1 H), 8.66 (s, 1 H), 8.73 (s, 1 H); IR (KBr, cm⁻¹): 3431, 2927, 1718, 1616, 1469, 1444, 1469, 1444, 1296, 1134, 747; MS m/e 443 (MH⁺); Anal. Calcd for $C_{21}H_{26}N_6O_3S \cdot H_2O$: C, 55.86; H, 6.03; N, 18.61 Found: C, 55.87; H, 5.88; N, 18.44.

EXAMPLE 45

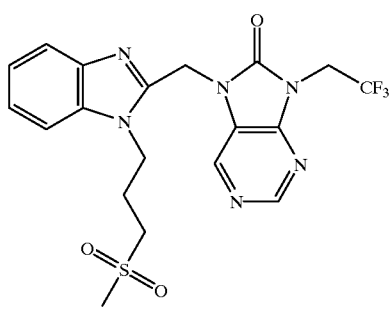

¹H NMR (CDCl₃) δ 2.25–2.29 (m, 2 H), 2.97 (s, 3 H), 3.14 (t, J=7.0 Hz, 2 H), 1 5 4.56–4.64 (m, 4 H), 5.49 (s, 2 H), 7.32–7.39 (m, 2 H), 7.44 (d, J=7.4 Hz, 1 H), 7.78–7.80 (dd, J=1.4, 7.2 Hz, 1 H), 8.76 (s, 1 H), 8.85 (s, 1 H); MS m/e 469 (MH⁺).

EXAMPLE 46

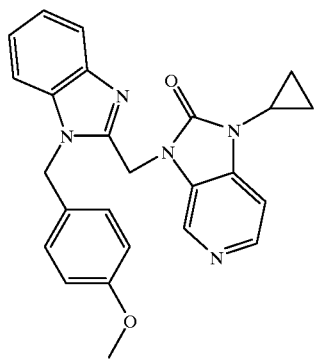

¹H NMR (CDCl₃) δ 0.71–0.74 (m, 2 H), 1.03–1.07 (m, 2 H), 2.63–2.66 (m, 1 H), 3.66 (s, 3 H), 5.39 (s, 2 H), 5.47 (s,

2 H), 6.50 (m, 4 H), 6.99 (d, J=5.3 Hz, 1 H), 7.20 (d, J=8.0 Hz, 1 H), 7.26 (m, 1 H), 7.31 (m, 1 H), 7.85 (d, J 8.0 Hz, 1 H), 8.27 (d, J=5.0 Hz, 1 H), 8.53 (s, 1 H); MS m/e 426 (MH+).

EXAMPLE 47

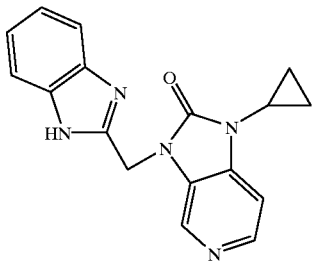

A stirred suspension of Example 46 (11.75 g, 27.6 mmol) in CH₃CN (150 mL) was treated with ceric ammonium nitrate (CAN, 60.60 g, 110 mmol) and diluted with water (25 mL) to give a homogeneous solution which was stirred at room temperature for 24 hours. The mixture was concentrated in vacuo to a volume of 50 mL, then diluted with H₂O (100 mL) and again concentrated until 100 mL remained and a yellow solid had precipitated from solution. The yellow solid was isolated from the chilled suspension by filtration and was identified as the 4-methoxybenzaldehyde by-product. The filtrate was then diluted with H₂O to 400 mL and MeOH (600 mL) was added. To the resulting solution was added a saturated aqueous solution of sodium potassium tartrate until the pH of the solution reached 6 and a very finely divided powder precipitated. The reaction mixture was centrifuged and the liquid was decanted away from the solid and concentrated in vacuo. The residue was redissolved in water (250 mL) and the resulting solution was extracted with CH₂Cl₂ (8×100 mL). The organic extracts were combined and concentrated in vacuo to a brown glassy solid which was redissolved in minimum CH₂Cl₂. After a few minutes, a beige powder precipitated from solution. Et₂O was added to the mixture and the solid was isolated by filtration, rinsed with Et₂O, and dried under high vacuum to give 6.62 g (79% yield) of Example 47 as a beige powder.

¹H NMR (DMSO-d₆) δ 0.92–0.97 (m, 2 H), 1.06–1.10 (m, 2 H), 2.97–3.01 (m, 1 H), 5.30 (s, 2 H), 7.14–7.17 (m, 2 H), 7.30 (d, J5.4Hz, 1 H), 7.50 bs, 2 H), 8.25–8.28 (m, 2 H), 12.54 (bs, 1 H); MS m/e 306 (MH+).

EXAMPLE 48

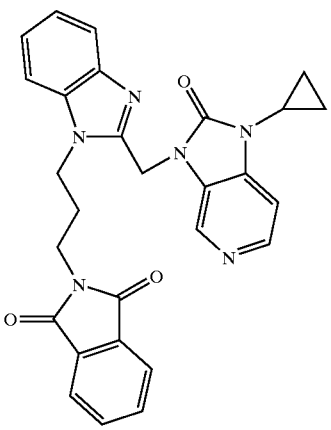

¹H NMR (CDCl₃) δ 0.97–1.00 (m, 2 H), 1.12–1.16 (m, 2 H), 2.09–2.15 (m, 2 H), 2.99–3.03 (m, 1 H), 3.82 (t, J=6.8 Hz, 2 H), 4.42 (t, J=7.9 Hz, 2 H), 5.36 (s, 2 H), 7.21–7.28 (m, 3 H), 7.32 (d, J=7.7 Hz, 1 H), 7.69–7.74 (m, 3 H), 7.81–7.85 (m, 2 H), 8.35 (d, J=5.0 Hz, 1 H), 8.79 (s, 1 H); MS m/e 493 (MH+).

EXAMPLE 49

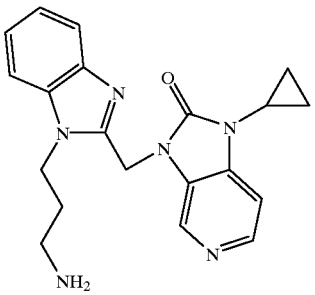

Example 48 (2.58 g, 5.24 mmol) was treated with hydrazirie hydrate (2.62 g, 52.4 mmol) in MeOH (100 mL) and the mixture was heated to reflux for 5 hours. The resulting mixture was passed through a 50 mL bed of AG 50W-X2 strong cation exchange resin (Bio-Rad Laboratories), and the bed was rinsed with MeOH (300 mL). The yellow eluent was discarded, and the product was eluted from the resin with 2M ammonia in MeOH (500 mL). The ammonia eluent was concentrated in vacuo to give 1.85 g (97% yield) of Example 49 as an off-white powder.

¹H NMR (DMSO-d₆) δ 0.92 (s, 2 H), 1.07 (d, J=5.8, 2 H), 1.74 (t, J=6.8 Hz, 2 H), 2,57 (t, J=6.2 Hz, 2 H), 2.99–3.01 (m, 1 H), 4.39 (t, J=7.1 Hz, 2 H), 5.43 (s, 2 H), 7.17 (t, J=7.4Hz, 1 H), 7.24 (t, J=7.5 Hz, 1 H), 7.29 (d, J=5.1 Hz, 1 H), 7.58 (t, J=8.6 Hz, 2 H), 8.25 (d, J=5.2 Hz, 1 H), 8.39 (s, 1 H); MS m/e 363 (MU+).

EXAMPLE 50

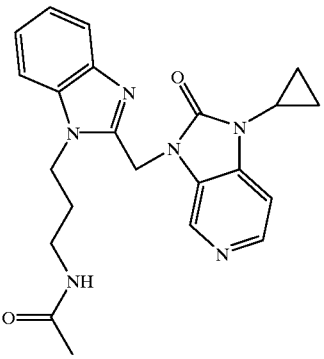

A mixture of Example 49 (0.0 50 g, 0. 14 mmol) and polystyrene diisopropylethylamine resin (PS-DIEA resin, Argonaut, 0.075 g, 0.28 mmol) in anhydrous $CH_2Cl_2$ (1 mL) was treated with acetic anhydride (0.141 g, 1.38 mmol) and stirred at room temperature for 18 hours. Solids which precipitated from solution were redissolved by the addition of chloroform (1 mL), and the reaction mixture was filtered to remove the resin. The filtrate was concentrated in vacuo, and the residue was purified by preparative HPLC (gradient, 10% MeOH in $H_2O$ with 0.1% TFA to 90% MeOH in $H_2O$ with 0.1% TFA) to give 0.074 g (>100% yield) of the trifluoroacetic acid salt of Example 50 as a glassy, colorless solid.

$^1$H NMR (DMSO-$d_6$) δ 0.99–1.02 (m, 2 H), 1.13–1.17 (m, 2 H), 1.84 (s, 3 H), 1.95 (t, J=7.3 Hz, 2 H), 3.14–3.17 (m, 3 H), 4.41 (t, J=7.5 Hz, 2 H), 5.57 (s, 2 H), 7.25 (t, J=7.4 Hz, 1 H), 7.33 (t, J=7.4 Hz, 1 H), 7.58 (d, J=8.0 Hz, 1 H), 7.68 (d, J=8.1 Hz, 1 H), 7.83 (d, J=6.4 Hz, 1 H), 7.99 (t, J=5.2 Hz, 1 H), 8.62 (d, J =6.2 Hz, 1 H), 8.83 (s, 1 H); MS m/e 405 (MH$^+$).

EXAMPLE 51

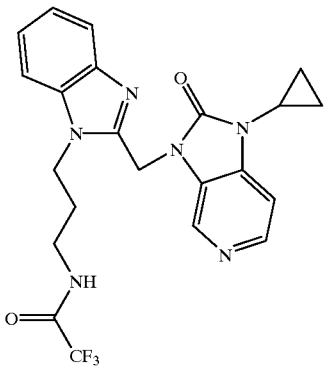

Example 51 was prepared according to the same procedure described for Example 50 using trifluoroacetic anhydride.

$^1$H NMR (DMSO-$d_6$) δ 0.98–1.01 (m, 2 H), 1.13–1.17 (m, 2 H), 2.03–2.08 (m, 2 H), 3.14–3.18 (m, 1 H), 3.33–3.37 (m, 2 H), 4.42 (t, J=7.5 Hz, 2 H), 5.54 (s, 2 H), 7.20–7.23 (m, 1 H), 7.29–7.23 (m, 1 H), 7.56 (d, J=8.0 Hz, 1 H), 7.65 (d, J=8.1 Hz, 1 H), 7.81 (d, J=6.3 Hz, 1 H), 8.61 (d, J=6.3 Hz, 1 H), 8.81 (s, 1 H), 9.54–9.56 (m, 1 H); MS m/e 459 (MH$^+$).

EXAMPLE 52

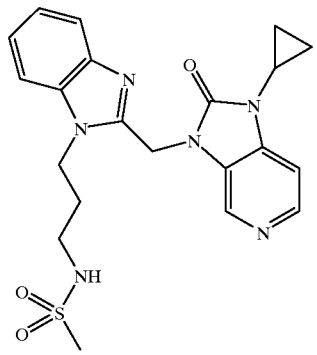

Example 52 was prepared according to the same procedure described for Example 50 using methanesulfonyl chloride.

$^1$H NMR (DMSO-$d_6$) δ 1.04–1.07 (m, 2 H), 1.14–1.17 (m, 2 H), 2.12 (t, J=7.4 Hz, 2 1H), 2.96 (s, 3 H), 3.16–3.18 (m, 3 H), 4.58 (t, J=7.6 Hz, 2 H), 5.82 (s, 2 H), 7.23–7.25 (m, 1 H), 7.47 (t, J=7.6 Hz, 1 H), 7.54 (t, J=7.7 Hz, 1 H), 7.75 (d, J=8.1 Hz, 1 H), 7.88 (d, J=6.5 Hz, 1 H), 7.94 (d, J=8.3 Hz, 1 H), 8.66 (d, J=6.5 Hz, 1 H), 8.90 (s, 1 H); MS m/e 441 (MH$^+$).

EXAMPLE 53

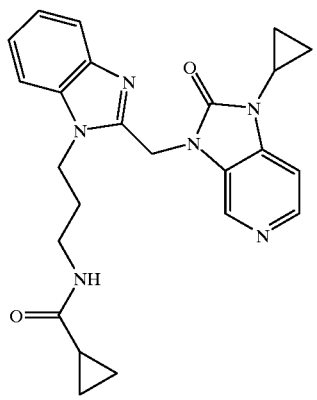

Example 53 was prepared according to the same procedure described for Example 50 using cyclopropanecarbonyl chloride.

$^1$H NMR (DMSO-$d_6$) δ 0.63–0.69 (m, 4 H), 0.98–1.02 (m, 2 H), 1.13–1.17 (m, 2 H), 1.53–1.58 (m, 1 H), 1.94–2.00 (m, 2 H), 3.14–3.20 (m, 3 H), 4.40 (t, J=7.4 Hz, 2 H), 5.55 (s, 2 H), 7.23 (t, J=7.5 Hz, 1 H), 7.31 (t, J=7.5 Hz, 1 H), 7.56 (d, J=8.0 Hz, 1 H), 7.65 (d, J=8.1 Hz, 1 H), 7.82 (d, J=6.3 Hz, 1 1H), 8.21 (t, J=5.1 Hz, 1 H), 8.61 (d, J=6.2 Hz, 1 H), 8.82 (s, 1 H); MS m/e 431 (MH$^+$).

EXAMPLE 54

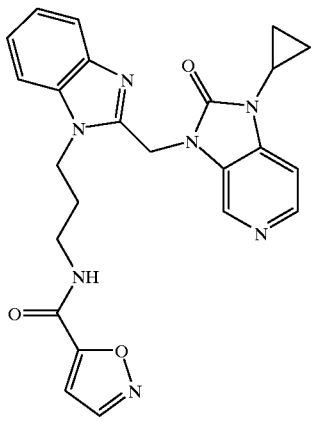

Example 54 was prepared according to the same procedure described for Example 50 using isoxazole-5-carbonyl chloride.

¹H NMR (DMSO-d$_6$) δ 0.97–1.00 (m, 2 H), 1.12–1.16 (m, 2 H), 2.06–2.12 (m, 2 H), 3.13–3.17 (m, 1 H), 3.39–3.43 (m, 2 H), 4.46 (t, J=7.5 Hz, 2 H), 5.56 (s, 2 H), 7.06 (s, 1 H), 7.22 (t, J=7.4 Hz, 1 H), 7.30 (t, J=7.4 Hz, 1 H), 7.56 (d, J=8.1 Hz, 1 H), 7.67 (d, J=8.1 Hz, 1 H), 7.81 (d, J=6.3 Hz, 1 H), 8.60 (d, J=6.2 Hz, 1 H), 8.75 (s, 1 H), 8.81 (s, 1 H), 9.08 (t, J=5.5 Hz, 1 H); MS m/e 458 (MH⁺).

EXAMPLE 55

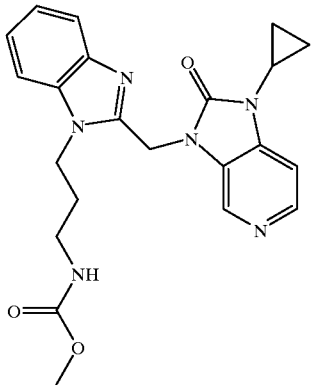

Example 55 was prepared according to the same procedure described for Example 50 using methyl chloroformate.

¹H NMR (DMSO-d$_6$) δ 0.90–0.93 (m, 2 H), 1.03–1.09 (m, 2 H), 1.80–1.86 (m, 2 H), 2.98–3.02 (m, 1 H), 3.05–3.08 (m, 2 H), 3.53 (s, 3 H), 4.35 (t, J=7.5 Hz, 2 H), 5.38 (s, 2 H), 7.17 (t, J=7.7 Hz, 1 H), 7.23–7.29 (m, 3 H), 7.57 (d, J8.2 Hz, 2 H), 8.25 (d, J=5.0 Hz, 1 H), 8.40 (s, 1 H); MS m/e 421 (MH⁺).

EXAMPLE 56

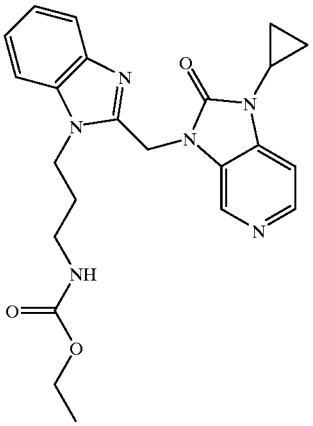

Example 56 was prepared according to the same procedure described for Example 50 using ethyl chloroformate.

¹H NMR (DMSO-d$_6$) δ 0.89–0.94 (m, 2 H), 1.03–1.09 (m, 2 H), 1.16 (t, J=7.1 Hz, 3 H), 1.80–1.86 (m, 2 H), 2.98–3.03 (m, 1 H), 3.04–3.08 (m, 2 H), 4.00 (q, J 7.1 Hz, 2 H), 4.35 (t, J=7.5 Hz, 2 H), 5.39 (s, 2 H), 7.23–7.29 (m,, 3 H), 7.29 (d, J =5.2 Hz, 1 H), 7.57 (d, J8.8 Hz, 2 H), 8.25 (d, J=5.1 Hz, 1 H), 8.40 (s, 1 H); MS m/e 435 (MH⁺).

EXAMPLE 57

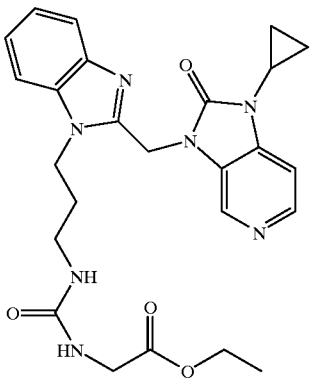

A solution of Example 49 (0.050 g, 0.14 mmol) in chloroform (2 mL) was treated with ethyl isocyanatoacetate (0.018 g, 0.14 mmol) and stirred for 15 minutes at room temperature. The mixture was concentrated in vacuo. The residue was purified by preparative HPLC (gradient, 10% MeOH in H$_2$O with 0.1% TFA to 90% MeOH in H$_2$O with 0.1% TFA) to give 0.08C0 g (96% yield) of the trifluoroacetic acid salt of Example 57 as a glassy, colorless solid.

¹H NMR (DMSO-d$_6$) δ 0.98–1.02 (m, 2 H), 1.13–1.17 (m, 5 H), 1.91–1.97 (m, 2 H), 3.10–3.12 (m, 2 H), 3.15–3.18 (m, 1 H), 3.76 (s, 2 H), 4.04 (q, J=7.1 Hz, 2 H), 4.39 (t, J=7.5 Hz, 2 H), 5.55 (s, 2 H), 6.31 (bs, 1 H), 6.43 (bs, 1 H), 7.23 (t, J =7.6 Hz, 1 H), 7.29–7.33 (m, 1 H), 7.56 (d, J=8.0 Hz, 1 H), 7.66 (d, J=8.1 Hz, 1 H), 7.83 (d, J=6.3 Hz, 1 H), 8.62 (d, J=5.8 Hz, 1 H), 8.83 (s, 1 H); MS m/e 492 (MH⁺).

EXAMPLE 58

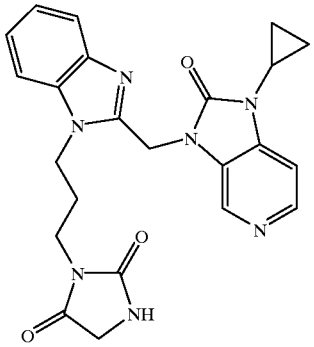

Example 57 (0.061 g, 0.14 mmol) was dissolved in glacial acetic acid (2 mL) and the resulting solution was heated to 120° C. in a sealed tube for several hours. The mixture was concentrated in vacuo and the residue was purified by preparative HPLC (gradient, 10% MeOH in H$_2$O with 0.1% TFA to 90% MeOH in H$_2$O with 0.1% TFA) to give 0.036 g (47% yield) of the trifluoroacetic acid salt of Example 58 as a glassy, colorless solid.

$^1$H NMR (DMSO-d$_6$) δ 0.98–1.01 (m, 2 H), 1.13–1.17 (m, 2 H), 2.01–2.07 (m, 1 H), 3.13–3.18 (m, 2 H), 3.52 (t, J=6.8Hz, 2 H), 3.92 (s, 2 H), 4.38–4.43 (m, 2 H), 5.55 (s, 2 H), 7.24 (t, J=7.6 Hz, 1 H), 7.29–7.33 (m, 1 H), 7.56–7.59 (m, 1 H), 7.67 (d, J=8.0 Hz, 1 H), 7.81–7.83 (m, 1 H), 8.09 (s, 1 H), 8.60–8.62 (m, 1 H), 8.80–8.82 (m, 1 H); MS m/e 446 (MH$^+$).

EXAMPLE 59

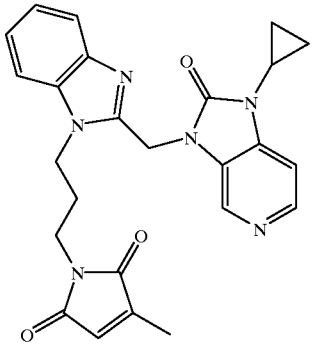

Example 49 (0.050 g, 0.14 mmol) was combined with citraconic anhydride (0.017 g, 0.15 mmol) and glacial acetic acid (2 mL). The resulting mixture was heated to 80° C. for 18 hours and then concentrated in vacuo. Purification by preparative HPLC (gradient, 10% MeOH in H$_2$O with 0.1% TFA to 90% MeOH in H$_2$O with 0.1% TFA) gave 0.052g (66% yield) of the trifluoroacetic acid salt of Example 59 as a glassy, colorless solid.

$^1$H NMR (DMSO-d$_6$) δ 0.97–1.00 (m, 2 H), 1.12–1.16 (m, 2 H), 2.00 (s, 3 H), 2.00–2.06 (m, 2 H), 3.12–3.17 (m, 1 H), 3.56 (t, J=6.8 Hz, 2 H), 4.40 (t, J=7.7 Hz, 2 H), 5.51 (s, 2 H), 6.62–6.63 (m, 1 H), 7.22 (t, J=7.4 Hz, 1 H), 7.29 (t, J=7.3 Hz, 1 H), 7.57 (d, J=8.0 Hz, 1 H), 7.65 (d, J=8.1 Hz, 1 H), 7.80 (d, J=6.2 Hz, 1 H), 8.59 (d, J=4.7 Hz, 1 H), 8.80 (s, 1 H); MS m/e 457 (MH$^+$).

EXAMPLE 60

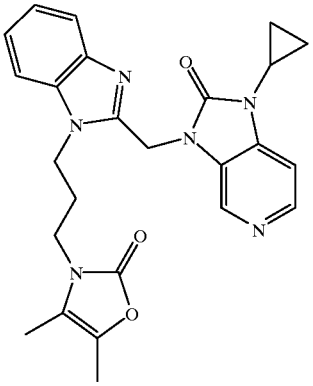

Example 49 (0.050g, 0.14 mmol) was combined with 4,5-dimethyl-1,3-dioxo-2-one (0.016 g, 0.14 mmol), sodium bicarbonate (0.024 g, 0.14 mmol) and anhydrous DMF (2 mL), and the resulting mixture was stirred at room temperature for 18 hours. The mixture was concentrated in vacuo and the residue was purified by preparative HPLC (gradient, 10% MeOH in H$_2$O with 0.1% TFA to 90% MeOH in H$_2$O with 0.1% TFA) to give 0.029 g (37% yield) of the trifluoroacetic acid salt of Example 60 as a glassy, colorless solid.

$^1$H NMR (DMSO-d$_6$) δ 0.98–1.00 (m, 2 H), 1.13–1.17 (m, 2 H), 1.96 (s, 3 H), 2.00 (s, 3 H), 2.06–2.12 (m, 2 H), 3.13–3.18 (m, 1 H), 3.61 (t, J=7.3Hz, 2 H), 4.44 (t, J=77 Hz, 2 H), 5.54 (s, 2 H), 7.22 (t, J=7.3 Hz, 1 H), 7.30 (t, J=7.3 Hz, 1 H), 7.56 (d, J=8.0 Hz, 1 H), 7.64 (d, J=8.1 Hz, 1 H), 7.81 (d, J=6.0 Hz, 1 H), 8.61 (d, J=5.3 Hz, 1 H), 8.81 (s, 1 H); MS m/e 459 (MH$^+$).

EXAMPLE 61

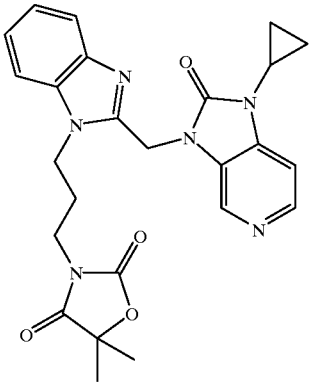

Example 49 (0.050 g, 0.14 mmol) was combined with methyl-2-hydroxyisobutyrate (0.018 g, 0.14 mmol), a catalytic amount of 50% sodium methoxide in MeOH and diethyl carbonate (1 mL) in a sealed tube and the mixture was heated to 175° C. for 18 hours. The mixture was concentrated in vacuo and the residue was purified by preparative HPLC (gradient, 10% MeOH in H$_2$O with 0.1% TFA to 90% MeOH in H$_2$O with 0.1% TFA) to give 0.018 g (21% yield) of the trifluoroacetic acid salt of Example 61 as a glassy, colorless solid.

$^1$H NMR (DMSO-d$_6$) δ 0.99–1.01 (m, 2 H), 1.13–1.15 (m, 2 H), 1.52 (s, 6 H), 2.11 (t, J=7.5 Hz, 2 H), 3.14–3.16 (m, 1

H), 3.60 (t, J=6.9 Hz, 2 H), 4.46 (t, J=7.7 Hz, 2 H), 5.54 (s, 2 H), 7.23 (t, J=7.5 Hz, 1 H), 7.31 (t, J=7.5 Hz, 1 H), 7.58 (d, J=8.0 Hz, 1 H), 7.69 (d, J=8.1 Hz, 1 H), 7.81 (d, J=6.1 Hz, 1 H), 8.61 (s, 1 H), 8.81 (s, 1 H); MS m/e 475 (MH$^+$).

EXAMPLE 62

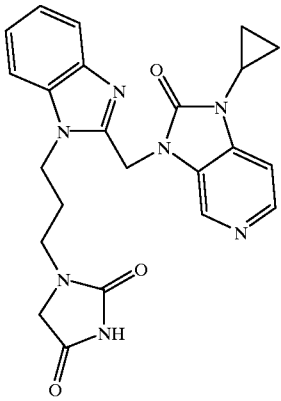

Example 49 (0.050 g, 0.14 mmol) was combined with N-chloroacetyl urethane (0.024 g, 0.14 mmol), sodium bicarbonate (0.023g, 0.28 mmol) and anhydrous acetonitrile (2 mL) in a sealed tube. The mixture was heated to 140° C for 1 hour. The mixture was concentrated in vacuo and the residue was purified by preparative HPLC (gradient, 10% MeOH in H$_2$O with 0.1% TFA to 90% MeOH in H$_2$O with 0.1% TFA) to give 0.030 g (39% yield) of the trifluoroacetic acid salt of Example 62 as a glassy, colorless solid.

$^1$H NMR (DMSO-d$_6$) δ 0.98–1.01 (m, 2 H), 1.13–1.17 (m, 2 H), 2.00–2.06 (m, 2 H), 3.13–3.18 (m, 1 H), 3.41 (t, J=6.8 Hz, 2 H), 4.00 (s, 2 H), 4.41 (t, J=7.7 Hz, 2 H), 5.56 (s, 2 H), 7.22 (t, J=7.6 Hz, 1 H), 7.30 (t, J=7.3 Hz, 1 H), 7.56 (d, J=8.0 Hz, 1 H), 7.71 (d, J=8.1 Hz, 1 H), 7.81 (d, J=6.3 Hz, 1 H), 8.60 (d, J=6.0 Hz, 1 H), 8.80 (s, 1 H), 10.77 (s, 1 H); MS m/e 446 (MH$^+$).

EXAMPLE 63

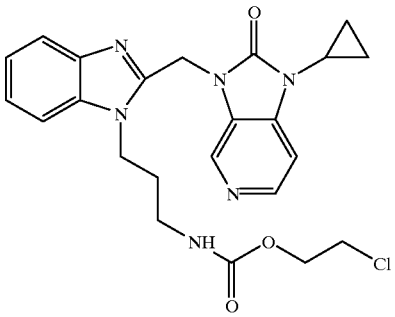

A mixture of Example 49 (100 mg, 0.27 mmol) and 2-bromoethylchloroformate (51.7 mg, 0.27 mmol) was stirred at room temperature for 18 hours. The reaction mixture was filtered to remove inorganic impurities and the solid was washed with MeOH. The MeOH solution was concentrated to give 126 mg (99% yield) of Example 63 as a hygroscopic solid.

$^1$H NMR (DMSO-d$_6$) δ 0.94 (bs, 2 H), 1.10 (d, J=5.4 Hz, 2 H), 1.21 (d, J=6.4 Hz, 2 H), 1.86–1.89 (m, 2 H), 3.09–3.11 (m, 1 H), .3.78–3.80 (m, 1 H), 3.85–3.87 I (m,1H), 4.21–4.23 (m, 2 H), 4.35–4.37 (m, 2 H), 5.43 (s, 2 H), 7.18 (t, J=7.7 Hz, 1 H), 7.25 (t, J=7.5 Hz, 1 H), 7.46–7.50 (m, 2 H), 7.55–7.60 (m, 1 H), 8.37 (d, J=5.0 Hz, 1 H), 8.54 (s, 1 H); MS m/e 469 (MH$^+$).

EXAMPLE 64

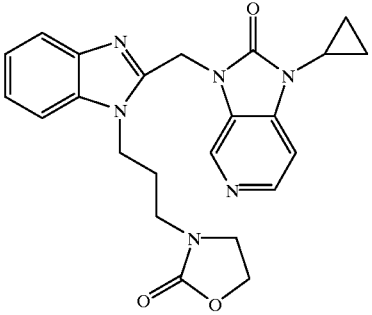

A mixture of Example 63 (70 mg, 0.149 mmol) and lithium bis(trimethylsilyl)amide (0.15 mL, 0.149 mmol) was stirred at reflux in dioxane (15 mL) for 16 hours. The solvent was evaporated and the residue was diluted with EtOAc, washed with H$_2$O, dried over Na$_2$SO$_4$, and evaporated to give 41 mg (63% yield) of Example 64.

$^1$H NMR (DMSO-d$_6$) δ 0.90–0.93 (m, 2 H), 1.01–1 .09 (m, 2 H), 1.92–1.98 (m, 2 H), 2.98–3.03 (m, 1 H), 3.27 (t, J=6.9 Hz, 2 H), 3.55 (t, J=8.1 Hz, 2 H), 4.27 (t, J=7.7 Hz, 2 H), 4.37 (t, J=7.7 Hz, 2 H), 5.40 (s, 2 H), 7.17–7.20 (t, J=7.4 Hz, 1 H), 7.22–7.29 (m, 2 H), 7.56–7.62 (m, 2 H), 8.25 (d, J=5.3 Hz, 1 H), 8.42 (s, 1 H); MS m/e 416 (MH$^+$).

EXAMPLE 65

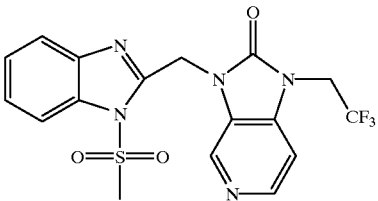

MS m/e 426 (MH$^+$).

EXAMPLE 66

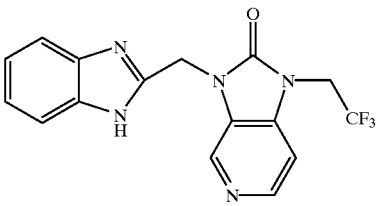

Example 65 was refluxed with hydrazine hydrate (5 mL) in MeOH (10 mL) for 1 hour. The solvent was evaporated and the oily residue was diluted with water and extracted with EtOAc. The combined organic extracts were dried over MgSO$_4$ and evaporated to give 467 mg (29% yield) of Example 665.

$^1$H NMR (DMSO-d$_6$) δ 4.91 (q, J=9.3 Hz, 2 H), 5.38 (s, 2 H), 7.12–7.21 (m, 2 H), 7.44 (d, J=5.3 Hz, 1 H), 7.45–7.50

(m, 1 H), 7.51–7.58 (m, 1 H), 8.32 (d, J 5.3 Hz, 1 H), 8.38 (s, 1 H), 12.60 (s, 1 H); MS m/e 348 (MH⁺).

EXAMPLE 67

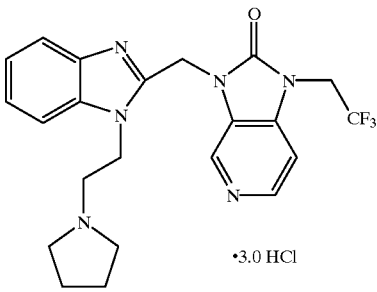

•3.0 HCl

¹H NMR (DMSO-d₆) δ 1.88–2.01 (m, 2 H), 2.01–2.13 (m, 2 H), 3.10–3.22 (m, 2 H), 3.58–3.65 (m, 2 H), 3.70–3.79 (m, 2 H), 4.90–4.99 (m, 2 H), 5.10–5.23 (m, 2 H), 5.95 (s, 2 H), 7.34 (t, J=7.6 Hz, 1 H), 7.43 (t, J=7.6 Hz, 1 H), 7.62 (d, J=8.0 Hz, 1 H), 7.98 (d, J=8.0 Hz, 1 H), 8.08 (d, J=6.1 Hz, 1 H), 8.76 (d, J=6.4 Hz, 1 H), 9.18 (s, 1 H); IR (KBr, cm⁻¹) 3416, 2927, 1754, 1653, 1627, 1518, 1462, 1264, 1168, 1121, 831, 755. MS m/e 445 (MH⁺).

EXAMPLE 68

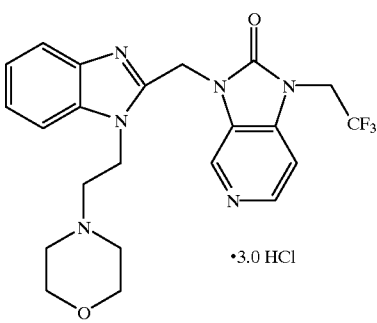

•3.0 HCl

¹H NMR (DMSO-d₆) δ 3.19–3.31 (m, 2 H), 3.56–3.63 (m, 2 H), 3.65–3.74 (m, 2 H), 3.86–3.95 (m, 2 H), 4.00–4.09 (m, 2 H), 5.01 (t, J=7.5 Hz, 2 H), 5.16 (q, J=9.0 Hz, 2 H), 5.93 (s, 2 H), 7.34 (t, J=7.6 Hz, 1 H), 7.43 (t, J=7.6 Hz, 1 H), 7.61 (d, J=8.3 Hz, 1 H), 7.99 (d, J=7.9Hz, 1 H), 8.08 (d, J=6.1 Hz, 1 H), 8.75 (d, J =6.4 Hz, 1 H), 9.18 (s, 1 H); IR (KBr, cm⁻¹) 3430, 1761, 1618, 1517, 1268, 1172, 823, 770; MS m/e 461 (MH⁺).

EXAMPLE 69

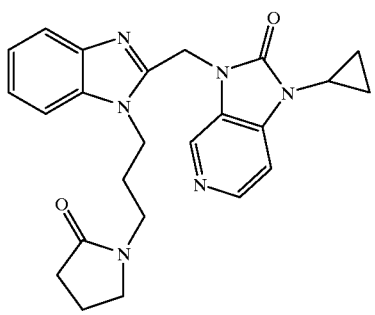

¹H NMR (DMSO-d₆) δ 1.03–1.08 (m, 2 H), 1.12–1.16 (m, 2 H), 2.01–2.17 (m, 2 H), 2.21–2.31 (m, 2 H), 2.31–2.41 (m, 2 H), 3.21–3.35 (m, 3 H), 3.40–50 (m, 1 H), 3.61–3.72 (m, 1 H), 4.45–4.51 (m, 2 H), 5.77(s, 2 H), 7.41–7.48 (m, 2 H), 7.67 (d, J=8.1 Hz, 1 H), 7.85–7.88 (m, 2 H), 8.64 (d, J=6.7 Hz, 1 H), 8.95 (s, 1 H); MS m/e 430 (MH⁺).

EXAMPLE 70

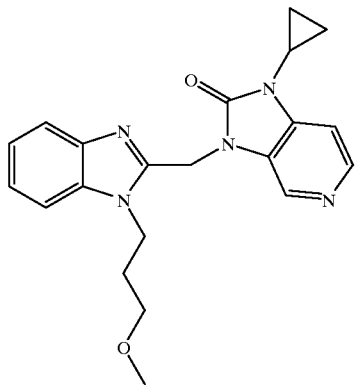

¹H NMR (CDCl₃) δ 1.14 (q, J=7.5 Hz, 2 H), 1.21 (q, J=6.4 Hz, 2 H), 2.20–2.23 (m, 2 H), 3.07 (m, 1 H), 3.38 (s, 3 H), 3.38 (t, J=5.4 Hz, 2 H), 4.56 (t, J=6.5 Hz, 2 H), 5.85 (s, 2 H), 7.40 (t, J=7.6 Hz, 1 H), 7.45 (t, J=7.7 Hz, 11 H), 7.53–7.55 (m, 2 H), 7.88 (d, J=82 Hz, 1 H), 8.38 (d, J=6.3 Hz, 1 H), 8.92 (s, 1 H); MS m/e 378 (MH⁺).

EXAMPLE 71

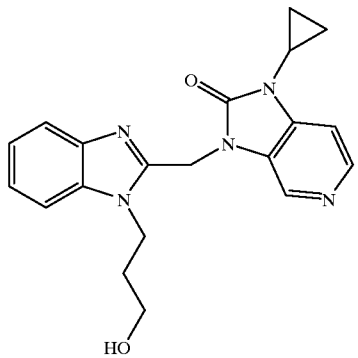

A solution of Example 70 (434 mg, 0.72 mmol) in CH₂Cl₂ (25 ML) was treated with boron tribromide 1 M in CH₂Cl₂, 7.2 mL, 7.2 mmol). The reaction mixture was stirred at room temperature for 40 minutes and then was quenched slowly with anhydrous MeOH. The solvent was evaporated and the residue was diluted with MeOH and evaporated two more times. Purification by flash column chromatography (CH$_2$Cl$_2$/MeOH, 9: 1) gave Example 71.

$^1$H NMR (DMSO-d$_6$) δ 1.07 (d, J=5.6 Hz, 2 H), 1.83 (t, J=6.2 Hz, 2 H), 2.99 (t, J=3.2 Hz, 1 H), 3.17 (d, J=5.0 Hz, 1 H), 3.40 (t, J=5.4 Hz, 2 H), 4.40 (t, J=6.8 Hz, 2 H), 4.75 (t, J=4.6, 1 H), 5.42 (s, 2 H), 7.16 (t, J=7.5 Hz, 1 H), 7.24 (t, J=7.6 Hz, 1 H), 7.29 (d, J=4.8 Hz, 1 H), 7.56 (d, J=8.1 Hz, 2 H), 8.25 (s, 1 H), 8.38 (s, 1 H); MS m/e 364 (MH$^+$).

EXAMPLE 72

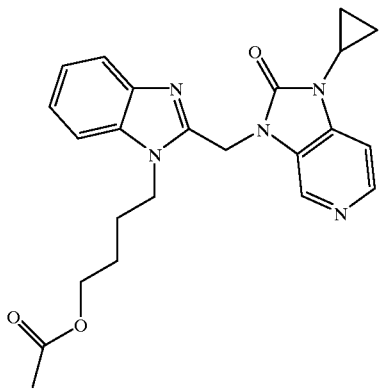

$^1$H NMR (CDCl$_3$) δ 0.99–1.03 (m, 2 H), 1.16–1.20 (m, 2 H), 1.65–1.69 (m,, 2 H), 1.71–1.75 (m, 2 H), 2.00 (s, 3 H), 2.92–2.95 (m, 1 H), 4.03 (t, J=6.2 Hz, 2 H), 4.35 (t, J=7.3 Hz, 2 H), 5.37 (s, 2 H), 7.14 (d, J=5.0 Hz, 1 H), 7.26–7.32 (m, 3 H), 7.56–7.77 (m, 1 H), 8.32 (d, J=5.4 Hz, 1 H), 8.72 (s, 1 H); MS m/e 420 (MH$^+$).

EXAMPLE 73

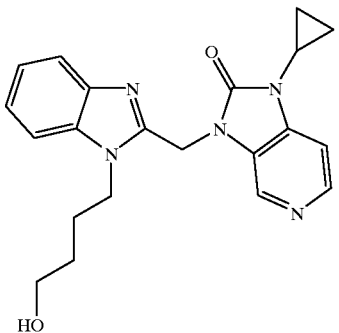

Example 72 (1.0 g, 2.48 mmol) and K$_2$CO$_3$ (1.03 g, 7.44 mmol) were stirred together in MeOH (5 mL) at room temperature for 1.5 hours. The mixture was diluted with H$_2$O and extracted with CH$_2$Cl$_2$ (3×25 mL). The combined extracts were washed with brine, dried over MgSO4, and evaporated. The product was then recrystallized from MeOH to give 650 mg (70% yield) of Example 73. Example 73 was converted to the HCl salt by treating a solution of 73 in MeOH with 4 N HCl in dioxane and then by evaporating the solvent.

$^1$H NMR (DMSO-d$_6$) δ 1.03–1.06 (m, 2 H), 1.12–1.16 (m, 2 H), 1.50–1.56 (m, 2 H), 1.89–1.83 (m, 2 H), 3.13–3.17 (m, 1 H), 3.46 (t, J=6.3 Hz, 2 H), 4.46 (t, J=7.5 Hz, 2 H), 5.70 (s, 2 H), 7.32 (t, J=7.3 Hz, 1 H), 7.39 (t, J=7.5 Hz, 1 H), 7.62 (d, J=8.0 Hz, 1 H), 7.78 (d, J=7.8 Hz, 1 H), 7.81 (d, J=6.4 Hz, 1 H), 8.61 (d, J =6.4 Hz, 1 H), 8.93 (s, 1 H); IR (KBr, cm$^{-1}$) 3350, 2907, 2443, 1736, 1516, 1421, 1172, 825; MS m/e 378 (MH$^+$). Anal. Calcd for C$_{29}$H$_{30}$N$_4$O$_3$•1.25 HCl: C, 59.63; H, 5.78; N, 16.56 Found: C, 59.52; H, 5.88; N, 16.57.

EXAMPLE 74

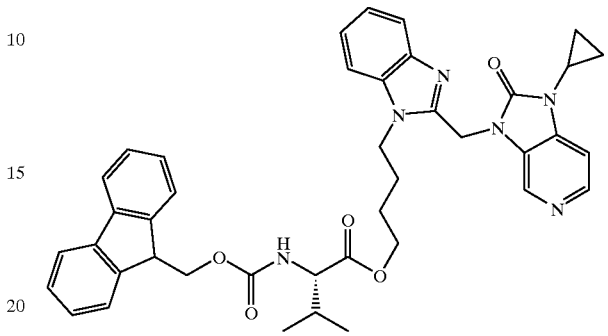

Fmoc-L-valine (0.690 g, 2.00 mmol) was combined with oxalyl chloride (0.508 g, 4.00 mmol) and dichloromethane (10 mL), and the resulting solution was stirred for 2 hours. The mixture was concentrated in vacuo to a yellow oil, which was then combined with Example 73 (0.252 g, 0.667 mmol) in dry CH$_3$CN (15 mL). The resulting mixture was stirred for 72 hours, then was diluted with H$_2$O (5 mL) and was concentrated in vacuo . The mixture was redissolved in EtOAc (50 mL) and the solution was washed successively with saturated aqueous NaHCO$_3$ (3×10 mL) and brine (10 mL). The aqueous extracts were combined and back-extracted with EtOAc. The combined organic extracts were dried over anhydrous MgSO$_4$ and concentrated in vacuo. Purification of the crude material by flash chromatography (CH$_2$Cl$_2$:MeOH, 25:1) gave 410 mg of Example 74 as an off-white solid which was used immediately upon isolation.

EXAMPLE 75

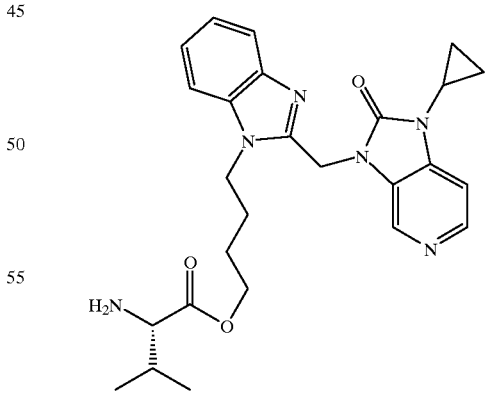

A solution of Example 74 (410 mg) and piperidine (4 ml) in DMF (15 mL) was stirred for 18 hours. The mixture was concentrated in vacuo. The crude solid was redissolved in CH$_2$Cl$_2$ and filtered to remove insolubles. Purification of the crude product by flash chromatography (gradient, CH$_2$Cl$_2$:MeOH, 20:1 to 10:1) gave a 184 mg of an 85:15 mixture of Examples 75 and 7.3. Repurification by preparative HPLC gave 284 mg (52% yield) of pure Example 75 as the tris-trifluoroacetic acid salt.

$^1$H NMR (DMSO) δ 0.93 (d, J=6.9 Hz, 3 H), 0.96 (d, J=6.9 Hz, 3 H), 0.99–1.01 (m, 2 H), 1.13–1.17 (m, 2 H), 1.74–1.78 (m, 2 H), 1.86–1.92 (m, 2 H), 2.11–2.17 (m, 1 H), 3.13–3.17 (m, 1 H), 3.93 (br s, 1 H), 4.20–4.31 (m, 2 11), 4.44 (t, J=7.4 Hz, 2 H), 5.56 (s, 2 H), 7.23 (dd, J=7.5 Hz, 7.5 Hz, 1 H), 7.30 (dd, J=7.5 Hz, 7.5 Hz, 1 H), 7.57 (d, J=8.0 Hz, 1 H), 7.67 (d, J=8.1 Hz, 1 H), 7.82 (d, J=6.3 Hz, 1 H), 8.37 (br s, 2 H), 8.62 (d, J=5.7 Hz, 1 H), 8.83 (s, 1 H); MS m/e 477 (MH$^+$).

EXAMPLE 76

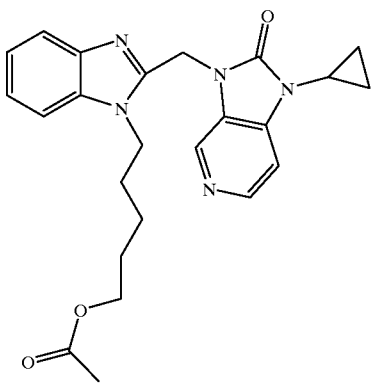

$^1$H NMR (DMSO-d$_6$) δ 0.89–0.93 (m, 2 H), 1.06–1.08 (m, 2 H), 1.31–1.34 (m, 2 H), 1.54–1.58 (m, 2 H), 1.58–1.66 (m, 2 H), 1.98 (s, 3 H), 2.97–3.00 (m, 1 H), 3.96 (t, J=6.6 Hz, 2 H), 4,32 (t, J=7.5 Hz, 1 H), 5.39 (s, 2 H), 7.16 (t, J=7.2 Hz, 1 H), 7.24 (t, J=7.0 Hz, 1 H), 7.29 (d, J=5.0 Hz, 1 H), 7.58 (t, J=7.8 Hz, 2 H), 8.22 (bs, 1 H), 8.42 (bs, 1 H); MS m/e 433 (MH$^+$).

EXAMPLE 77

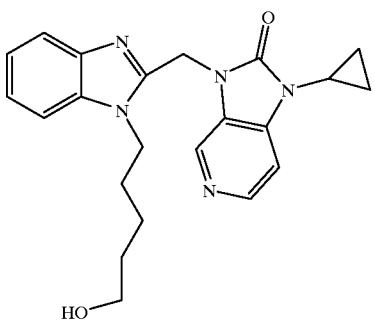

Example 76 (115 mg, 0.27 mmol) in 1 N HCl (20 mL) was heated to reflux for 1 hour then concentrated. The oily residue was triturated with EtOAc/MeOH to give 106 mg (94% yield) of Example 77 106 mg (94% yield) as the HCl salt.

$^1$H NMR (DMSO-d$_6$) δ 1.04–1.10 (m, 2 H), 1.10–1.17 (m, 2 H), 1.42–1.53 (m, 4 H), 1.85–1.91 (m, 2 H), 3.13–3.17 (m, 1 H), 3.40–3.50 (m, 2 H), 4.51 (t, J=7.5 Hz, 2 H), 5.82 (s, 2 H), 7.43–7.46 (m, 1 H), 7.46–7.52 (m, 1 H), 7.69 (d, J=8.0 Hz, 1 H), 7.85 (d, J=6.4 Hz, 1 H), 7.91 (d, J=8.0 Hz, 1 H), 8.64 (d, J=6.4 Hz, 1 H), 8.97 (s, 1 H); MS m/e 391 (MH$^+$).

EXAMPLE 78

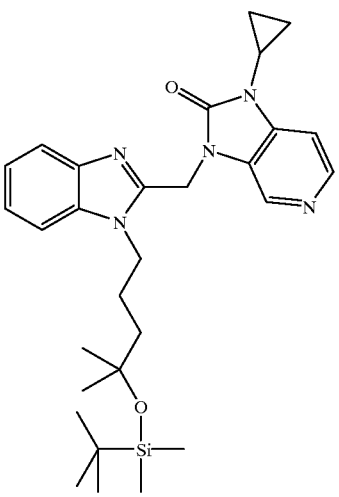

Example 78 was prepared according to the general coupling procedure shown in Scheme I–C and was used immediately upon isolation.

EXAMPLE 79

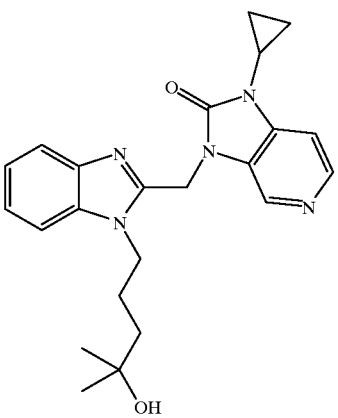

To a solution of Example 79 (86 mg, 0.17 mmol) in THF (3 mL) was added tetrabutylammonium fluoride (TBAF, 1 M in THF, 0.25 mL, 0.25 mmol). The reaction mixture was stirred at room temperature for 18 hours at which time more tetrabutylammonium fluoride (TBAF, 1 M in THF, 0.50 mL, 0.50 mmol) was added and stirring was continued at room temperature for an additional 18 hours. Purification by flash column chromatography (CH$_2$Cl$_2$/MeOH, 9:1) gave Example 79.

$^1$H NMR (CDCl$_3$) δ 0.94–0.97 (m, 2 H), 1.07 (s, 6 H), 1.09–1.11 (m, 2 H), 1.40 (t, J=3.6 Hz, 2 H), 1.67–1.70 (m, 1 H), 2.86–2.87 (m, 1 H), 4.25 (t, J=7.7 Hz, 2 H), 5.31 (s, 2 H), 7.05 (d, J=5.3 Hz, 1 H), 7.18–7.21 (m, 2 H), 7.27 (t,

J=4.6 Hz, 1 H), 7.71 (t, J=4.6 Hz, 1 H), 8.24 (d, J=5.3 Hz, 1 H), 8.65 (s7 1 H); IR (KBr, cm⁻¹) 3373, 2966, 1720, 1609, 1499, 1410, 913, 742; MS m/e 406 (MH⁺).

EXAMPLE 80

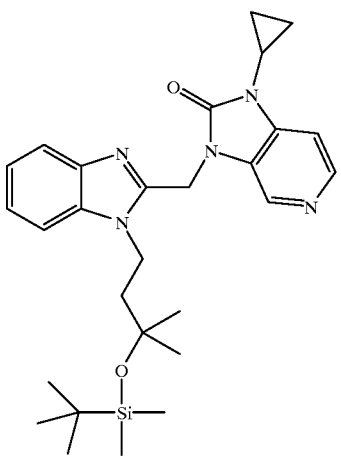

Example 80 was prepared according to the general coupling procedure shown in Scheme I–C and was used immediately upon isolation.

EXAMPLE 81

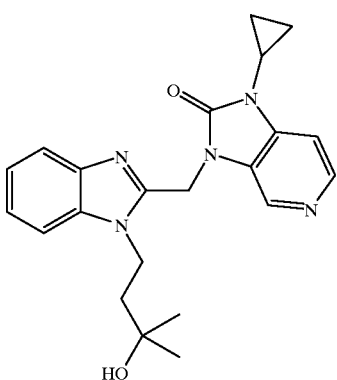

Example 81 was prepared according to the same deprotection procedure as Example 79 from Example 80.

$^1$H NMR (CDCl$_3$) δ 1.02–1.04 (m, 2 H), 1.16 (q, J=6.9 Hz, 2 HI), 1.32 (s, 6 H), 1.81 (t, J=3.2 Hz, H), 2.49 (s, 1 H), 2.93 (m, 1 H), 4.45 (t, J=3.4 Hz, 2 H), 5.41 (s, 2 H), 7.14 (d, J=5.25 Hz, 1 H), 7.27–7.30 (m, 2 H), 7.33 (d(1, J=2.5, 3.5 Hz, 1 H), 7.77 (dd, J=2.9, 3.1 Hz, 1 H), 8.34 (d, J=5.3, 1 H), 8.77 (s, 1 H); MS m/e 392 (MH⁺).

EXAMPLE 82

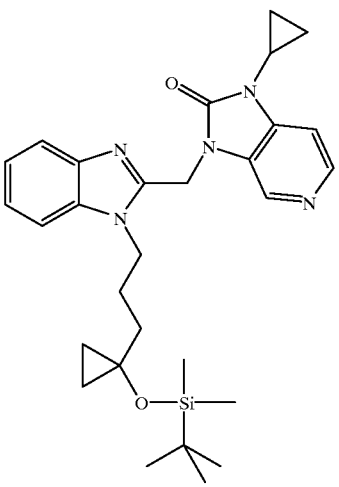

$^1$H NMR (CDCl$_3$) δ 0.03 (s, 6 H), 0.80–0.86 (m, 2 H), 0.89 (s, 9 H), 1.00–1.02 (m, 2 H), 1.15–1.17 (m, 2 H), 1.48–1.51 (m, 2 H), 1.77–1.86 (m, 2 H), 2.05 (t, J=7.4 Hz, 2 H), 2.89–2.97 (m, 1 H), 4.29 (t, J=7.4 Hz, 2 H), 5.35 (s, 2 H), 7.10 (d, J=5.2 Hz, 1 H), 7.24–7.26 (m, 2 H), 7.31–7.33 (m, 1 H), 7.74–7.77 (m, 1 H), 8.31 (d, J=5.2 Hz, 1 H), 8.69 (s, 1 H); MS m/e 518 (MH⁺).

EXAMPLE 83

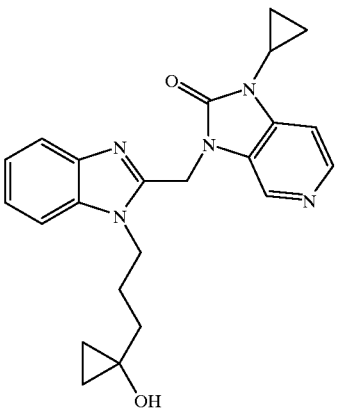

Example 83 was prepared from Example 82 according to the same deprotection procedure described for Example 79.

$^1$H NMR (DMSO-d$_6$) δ 0.91–1.05 (m, 4 H), 1.13–1.22 (m, 2 H), 1.77–1.84 (m, 2 H), 2.27 (q, J=7.4 Hz, 2 H), 2.39 (t=6.8 Hz, 2 H), 2.89–2.95 (m, 1 H), 4.23 (t, J =7.7Hz, 2 H), 5.27 (s, 2 H), 7.03 (d, J=5.1 Hz, 1 H), 7.24–7.31 (m, 2 H), 7.34 (dd, J=1.9, 6.4 Hz, 1 H), 7.66 (dd, J=1.4, 7.1 Hz, 1 H), 8.23 (d, J=5.2 Hz, I H), 8.60 (s, 1 H); IR (KBr, cm⁻¹) 3392, 2938, 1721, 1609, 1499, 1410, 913, 743; MS m/e 404 (MH⁺).

EXAMPLE 84

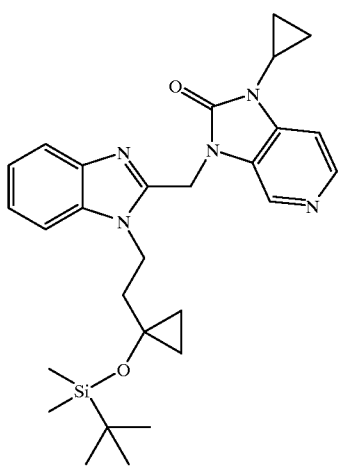

$^1$H NMR (CDCl$_3$) δ 0.05 (t, J=5.8 Hz, 2 H), 0.14 (s, 6 H), 0.63 (t, J=6.1 Hz, 2 H), 0.90 (s, 9 H), 1.00–1.03 (m, 2 H), 1.13–1.17 (m, 2 H), 1.86 (t, J=6.6 Hz, 2 H), 2.89–2.92 (m, 1 H), 4.61 (t, J=6.6 Hz, 2 H), 5.42 (s, 2 H), 7.12 (d, J=4.9 Hz, 1 H), 7.22–7.24 (m, 2 H), 7.38–7.40 (m, 1 H), 7.72–7.74 (m, 1 H), 8.32 (d, J=5.5 Hz, 1 H), 8.66 (s, 1 H); MS m/e 504 (MH$^+$).

EXAMPLE 85

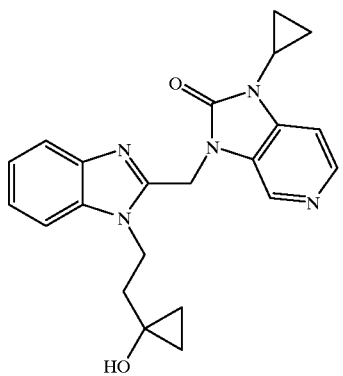

Example 85 was prepared from Example 84 according to the same deprotection procedure described for Example 79.

$^1$H NMR (DMSO-d$_6$) δ 0.10 (q, J=4.8 Hz, 2 H), 0.49 (q, J=4.91 Hz, 2 H), 0.90–0.94 (m, 2 H), 1.04–1.07 (m, 2 H), 1.85 (t, J=7.0 Hz, 2 H), 2.99 (m, 1 H), 4.54 (t, J=7.0 Hz, 2 H), 5. 42 (s, 1 H), 5.46 (s, 2 H), 7.16 (dt, J=1.0, 7.6 Hz, 1 H), 7.23 (dt, J=1.0, 7.6 Hz, 1 H), 7.28 (d, J=5.2 Hz, 1 H), 7.54 (dd, J=8.0, 23.0 Hz, 2 H), 8.25 (d, J=5.25 Hz. 1 H), 8.39 (s, 1 H); MS m/e 390 (MH$^+$).

EXAMPLE 86

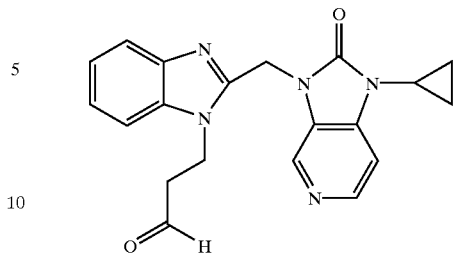

To a solution of oxalyl chloride (326 mg, 2.57 mmol) in, CH$_2$Cl$_2$ (5 mL) cooled to −78° C. with a dry ice/acetone bath was added a solution of DMSO (268 mg, 3.42 mmol) in CH$_2$Cl$_2$ (10 mL) slowly over 15 minutes. After stirring for 10 minutes, a solution of Example 71 (622 mg, 1.71 mmol) in CH$_2$Cl$_2$ (5 mL) was slowly added to the reaction mixture. The reaction was monitored for completion by thin layer chromatography and LC/MS. The solution became cloudy upon completion and the reaction was quenched at 31 78° C. by adding triethylamine (693 mg, 6.85 mmol). The solution became clear and was then warmed to room temperature. The reaction mixture was diluted with more CH$_2$Cl$_2$, washed with water and brine, dried over MgSO$_4$, and evaporated. Purification by flash column chromatography (gradient, EtOAc/MeOH, 10:1 to 3:1) gave 185 mg (19% yield) of Example 86 which was used immediately upon isolation.

EXAMPLE 87

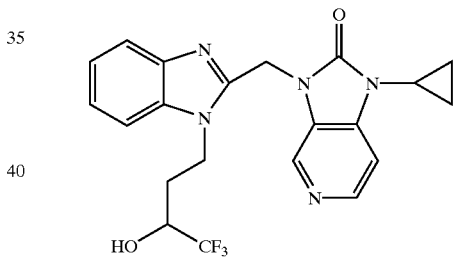

Example 87 was prepared according to the procedure described in *J. Med. Chem.*, 1996, 39, 2411–2421 by Yu, K.-L. et al. using aldehyde :86:

A fresh solution of anhydrous 1 M tetrabutylammonium fluoride in THF was prepared according to the procedure described by Cox et al in *J. Organic Chemistry*, 1984, 49, 3219–3220.

To a solution of Example 86 (150 mg, 0.42 mmol) in TIFF (10 mL) was added trimethyl(trifluoromethyl) silane (0.5M in THF, 1.25 mL, 0.62 mmol) followed by a catalytic amount of tetrabutylammonium fluoride (TBAF, 1M in THF, 8 μL) at 0° C. The reaction mixture was stirred at 0° C. for 1.5 hours and then warmed to room temperature. Additional trimethyl(triflucoromethyl) silane (0.5M in THF, 1.05 mL, 0.53 mmol) and TBAF (1M in THF, 8 μL) were added to push the reaction toward completion. The reaction was quenched with excess TBAF (1M in THF, 2.88 mL, 2.88 mmol) and the reaction mixture was allowed to stir for 18 hours. The solvent was evaporated and the residue was purified by flash column chromatography (gradient, straight EtOAc to EtOAc/MeOH, 5:1) to give 106 mg (59% yield) of Example 87.

¹H NMR (CD₃OD) δ 0.98–1.07 (m, 2 H), 1.08–1.16 (m, 1 H), 1.89–1.97 (m, 1 H), 2.08–2.14 (m, 1 H), 2.99–3.04 (m, 2 H), 3.91–3.95 (m, 1 H), 4.53–4.63 (m, 2 H), 5.46–5.55 (m, 2 H), 7.25–7.28 (m, 1 H), 7.33 (dt, J=0.9, 7.8 Hz, 1 H), 7.40 (d, J 5.5 Hz, 1 H), 7.58 (d, J=8.1 Hz, 2 H), 8.26 (d, J=5.4 Hz, 1 H), 8.30 (s, 1 H); IR (KBr, cm⁻¹) 3422, 1723, 1613, 1504, 1412, 1173, 1131, 745; MS m/e 432 (MH⁺).

EXAMPLE 88

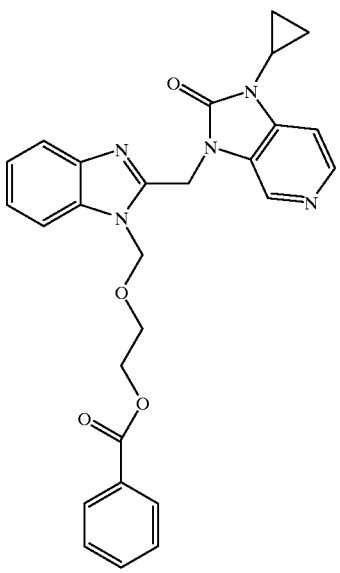

¹H NMR (CDCl₃) δ 0.92–0.95 (m, 2 H), 1.03–1.07 (m, 2 H), 2.81–2.85 (m, 1 H), 3.53 (t, J=4.8 Hz, 2 H), 4.07 (t, J=4.8 Hz, 2 H), 5.36 (s, 2 H), 5.69 (s, 2 H), 7.04 (d, J=5.5 Hz, 1 H), 7.19–7.23 (m, 3 H), 7.33–7.39 (m, 3 H), 7.48–7.51 (m, 1 H), 7.70–7.72 (m, 1 H), 7.86 (d, J=8.3 Hz, 1 H), 8.22 (d, J=5.2 Hz, 1 H), 8.52 (s, 1 H); MS m/e 484 (MH⁺).

EXAMPLE 89

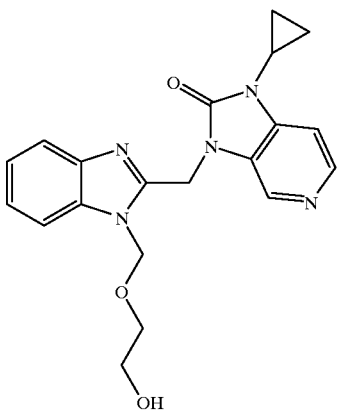

To a solution of Example 88 (30.5 mg, 0.06 mmol) in MeOH (1 mL) was added ammonia (2 M in MeOH, 1 mL). The reaction mixture was stirred at room temperature for 16 hours. The solvent was concentrated. Purification by preparative HPLC (gradient, 10% MeOH in H₂O with 0.1% TFA to 90% MeOH in H₂O with 0.1% TFA) followed by treatment with excess 4 N HCl in dioxane gave Example 89 as the HCl salt.

¹H NMR (CD₃OD) δ1.11–1.17 (m, 2 H), 1.21–1.26 (m, 2 H), 3.13–3.20 (m, 1 H), 3.59–3.66 (m, 2 H), 3.72–3.77 (m, 2 H), 5.98 (s, 2 H), 6.11 (s, 2 H), 7.62 (t, J7.4 Hz, 1 H), 7.66 (t, J=7.6 Hz, 1 H), 7.78 (d, J=8.0 Hz, 1 H), 7.92 (d, J=4.2 Hz, 1 H), 8.04 (d, J=8.0 Hz, 1 H), 8.58 (d, J=3.9 Hz, 1 H), 8.89 (s, 1 H); MS m/e 380 (MH⁺).

EXAMPLE 90

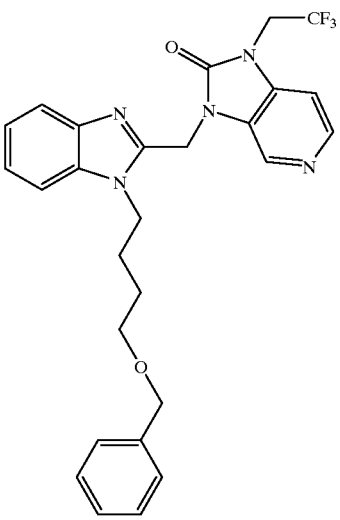

MS m/e 510 (MH⁺).

EXAMPLE 91

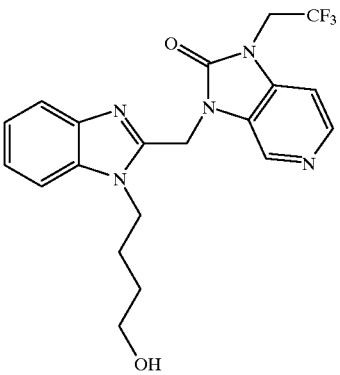

Example 91 was prepared from Example 90 according to the same procedure described for Example 71.

¹H NMR (DMSO-d₆) δ 1.53–1.59 (m, 2 H), 1.87–1.92 (m, 2 H), 3.47 (t, J=6.4 Hz, 2 H), 4.54 (t, J=7.6 Hz, 2 H), 5.17 (q, J=9.0 Hz, 2 H), 5.89 (s, 2 H), 7.44 (t, J=7.6 Hz, 1 H), 7.51 (t, J=7.6 Hz, 1 H), 7.70 (d, J=8.1 Hz, 1 H), 7.91 (d, J=8.2 Hz, 1 H), 8.10 (d, J=6.4 Hz, 1 H), 8.80 (d, J=6.5 Hz, 1 H), 9.11 (s, 1 H). MS m/e 420 (MH⁺).

EXAMPLE 92

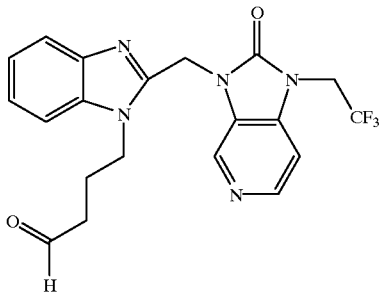

Example 92 was prepared from Example 91 according to the same procedure described for Example 86.

¹H NMR (CDCl₃) δ 1.94–1.99 (m, 2 H), 2.59 (t, J=6.7Hz, 2 H), 4.31–4.35 (m, 2 H), 4.53 (q, J=8.5 Hz, 2 H), 5.46 (s, 2 H), 7.07 (d, J=6.4 Hz, 1 H), 7.27–7.34 (m, 2 H), 7.44 (d, J=7.5 Hz, 1 H), 8.78 (dd, J=0.9, 7.2 Hz, 1 H), 8.39 (d, J=5.4 Hz, 1 H), 8.85 (s, 1 H), 9.78 (s, 1 H); MS m/e 418 (MH⁺).

EXAMPLE 93

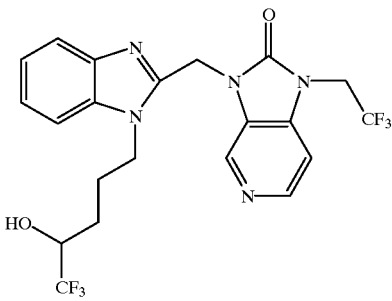

Example 93 was prepared from Example 92 according to the same procedure described for Example 87.

¹H NMR (CD₃OD) δ 1.60–1.73 (m, 1 H), 1.78–1.90 (m, 1 H), 2.00–2.14 (m, 2 H), 3.96–4.01 (m, 1 H), 4.53 (t, J=7.8 Hz, 2 H), 4.94 (q, J=8.9 Hz, 2 H), 5.69 (s, 2 H), 7.34–7.44 (m, 2 H), 7.60 (d, J=7.8 Hz, 1 H), 7.68 (d, J=7.5 Hz, 1 H), 7.92 (d, J=6.3 Hz, 1 H), 8.60 (d, J=5.7 Hz, 1 H), 8.82 (s, 1 H); MS m/e 488 (MH⁺).

EXAMPLE 94

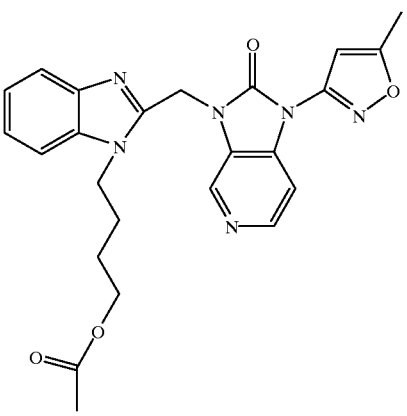

¹H NMR (CDCl₃) δ 1.68–1.73 (m, 2 H), 1.74–1.80 m, 2 H), 1.99 (s, 3 H), 2.54 (s, 3 H), 4.04–6.3 Hz, 2 H), 4.35 (t, J=7.5 Hz, 2 H), 5.48 (s, 2 H), 6.97 (s, I H), 7.27–7.35 (m, 3 H), 7.78–7.80 (m, 1 H), 8.00 (d, 3J=5.4 Hz, 1 H), 8.46 (d, 3J 5.4 Hz, 1 H), 8.86 (s, 1 H); IR (KBr, cm⁻¹) 3421, 1727, 1599, 1527, 1484, 1457, 1257, 751; MS m/e 461 (MH⁺); Anal. Calcd for C₂₄H₂₄N₆O₄·2.0 H₂O: C, 58.06; H, 5.68; N, 16.93. Found: C, 58.36; H, 5.55; N, 16.97.

EXAMPLE 95

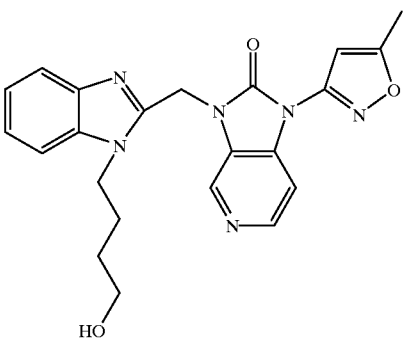

Example 95 was prepared from Example 94 according to the same procedure described for Example 73.

¹H NMR (CDCl₃) δ 1.60–1.66 (m, 2 H), 1.79–1.85 (m, 2 H), 3.65 (t, J=6.1 Hz, 2 H), 4.35 (t, J=7.9 Hz, 2 H), 5.50 (s, 2 H), 6.95 (s, 1 H), 7.28–7.36 (m, 3 H), 7.77–7.79 (m, 1 H), 8.00 (d, J=5.4 Hz, 1 H), 8.45 (d, J=5.4 Hz, 1 H), 8.87 (s, 1 H); IR (KBr, cm⁻¹) 3309, 1728, 1602, 1528, 1483, 1452, 1385, 1171, 827, 739; MS m/e 419 (MH⁺).

EXAMPLE 96

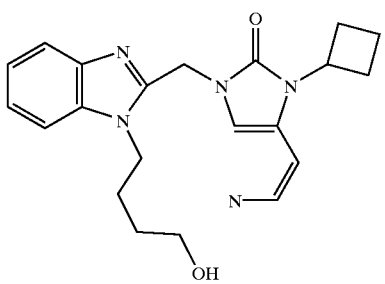

Example 96 was prepared via synthesis of the acetate intermediate according to the same procedure described for Example 72 followed immediately by deprotection of the alcohol according to the same procedure described for Example 73.

$^1$H NMR (CDCl$_3$) δ 1.61–1.67 (m, 2 H), 1.79–1.85 (m, 2 H), 1.90–2.05 (m, 2 H), 2.43–2.49 (m, 2 H), 2.81–2.89 (m, 2 H), 3.68 (t, J=6.0 Hz, 2 H), 4.34 (t, J=7.8 Hz, 2 H), 4.85–4.92 (m, 1 H), 5.43 (s, 2 H), 7.22–7.35 (m, 4 H), 7.75–7.77 (m, 1 H), 8.33 (d, J=5.5 Hz, 1 H), 8.82 (s, 1 H); MS m/e 392 (MH$^+$); Anal. Calcd for C$_{22}$H$_{25}$N$_5$O$_2$•0.5 H$_2$O: C, 65.98; H, 6.54; N, 17.49 Found: C, 65.71; H, 6.62; N, 17.37.

EXAMPLE 97

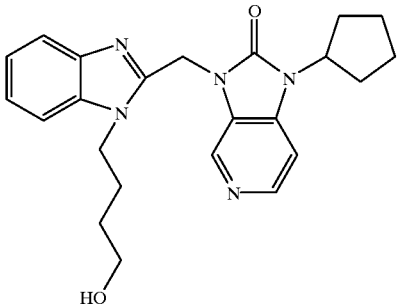

Example 97 was prepared via synthesis of the acetate intermediate according to the same procedure described for Example 72 followed immediately by deprotection of the alcohol according to the same procedure described for Example 73.

$^1$H NMR (CDCl$_3$) δ 1.61–1.67 (m, 2 H), 1.75–1.83 (m, 4 H), 1.95–2.02 (mi, 2 H), 2.05–2.11 (m, 4 H), 3.68 (t, J=6.0 Hz, 2 H), 4.35 (t, J=7.9 Hz, 2 H), 4.82–4.89 (mi, 1 H), 5.43 (s, 2 H), 7.04 (d, J=5.5 Hz, 1 H), 7.22–7.30 (m, 2 H), 7.32–7.35 (m, 1 H), 7.76–7.78 (mi, 1 H), 8.30 (d, J=5.5 Hz, 1 H), 8.82 (s, 1 H); IR (KBr, cm$^{-1}$) 3272, 2945, 2870, 1710, 1607, 1496, 1395, 742; MS m/e 406 (MH$^+$); Anal. Calcd for C$_{23}$H$_{28}$N$_5$O$_2$: C, 67.95; H, 6.94; N, 17.22 Found: C, 67.78; H, 6.72; N, 16.92.

EXAMPLE 98

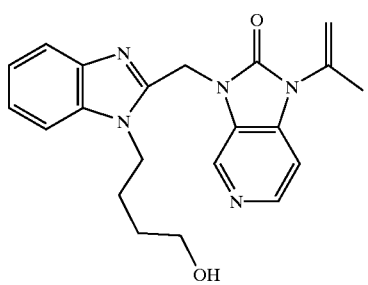

Example 98 was prepared via synthesis of the acetate intermediate according to the same procedure described for Example 72 followed immediately by deprotection of the alcohol according to the same procedure described for Example 73.

$^1$H NMR (DMSO-d$_6$) δ 1.43–1.48 (m, 2 H), 1.66–1.69 (m, 2 H), 2.18 (s, 3 H), 3.37–3.41 (m, 2 H), 4.35 (t, J=7.3 Hz, 2 H), 4.47 (t, J=5.1 Hz, 1 H), 5.25 (s, 1 H), 5.44 (s, 2 H), 5.46 (d, J=1.0 Hz, 1 H), 7.17–7.27 (m, 3 H), 7.57–7.60 (m, 2 H), 8.25 (d, J=5.2 Hz, 1 H), 8.48 (s, 1 H); MS m/e 378 (MH$^+$).

EXAMPLE 99

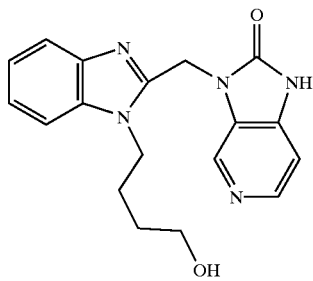

Example 99 was prepared from Example 98 according to the same procedure described for Example 17.

$^1$H NMR (DMSO-d$_6$) δ 1.44–1.48 (m, 2 H), 1.65–1.68 (m, 2 H), 3.38–3.42 (m, 2 H), 4.34 (t, J=7.5 Hz, 2 H), 4.47 (t, J=5.1 Hz, 1H), 5.38 (s, 1 H), 7.07 (d, J=5.2 Hz, 1 H), 7.19 (t, J=7.0 Hz, 1 H), 7.23 (t, J=7.0 Hz, 1 H), 7.57 (t, J=8.0 Hz, 1 H), 8.15 (d, J=5.1 Hz, 1 H), 8.34 (s, 1 H), 11.59 (s, 1 H); MS m/e 338 (MH$^+$).

EXAMPLE 100

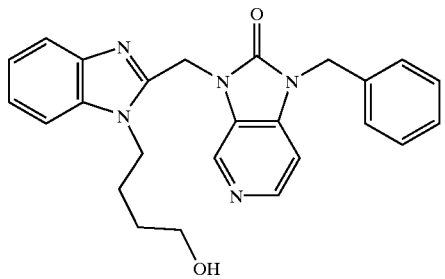

$^1$H NMR (CD$_3$OD) δ 1.54–1.60 (m, 2 H), 1.86–1.92 (m, 2 H), 3.52 (t, J=6.2 Hz, 2 H), 4.45 (t, J=7.7 Hz, 2 H), 5.20 (s, 1 H), 5.65 (d, J=6.8 Hz, 2 H), 7.21–7.32 (m, 4 H), 7.34–7.37 (m, 3 H), 7.52–7.55 (m, 1 H), 7.63 (t, J=8.4 Hz, 1 H), 8.37 (d, J=6.5 Hz, 1 H), 8.68 (s, 1 H); MS m/e 428 (MH$^+$).

EXAMPLE 101

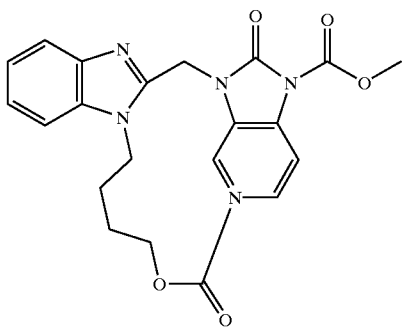

To a solution of Example 99 (34 mg, 0.1 mmol) and 4-dimethylaminopyridine (DMAP, 2.0 mg, 0.02 mmol) in pyridine (1 ml) was added acetic anhydride (22 mg, 0.22 mmol) at room temperature. After stirring for 12 hours, the reaction mixture was diluted with EtOAc (10 ml) and washed twice with $H_2O$ and brine. The combined organic extracts were dried over $MgSO_4$, and concentrated. The residue was purified by flash column chromatagraphy ($CH_2Cl_2$/MeOH, 20:1) to yield 35 mg (82%yield) of Example 101 as a white solid.

$^1$H NMR (CDCl$_3$) δ 1.69–1.82 (m, 4 H), 2.00 (s, 3 H), 2.80 (s, 3 H), 4.06 (t, J=6.2 Hz, 2 H), 4.34 (t, J=6.6 Hz, 2 H), 5.39 (s, 2 H), 7.26–7.32 (m, 3 H), 7.75–7.78 (m, 1 H), 8.03 (d, J=5.1 Hz, 1 H), 8.42 (d, J=3.2 Hz, 1 H), 8.82 (s, 1 H); MS m/e 422 (MH$^+$).

EXAMPLE 102

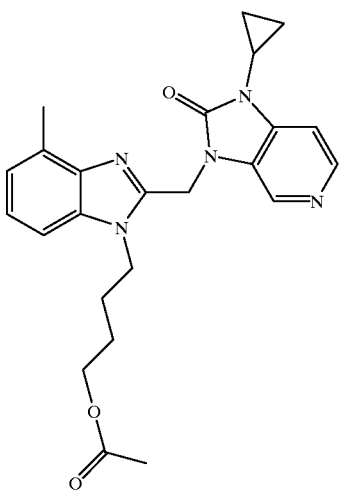

$^1$H NMR (DMSO-d$_6$) δ 0.64–0.68 (m, 2 H), 0.81–0.86 (m, 2 H), 1.28–1.37 (m, 4 1 5 H), 1.72 (s, 3 H), 2.27 (s, 3 H), 2.73–2.77 (m, 1 H), 3.72 (t, J=6.2 Hz, 2 H), 4.07 (t, J=7.1 Hz, 2 H), 5.14 (s, 2 H), 6.76 (d, J=7.3 Hz, 1 H), 6.90 (t, J=7.7 Hz, I H), 7.03 (d, J=5.25 Hz, 1 H), 7.13 (d, J=8.1 Hz, 1 H), 8.00 (d, J=5.25 Hz, I H), 8.23 (s, 1 H); MS m/e 434 (MH$^+$).

EXAMPLE 103

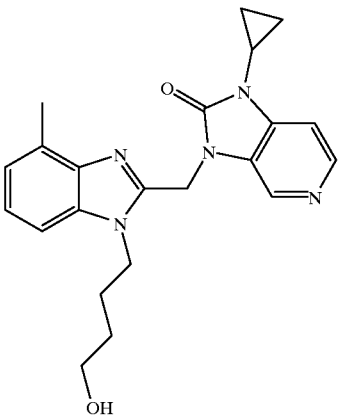

Example 103 was prepared from Example 102 according to the same procedure described for Example 73.

$^1$H NMR (DMSO-d$_6$) δ 0.90–0.95 (m, 2 H), 1.05–1.10 (m, 2 H), 1.35–1.41 (m, 2 H), 1.50–1.55 (m, 2 H), 2.51 (s, 3 H), 2.97–3.00 (m, 1 H), 4.27 (t, J=7.5 Hz, 2 H), 4.43 (t, J=5.0Hz, 2 H), 5.38 (s, 2 H), 7.00 (d, J=7.2Hz, 1 H), 7.13 (t, J=7.7 Hz, 1 H), 7.27 (d, J=5.2 Hz, 1 H), 7.34 (d, J=8.1 Hz, 1 H), 8.23 (d, J=5.2 Hz, 1 H), 8.45 (s, 1 H); MS m/e 392 (MH$^+$).

EXAMPLE 104

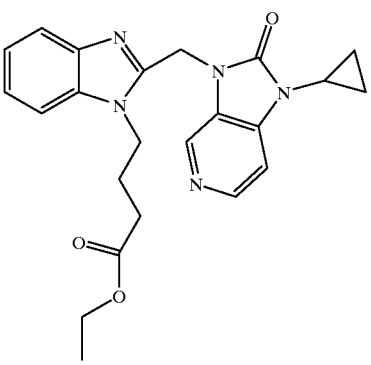

$^1$H NMR (CDCl$_3$) δ 1.00–1.02 (m, 2 H), 1.14–1.18 (m, 2 H), 1.22 (t, J=7.1 Hz, 3 H), 2.38 (t, J=7.15 Hz, 2 H), 2.91–2.96 (m, 1 H), 4.10 (q, J=7.2Hz, 2 H), 4.38 (t, J=7.6 Hz, 2 H), 5.37 (s, 2 H), 7.16 (d, J=5.4 Hz, 1 H), 7.24–7.30 (m, 4 H), 7.39 (d, J=6.6 Hz, 1 H), 7.75 (d, J=7.0 Hz, 1 H), 8.33 (d, J=5.3 Hz, 1 H), 8.71 (s, 1 H); MS m/e 419 (MH$^+$).

EXAMPLE 105

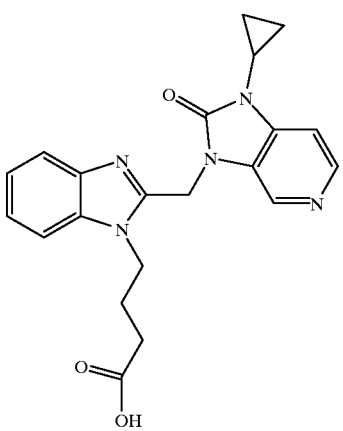

A mixture of Example 104 (346 mg, 0.83 mmol) and aqueous sodium hydroxide (1N, 4.1 mL, 4.13 mmol) were stirred in MeOH (5 mL) for 14 hours at room temperature. The mixture was neutralized with HCl followed by flash column chromatography to give Example 105.

$^1$H NMR (CDCl$_3$) δ 1.13–1.16 (m, 2 H), 1.22–1.25 (m, 2 H), 2.36–2.41 (m, 4 H), 3.09–3.12 (m, 1 H), 4.56 (t, J=6.6 Hz, 2 H), 5.91 (s, 2 H), 7.47–7.57 (m, 4 H), 7.93 (d, J=7.6 Hz, 1 H), 8.37 (d, J=6.4 Hz, 1 H), 9.17 (s, 1 H); MS m/e 392 (MH$^+$).

EXAMPLE 106

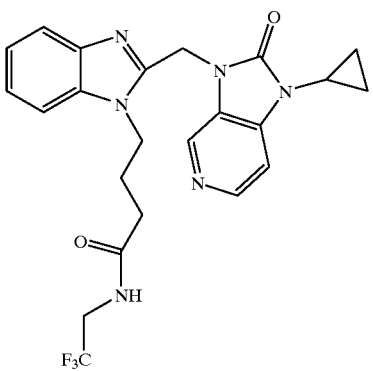

A solution of Example 105 (0.23 g, 0.50 mmol), 1-hydroxybenzotriazole hydrate (HOBT, 75 mg, 0.54 mmol), trifluoroethylamine hydrocloride (75 mg, 0.54 mmol), and N-methylmorpholine (0.21 g, 2.16 mmol) was stirred at room temperature for 30 minutes until a homogeneous solution resulted. 1-[3-(Dimethylamino)propyl]-3-ethylcarbodiimide hydrochloride (EDAC ,103 mg, 0.54 mmol) was added and the mixture was stirred for 12 hours. The solution was concentrated and the residue dissolved in EtOAc and washed with water and saturated NaHCO$_3$, dried over MgSO$_4$ and concentrated to give 35 mg (18% yield) of Example 106 as a white solid.

$^1$H NMR (DMSO-d$_6$) δ 0.89–0.93 (m, 2 H), 1.06–1.08 (m, 2 H), 1.86–1.89 (m, 2 H), 2.27–2.30 (m, 2 H), 2.98–3.00 (m, 1 H), 4.31–4.34 (m, 2 H), 5.40 (s, 2 H), 7.18–7.23 (m, 1 H), 7.25–7.29 (m, 2 H), 7.57–7.58 (m, 2 H) 8.25–8.26 (m, 1 H) 8.41 (s, 1 H), 8.57–8.60 (m, 1 H); MS m/e 472 (MH$^+$).

EXAMPLE 107

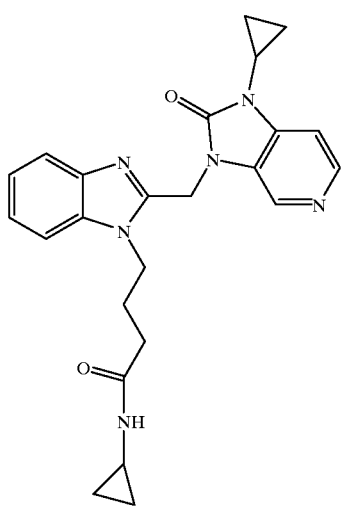

Example 104 (100 mg, 0.24 mmol) in neat cyclopropylamine (1.22 g, 21.40 mmol) was heated at 105° C. in a sealed tube for 18 hours. The reaction mixture was concentrated and the residue was purified by flash column chromatography to give Example 107.

$^1$H NMR (CDCl$_3$) δ 0.45–0.48 (m, 2 H), 0.74–0.78 (m, 2 H), 0.98–1.03 (m, 2 H), 1.14–1.18 (m, 2 H), 1.99–2.04 (m, 2 H), 2.20 (t, J=6.9Hz, 2 H), 2.67–2.70 (m, 1 H), 2.92–2.96 (m, 1 H), 4.37 (t, J=7.6 Hz, 2 H), 5.36 (s, 2 H), 7.14 (d, J=5.2 Hz, 1 H0, 7.24–7.29 (m, 2 H), 7.44 (d, J=7.0 Hz, 1 H), 7.75 (d, J=7.4 Hz, 1 H), 8.34 (d, J=5.2 Hz, 1 H), 8.70 (s, 1 H); MS m/e 431 (MH$^+$).

EXAMPLE 108

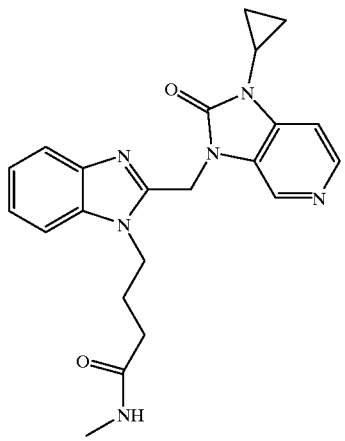

Example 104 (52 mg, 0.12 mmol) in methylamine (40% aqueous solution, 4 mL) was heated at 120° C. in a sealed tube for 18 hours. The solvent was evaporated and the residue purified by flash column chromatography to give Example 108 as a 2:1 mixture of cis/trans rotomers.

$^1$H NMR (CDCl$_3$) δ 0.96–1.00 (m, 2 H), 1.08–1.14 (m, 2 H), 1.94–2.02 (m, 2 H), 2.19–2.23 (m, 2 H), 2.75 (d, J=6.0 Hz, 3 H), 2.88–2.92 (m, 1 H), 4.29–4.36 (m, 2 H), 5.33, 5.34 (s, 2 H), 7.07, 7.10 (d, J6.5 Hz, 1 H), 7.11–7.27 (m, 2 H), 7.66–7.71 (m, 1 H), 8.25, 8.28 (d, J=6.7 Hz, 1 H), 8.57, 8.63 (s, 1 H); MS m/e 405 (MH$^+$).

EXAMPLE 109

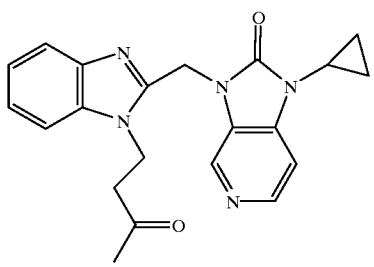

A mixture of Example 47 (500 mg, 1.64 mmol) and methyl vinyl ketone (574 mg, 8.2 mmol) in EtOH (10 ml) was heated to reflux for 8 hours. After cooling, the solid was collected by filtration to give 378 mg (61%) of Example 109 as a white solid.

$^1$H NMR (CDCl$_3$) δ 1.01–1.05 (m, 2 H), 1.15–1.19 (m, 2 H), 2.10 (s, 3 H), 2.91–2.96 (m, 3 H), 4.60 (t, J=6.4 Hz, 2 H), 5.53 (s, 2 H), 7.17 (d, J=5.4 Hz, 1 H), 7.24–7.30 (m, 2 H), 7.32–7.34 (m, 1 H), 7.73–7.75 (m, 1 H), 8.34 (d, J=5.4 Hz, 1 H), 8.69 (s, 1 H); MS m/e 376 (MH$^+$).

EXAMPLE 110

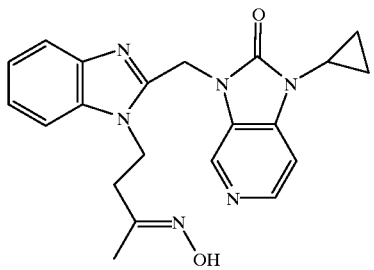

A mixture of Example 109 (37 mg, 0.10 mmol) and hydroxylamine hydrochloride (7.6 mg, 0.11 mmol) in MeOH (2 ml) was heated to reflux for 2 hours, diluted with EtOAc (20 ml) and washed with aqueous saturated NaHCO$_3$. The organic layer was separated, dried over MgSO$_4$, and evaporated to give 34 mg (87% yield) of Example 110 as white solid.

$^1$H NMR (CDCl$_3$) δ 1.01–1.05 (m, 2 H), 1.15–1.19 (m, 2 H), 1.89 (s, 3 H), 2.64 (t, J=6.5 Hz, 2 H), 2.89–2.92 (m, 1 H), 4.58 (t, J=6.6 Hz, 2 H), 5.41 (s, 2 H), 7.12–7.31 (m, 4 H), 7.69–7.72 (m, 1 H), 8.29 (d, J=4.8 Hz, 1 H), 8.57 (s, 1 H); MS m/e 391 (MH$^+$).

EXAMPLE 111

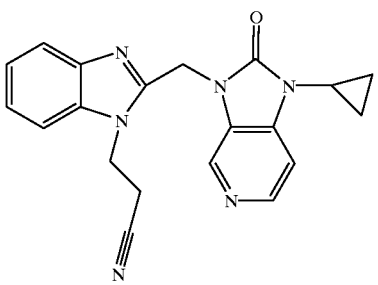

$^1$H NMR (CDCl$_3$) δ 1.03–1.07 (m, 2 H), 1.16–1.20 (m, 2 H), 2.86 (t, J=6.5 Hz, 2 H), 2.93–2.97 (m, 1 H), 4.78 (t, J=6.5 Hz, 2 H), 5.43 (s, 2 H), 7.18 (d, J=5.4 Hz, 1 H), 7.30–7.36 (m, 3 H), 7.81–7.82 (m, 1 H), 8.36 (d, J=5.4 Hz, 1 H), 8.84 (s, 1 H); IR (KBr, cm$^{-1}$) 3405, 1709, 1605, 1500, 1466, 1455, 1411, 1179, 750; MS m/e 359 (MH$^+$); Anal. Calcd for C$_{20}$H$_{18}$N$_6$O•0.5H$_2$O: C, 65.38; H, 5.21; N, 22.87 Found: C, 65.49; H, 5.09; N, 22.41.

EXAMPLE 112

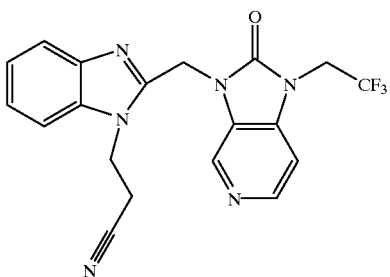

$^1$H NMR (CD$_3$OD) δ 3.11 (t, J=6.6 Hz, 2 H), 4.72–4.82 (m, 4 H), 5.59 (s, 2 H), 7.28–7.38 (m, 3 H), 7.60–7.64 (m, 2 H), 8.29 (d, J=5.7 Hz, 1 H), 8.53 (s, 1 H).

EXAMPLE 113

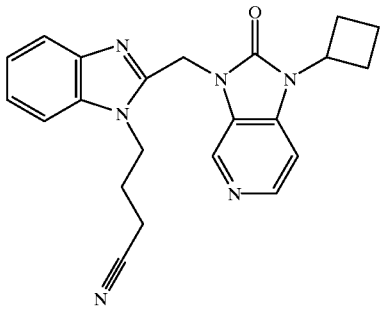

$^1$H NMR (CDCl$_3$) δ 1.90–2.10 (m, 4 H), 2.43–2.49 (m, 4 H), 2.80–2.89 (m, 2 H), 4.48 (t, J=7.4 Hz, 2 H), 4.84–4.90 (m, 1 H), 5.40 (s, 2 H), 7.21–7.38 (m, 4 H), 7.77–7.79 (m, 1 H), 8.34 (d, J=5.5 Hz, 1 H), 8.82 (s, 1 H); MS m/e 387 (MH$^+$); Anal. Calcd for C$_{22}$H$_{22}$N$_6$O: C, 68.37; H, 5.73; N, 21.74 Found: C, 68.21; H, 5.83; N, 21.71.

EXAMPLE 114

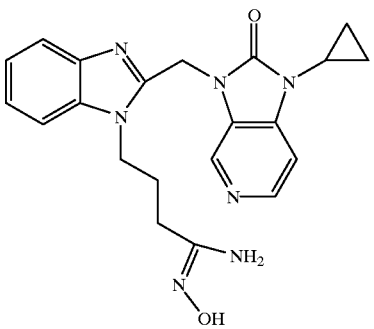

A mixture of Example 26 (610 mg, 1.62 mmol), hydroxylamine hydrochloride (408 mg, 5.87 mmol) and potassium carbonate (450 mg, 3.24 mmol) were stirred in a EtOH and H20 (2:1 ratio mixture, 60 mL) at 80° C. for 18 hours. The solvent was evaporated and the residue was diluted with H20 to dissolve inorganic salts. The white solid was filtered and dried under high vacuum to give 545 mg (83% yield) of Example 114 as a white solid.

$^1$H NMR (DMSO-$d_6$) δ 0.90–0.93 (m, 2 H), 1.05–1.07 (m, 2 H), 1.87–1.90 (m, 2 H), 2.06 (t, J=7.5 Hz, 2 H), 3.00–3.02 (m, 1 H), 4.32 (t, J=7.6 Hz, 2 H), 5.41 (s, 2 H), 5.46 (bs, 2 H), 7.17 (t, J=7.3 Hz, 1 H), 7.24 (t, J=7.3 Hz, 1 H), 7.29 (d, J =5.2 Hz, 1 H), 7.57 (d, J=7.9 Hz, 1 H), 7.60 (d, J=8.0 Hz, 1 H), 8.25 (d, J=5.2 Hz, 1 H), 8.40 (s, 1 H), 8.84 (s, 1 H).

EXAMPLE 115

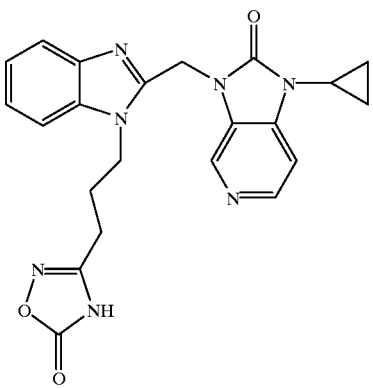

Example 114 (210 mg, 0.52 mmol) was treated with phosgene (20% in toluene, 2.56 g, 5.2 mmol) and heated to reflux for 12 hours. Additional phosgene (20% in toluene 2.56 g, 5.2 mmol) was added and the mixture heated to reflux for another 6 hours. The solution was concentrated to half volume and the white solid was isolated by filtration to give 138 mg (62% yield) of Example 115.

$^1$H NMR (DMSO-$d_6$) δ 1.05–1.05 (bs, 2 H), 1.15–1.16 (m, 2 H), 2.21–2.26 (m, 2 H), 2.71–2.75 (m, 2 H), 3.15–3.17 (m, 1 H), 4.51–4.58 (m, 2 H), 5.74–5.78 (m, 2 H), 7.37–7.40 (m, 1 H), 7.45–7.47 (m, 1 H), 7.63–7.66 (m, 1 H), 7.84–7.89 (m, 2 H), 8.64 (d, J=6.4 Hz, 1 H), 8.92–8.95 (m, 1 H); MS m/e 432 (MH$^+$).

EXAMPLE 116

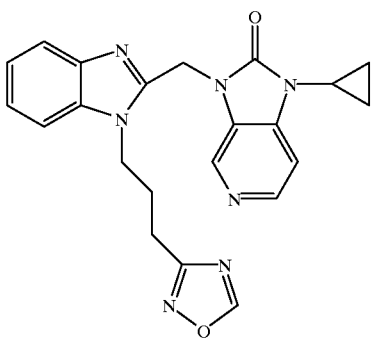

A mixture of the Example 114 (100 mg, 0.24 mmol) was heated to reflux in triethylorthoformate (2.5 mL) for 12 hours. The solution was concentrated and the residue purified by preparative HPLC (C 18, gradient 0–100% MeOH/H$_2$O with 0. 1% trifluoroacetic acid). The product was treated with 4 N HCl in dioxane and concentrated to give 38 mg (35% yield) of the Example 116 as the hydrochloride salt.

$^1$H NMR (DMSO-$d_6$) δ 0.97–1.02 (m, 2 H), 1.10–1.16 (m, 2 H), 2.25–2.35 (m, 2 H), 2.95–2.99 (m, 2 H), 3.14–3.16 (m, 1 H), 4.55–4.65 (m, 2 H), 5.77 (s, 2 H), 7.39–7.41 (m, 1 H), 7.46–7.48 (m, 1 H), 7.66–7.68 (m, 1 H), 7.84–7.90 (m, 2 H), 8.64 (d, J=6.1 Hz, 1 H), 8.94 (s, 1 H), 9.57 (s, 1 H); MS m/e 416 (MH$^+$).

EXAMPLE 117

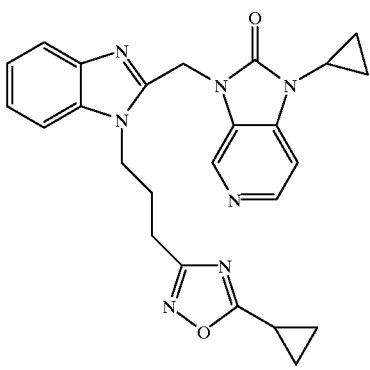

A mixture of Example 114 (250 mg, 0.62 mmol) was heated to reflux with cyclopropanecarbonyl chloride (354 mg, 3.39 mmol) and pyridine (2 mL) for 12 hours. The solution was concentrated and the residue purified by preparative HPLC (C18, gradient 0–100% MeOH/H$_2$O with 0.1% trifluoroacetic acid). The product was treated with 4N HCl in dioxane and concentrated to give 80 mg (28% yield) of Example 117 as the hydrochloride salt.

$^1$H NMR (DMSO-$d_6$) δ 1.04–1.06 (m, 4H), 1.13–1.15 (m, 2 H), 1.20–1.23 (m, 2 H), 2.21–2.31 (m, 2 H), 2.83–2.85 (m, 2 H), .3.11–3.19 (m, 1 H), 3.65–3.75 (m, 1 H), 4.55–4.57 (m, 2 H), 5.75 (s, 2 H), 7.35–7.42 (m, 1 H), 7.45–7.52 (m, 1 H), 7.65 (d, J=8.1 Hz, 1 H), 7.83–7.85 (m, 2 H), 8.62 (d, J=8.1 Hz, 1 H), 8.92 (s, 1 H); MS m/e 456 (MH$^+$).

EXAMPLE 118

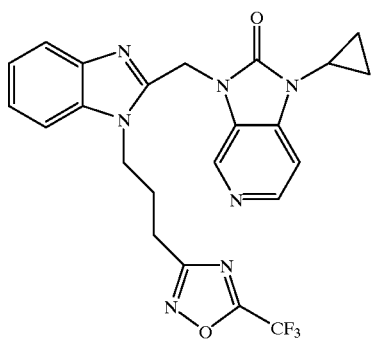

Example 118 was prepared according to the same procedure described for Example 117 using trifluoroacetic anhydride.

$^1$H NMR (DMSO-d$_6$) δ 1.02–1.05 (m, 2 H), 1.12–1.16 (m, 2 H), 2.31–2.34 (m, 2 H), 3.10 (t, J=7.3 Hz, 2 H), 3.13–3.16 (m, 1 H), 4.59 (t, J=7.6 Hz, 2 H), 5.74 (s, 2 H), 7.38 (t, J=7.8 Hz, 1 H), 7.45 (t, J=7.4 Hz, 1 H), 7.65 (d, J=8.0 Hz, 1 H), 7.85 (d, J=7.7 Hz, 1 H), 7.88 (d, J=8.2 Hz, 1 H), 8.63 (d, J=8.2 Hz, 1 H), 8.94 (s, 1 H); MS m/e 483 (MH$^+$).

EXAMPLE 119

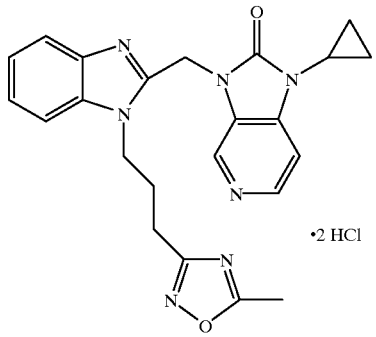

Example 119 was prepared according to the same procedure described for Example 117 using acetic anhydride.

$^1$H NMR (DMSO-d$_6$) δ 1.01–1.05 (m, 2 H), 1.13–1.15 (m, 2 H), 2.24–2.28 (m, 2 H), 2.55 (s, 3 H), 2.85–2.88 (m, 1 H), 3.15–3.18 (m, 2 H), 4.55 (t, J7.4 Hz, 2 H), 5.71 (bs, 2 H), 7.29–7.38 (m, 1 H), 7.40–7.47 (m, 1 H), 7.64 (d, J=7.4 Hz, 1 H), 7.80–7.86 (m, 2 H), 8.63 (d, J=6.4 Hz, 1 H), 8.90 (s, 1 H); MS m/e 430 (MH$^+$).

EXAMPLE 120

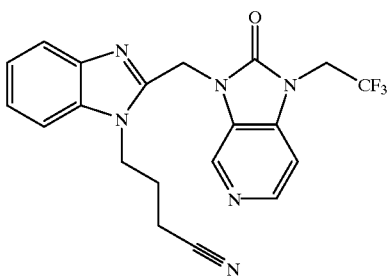

$^1$H NMR (DMSO-d$_6$) δ 2.06–2.12 (m, 2 H), 2.63 (t, J=7.3 Hz, 2 H), 4.42 (t, J 7.5 Hz, 2 H), 4.92 (q, J=9.3 Hz, 2 H), 5.51 (s, 2 H), 7.18 (t, J=7.5Hz, 1 H), 7.27 (t, J=7.5 Hz, 1 H), 7.45 (d, J=5.2 Hz, 1 H), 7.56 (d, J=8.0 Hz, 1 H), 7.62 (d, J=8.2 Hz, 1 H), 8.33 (d, J=5.5 Hz, 1 H), 8.51 (s, 1 H).

EXAMPLE 121

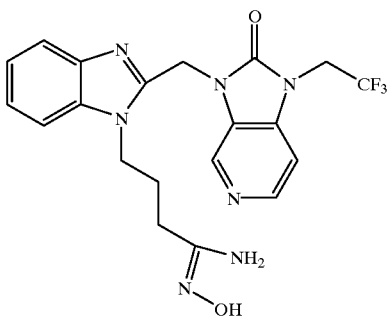

Example 121 was prepared from Example 120 according to the same procedure as Example 114.

$^1$H NMR (DMSO-d$_6$) δ 1.91–1.98 (m, 2 H), 2.30 (t, J=7.0Hz, 2 H), 4.37 (t, J=7.7Hz, 2 H), 4.91 (q, J=9.1 Hz, 2 H), 5.51 (s, 2 H), 7.15–7.18 (m, 1 H), 7.23–7.27 (m, 1 H), 7.44 (d, J=5.2 Hz, 1 H), 7.55 (d, J=7.9 Hz, 1 H), 7.61 (d, J=8.0 Hz, 1 H), 8.06 (bs, 1 H), 8.31 (d, J=5.2 Hz, 2 H), 8.46 (s, 1 H), 9.48 (s, 1 H); MS m/e 448 (MH$^+$).

EXAMPLE 122

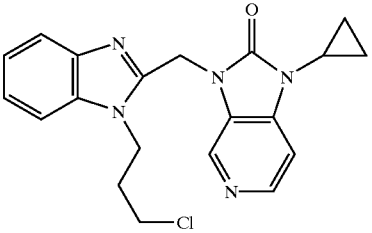

$^1$H NMR (CDCl$_3$) δ 1.00–1.06 (m, 2 H), 1.15–1.19 (m, 2 H), 2.14–2.19 (m, 2 H), 2.91–2.95 (m, 1 H), 3.55 (t, J=6.0 Hz, 2 H), 4.52 (t, J=6.7 Hz, 2 H), 5.40 (s, 2 H), 7.14–7.15 (m, 1 H), 7.26–7.32 (m, 2 H), 7.39–7.40 (m, 1 H), 7.76–7.78 (m, 1 H), 8.34 (d, J=5.0 Hz, 1 H), 8.72 (s, 1 H); MS m/e 382 (MH$^+$); Anal. Calcd for C$_{20}$H$_{20}$ClN$_5$O: C, 62.90; H, 5.27; N, 18.34 Found: C, 62.58; H, 5.17; N, 18.18.

EXAMPLE 123

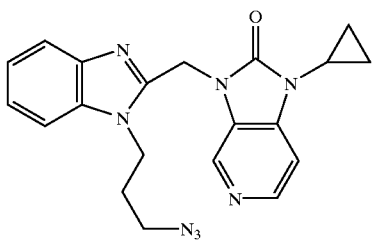

A mixture of Example 122 (38 mg, 0.10 mmol) and sodium azide (20 mg, 0.30 mmol) in DMF (2 ml) was heated to 70° C. for 2 hours. The final solution was diluted with EtOAc (10 ml) and washed with $H_2O$ (3×10 ml) and brine. The combined organic extracts were dried over $MgSO_4$, concentrated, and purified by flash chromatography, (gradient, $CH_2Cl_2$/MeOH, 40:1 to 20:1) to yield 33 mg (85% yield) of Example 123 as a white solid.

$^1$H NMR (CDCl$_3$) δ 1.00–1.05 (m, 2 H), 1.13–1.19 (m, 2 H), 1.91–1.97 (m, 2 H), 2.90–2.94 (m, 1 H), 3.35 (t, J=6.3 Hz, 2 H), 4.43 (t, J=7.2 Hz, 2 H), 5.37 (s, 2 H), 7.12 (d, J=5.2 Hz, 1 H), 7.26–7.30 (m, 2 H), 7.33–7.35 (m,1 H), 7.77 (d, J=7.2 Hz, 1 H), 8.32 (d, J=5.0 Hz, 1 H), 8.72 (s, 1 H); MS m/e 388 (MH$^+$); Anal. Calcd for $C_{20}H_{20}N_8O$: C, 61.84; H, 5.19; N, 28.84 Found: C, 61.59; H, 5.27; N, 28.50.

EXAMPLE 124

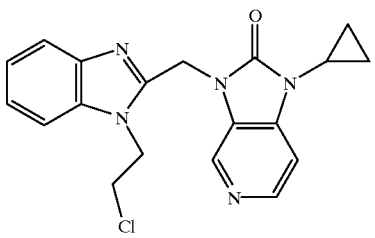

$^1$H NMR (CDCl$_3$) δ 1.02–1.05 (m, 2 H), 1.15–1.19 (m, 2 H), 2.90–2.95 (m, 1 H), 3.77 (t, J=6.0Hz, 2 H), 4.76 (t, J=6.1 Hz, 2 H), 5.44 (s, 2 H), 7.14 (d, J=5.2 Hz, 1 H), 7.28–7.32 (m, 3 H), 7.78–7.80 (m, 1 H), 8.34 (d, J=4.8 Hz, 1 H), 8.77 (s, 1 H); MS m/e 368 (MH$^+$).

EXAMPLE 125

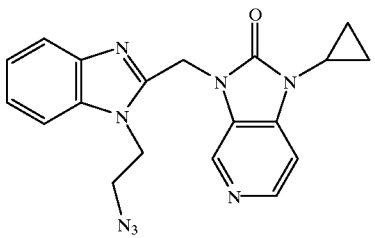

Example 125 was prepared from Example 124 according to the same procedure described for Example 123.

$^1$H NMR (CDCl$_3$) δ 1.01–1.06 (m, 2 H), 1.16–1.20 (m, 2 H), 2.92–2.96 (m, 1 H), 3.70 (t, J=6.0Hz, 2 H), 4.54 (t, J=6.1 Hz, 2 H), 5.43 (s, 2 H), 7.15 (d, J=5.2 Hz, 1 H), 7.29–7.32 (m, 3 H), 7.78–7.81 (m, 1 H), 8.34 (d, J=4.8 Hz, 1 H), 8.79 (s,1H); MS m/e 375 (MH$^+$); Anal. Calcd for $C_{19}H_{18}N_8O$•0.25 $H_2O$: C, 60.23; H, 4.92; N, 29.57 Found: C, 60.30; H, 4.85; N, 29.44.

EXAMPLE 126

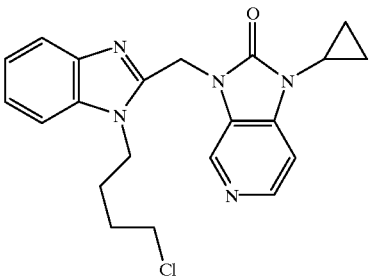

$^1$H NMR (CDCl$_3$) δ 1.00–1.04 (m, 2 H), 1. 16–1.20 (m, 2 H), 1.79–1.81 (m, 4 H), 2.92–2.96 (m, 1 H), 3.49–3.50 (m, 2 H), 4.35 (s, 2 H), 5.37 (s, 2 H), 7.13 (d, J=5.2 Hz, 1 H), 7.26–7.33 (m, 3 H), 7.76–7.79 (m, 1 H), 8.83 (d, J=5.2 Hz, 1 H), 8.72 (s, 1 H); MS m/e 396 (MH$^+$); Anal. Calcd for $C_{21}H_{22}ClN_5O$•0.20 $H_2O$: C, 63.14; H, 5.64; N, 17.53 Found: C, 62.74; H, 5.54; N, 17.57.

EXAMPLE 127

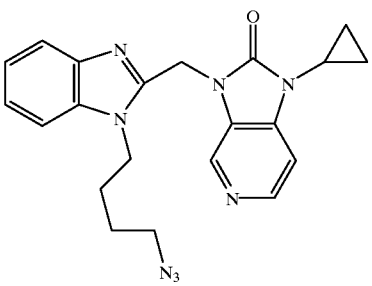

Example 127 was prepared from Example 126 according to the same procedure described for Example 123.

$^1$H NMR (CDCl$_3$) δ 0.99–1.02 (m, 2 H), 1. 15–1.19 (m, 2 H), 1.58–1.63 (m, 2 H), 1.69–1 .75 (m, 2 H), 2.90–2.95 (m, 1 H), 3.27 (t, J=6.5 Hz, 2 H), 4.32 (t, J=7.3 Hz, 2 H), 5.35 (s, 2 H), 7.12 (d, J=5.0 Hz, 1 H), 7.25–7.31 (m, 3 H), 7.76–7.77 (m, 1 H), 8.32 (d, J=4.8 Hz, 1 H), 8.71 (s, 1 H); MS m/e 403 (MH$^+$).

EXAMPLE 128

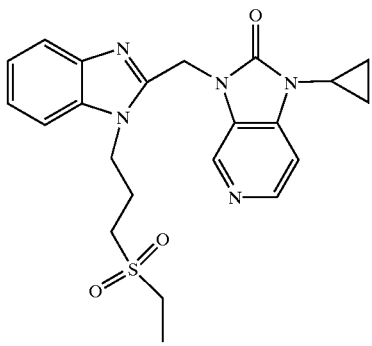

$^1$H NMR (DMSO-d$_6$) δ 0.91–0.94 (m, 2 H), 1.04–1.09 (m, 2 H), 1.20 (t, J=7.5 Hz, 3 H), 2.06–2.13 (m, 2 H), 2.98–3.02 (m, 1 H), 3.11 (q, J=7.5 Hz, 2 H), 3.16–3.21 (m, 2 H), 4.86 (t, J=7.6 Hz, 2 H), 5.42 (s, 2 H), 7.18–7.21 (m, 1 H), 7.26–7.30 (m, 2 H), 7.59 (d, J=8.0 Hz, 1 H), 7.64 (d, J=8.1 Hz, 1 H), 8.26 (d, J=5.3 Hz, 1 H), 8.44 (s, 1 H); IR (KBr, cm$^{-1}$) 3421, 1610, 1706, 1500, 1458, 1409, 1298, 1131, 751; MS m/e 440 (MH$^+$); Anal. Calcd for C$_{22}$H$_{25}$N$_5$O$_3$S•2 H$_2$O: C, 55.56; H, 6.15; N, 14.73 Found: C, 55.29; H, 5.89; N, 14.59.

EXAMPLE 129

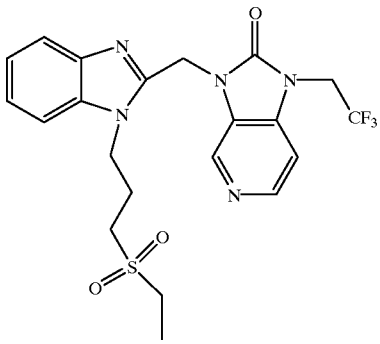

$^1$H NMR (DMSO-d$_6$) δ 1.21 (t, J=7.4 Hz, 3 H), 2.14–2.16 (m, 2 H), 3.13 (q, J=7.4 Hz, 2 H), 3.22 (t, J=7.5 Hz, 2 H), 4.50 (t, J=7.5 Hz, 2 H), 4.91 (q, J=9.3 Hz, 2 H), 5.53 (s, 2 H), 7.19 (t, J=7.7 Hz, 1 H), 7.28 (t, J=7.7 Hz, 1 H), 7.46 (d, J=5.3 Hz, 1 H), 7.57 (d, J=8.0 Hz, 1 H), 7.65 (d, J=8.0 Hz, 1 H), 8.33 (d, J=5.0 Hz, 1 H), 8.52 (s, 1 H); IR (Br,cm$^{-1}$) 3430, 2945, 1726, 1615, 1500, 1411, 1266, 1170, 1125, 745; MS m/e 482 (MH$^+$); Anal. Calcd for C$_{21}$H$_{22}$F$_3$N$_5$O$_3$S•0.25 H$_2$O: C, 51.90; H, 4.67; N, 14.41 Found: C, 51.69; H, 4.74; N, 14.17.

EXAMPLE 130

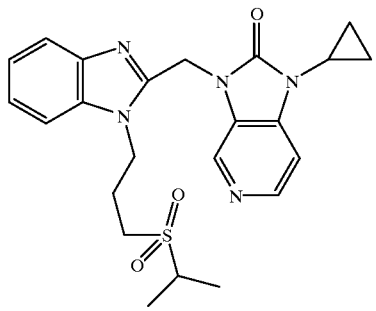

$^1$H NMR (DMSO-d$_6$) δ 0.92–0.93 (m, 2 H), 1.05–1.07 (m, 2 H), 1.23 (d, J=6.8 Hz, 6 H), 2.06–2.12 (m, 2 H), 2.98–3.02 (m, 1 H), 3.16–3.20 (m, 2 H), 3.28–3.30 (m, 1 H), 4.49 (t, J=7.6 Hz, 2 H), 5.42 (s, 2 H), 7.21 (t, J=7.1 Hz, 1 H), 7.26–7.30 (m, 2 H), 7.59 (d, J=8.0 Hz, 1 H), 7.64 (d, J=8.0 Hz, 1 H), 8.25 (d, J=5.2 Hz, 1 H), 8.44 (s, 1 H); IR (KBr, cm$^{-1}$) 2926, 1720, 1604, 1498, 1471, 1420, 1267, 1126, 746; MS m/e 454 (MH$^+$); Anal. Calcd for C$_{23}$H$_{27}$N$_5$O$_3$S•0.7 H$_2$O: C, 59.26; H, 6.14; N, 15.02 Found: C, 59.58; H, 6.10; N, 14.63.

EXAMPLE 131

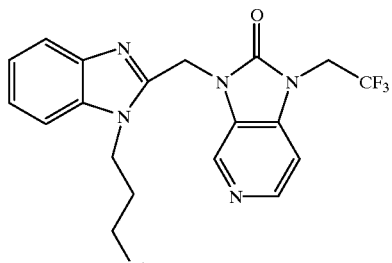

$^1$H NMR (CDCl$_3$) δ 2.03–2.17 (m, 2 H), 3.53 (t, J=6.2 Hz, 2 H), 4.45–4.54 (m, 4 H), 5.44 (s, 2 H), 7.01 (d, J=5.1 Hz, 1 H), 7.24–7.32 (m, 2 H), 7.37–7.41 (m, 2 H), 7.73–7.78 (m, 1 H), 8.36 (d, J=5.4 Hz, 1 H), 8.79 (s, 1 H); MS m/e 424 (MH$^+$).

EXAMPLE 132

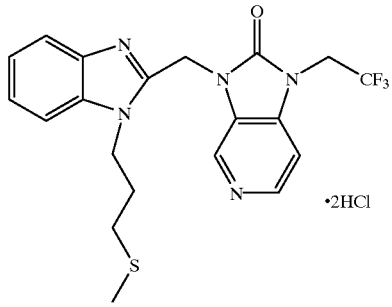

To a volume of DMF (1 0 mL) saturated with excess methanethiol at −78° C. was added sodium hydride (60% suspension in mineral oil, 56 mg, 1.39 mmol). The mixture was warmed to 0° C. and stirred for 30 minutes. The mixture was then added to a solution of Example 131 (3 94 mg, 0.93 mmol) in DMF (2 mL) and was stirred at 0° C. for 30 minutes. The solvent was evaporated under high vacuum. The residue was neutralized with concentrated HCl and the solvent was evaporated. The residue was diluted with $CH_2Cl_2$ and was washed with saturated aqueous $NaHCO_3$ and $H_2O$, dried over $MgSO_4$, and evaporated. Purification by flash column chromatography (gradient, straight EtOAc to EtOAc/MeOH, 10:1) gave 374 mg (93% yield) of Example 132. Example 132 (200 mg, 0.46 mmol) was converted to the HCl salt by treating a solution of Example 132 in MeOH with excess 4N HCl in dioxane and then by evaporating the solvent to give 223 mg (96% yield).

$^1$H NMR (CD$_3$OD) δ 2.14 (s, 3 H), 2.30–2.39 (m, 2 H), 2.70 (t, J=6.6 Hz, 2 H), 25 4.78 (t, J=7.4 Hz, 2 H), 5.01 (q, J=8.7 Hz, 2 H), 6.05 (s, 2 H), 7.62–7.75 (m, 2 H), 7.76 (d, J=7.5 Hz, 1 H), 7.99–8.04 (m, 2 H), 8.71 (d, J=6.6 Hz, 1 H), 9.09 (s, 1 H); IR (KBr, cm$^{-1}$) 3412, 2762, 1760, 1655, 1624, 1519, 1264, 1169, 1119, 834, 752; MS m/e 436 (MH$^+$).

EXAMPLE 133

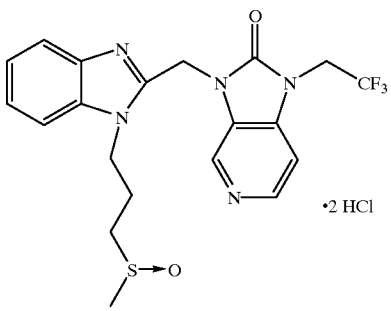

A mixture of Example 132 (174 mg, 0.40 mmol) and sodium periodate (94 mg, 0.44 mmol) in $H_2O$ (5 mL) was stirred at 0° C. To this mixture was added DMF (2 mL) in order to dissolve the solids and the resulting solution was stirred at room temperature for 48 hours The reaction mixture was diluted with $CH_2Cl_2$, washed with water, dried over $MgSO_4$ and evaporated. Purification by flash column chromatography (gradient, straight EtOAc to EtOAc/MeOH, 5:1) gave 145 mg (81% yield) of Example 133 which was converted to the HCl salt by treating a solution of Example 133 in MeOH with 4N HCl in dioxane and then by evaporating the solvent.

$^1$H NMR (CD$_3$OD) δ 2.02–2.15 (m, 2 H), 2.53 (s, 3 H), 2.68 (t, J=7.4 Hz, 2 H), 4.43–4.56 (m, 4 H), 5.43 (s, 2 H), 7.02 (d, J=5.1 Hz, 1 H), 7.26–7.31 (m, 2 H), 7.35–7.38 (m, 1 H), 7.74–7.77 (m, 1 H), 8.35 (d, J=5.4 Hz, 1 H), 8.79 (s, 1 H); IR(KBr,cm$^1$)3412,2854, 1760, 1656, 1624, 1519, 1264, 1169, 1120, 753; MS m/e 452 (MH$^+$); Anal. Calcd for $C_{20}H_{20}F_3N_5O_2S\cdot 2HClH_2O$: C, 44.29; H, 4.46; N, 12.91 Found: C, 44.08; H, 4.93; N, 11.54.

EXAMPLE 135

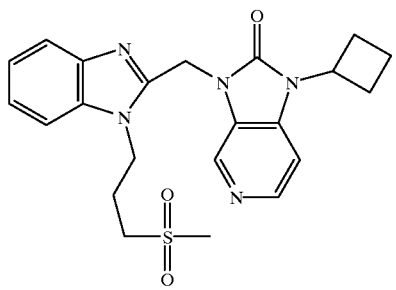

$^1$H NMR (DMSO-d$_6$) δ 1.73–1.92 (m, 2 H), 2.13–2.16 (m, 2 H), 2.31–2.33 (m, 2 H), 2.79–2.83 (m, 2 H), 3.00 (s, 3 H), 3.24 (t, J=7.7 Hz, 2 H), 4.49 (t, J=7.4 Hz, 2 H), 4.85–4.92 (m, 1 H), 5.44 (s, 2 H), 7.19–7.20 (m, 1 H), 7.26–7.27 (m, 1H), 7.49 (d, J=5.3 Hz, 1 H), 7.57 (d, J=8.0 Hz, 1 H), 7.63 (d, J=8.05 Hz, 1 H), 8.25 (d, J=5.3 Hz, 1 H), 8.46 (s, 1 H); MS m/e 440 (MH$^+$); Anal. Calcd for $C_{22}H_{25}N_5O_3S$: C, 60.11; H, 5.73; N, 15.93 Found: C, 60.09; H, 5.76; N, 15.89.

EXAMPLE 136

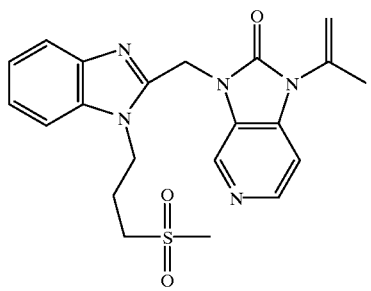

$^1$H NMR (DMSO-d$_6$) δ 2.12–2.18 (m, 5 H), 3.00 (s, 3 H), 3.24 (t, J=7.6 Hz, 2 H), 4.51 (t, J=7.6 Hz, 2 H), 5.45–5.48 (m, 3 H), 7.19–7.28 (m, 3 H), 7.59 (d, J=8.0 Hz, 1 H), 7.64 (d, J=8.1 Hz, 1 H), 8.26 (d, J=5.3 Hz, 1 H), 8.52 (s, 1 H); MS m/e 426 (MH$^+$).

EXAMPLE 137

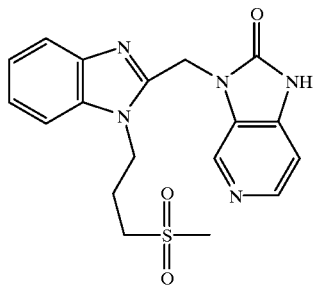

Example 137 was prepared from Example 136 according to the same procedure described for Example 17.

$^1$H NMR (DMSO-d$_6$) δ 2.12–2.16 (m, 2 H), 3.00 (s, 3 H), 3.24 (t, J=7.6 Hz, 2 H), 4.49 (t, J=7.6 Hz, 2 H), 5.41 (s, 2 H), 7.08 (d, J=7.0 Hz, 1 H), 7.17–7.20 (m, I H), 7.25–7.29 (m, 1 H), 7.58 (d, J=8.0 Hz, 1 H), 7.63 (d, J=8.0 Hz, 1 H), 8.17 (d, J=5.2 Hz, 1 H), 8.39 (s, 1 H); MS m/e 386 (MH$^+$).

EXAMPLE 138

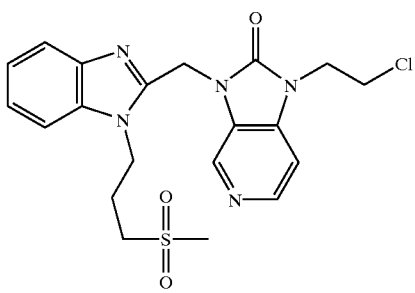

$^1$H NMR (CDCl$_3$) δ 2.16–2.22 (m, 2 H), 2.91 (s, 3 H), 3.09 (t, J=7.3 Hz, 2 H), 3.88 (t, J=5.9Hz, 2 H), 4.26 (t, J=6.0Hz, 2 H), 4.51 (t, J=7.6Hz, 2 H), 5.44 (s, 2 H), 7.20 (d, J=5.3 Hz, 1 H), 7.28–7.34 (m, 2 H), 7.37–7.39 (m, 1 H), 7.78–7.80 (m, 1 H), 8.36 (d, J=5.1 Hz, 1 H), 8.78 (s, 1 H); MS m/e 448 (MH$^+$).

EXAMPLE 139

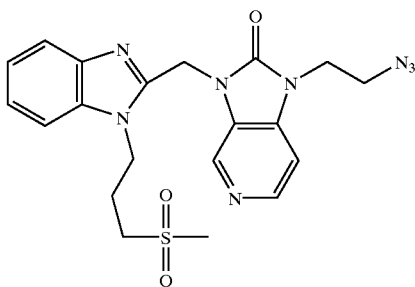

Example 139 was prepared from Example 138 according to the same procedure described for Example 123.

$^1$H NMR (CDCl$_3$) δ 2.18–2.24 (m, 2 H), 2.91 (s, 3 H), 3.09 (t, J=7.3 Hz, 2 H), 3.73 (t, J=5.9 Hz, 2 H), 4.08 (t, J=6.0 Hz, 2 H), 4.51 (t, J=7.6 Hz, 2 H), 5.44 (s, 2 H), 7.07 (d, J=5.3 Hz, 1 H), 7.26–7.33 (m, 2 H), 7.33–7.38 (m, 1 H), 7.77–7.79 (m, 1 H), 8.36 (d, J=5.1 Hz, 1 H), 8.79 (s, 1 H); MS m/e 455 (MH$^+$); Anal. Calcd for C$_{20}$H$_{22}$N$_8$O$_3$S•0.5 H$_2$O: C, 51.83; H, 5.00; N, 24.17 Found: C, 51.85; H, 4.82; N, 23.97.

EXAMPLE 140

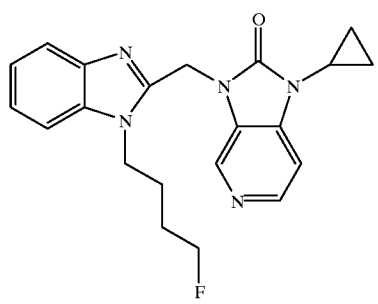

$^1$H NMR (DMSO-d$_6$) δ 0.89–0.92 (m, 1 H), 1.06–1.08 (m, 1 H), 1.65–1.72 (m, 2 H), 2.96–2.99 (m, 1 H), 4.35–4.50 (m, 3 H), 5.40 (s, 2 H), 7.17–7.20 (m, 1 H), 7.24–7.29 (m, 2 H), 7.59 (d, J=8.2 Hz, 2 H), 8.25 (d, J=5.1 Hz, 1 H), 8.41 (s, 1 H); MS m/e 380 (MH$^+$).

EXAMPLE 141

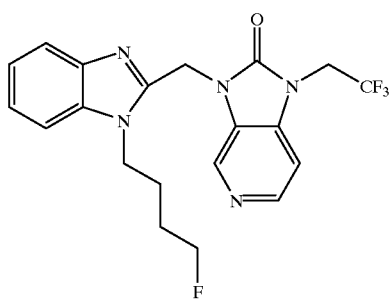

$^1$H NMR (DMSO-d$_6$) δ 1.67–1.77 (m, 4 H), 4.37–4.42 (m, 3 H), 4.49–4.51 (m, 1 H), 4.92 (q, J9.2 Hz, 2 H), 5.50 (s, 2 H), 7.18 (t, J7.6Hz, 1 H), 7.26 (t, J=7.7, 1 H), 7.44 (d, J=4.3, 1 H), 7.57–7.61 (m, 2 H), 8.30–8.33 (bs, 1 H), 8.49–8.51 (bs, 1 H); MS m/e 422 (MH$^r$).

EXAMPLE 142

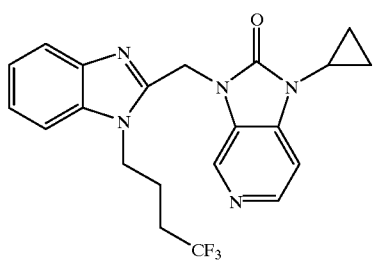

$^1$H NMR (DMSO-d$_6$) δ 1.03–1.04 (m, 2 H), 1.14–1.16 (m, 2 H), 2.06–2.08 (m, 2 H), 3.11–3.18 (m, 1 H), 4.52–4.55 (m, 4 H), 5.70 (s, 2 H), 7.34–7.39 (m, 1 H), 7.43–7.47 (m, 1 H), 7.63 (d, J=8.1 Hz, 1 H), 7.84 (d, J=6.4 Hz, 2 H), 8.63 (d, J=6.4 Hz, 1 H), 8.92 (s, 1 H); MS m/e 416 (MH$^+$).

EXAMPLE 143

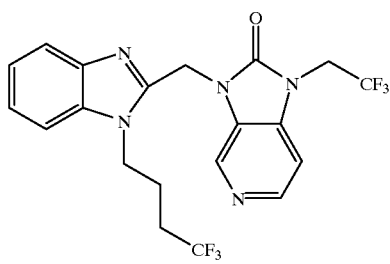

$^1$H NMR (DMSO-d$_6$) δ 1.84–1.87 (m, 2 H), 4.50–4.53 (m, 4 H), 5.14 (q, J=9.0 Hz, 2 H), 5.74 (s, 2 H), 7.30–7.32 (m, 1 H), 7.37–7.40 (m, 1 H), 7.60 (d, J=8.2 Hz, 1 H), 7.80 (d, J=8.0, 1 H), 8.05 (d, J=6.2 Hz, 1 H), 8.74 (d, J=6.3 Hz, 1 H), 9.04 (s, 1 H); MS m/e 458 (MH$^+$).

EXAMPLE 144

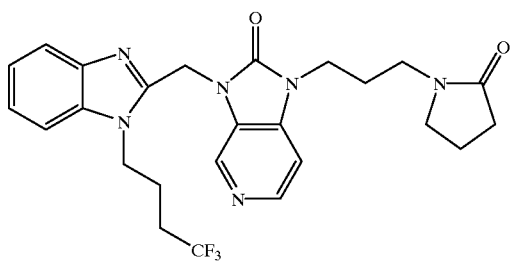

¹H NMR (DMSO-d₆) δ 1.85–1.92 (m, 6 H), 2.18 (t, J=8.1 Hz, 2 H), 2.36–2.41 (m, 2 H), 2.34 (t, J=7.3 Hz, 2 H), 3.88 (t, J=7.3 Hz, 2 H), 4.43 (t, J=7.6 Hz, 2 H), 5.46 (s, 2 H), 7.19 (t, J=7.0 Hz, 1 H), 7.27 (t, J=7.0 Hz, 1 H), 7.38 (d, J=5.5 Hz, 1 H), 7.58 (d, J=8.0 Hz, 1 H), 7.64 (d, J=7.9 Hz, 1 H), 8.26 (d, J=5.2 Hz, 1 H), 8.46 (s, 1 H); MS m/e 501 (MH⁺).

EXAMPLE 145

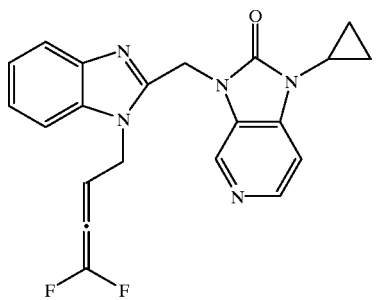

Example 145 was prepared according to the general coupling procedure described in Scheme I–C with 4-bromo-1,1,2-trifluoro-I-butene which gave an elimination product.

¹H NMR (DMSO-d₆) δ 0.96–0.99 (m, 2 H), 1.14–1.16 (m, 2 H), 3.15–3.17 (m, 1 H), 5.53 (s, 2 H), 5.72 (d, J=11.6 Hz, 1 H), 5.81 (d, J=17.4 Hz, 1 H), 6.77–6.86 (m, 1 H), 7.34–7.42 (m, 2 H), 7.54 (d, J=7.9 Hz, 1 H), 7.69 (d, J=7.9 Hz, 1 H), 7.85 (d, J=6.4 Hz, 1 H), 8.64 (d, J=6.1 Hz, 1 H), 8.90 (s, 1 H); MS m/e 394 (MH⁺).

EXAMPLE 146

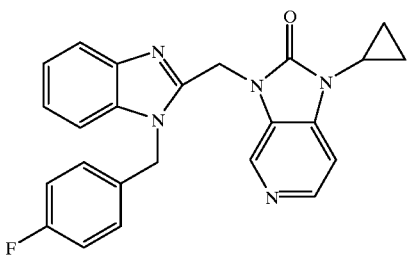

¹H NMR (DMSO-d₆) δ 0.64–0.66 (m, 2 H), 0.97–0.98 (m, 2 H), 2.77–2.78 (m, I H), 5.40 (s, 2 H), 5.59 (s, 2 H), 6.77–6.81 (m, 2 H), 6.94 (t, J=8.9 Hz, 2 H), 7.15 (d, J=5.2 Hz, 1 H), 7.21–7.23 (m, 2 H), 7.40–7.42 (m, 1 H), 7.68–7.70 (m, 1H), 8.20 (d, J=5.2 Hz, 1 H), 8.31 (s, 1 H);MS m/e 413 (MH⁺).

EXAMPLE 147

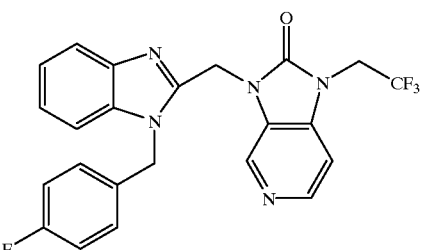

¹H NMR (DMSO-d₆) δ 4.74–4.79 (m, 2 H), 5.49 (s, 2 H), 5.60 (s, 2 H), 6.96–7.04 (m9 4 H), 7.17–7.25 (m, 2 H), 7.36 (d, J=5.2 Hz, 1 H), 7.48 (d, J=7.3 Hz, 1 H), 7.65 (d, J=6.7 Hz, 1 H), 8.28 (d, J=5.5 Hz, 1 H), 8.36 (s, 1 H); MS m/e 456 (MH⁺).

EXAMPLE 148

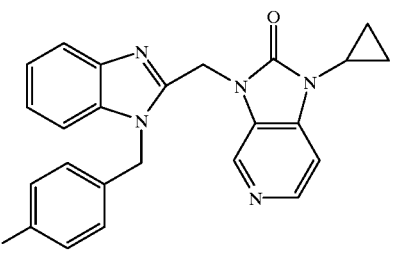

¹H NMR (DMSO-d₆) δ 0.53–0.56 (m, 2 H), 0.92–0.96 (m, 2 H), 2.66–2.69 (m, 1 H), 5.41 (s, 2 H), 5.71 (s, 2 H), 6.83 (d, J=8.2 Hz, 2 H), 7.06 (d, J=5.2 Hz, 1 H), 7.23–7.25 (m, 2 H), 7.40–7.42 (m, 3 H), 7.72–7.74 (m, 1 H), 8.18 (d, J=5.1 Hz, 1 H), 8.30 (s, 1 H); MS m/e 464 (MH⁺).

EXAMPLE 149

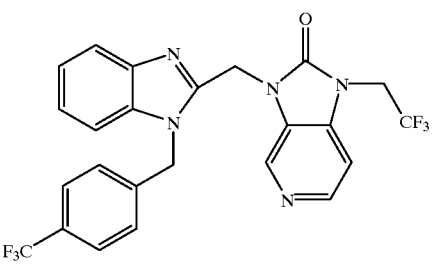

¹H NMR (DMSO-d₆) δ 4.68–4.70 (m, 2 H), 5.49 (s, 2 H), 5.74 (s, 2 H), 7.04 (d, J =8.1 Hz, 2 H), 7.22–7.23 (m, 2H), 7.31 (d, J=5.3 Hz, 1 H), 7.40–7.50 (m, 1H), 7.51 (d, J=8.2 Hz, 2 H), 7.64–7.70 (m, 1 H), 8.25 (d,J=5.2 Hz, 1 H), 8.38 (s, 1 H); MS m/e 464 (MH⁺).

EXAMPLE 150

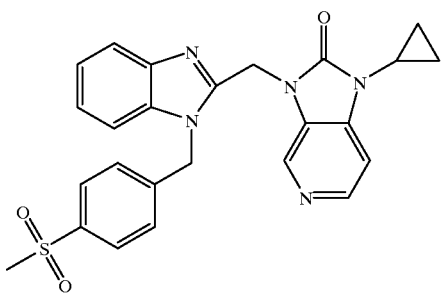

¹H NMR (DMSO-d₆) δ 0.76–0.77 (m, 2 H), 1.05–1.07 (m, 2 H), 2.92–2.96 (m, 1 H), 3.56 (s, 3 H), 5.56 (s, 2 H), 5.81 (s, 2 H), 7.14 (d, J=8.3 Hz, 2 H), 7.26–7.28 (m, 2 H), 7.47–7.49 (m, 1 H), 7.68–7.71 (m, 2 H), 7.77 (d, J=8.4 Hz, 2 H), 8.58 (d, J=6.4 Hz, 1 H), 8.72 (s, 1 H); MS m/e 474 (MH⁺).

EXAMPLE 151

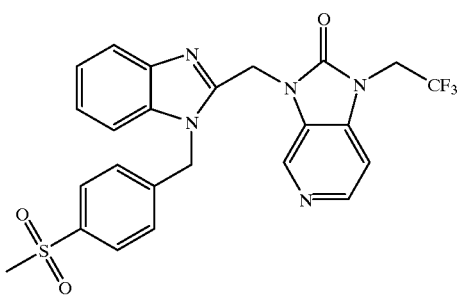

¹H NMR (DMSO-d₆) δ 3.20 (s, 3 H), 4.95–5.02 (m, 2 H), 5.66 (s, 2 H), 5.84 (s, 2 H), 5.56 (s, 2 H), 5.81 (s, 2 H), 7.26–7.29 (m, 2 H), 7.34 (d, J=8.3 Hz, 2 H), 7.51–7.53 (m, 1 H), 7.64–7.66 (m, 1 H), 7.85 (d, J=8.4 Hz, 2 H), 7.99 (d, J=6.3 Hz, 1 H), 8.71 (d, J=6.4 Hz, 1 H), 8.93 (s, 1 H); MS m/e 516 (MH⁺).

EXAMPLE 152

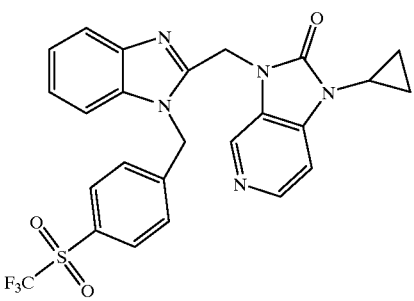

¹H NMR (DMSO-d₆) δ 0.78–0.81 (m, 2 H), 1.05–1.09 (m, 2 H), 2.95–2.98 (m, 1 H), 5.60 (s, 2 H), 5.95 (s, 2 H), 7.30 (dd, J=3.0, 6.1 Hz, 2 H), 7.39 (d, J=8.6 Hz, 2 H), 7.48–7.51 (m, 2 H), 7.71 (dd, J=3.0, 6.1 Hz, 2 H), 7.73 (d, J=6.4 Hz, 1 H), 8.04 (d, J=8.6 Hz, 1 H), 8.60 (d, J=6.4 Hz, 1 H), 8.82 (s, 1 H); MS m/e 528 (MH⁺).

EXAMPLE 153

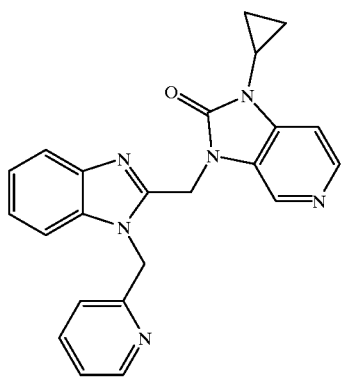

¹H NMR (DMSO-d₆) δ 0.68–0.71 (m, 2 H), 0.96–1.00 (m, 2 H), 2.79–2.82 (m, 1 H), 5.49 (s, 2 H), 5.69 (s, 2 H), 7.02 (d, J=7.9 Hz, 1 H), 7.16–7.21 (m, 4 H), 7.43–7.45 (m, 1 H), 7.59–7.65 (m, 2 H), 8.21 (d, J=5.0 Hz, 1 H), 8.24 (d, J=3.9 Hz, 1 H), 8.35 (s,1 H);

EXAMPLE 154

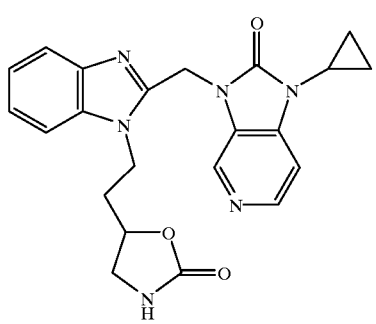

¹H NMR (CD₃OD) δ 1.16–1.20 (m, 2 H), 1.21–1.27 (m, 2 H), 2.44–2.48 (m, 1 H), 2.51–2.56 (m, 1 H), 3.18–3.22 (m, 1 H), 3.32–3.34 (m, 1 H), 3.74–3.78 (m, 1 H), 4.73–4.78 (m, 1 H), 4.81–4.89 (m, 2 H), 6.01 (d, 2 H), 7.63–7.67 (m, 1 H), 7.68–7.72 (m, 1 H), 7.79 (d, J=8.2 Hz, 1 H), 7.94 (d, J=6.4 Hz, 1 H), 8.02 (d, J=8.3 Hz, 1 H), 8.61 (d, J=6.4 Hz, 1 H), 8.96 (s, 1 H); MS m/e 419 (MH⁺).

EXAMPLE 155

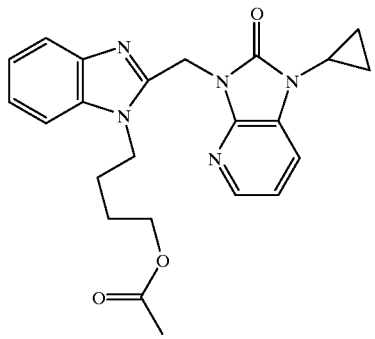

¹H NMR (CDCl₃) δ 1.00–1.03 (m, 2 H), 1.08–1.12 (m, 2 H), 1.68–1.74 (m, 2 H), 1.84–1.90 (m, 2 H), 2.06 (s, 3 H), 3.47–3.51 (m, 2 H), 4.09 (t, J=6.3 Hz, 2 H), 4.46 (t, J=7.5 Hz, 2 H), 5.42 (s, 2 H), 6.99–7.01 (m, 1 H), 7.20–7.27 (m, 2 H), 7.33–7.37 (m, 2 H), 7.76 (d, J=7.6 Hz, 1 H), 8.06–8.07 (m, 1 H); MS m/e 420 (MH$^+$).

EXAMPLE 156

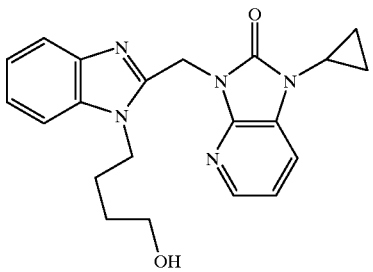

Example 156 was prepared from Example 155 according to the same procedure described for Example 73.

$^1$H NMR (CD$_3$OD) δ 1.01–1.04 (m, 2 H), 1.13–1.68 (m, 2 H), 1.63–1.68 (m, 2 H), 1.94–2.01 (m, 2 H), 2.68 (s, 3 H), 3.01–3.04 (m, 1 H), 3.60 (t, J=6.2 Hz, 2 H), 4.69 (t, J=7.9 Hz, 2 H), 5.73 (s, 2 H), 7.19–7.22 (m, 1 H), 7.63–7.69 (m, 3 H), 7.74–7.76 (m, 1 H), 7.98 (d, J=7.6 Hz, 1 H), 8.03–8.04 (m, 1 H); MS m/e 478 (MH$^+$); Anal. Calcd for C$_{21}$H$_{23}$N$_5$O$_2$•CH$_4$O$_3$S•0.75 H$_2$O: C, 54.21; H, 5.85; N, 14.22 Found: C, 54.25; H, 5.90; N, 14.38.

EXAMPLE 157

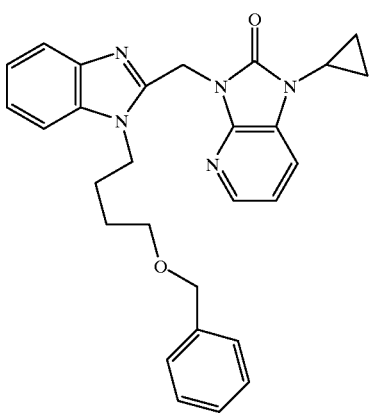

$^1$H NMR (CDCl$_3$) δ 0.98–1.01 (m, 2 H), 1.07–1.10 (m, 2 H), 1.65–1.71 (m, 2 H), 1.84–1.90 (m, 2 H), 2.86–2.90 (m, 1 H), 3.47–3.51 (m, 2 H), 4.43 (t, J=7.6 Hz, 2 H), 4.47 (s, 2 H), 5.37 (s, 2 H), 6.97–6.99 (m, 1 H), 7.18–7.33 (m, 9 H), 7.72–7.74 (m, 1 H), 8.03–8.06 (m, 1 H); MS m/e 468 (MH$^+$).

EXAMPLE 158

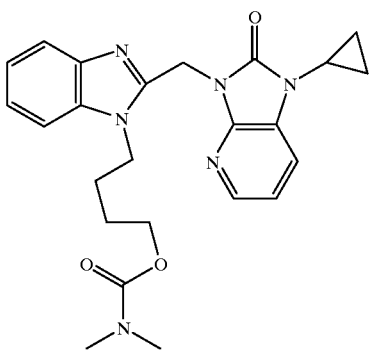

To a suspension of Example 156 (52 mg, 0.14 mmol) and sodium hydride (6.6 mg, 0.16 mmol) in DMF (2 mL) was added N,N-dimethylcarbamoyl chloride (16.2 mg, 0.15 mmol) at 0° C. The resulting mixture was stirred at room temperature for 12 hours. The mixture was diluted with EtOAc and washed with water. The organic extracts were dried with MgSO$_4$ and evaporated. The residue was purified by flash chromatography (gradient, CH$_2$Cl$_2$/MeOH, 40:1 to 20:1) to give 35 mg (56% yield) of Example 158 as a off-white solid.

$^1$H NMR (CDCl$_3$) δ 1.00–1.03 (m, 2 H), 1.08–1.12 (m, 2 H), 1.68–1.74 (m, 2 H), 1.84–1.90 (m, 2 H), 2.84 (s, 3 H), 2.90–2.93 (m, 4 H), 4.09 (t, J=6.3 Hz, 2 H), 4.46 (t, J=7.5 Hz, 2 H), 5.42 (s, 2 H), 6.99–7.01 (m, 1 H), 7.20–7.27 (m, 2 H), 7.33–7.37 (m, 2 H), 7.76 (d, J=7.6 Hz, 1 H), 8.06–8.07 (m, 1 H); MS m/e 449 (MH$^+$).

EXAMPLE 159

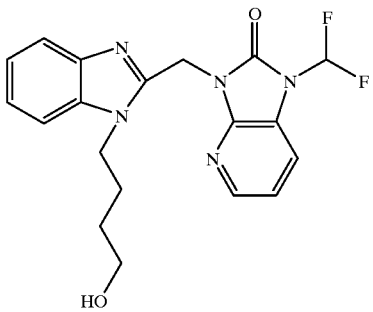

Example 159 was prepared via synthesis of the acetate intermediate according to the same procedure described for Example 72 followed immediately by deprotection of the alcohol according to the same procedure described for Example 73.

$^1$H NMR (d$_6$-DMSO) δ 1.44–1.54 (m, 2 H), 1.77–1.86 (m, 2 H), 3.41 (t, J=6.3 Hz, 2 H), 4.46 (t, J=7.2 Hz, 2 H), 5.53 (s, 2 H), 7.21 (dd, J=5.3, 8.0 Hz, 1 H), 7.28–7.40 (m, 2 H), 7.59 (d, J=7.8 Hz, 1 H), 7.76 (d, J=7.8 Hz, 2 H), 7.84 (t, J=57.6 Hz, 1 H), 8.10 (d, J=4.8 Hz, 1 H); IR (KBr, cm$^{-1}$) 3275, 2941, 1751, 1623, 1606, 1466, 2503, 1031, 772, 746; MS m/e 388 (MH$^+$); Anal. Calcd for C$_{19}$H$_{19}$F$_2$N$_5$O$_2$•0.25 H$_2$O: C, 58.23; H, 5.02; N, 17.87 Found: C, 58.42; H, 4.79; N, 17.64.

EXAMPLE 160

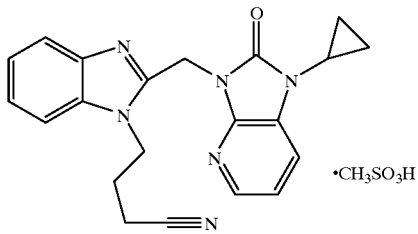

¹H NMR (CD₃OD) δ 1.02–1.05 (m, 2 H), 1.11–1.17 (m, 2 H), 2.32–2.38 (m, 2 H), 2.68 (s, 3 H), 2.71 (t, J=7.2 Hz, 2 H), 3.01–3.05 (m, 1 H), 5.79 (s, 2 H), 7.20–7.22 (m, 1 H), 7.64–7.76 (m, 4 H), 7.99–8.05 (m, 2 H); MS m/e 373 (MH⁺); Anal. Calcd for $C_{19}H_{18}N_8O \cdot 1.0\ H_2O \cdot 1.0\ CH_4SO_3$: C, 54.31; H, 5.39; N, 17.27 Found: C, 54.58; H, 5.37; N, 17.37.

EXAMPLE 161

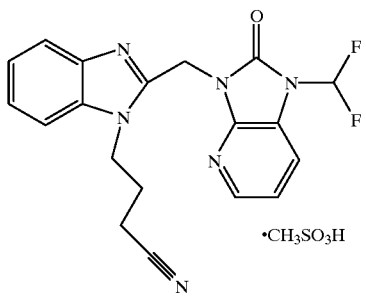

¹H NMR (CD₃OD) δ 2.37–2.40 (m, 2 H), 2.68 (s, 3 H), 2.73 (t, J=7.3 Hz, 2 H), 4.82 (t, J=7.6 Hz, 2 H), 5.80 (s, 2 H), 7.26–7.28 (m, 1 H), 7.62 (t, J=58.0 Hz, 1 H), 7.65–7.79 (m, 4 H), 8.00 (d, J=8.3 Hz, 1 H), 8.17 (dd, J=1.3, 5.3 Hz, 1 H); IR (KBr, cm⁻¹) 3449, 3064, 2953, 1758, 1466, 1410, 1230, 1156, 1048, 771, 551; MS m/e 383 (MH⁺); Anal. Calcd for $C_{19}H_{16}F_2N_6O \cdot 0.5\ H_2O \cdot 1.0\ CH_3SO_3H$: C, 49.28; H, 4.34; N, 17.24 Found: C, 49.36; H, 4.42; N, 16.95.

EXAMPLE 162

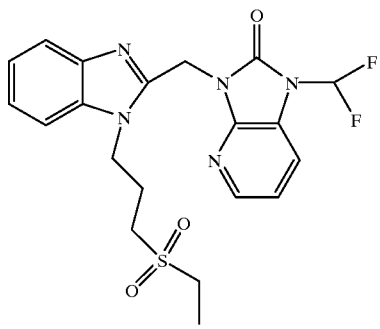

¹H NMR (CD₃OD) δ 1.35 (t, J=7.5 Hz, 3 H), 2.50–2.57 (m, 2 H), 3.15 (q, J=7.5 Hz, 2 H), 3.35 (t, J=7.2 Hz, 2 H), 4.86 (t, J=7.2 Hz, 2 H), 5.77 (s, 2 H), 7.24–7.27 (m, 1 H), 7.59–7.68 (m, 3 H), 7.62 (t, J=58.0 Hz, 1 H), 7.71 (d, J=8.3 Hz, 1 H), 7.78 (d, J=7.8 Hz, 1 H), 7.98 (d, J=8.1 Hz, 1 H), 8.16 (d, J=5.2 Hz, 1 H); MS m/e 450 (MH⁺).

EXAMPLE 163

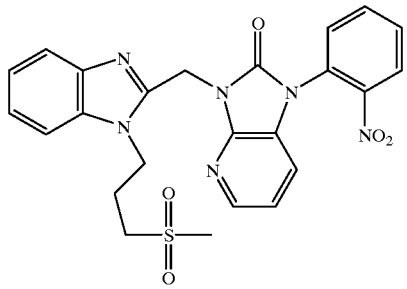

¹H NMR (DMSO-d₆, 65° C.) δ 2.81–2.34 (m, 2 H), 2.99 (s, 3 H), 3.28 (t, J=7.7 Hz, 2 H), 4.57 (t, J=7.4 Hz, 2 H), 5.50 (s, 2 H), 7.14–7.19 (m, 2 H), 7.25–7.27 (m, 1 H), 7.41 (d, J=8.0 Hz, 1 H), 7.53 (d, J=7.9 Hz, 1 H), 7.63 (d, J=8.1 Hz, 1 H), 7.80–7.84 (m, 1 H), 7.91 (d, J=7.6 Hz, 1 H), 7.98–8.02 (m, 1 H), 8.09 (d, J=5.0 Hz, 1 H), 8.25–8.27 (m, 1 H); MS m/e 507 (MH⁺).

EXAMPLE 164

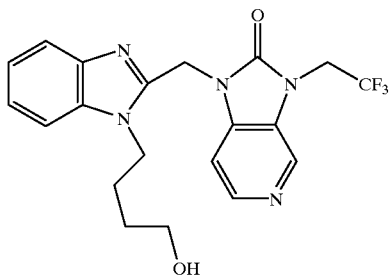

Example 164 was prepared via synthesis of the acetate intermediate according to the same procedure described for Example 72 followed immediately by deprotection of the alcohol according to the same procedure described for Example 73.

¹H NMR (CDCl₃) δ 1.60–1.65 (m, 2 H), 1.73–1.80 (m, 2 H), 3.64–3.70 (m, 2 H), 4.33 (t, J=8.0 Hz, 2 H), 4.53–4.60 (m, 2 H), 5.44 (s, 2 H), 7.24–7.37 (m, 3 H), 7.60 (d, J=5.3 Hz, 1 H), 7.77–7.81 (I, 1 H), 8.35–8.38 (m, 2 H);

MS m/e 420 (MH⁺).

EXAMPLE 165

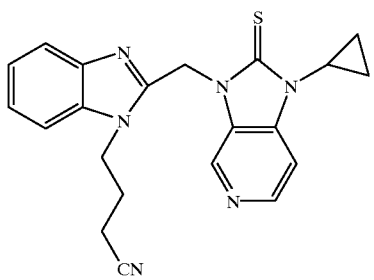

A mixture of Example 26 (100 mg, 0.27 mmol) and 2,4-bis(4-methoxyphenyl)-1,3-dithia-2,4-diphosphetane-2,4-disulfide (Lawesson's reagent, 130 mg, 0.32 mmol) in a mixture of toluene and dioxane (9:1 ratio, 10 mL) was heated in a sealed tube at 130° C. for 15 hours. The solvents were removed in vacuo and the residue was suspended in H$_2$O and extracted with CH$_2$Cl$_2$. The organic phase was washed with brine, dried over MgSO$_4$ and evaporated. The residue was purified by preparative TLC (5% MeOH in CH$_2$Cl$_2$), followed by trituration from Et$_2$O to give 5 mg (5% yield) of Example 165 as an off white solid.

$^1$H NMR (DMSO-d$_6$) δ 1.05–1.10 (m, 2 H), 1.21–1.25 (m, 2 H), 2.07–2.15 (m, 2 H), 2.67 (t, J=7.4 Hz, 2 H), 3.23–3.26 (m, 1 H), 4.49 (t, J=7.5 Hz, 2 H), 5.90 (s, 2 H), 7.18 (t, J=7.5 Hz, 1 H), 7.27 (t, J=7.5Hz, 1 H), 7.53 (d, J=7.9Hz, 1 H), 7.59 (d, J=5.5 Hz, 1 H), 7.63 (d, J=7.9 Hz, 1 H), 8.42 (d, J=5.5 Hz, 1 H), 8.76 (s, 1 H); MS m/e 389 (MH$^+$).

EXAMPLE 166

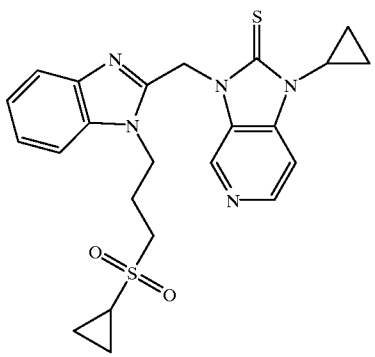

$^1$H NMR (CDCl$_3$) δ 1.00–1.07 (m, 4 H), 1.15–1.18 (m, 2 H), 1.16–1.23 (m, 2 H), 2.20–2.26 (m, 2 H), 2.32–2.38 (m, 1 H), 2.96–2.30 (m, 1 H), 3.09 (t, J=7.2 Hz, 2 H), 4.53 (t, J=7.5 Hz, 2 H), 5.38 (s, 2 H), 7.18 (d, J=5.3 Hz, 1 H), 7.27–7.33 (m, 2 H), 7.38–7.39 (m, 1 H), 7.77–7.79 (m, 1 H), 8.34 (d, J=5.3 Hz, 1 H), 8.74 (s, 1 H); MS m/e 452 (MH$^+$).

The compounds of the present invention may be administered orally, parenterally (including subcutaneous injections, intravenous, intramuscular, intrasternal injection or infusion techniques), intranasally, by inhalation spray, or rectally, in dosage unit formulations containing conventional non-toxic pharmaceutically-acceptable carriers, adjuvants and vehicles.

Thus, in accordance with the present invention there is further provided a method of treating and a pharmaceutical composition for treating viral infections such as RSV infection. The treatment involves administering to a patient in need of such treatment a pharmaceutical composition comprising a pharmaceutical carrier and a therapeutically-effective amount of a compound of the present invention.

The pharmaceutical composition may be in the form of orally-administrable suspensions or tablets; nasal sprays, sterile injectable preparations, for example, as sterile injectable aqueous or oleagenous suspensions or suppositories.

When administered orally as a suspension, these compositions are prepared according to techniques well-known in the art of pharmaceutical formulation and may contain microcrystalline cellulose for imparting bulk, alginic acid or sodium alginate as a suspending agent, methylcellulose as a viscosity enhancer, and sweetners/flavoring agents known in the art. As immediate release tablets, these compositions may contain microcrystalline cellulose, dicalcium phosphate, starch, magnesium stearate and lactose and/or other excipients, binders, extenders, disintegrants, diluents and lubricants known in the art.

The injectable solutions or suspensions may be formulated according to known art, using suitable non-toxic, parenterally-acceptable diluents or solvents, such as mannitol, 1,3-butanediol, water, Ringer's solution or isotonic sodium chloride solution, or suitable dispersing or wetting and suspending agents, such as sterile, bland, fixed oils, including synthetic mono- or diglycerides, and fatty acids, including oleic acid.

The compounds of this invention can be administered orally to humans in a dosage range of 0.1 to 100 mg/kg body weight in divided doses. One preferred dosage range is 0.1 to 10 mg/kg body weight orally in divided doses. Another preferred dosage range is 0.1 to 20 mg/kg body weight orally in divided doses. It will be understood, however, that the specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

BIOLOGICAL ACTIVITY

The antiviral activity of these compounds against respiratory syncytial virus was determined in HEp-2 (ATCC CCL 23) cells that were seeded in 96 well microtiter plates at 1.5×10$^4$ cells/100 μL/well in DMEM (Dulbecco's Modified Eagle's Medium) supplemented with penicillin, streptomycin, glutamine, and 10% fetal bovine serum. The cells were incubated overnight at 37° C., the culture medium was removed, and cells were infected (100 μL volume in medium containing 2% fetal bovine serum) with respiratory syncytial virus Long strain at 5000 plaque forming units/mL. The compounds, 100 μL at appropriate dilution, were added to the cells 1 hour post infection. After incubation for 4 days at 37° C., the plates were stained with MTT solution (3-[4,5-dimethlythiazol-2-yl]-2,5-diphenyltetrazolium bromide) and incubated for 4 hours at 37° C. The media was aspirated from the cells and 100 μL/well of acidified isopropanol (per liter: 900 mL isopropanol, 100 mL Triton X100, and 4 mL conc. HCl) was added. Plates were incubated for 15 minutes at room temperature with shaking, and an optical density (OD 540) reading at 540 nanometer (nm) was obtained. The optical density reading is proportional to the number of viable cells. The increase in the number of viable cells reflects the protective, antiviral activity of the compound. Assays comparing MTT staining in uninfected cells containing compound with uninfected cells in the absence of compound provide a measure of cellular toxicity. The control compound in this assay is Ribavirin which exhibits 100% cell protection at 2.5 μg/mL (corresponding to 10.2 μM).

The antiviral activity of compounds, designated as EC$_{50}$, is presented as a concentration that produces 50% cell protection in the assay. The compounds disclosed in this application show antiviral activity with EC$_{50}$'s between 50 μM and 0.001 μM. Ribavirin has an EC$_{50}$ of 3 μM.

What is claimed is:

1. A compound of Formula I, and pharmaceutically acceptable salts thereof,

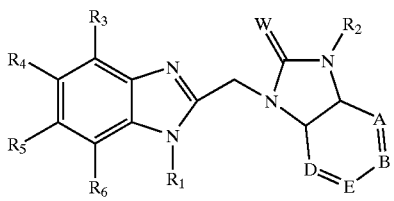

Formula I wherein:

W is O or S;

$R_1$ is -(CR'R")$_n$-X;

X is H, $C_{1-12}$ alkyl, $C_{2-12}$ alkenyl, $C_{2-12}$ alkynyl, $C_{3-7}$ cycloalkyl, $C_{4-7}$ cycloalkenyl, each of said alkyl, alkenyl, alkynyl, cycloalkyl and cycloalkenyl being optionally substituted with one to six of the same or different halogen atoms; halogen, CN, OR', OCOR"", NR'R", NR'COR", NR'CONR"R'", NR'SO$_2$R", NR'COOR", NR'COOR", COR', CR'"NNR'R", CR'NOR", COOR', CONR'R", SO$_m$R', PO(OR')$_2$, aryl, heteroaryl or non-aromatic heterocycle;

m is 0–2; n is 2–6;

$R_2$ is (i) H, $C_{1-12}$ alkyl, $C_{2-12}$ alkenyl, $C_{2-12}$ alkynyl, $C_{3-7}$ cycloalkyl, $C_{4-7}$ cycloalkenyl, -(CH$_2$)$_t$ $C_{3-7}$ cycloalkyl, -(CH$_2$)$_t$ $C_{4-7}$ cycloalkenyl, each of said alkyl, alkenyl, alkynyl, cycloalkyl and cycloalkenyl being optionally substituted with one to six of the same or different halogen atoms;

SO$_2$R", SO$_2$NR'R" or CN; wherein t is 1–6;

(ii) -(CR'R")$_{n'}$-Y, wherein Y is CN, OR',OCONR'R", NR'R", NCOR', NR'SO$_2$R", NR'COOR", NR'CONR"R'", COR', CR'"NNR'R", CR'NOR", COOR', CONR'R", SO$_m$R', SO$_2$NR'R" or PO(OR')$_2$; wherein m is –2 and n' is 1–6;

(iii) -(CR'R")$_{n''}$-C$_6$H$_4$-Z, wherein the Z group may be in the ortho, meta or para position relative to the -(CH$_2$)$_{n''}$ group; Z is CN, OR', OCONR'R", NO$_2$, NCOR', NR'SO$_2$R", NR'COOR", NR'CONR"R'", COR', CR'"NNR'R", CR'NOR", COOR', CONR'R", SO$_m$R', SO$_2$NR'R" or PO(OR')$_2$;

m is 0–2; n" is 0–6; or (iv) -(CR'R")N'"-heteroaryl, wherein n'" is 0–6;

(v) -(CR'R")$_{n''''}$-non-aromatic heterocycle, wherein n$_{40}$ " $_{is}$ 0–6;

$R_3$, $R_4$, $R_5$ and $R_6$ are each independently hydrogen, halogen, $C_{1-6}$ alkyl, $C_{1-6}$ alkyl substituted with one to six of the same or different halogen atoms, OR', CN, COR', COOR', CON'R", or NO$_2$;

A, B, E, D are each independently C—H, C—Q—, N, or N—O; provided only one of A, B, E or D is not C—H or C—Q; wherein Q is halogen, $C_{1-3}$ alkyl or $C_{1-3}$ alkyl substituted with one to three of the same or different halogen atoms;

R', R", R'" are each independently H, $C_{1-6}$ alkyl, $C_{2-6}$ alkenyl, $C_{2-6}$ alkynyl, $C_{3-7}$ cycloalkyl, $C_{4-7}$ cycloalkenyl, each of said alkyl, alkenyl, alkynyl, cycloalkyl and cycloalkenyl being optionally substituted with one to six of the same or different halogen atoms; or R' and R" taken together form a cyclic alkyl group having 3 to 7 carbon atoms; benzyl, or aryl;

R"" is $C_{1-6}$ alkyl, $C_{2-6}$ alkenyl, $C_{2-6}$ alkynyl, $C_{3-7}$ cycloalkyl, $C_{4-7}$ cycloalkenyl, NR'R", CR'NR"R'", aryl, heteroaryl, non-aromatic hetercycle; and Non-aromatic heterocycle is a 3–7 membered non-aromatic ring containing at least one and up to 4 non-carbon atoms selected from the group consisting of O, S, N, and NR';

Aryl is phenyl, naphthyl, indenyl, azulenyl, fluorenyl and anthracenyl;

Heteroaryl is a 4–7 membered aromatic ring which contains one to five heteroatoms independently selected from the group consisting of O, S, N and NR', wherein sadi aromatic ring is optionally fused to group B';

B' is an aromatic group selected from the group consisting of phenyl, 1-naphthyl, 2-naphthyl, idenyl, azulenyl, flurenyl, and anthracenyl;

Aryl, B', said 4-7 membered aromatic ring, and said 3-7 membered non-aromatic ring may each independently contain one to five substituents which are each independently selected from $R_7$, $R_8$, $R_9$, $R_{10}$ or $R_{11}$; and $R_7$, $R_8$, $R_9$, $R_{10}$ and $R_{11}$ are each independently (i) H, $C_{1-6}$ alkyl, $C_{2-6}$ alkenyl, $C_{2-6}$ alkynyl, $C_{3-7}$ cycloalkyl, $C_{4-7}$ cycloalkenyl, each of said alkyl, alkenyl, alkynyl, cycloalkyl, cycloalkenyl, being optionally substituted with one to six of the same or different halogen atoms; and (ii) halogen, CN, NO$_2$, OR', NR'R", COR', COOR', CONR'R", OCOR', NR'COR", SO$_m$R', SO$_2$NR'R", PO(OR')$_2$.

2. The compound of claim 1 wherein heteroaryl is selected from the group consisting of 2-furyl, 3-furyl, 2-thienyl, 3-thienyl, 2-pyridyl, 3-pyridyl, 4-pyridyl, pyrrolyl, oxazolyl, thiazolyl, imidazolyl, pyrazolyl, isoxazolyl, isothiazolyl, 1,2,3-oxadiazolyl, 1,2,4-oxadiazolyl, 1,2,4-oxadiazol-5-one, 1,2,3-triazolyl, 1,3,4-thiadiazolyl, pyridazinyl, pyrimidinyl, pyrazinyl, 1,3,5-triazinyl, 1,3,5-trithianyl, indolizinyl, indolyl, isoindolyl, 3H-indolyl, indolinyl, benzoylfuranyl, benzo[b]thiophenyl, 1H-indazolyl, benzimidazolyl, benzthiazolyl, purinyl, 4H-quinolizinyl, quinolinyl, isoquinolinyl, cinnolinyl, phthalazinyl, quinazolinyl, quinoxalinyl, 1,8-naphthyridinyl, pteridinyl, carbazolyl, acridinyl, phenazinyl, phenothiazinyl, tetrazole and phenoxazinyl.

3. A compound of claim 2 wherein:

$R_1$ is —(CH$_2$)$_n$—X;

X is H, $C_{1-6}$ alkyl, $C_{2-6}$ alkenyl, $C_{2-6}$ alkynyl, $C_{3-6}$ cycloalkyl, $C_{3-6}$ cycloalkenyl, each of said alkyl, alkenyl, alkynyl, cycloalkyl and cycloalkenyl being optionally substituted with one to six of the same or different halogen atoms; halogen, CN, OR', OCOR"", NR'R", NR'COR", NR'COOR", COR', CR'"NNR'R'R", CR'NOR", COOR', CONR'R", SO$_m$R', aryl or heteroaryl;

m is 0–2; n is 2–4;

$R_2$ is (i) H, $C_{1-6}$ alkyl, $C_{2-6}$ alkenyl, $C_{2-6}$ alkynyl, $C_{3-6}$ cycloalkyl, C3–6 cycloalkenyl, —(CH$_2$)$_t$ $C_{3-7}$ cycloalkyl, —(CH$_2$)$_t$ $C_{4-7}$ cycloalkenyl, each of said alkyl, alkenyl, alkynyl, cycloalkyl and cycloalkenyl being optionally substituted with one to six of the same or different halogen atoms; SO$_2$R", SO$_2$NR'R" or CN; wherein t is 1–6;

(ii) —(CH$_2$)$_{n'}$—Y, wherein Y is CN, OR', COR', COOR', CONR'R", SO$_m$R', SO$_2$NR!R", PO(OR')$_2$ wherein m is 0–2 and n' is 1–6; or (iii) —$(CH_2)n''$—$C_6H_4$—Z, wherein the Z group may be in the ortho, meta or para position relative to the —$(CH_2)n''$ group; Z is CN, OR', COR' or $SO_mR'$; m is 0–2; n" is 0–3;

$R_3$, $R_4$, $R_5$, and $R_6$ are each independently hydrogen, halogen, $C_1$–$I_6$ alkyl, optionally substituted with one to six of the same or different halogen atoms; and A, B, E, D are each independently C—H or N; provided at least one of A, B, E or D is not C—H.

4. A compound of claim 2 wherein:

$R_3$, $R_4$, $R_5$ and $R_6$ are each H;

A, B and D are each C—H; and

E is N.

5. A compound of claim 2 wherein:

$R_3$, $R_4$, $R_5$ and $R_6$ are each H;

A, B and D are each C—H; and

E is N.

6. A pharmaceutical composition which comprises a therapeutically effective amount of an anti-RSV compound having Formula I, and pharmaceutically acceptable salts thereof, as claimed in any one of claims 1–5, and a pharmaceutically acceptable carrier.

7. A method for treating mammals infected with RSV, and in need thereof, which comprises administering to said mammal a therapeutically effective amount of a compound having the Formula I, and pharmaceutically acceptable salts thereof, as claimed in any one of claims 1–5.

\* \* \* \* \*